(12) United States Patent
Kossen et al.

(10) Patent No.: US 9,726,677 B2
(45) Date of Patent: Aug. 8, 2017

(54) PROTEOMIC IPF MARKERS

(71) Applicant: Intermune, Inc., Brisbane, CA (US)

(72) Inventors: Karl Kossen, Burlingame, CA (US);
Xiaoli Qin, San Mateo, CA (US);
Sharlene R. Lim, San Mateo, CA (US);
Scott S. Seiwert, Half Moon Bay, CA (US); Donald Ruhrmund, San Francisco, CA (US)

(73) Assignee: INTERMUNE, INC., Brisbane, CA (US)

( * ) Notice: Subject to any disclaimer, the term of this patent is extended or adjusted under 35 U.S.C. 154(b) by 0 days.

(21) Appl. No.: 14/213,970

(22) Filed: Mar. 14, 2014

(65) Prior Publication Data

US 2014/0286929 A1 Sep. 25, 2014

Related U.S. Application Data

(60) Provisional application No. 61/801,290, filed on Mar. 15, 2013, provisional application No. 61/801,476, filed on Mar. 15, 2013, provisional application No. 61/874,947, filed on Sep. 6, 2013.

(51) Int. Cl.
*A61K 38/44* (2006.01)
*G01N 33/68* (2006.01)
*C12Q 1/68* (2006.01)

(52) U.S. Cl.
CPC ....... *G01N 33/6893* (2013.01); *C12Q 1/6883* (2013.01); *G01N 33/6854* (2013.01); *C12Q 2600/118* (2013.01); *C12Q 2600/158* (2013.01); *G01N 2800/12* (2013.01)

(58) Field of Classification Search
CPC ........... G01N 2800/12; G01N 33/6893; G01N 33/6854; C12Q 1/6883; C12Q 2600/118; C12Q 2600/158
See application file for complete search history.

(56) References Cited

U.S. PATENT DOCUMENTS

| | | | |
|---|---|---|---|
| 5,034,506 A | 7/1991 | Summerton et al. | |
| 5,235,033 A | 8/1993 | Summerton et al. | |
| 5,582,981 A | 12/1996 | Toole et al. | |
| 5,595,877 A | 1/1997 | Gold et al. | |
| 5,637,459 A | 6/1997 | Burke et al. | |
| 6,019,988 A | 2/2000 | Parab et al. | |
| 7,981,621 B2* | 7/2011 | Darbouret | G01N 33/573 435/7.1 |
| 2004/0234519 A1* | 11/2004 | Tso | A61K 47/48546 424/141.1 |
| 2010/0227335 A1* | 9/2010 | Baker | C07K 16/40 435/7.4 |
| 2011/0076280 A1* | 3/2011 | Nakamura | C07K 16/3046 424/158.1 |
| 2011/0250589 A1 | 10/2011 | Lama | |
| 2011/0280865 A1 | 11/2011 | Marsh et al. | |
| 2012/0035067 A1 | 2/2012 | Kaminski et al. | |
| 2012/0282276 A1 | 11/2012 | Hogaboam et al. | |
| 2013/0078252 A1* | 3/2013 | Wilson | A61K 31/437 424/138.1 |

FOREIGN PATENT DOCUMENTS

| | | |
|---|---|---|
| WO | WO-2004/009776 A2 | 1/2004 |
| WO | WO-2004/009776 A3 | 1/2004 |
| WO | WO-2010/028274 A1 | 3/2010 |
| WO | WO-2011/054893 A2 | 5/2011 |
| WO | WO-2014/144821 A1 | 9/2014 |

OTHER PUBLICATIONS

Ishii et al. J. Biol. Chem. (2002) 277(42): 39696-39702.*
Pavan et al. Endocrinology (2004) 145(10): 4583-4591.*
Entrez entry for gene ID No. 8578 downloaded from NCBI https://www.ncbi.nlm.nih.gov/gene/?term=8578 on Mar. 30, 2017.*
Desai, B. et al. (Jan. 2009). "Differential Cellular and Molecular Markers in Idiopathic Pulmonary Fibrosis," *American Journal of Respiratory and Critical Care Medicine; American Thoracic Society 2009 international Conference, American Lung Association* vol. 179, p. A3488, Meeting Abstracts.
Fingerlin, T.E. et al. (Jun. 2013, e-published Apr. 14, 2013). "Genome-wide association study identifies multiple susceptibility loci for pulmonary fibrosis," Nature Genetics 45(6):613-620.
Selman, M. et al. (2000). "TIMP-1, -2, -3 and -4 in idiopathic pulmonary fibrosis. A prevailing nondegradative lung microenvironment?" *American Journal of Physiology-Lung Cellular and Molecular Physiology* Sep 279(3):L562-L574.
Rosas, I.O. et al. (Apr. 29, 2008). "MMP1 and MMP7 as potential peripheral blood biomarkers in idiopathic pulmonary fibrosis," *PLoS Med* 5(4):623-633.
Thomeer, M. et al. (Jun. 28, 2010). "Clinical use of biomarkers of survival in pulmonary fibrosis," *Respiratory Research* 11:89.
Tzouvelekis, A. et al. (Jul. 21, 2005). "Serum biomarkers in interstitial lung diseases," *Respiratory Research* 6(1):78.
American Thoracic Society et al. (Jan. 15, 2002). "American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, Jun. 2001 and by the ERS Executive Committee, Jun. 2001," *Am J Respir Crit Care Med* 165(2):277-304.
Brody, E.N. et al. (Nov. 2010). "High-content affinity-based proteomics: unlocking protein biomarker discovery," *Expert Rev Mol Diagn* 10(8):1013-1022.
Coche, E. et al. (Feb. 2001). "Non-specific interstitial pneumonia showing a "crazy paving" pattern on high resolution CT," *Br J Radiol* 74(878):189-191.
International Search Report mailed on Jul. 17, 2014, for PCT Application No. PCT/US2014/029392, filed Mar. 14, 2014, 4 pages.

(Continued)

*Primary Examiner* — Susan Hanley
(74) *Attorney, Agent, or Firm* — Mintz Levin Cohn Ferris Glovsky and Popeo, P.C.

(57) ABSTRACT

Provided herein are novel biomarkers for the identification, prediction or monitoring of fibrotic pulmonary diseases (e.g. idiopathic pulmonary fibrosis (IPF)). The biomarkers provided herein may further be used for therapeutic treatment of IPF.

12 Claims, 57 Drawing Sheets

(56) References Cited

OTHER PUBLICATIONS

Ma, S. et al. (Jul. 1, 2011, e-published May 13, 2011). "Quantitation of desmosine and isodesmosine in urine, plasma, and sputum by LC-MS/MS as biomarkers for elastin degradation" *J Chromatogr B Analyt Technol Biomed Life Sci* 879(21):1893-1898.

Raghu, G. et al. (Oct. 1, 2006, e-published Jun. 29, 2006). "Incidence and prevalence of idiopathic pulmonary fibrosis," *Am J Respir Crit Care Med* 174(7):810-816.

Tazelaar, H.D. et al. (Mar. 2011, e-published Sep. 21, 2010). "Desquamative interstitial pneumonia," *Histopathology* 58(4):509-516.

Wells, A.U. et al. (Oct. 2003). "Respiratory bronchiolitis-associated interstitial lung disease," *Semin Respir Crit Care Med* 24(5):585-594.

White, K.A. et al. (Jun. 2007). "Bronchiolitis obliterans organizing pneumonia," Crit Care Nurse 27(3):53-66.

Written Opinion mailed on Jul. 17, 2014, for PCT Application No. PCT/US2014/029392, filed Mar. 14, 2014, 7 pages.

\* cited by examiner

PROTEOMIC IPF MARKERS

CROSS-REFERENCES TO RELATED APPLICATIONS

This application claims priority to U.S. Provisional Application No. 61/801,290, filed Mar. 15, 2013, U.S. Provisional Application No. 61/801,476, filed Mar. 15, 2013, and U.S. Provisional Application No. 61/874,947, filed Sep. 6, 2013, the disclosures of which are incorporated herein in their entireties.

BACKGROUND OF THE INVENTION

The idiopathic interstitial pneumonias (IIPs) represents a class of chronic pulmonary fibrotic disorders characterized by progressive scarring of the alveolar interstitium leading to severe dyspnea, hypoxemia, and death. Among interstitial lung disease idiopathic pulmonary fibrosis (IPF) is the most progressive disease with median survival of 2.5-3 years (ATS/ERS. Am J Respir Crit Care Med 2002: 165(2): 277-304). Patients diagnosed with IPF typically experience progressive pulmonary insufficiency, and most die of respiratory failure. The ratio of the estimated prevalence (90,000 individuals) and incidence (30,000 individuals) of IPF in the United States reflects this poor prognosis (Raghu G, Weycker D, Edelsberg J, Bradford W Z, Oster G. Incidence and prevalence of idiopathic pulmonary fibrosis. Am J Respir Crit Care Med 2006: 174(7): 810-816). The clinical course of IPF is highly variable and may be characterized by periods of relative stability, chronic decline, or periods of rapid decline (known as acute exacerbations).

Clinical and physiological parameters (e.g., forced vital capacity, diffusing capacity of carbon monoxide DLco, six minute walk test distance) are currently used to monitor disease state and progression. These clinical assessments of IPF and risk prediction models that incorporate these components (or change therein) are relatively successful in staging patients and predicting risk of mortality. However, management approaches that are based on molecular information (such as that derived from protein markers) may enable better monitoring of disease progression and risk of progression in patients with IPF.

There is a need in the art for well-defined biomarkers to determine if a patient has or is at risk for developing a fibrotic pulmonary disease, to indicate the progressiveness of the disease, and/or to facilitate evaluation of responsiveness to therapy. The invention provided herein addresses these and other needs in the art by providing, inter alia, novel protein biomarkers of fibrotic pulmonary diseases (e.g. IPF).

BRIEF SUMMARY OF THE INVENTION

In one aspect, a method of determining an expression level of a fibrotic pulmonary disease marker protein set forth in Table 1A or Table 1B in a subject that has or is at risk for developing a fibrotic pulmonary disease is provided. The method includes (i) obtaining a biological sample from said subject and (ii) determining an expression level of a fibrotic pulmonary disease marker protein set forth in Table 1A or Table 1B in the biological sample.

In another aspect, a method of determining whether a subject has or is at risk of developing a fibrotic pulmonary disease is provided. The method includes (i) detecting an expression level of one or more fibrotic pulmonary disease marker proteins set forth in Table 1A or Table 1B in a subject; (ii) determining whether the expression level is increased or decreased relative to a standard control, wherein an elevated expression level of a fibrotic pulmonary disease marker protein in Table 1A or a decreased expression level of a fibrotic pulmonary disease marker protein in Table 1B relative to the standard control indicates that the subject has or is at risk of developing a fibrotic pulmonary disease; and (iii) based at least in part on the expression level in step (ii), determining whether the subject has or is at risk for developing a fibrotic pulmonary disease.

In another aspect, a method of determining whether a fibrotic pulmonary disease patient is at risk for progression of the fibrotic pulmonary disease is provided. The method includes (i) detecting an expression level of one or more fibrotic pulmonary disease marker protein set forth in Table 1A or Table 1B in a fibrotic pulmonary disease patient (ii) determining whether the expression level is modulated relative to a standard control, wherein a modulated expression level of a fibrotic pulmonary disease marker protein in Table 1A or Table 1B relative to the standard control indicates that the fibrotic pulmonary disease patient is at risk for progression of the fibrotic pulmonary disease, and (iii) based at least in part on the expression level in step (ii), determining whether the fibrotic pulmonary disease patient is at risk for progression of the fibrotic pulmonary disease.

In another aspect, a method of determining whether a fibrotic pulmonary disease patient is at risk for progression of the fibrotic pulmonary disease is provided. The method includes (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, wherein when the second expression level of a protein set forth in Table 1A is greater than the first level of a protein set forth in Table 1A; or wherein when the second expression level of a protein set forth in Table 1B is smaller than the first level of a protein set forth in Table 1B, the patient is at risk for progression of the fibrotic pulmonary disease.

In another aspect, a method of determining a fibrotic pulmonary disease activity in a patient is provided. The method includes (i) detecting an expression level of one or more fibrotic pulmonary disease marker proteins set forth in Table 1A or Table 1B in a subject; (ii) determining whether the expression level is modulated relative to a standard control, thereby determining a fibrotic pulmonary disease activity in the patient; and (iii) based at least in part on the expression level in step (ii), determining the fibrotic pulmonary disease activity in the patient.

In another aspect, a method of determining a fibrotic pulmonary disease activity in a patient is provided. The method includes (i) determining a first expression level of a protein set forth in Table 1A or Table 1B in the patient at a first time point; (ii) determining a second expression level of a protein set forth in Table 1A or Table 1B in the patient at a second time point; (iii) comparing the second expression level of a protein set forth in Table 1A or Table 1B to the first expression level of a protein set forth in Table 1A or Table 1B, thereby determining the fibrotic pulmonary disease activity in the patient.

In another aspect, a method of determining a change in fibrotic pulmonary disease activity in a patient is provided. The method includes (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, thereby determining the a change in fibrotic pulmonary disease activity in the patient.

In another aspect, a method of determining a change in fibrotic pulmonary disease activity in a patient is provided. The method includes (i) detecting an expression level of one or more fibrotic pulmonary disease marker proteins set forth in Table 1A or Table 1B in a subject; (ii) determining whether the expression level is modulated relative to a standard control, thereby determining a change in fibrotic pulmonary disease activity in the patient; and (iii) based at least in part on the expression level in step (ii), determining the change in fibrotic pulmonary disease activity in the patient.

In another aspect, provided herein is a method of monitoring the effect of treatment for a fibrotic pulmonary disease in a patient undergoing fibrotic pulmonary disease therapy or a patient that has received fibrotic pulmonary disease therapy. The method includes (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, thereby determining the effect of treatment for a fibrotic pulmonary disease in the patient.

In another aspect, provided herein is a method of monitoring the effect of treatment for a fibrotic pulmonary disease in a patient undergoing fibrotic pulmonary disease therapy or a patient that has received fibrotic pulmonary disease therapy. The method includes (i) detecting an expression level of one or more fibrotic pulmonary disease marker proteins set forth in Table 1A or Table 1B in a subject; (ii) determining whether the expression level is modulated relative to a standard control, thereby monitoring the effect of treatment for a fibrotic pulmonary disease in the patient; and (iii) based at least in part on the expression level in step (ii), monitoring the effect of treatment for a fibrotic pulmonary disease in the patient.

In another aspect, a method of treating a fibrotic pulmonary disease in a subject in need thereof is provided. The method includes administering to the subject an effective amount of an modulator of a fibrotic pulmonary disease marker protein set forth in Table 1A or Table 1B, thereby treating a fibrotic pulmonary disease in said subject.

In one aspect, a method of treating a fibrotic pulmonary disease in a subject in need thereof is provided. The method includes (i) determining whether a subject expresses an elevated level of a fibrotic pulmonary disease marker protein as set forth in Table 1A or a decreased level of a fibrotic pulmonary disease marker protein as set forth in Table 1B relative to a standard control, and (ii) when an elevated expression level of the fibrotic pulmonary disease marker protein of Table 1A or a decreased expression level of the fibrotic pulmonary disease marker protein of Table 1B is found relative to the standard control, administering to the subject a fibrotic pulmonary disease treatment, an antagonist of a fibrotic pulmonary disease marker protein set forth in Table 1A or an agonist of a fibrotic pulmonary disease marker protein set forth in Table 1B, thereby treating the subject.

In another aspect, a method of determining an expression level of a fibrotic pulmonary disease marker protein set forth in Table 3A or Table 3B in a subject that has or is at risk for developing a fibrotic pulmonary disease is provided. The method includes (i) obtaining a biological sample from the subject, and (ii) determining an expression level of a fibrotic pulmonary disease marker protein set forth in Table 3A or Table 3B in the biological sample.

In another aspect, a method of determining whether a subject has or is at risk of developing a fibrotic pulmonary disease is provided. The method includes (i) detecting an expression level of one or more fibrotic pulmonary disease marker proteins set forth in Table 3A or Table 3B in a subject, (ii) determining whether said expression level is increased or decreased relative to a standard control, wherein an elevated expression level of a fibrotic pulmonary disease marker protein in Table 3A or a decreased expression level of a fibrotic pulmonary disease marker protein in Table 3B relative to the standard control indicates that the subject has or is at risk of developing a fibrotic pulmonary disease, and (iii) based at least in part on the expression level in step (ii), determining whether the subject has or is at risk for developing a fibrotic pulmonary disease.

In another aspect, a method of determining whether a fibrotic pulmonary disease patient is at risk for progression of the fibrotic pulmonary disease is provided. The method includes (i) detecting an expression level of one or more fibrotic pulmonary disease marker protein set forth in Table 3A or 3B in a fibrotic pulmonary disease patient, (ii) determining whether the expression level is modulated relative to a standard control, wherein a modulated expression level of a fibrotic pulmonary disease marker protein in Table 3A or 3B relative to the standard control indicates that the fibrotic pulmonary disease patient is at risk for progression of the fibrotic pulmonary disease, and (iii) based at least in part on the expression level in step (ii), determining whether the fibrotic pulmonary disease patient is at risk for progression of the fibrotic pulmonary disease.

In one aspect, a method of determining whether a fibrotic pulmonary disease patient is at risk for progression of the fibrotic pulmonary disease is provided. The method includes (i) determining a first expression level of a protein set forth in Table 3A or Table 3B in the patient at a first time point, (ii) determining a second expression level of a protein set forth in Table 3A or Table 3B in the patient at a second time point, (iii) comparing the second expression level of a protein set forth in Table 3A or Table 3B to the first expression level of a protein set forth in Table 3A or Table 3B, wherein when the second expression level of a protein set forth in Table 3A is greater than the first level of a protein set forth in Table 3A, or wherein when the second expression level of a protein set forth in Table 3B is smaller than the first level of a protein set forth in Table 3B, the patient is at risk for progression of the fibrotic pulmonary disease.

In another aspect, a method of determining a fibrotic pulmonary disease activity in a patient is provided. The method includes, (i) detecting an expression level of one or more fibrotic pulmonary disease marker proteins set forth in Table 3A or Table 3B in a subject; (ii) determining whether the expression level is modulated relative to a standard control, thereby determining a fibrotic pulmonary disease activity in the patient; and (iii) based at least in part on the expression level in step (ii), determining said fibrotic pulmonary disease activity in the patient.

In another aspect, a method of determining a fibrotic pulmonary disease activity in a patient is provided. The method includes (i) determining a first expression level of a protein set forth in Table 3A or Table 3B in the patient at a first time point, (ii) determining a second expression level of a protein set forth in Table 3A or Table 3B in the patient at a second time point, (iii) comparing the second expression level of a protein set forth in Table 3A or Table 3B to the first expression level of a protein set forth in Table 3A or Table 3B, thereby determining the fibrotic pulmonary disease activity in the patient.

In another aspect, a method of determining a change in fibrotic pulmonary disease activity in a patient is provided. The method includes (i) determining a first expression level of a protein set forth in Table 3A or Table 3B in the patient at a first time point; (ii) determining a second expression level of a protein set forth in Table 3A or Table 3B in the patient at a second time point; and (iii) comparing the second expression level of a protein set forth in Table 3A or Table 3B to the first expression level of a protein set forth in Table 3A or Table 3B, thereby determining a change in fibrotic pulmonary disease activity in a patient.

In another aspect, a method of determining a change in fibrotic pulmonary disease activity in a patient is provided. The method includes (i) detecting an expression level of one or more fibrotic pulmonary disease marker proteins set forth in Table 3A or Table 3B in a subject; (ii) determining whether the expression level is modulated relative to a standard control, thereby determining a change in fibrotic pulmonary disease activity in the patient; and (iii) based at least in part on the expression level in step (ii), determining the change in fibrotic pulmonary disease activity in the patient.

In another aspect, provided herein is a method of monitoring the effect of treatment for a fibrotic pulmonary disease in a patient undergoing fibrotic pulmonary disease therapy or a patient that has received fibrotic pulmonary disease therapy. The method includes (i) determining a first expression level of a protein set forth in Table 3A or Table 3B in the patient at a first time point; (ii) determining a second expression level of a protein set forth in Table 3A or Table 3B in the patient at a second time point; and (iii) comparing the second expression level of a protein set forth in Table 3A or Table 3B to the first expression level of a protein set forth in Table 3A or Table 3B, thereby monitoring the effect of treatment for a fibrotic pulmonary disease in the patient.

In another aspect, provided herein is a method of monitoring the effect of treatment for a fibrotic pulmonary disease in a patient undergoing fibrotic pulmonary disease therapy or a patient that has received fibrotic pulmonary disease therapy. The method includes (i) detecting an expression level of one or more fibrotic pulmonary disease marker proteins set forth in Table 3A or Table 3B in a subject; (ii) determining whether the expression level is modulated relative to a standard control, thereby monitoring the effect of treatment for a fibrotic pulmonary disease in the patient; and (iii) based at least in part on the expression level in step (ii), monitoring the effect of treatment for a fibrotic pulmonary disease in the patient In another aspect, a method of treating a fibrotic pulmonary disease in a subject in need thereof is provided. The method includes administering to the subject an effective amount of an modulator of a fibrotic pulmonary disease marker protein set forth in Table 3A or Table 3B, thereby treating a fibrotic pulmonary disease in the subject.

In another aspect, a method of treating a fibrotic pulmonary disease in a subject in need thereof is provided. The method includes (i) determining whether a subject expresses an elevated level of a fibrotic pulmonary disease marker protein as set forth in Table 3A or a decreased level of a fibrotic pulmonary disease marker protein as set forth in Table 3B relative to a standard control, and (ii) when an elevated expression level of the fibrotic pulmonary disease marker protein of Table 3A or a decreased expression level of the fibrotic pulmonary disease marker protein of Table 3B is found relative to the standard control, administering to the subject a fibrotic pulmonary disease treatment, an antagonist of a fibrotic pulmonary disease marker protein set forth in Table 3A or an agonist of a fibrotic pulmonary disease marker protein set forth in Table 3B, thereby treating the subject.

In one aspect a kit is provided. The kit includes a marker protein binding agent capable of binding to a substance within a biological sample from a human subject having or at risk of developing a fibrotic pulmonary disease, wherein the substance is a fibrotic pulmonary disease marker protein or fragment thereof set forth in the tables provided herein (e.g., Table 1A, 1B, 2A, 2B, 3A, 3B, 4A, or 4B); and a detecting reagent or a detecting apparatus capable of indicating binding of the marker protein binding agent to the substance.

In one aspect a kit is provided. The kit includes a marker protein binding agent capable of binding to a substance within a biological sample from a human subject having a fibrotic pulmonary disease, wherein the substance is a fibrotic pulmonary disease marker protein or fragment thereof set forth in the tables provided herein (e.g., Table 1A, 1B, 2A, 2B, 3A, 3B, 4A, or 4B); and a detecting reagent or a detecting apparatus capable of indicating binding of the marker protein binding agent to the substance.

In another aspect, a complex in vitro is provided. The complex includes a marker protein binding agent bound to a fibrotic pulmonary disease marker protein or fragment thereof set forth in the tables provided herein (e.g., Table 1A, 1B, 2A, 2B, 3A, 3B, 4A, or 4B), wherein the fibrotic pulmonary disease marker protein is extracted from a human subject having or at risk of developing a fibrotic pulmonary disease.

In another aspect, a complex in vitro is provided. The complex includes a marker protein binding agent bound to a fibrotic pulmonary disease marker protein or fragment thereof set forth in the tables provided herein (e.g., Table 1A, 1B, 2A, 2B, 3A, 3B, 4A, or 4B), wherein the fibrotic pulmonary disease marker protein is extracted from a human subject having a fibrotic pulmonary disease.

Figure 1:
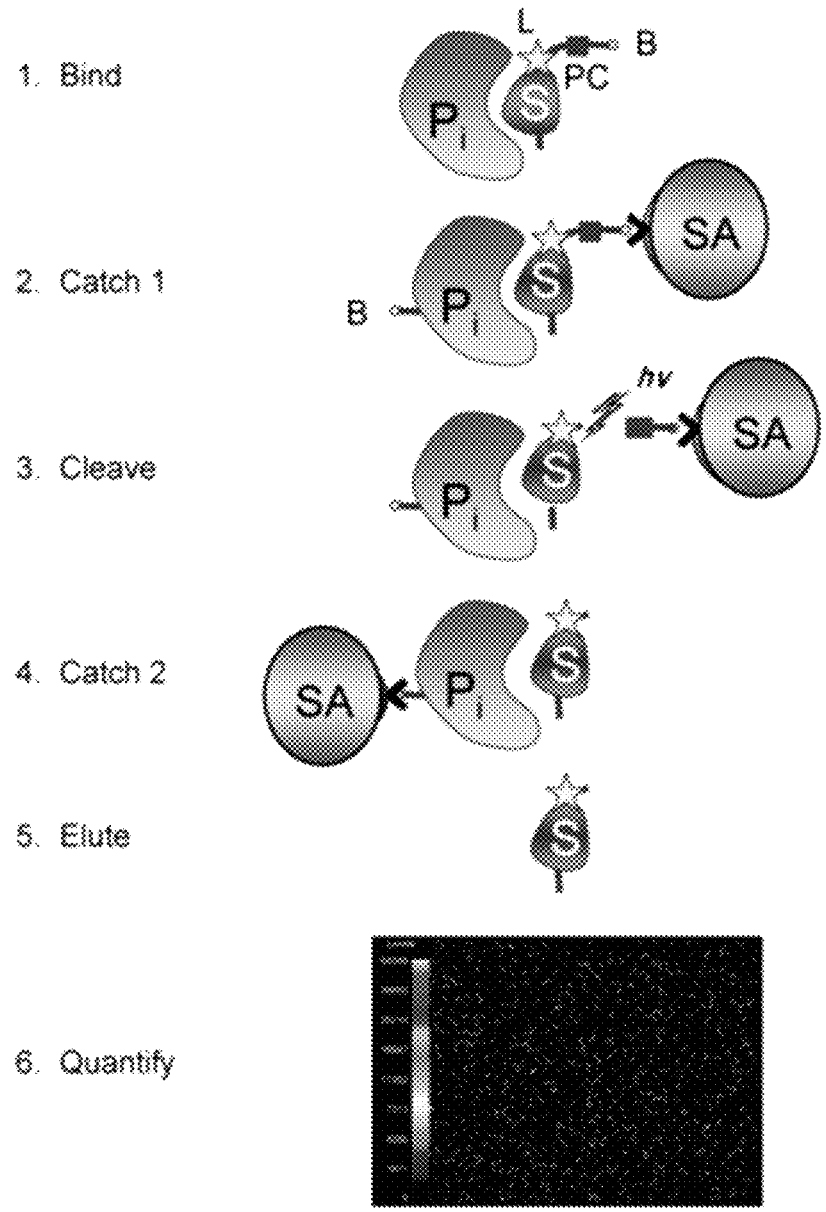
FIG. 1. Overview of the proteomics assay. (Step 1) The specific protein to be measured (P,) binds tightly to its cognate SOMAmer binding molecule (S), which includes a photo-cleavable biotin (PCB) and fluorescent label (L) at the 5' end. (Step 2) Bound protein-SOMAmer complexes are captured onto streptavidin coated beads (SA) by photo-cleavable biotin on the SOMAmer. Unbound proteins are washed away. Bound proteins are tagged with biotin (B). (Step 3) The photo-cleavable biotin is cleaved by UV light (hn) and the protein-SOMAmer complexes are released into solution. (Step 4) The protein-SOMAmer complexes are captured onto SA and the SOMAmers are eluted into solution (Step 5) and recovered for quantification in Step 6, hybridization to a custom DNA microarray. Each probe spot contains DNA with sequence complementary to a specific SOMAmer, and the fluorescent intensity of each probe spot is proportional to the amount of SOMAmer recovered, which is proportional to the amount of protein present in the original sample. PCB: Photo-cleavable biotin; SOMAmer: Slow off-rate modified aptamer. (reference: High-content affinity-based proteomics: unlocking protein biomarker discovery, Edward N Brody1, Larry Gold† 1,2, Richard M Lawn1, Jeffrey J Walker1 and Dom Zichi1 Expert Review of Molecular Diagnostics, November 2010, Vol. 10, No. 8, Pages 1013-1022, DOI 10.1586/erm.10.89).

(Upper left histogram) Kaplan-Meier curve for Progression Free Survival (PFS). X-axis indicates days, y-axis indicates percent survival. Subjects are grouped based on a protein level cut-off suggested by CART analysis. Number of subjects above and below cut-off are indicated (i.e. "high N" and "low N"). Unadjusted p-value for significance is shown.

(Upper right histogram) Kaplan-Meier curve for Progression Free Survival (PFS). X-axis indicates days, y-axis indicates percent survival. Subjects are grouped based on quartiles of protein levels (i.e. Q1 indicates the lowest quartile). Unadjusted p-values for significance compared to Q1 are shown.

(Lower left histogram) Kaplan-Meier curve for All-Cause Mortality. X-axis indicates days, y-axis indicates percent survival. Subjects are grouped based on a protein level cut-off suggested by CART analysis. Number of subjects above and below cut-off are indicated (i.e. "high N" and "low N"). Unadjusted p-value for significance is shown.

(Lower right histogram) Kaplan-Meier curve for All-Cause Mortality. X-axis indicates days, y-axis indicates percent survival. Subjects are grouped based on quartiles of protein levels (i.e. Q1 indicates the lowest quartile). Unadjusted p-values for significance compared to Q1 are shown.

FIG. 48-FIG. 57: Selected fibrotic pulmonary disease biomarker proteins that predict disease progression in two independent patient cohorts. Plasma protein level was quantitated by ELISA. The following description applies to the plots shown in FIG. 48-FIG. 57:

(Upper left plot) Kaplan-Meier Curve for Progression Free Survival (PFS). X-axis indicates days, Y-axis indicates proportion of survival. Subjects are grouped based on median (FIG. 48-FIG. 53 and FIG. 56-57) or tertiles (FIGS. 54 and 55) of protein levels. p-values of Log-rank test are shown.

(Upper right plot) Kaplan-Meier Curve for Progression Free Survival (PFS). X-axis indicates days, Y-axis indicates proportion of survival. Subjects are grouped based on a protein level cut-off determined by CART analysis. Number of subjects above and below cut-off are indicated (i.e. "High N" and "Low N"). p-values of Log-rank test are shown.

(Lower left plot) Kaplan-Meier Curve for All-Cause Mortality. X-axis indicates days, Y-axis indicates proportion of survival. Subjects are grouped based on median (FIG. 48-FIG. 53 and FIG. 56-FIG. 57) or tertiles (FIG. 54 and FIG. 55) of protein levels. p-values of Log-rank test are shown.

(Lower right plot) Kaplan-Meier Curve for All-Cause Mortality. X-axis indicates days, Y-axis indicates proportion of survival. Subjects are grouped based on a protein level cut-off determined by CART analysis. Number of subjects above and below cut-off are indicated (i.e. "High N" and "Low N"). p-values of Log-rank test are shown.

DETAILED DESCRIPTION OF THE INVENTION

I. Definitions

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

The terms "pulmonary disease," "pulmonary disorder," "lung disease," etc. are used interchangeably herein. The term is used to broadly refer to lung disorders characterized by difficulty breathing, coughing, airway discomfort and inflammation, increased mucus, and/or pulmonary fibrosis.

An "airway mucosal sample" can be obtained using methods known in the art, e.g., a bronchial epithelial brush as described herein. Additional methods include endobronchial biopsy, bronchial wash, bronchoalveolar lavage, whole lung lavage, transendoscopic biopsy, and transtracheal wash.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom prone to suffering from the indicated disorder. In some aspects, the subject is a mammal, and in some aspects, the subject is a human.

A "control" sample or value refers to a sample that serves as a reference, usually a known reference, for comparison to a test sample. For example, a test sample can be taken from a patient suspected of having a given pulmonary disease and compared to samples from a known pulmonary disease patient, or a known normal (non-disease) individual. A control can also represent an average value gathered from a population of similar individuals, e.g., pulmonary disease patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "pharmaceutically" acceptable is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose will generally refer to the amount of pulmonary disease treatment, anti-inflammatory agent, agonist or antagonist. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" are not intended to be absolute terms. Treatment can refer to any delay in onset, reduction in the frequency or severity of symptoms, amelioration of symptoms, improvement in patient comfort and/or respiratory function, etc. The effect of treatment can be compared to an individual or pool of individuals not receiving a given treatment, or to the same patient prior to, or after cessation of, treatment.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of pulmonary disease symptoms in a patient. As indicated above, the prevention may be complete (no detectable symptoms) or partial, such that fewer symptoms are observed than would likely occur absent treatment.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability that a pulmonary disease is present in the subject. Similarly, the term "prognosis" refers to a relative probability that a certain future outcome may occur in the subject. For example, in the context of the present invention, prognosis can refer to the likelihood that an individual will develop a pulmonary disease, or the likely severity of the disease (e.g., severity of symptoms, rate of functional decline, survival, etc.). The terms are not intended to be absolute, as will be appreciated by any one of skill in the field of medical diagnostics.

The terms "correlating" and "associated," in reference to determination of a pulmonary disease risk factor, refers to comparing the presence or amount of the risk factor (e.g., decreased or increased expression of an IPF biomarker protein) in an individual to its presence or amount in persons known to suffer from, or known to be at risk of, the pulmonary disease, or in persons known to be free of pulmonary disease, and assigning an increased or decreased probability of having/developing the pulmonary disease to an individual based on the assay result(s).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The terms "identical" or percent "identity," in the context of two or more nucleic acids (e.g., genomic sequences or subsequences or coding sequences) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

An example of algorithms suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. As will be appreciated by one of skill in the art, the software for performing BLAST analyses is publicly available through the website of the National Center for Biotechnology Information (ncbi.nlm.nih.gov).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, y-carboxyglutamate, and 0-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Antibody" refers to a polypeptide comprising a framework region from an immunoglobulin gene or fragments thereof that specifically binds and recognizes an antigen, e.g., a specific bacterial antigen. Typically, the "variable region" contains the antigen-binding region of the antibody (or its functional equivalent) and is most critical in specificity and affinity of binding. See Paul, Fundamental Immunology (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The term "aptamer" as provided herein refers to short oligonucleotides (e.g. deoxyribonucleotides), which fold into diverse and intricate molecular structures that bind with high affinity and specificity to proteins, peptides, and small molecules in a non-Watson Crick manner. An aptamer can thus be used to detect or otherwise target nearly any molecule of interest, including a fibrotic pulmonary disease marker protein. Methods of constructing and determining the binding characteristics of aptamers are well known in the art. For example, such techniques are described in U.S. Pat. Nos. 5,582,981, 5,595,877 and 5,637,459. Aptamers are typically at least 5 nucleotides, 10, 20, 30 or 40 nucleotides in length, and can be composed of modified nucleic acids to improve stability. Flanking sequences can be added for structural stability, e.g., to form 3-dimensional structures in the aptamer. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified.

A "biomarker", "marker protein" or "biomarker protein" as provided herein refers to any assayable characteristics or compositions that is used to identify, predict, or monitor a condition (e.g., a fibrotic pulmonary disease or lack thereof) or a therapy for said condition in a subject or sample. A biomarker is, for example, a protein or combination of proteins whose presence, absence, or relative amount is used to identify a condition (e.g. IPF) or status of a condition (e.g. IPF) in a subject or sample. Biomarkers identified herein are measured to determine levels, expression, activity, or to detect fragments, variants or homologs of said biomarkers. Variants include amino acid or nucleic acid variants or post translationally modified variants. In embodiments, the marker protein is a protein or fragment thereof as set forth in Table 1A, 1B, 2A, 2B, 3A, 3B, 4A, or 4B. In embodiments, the marker protein is a homolog of the protein listed in Table 1A, 1B, 2A, 2B, 3A, 3B, 4A, or 4B. The marker proteins provided herein are identified by accession numbers referring to the corresponding amino acid and/or nucleic acid sequence of the individual marker proteins. Therefore, a person of ordinary skill in the art will immediately recognize the sequences of the marker proteins provided herein.

In some examples of the disclosed methods, when the expression level of a biomarker(s) is assessed, the level is compared with control expression level of the biomarker(s). By control level is meant the expression level of a particular biomarker(s) from a sample or subject lacking a disease (e.g. IPF), at a selected stage of a disease or disease state, or in the absence of a particular variable such as a therapeutic agent. Alternatively, the control level comprises a known amount of biomarker. Such a known amount correlates with an average level of subjects lacking a disease, at a selected stage of a disease or disease state, or in the absence of a particular variable such as a therapeutic agent. A control level also includes the expression level of one or more biomarkers from one or more selected samples or subjects as described herein. For example, a control level includes an assessment of the expression level of one or more biomarkers in a sample from a subject that does not have a disease (e.g. IPF), is at a selected stage of progression of a disease (e.g. IPF), or has not received treatment for a disease. Another exemplary control level includes an assessment of the expression level of one or more biomarkers in samples taken from multiple subjects that do not have a disease, are at a selected stage of progression of a disease, or have not received treatment for a disease.

When the control level includes the expression level of one or more biomarkers in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

In one particular example, a biomarker is a protein or combination of proteins whose expression level in a subject or sample is indicative of a fibrotic pulmonary disease or a fibrotic pulmonary disease activity. The expression level of a biomarker or a combination of a plurality of biomarkers may be increased or decreased compared to a control level. For example, the expression level of a biomarker or a combination of a plurality of biomarkers as provided herein may be increased or decreased in a subject compared to the expression level of the same subject at an earlier time point. Therefore, the expression level of a biomarker as provided herein may be indicative of a specific disease stage. Alternatively, the biomarker may be indicative of the efficacy of treatment. In other words, the expression level of a biomarker may be indicative of whether a patient is responsive to a treatment. The biomarker may further be indicative of the activity of a disease, wherein the activity of a disease refers to the change of one or more biomarker expression levels over the course of the disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The pulmonary diseases contemplated herein can include any pulmonary disorders, lung fibrosis diseases, interstitial lung diseases, idiopathic interstitial pneumonias (BP), idiopathic pulmonary fibrosis, familial interstitial pneumonia (FIP), non-specific interstitial pneumonia (NSIP), hypersensitivity pneumonitis, acute respiratory distress syndrome (ARDS), scleroderma associated interstitial lung disease (SSc-ILD), Sarcoidosis, Beryllium disease, rheumatoid arthritis associated lung disorder, collagen vascular associated lung disorder, cigarette smoke associated lung disorders, Sjögren's syndrome, mixed connective tissue disease, etc.

Pulmonary fibrotic conditions, e.g., interstitial lung diseases (ILD) are characterized by shortness of breath, chronic coughing, fatigue and weakness, loss of appetite, and rapid weight loss. Pulmonary fibrosis is commonly linked to interstitial lung diseases (e.g., autoimmune disorders, viral infections or other microscopic injuries), but can be idiopathic. Fibrosis involves exchange of normal lung tissue with fibrotic tissue (scar tissue) that leads to reduced oxygen capacity.

Idiopathic interstitial pneumonias (IIP) are a subset of diffuse interstitial lung diseases of unknown etiology (the term "idiopathic" indicates unknown origin). IIPs are characterized by expansion of the interstitial compartment (i.e., that portion of the lung parenchyma sandwiched between the epithelial and endothelial basement membranes) with an infiltrate of inflammatory cells. The inflammatory infiltrate is sometimes accompanied by fibrosis, either in the form of abnormal collagen deposition or proliferation of fibroblasts capable of collagen synthesis.

Idiopathic Pulmonary Fibrosis (IPF) occurs in thousands of people worldwide with a doubling of prevalence over the past 10 years. Onset of IPF occurs around 50 to 70 years of age and starts with progressive shortness of breath and hypoxemia. IPF median survival is around 3-5 years and is to date untreatable. The etiology and pathogenesis of the condition is not well understood. About 5-20 percent of all cases of IPF have a family history and inheritance appears to be autosomal dominant. The clinical course of IPF is highly variable. Individuals diagnosed with IPF can experience a slow and steady decline, whereas others may decline more rapidly, thereby exhibiting a progressive form of idiopathic pulmonary fibrosis. Patients may also experience periods of relative stability interrupted by periods of rapid decline (known as acute exacerbations). A progressive form of idiopathic pulmonary fibrosis is characterized by the rapid decline of clinical and physical markers (e.g., FEV1, VC, FVC, $DL_{CO}$ as defined below).

Additional fibrotic pulmonary diseases include Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Bronchiolitis obliterans, with Organizing Pneumonia (BOOP).

AIP is a rapidly progressive and histologically distinct form of interstitial pneumonia. The pathological pattern is an organizing form of diffuse alveolar damage (DAD) that is also found in acute respiratory distress syndrome (ARDS) and other acute interstitial pneumonias of known causes (see Clinical Atlas of Interstitial Lung Disease (2006 ed.) pp 61-63).

RBILD is characterized by inflammatory lesions of the respiratory bronchioles in cigarette smokers. The histologic appearance of RBILD is characterized by the accumulation of pigmented macrophages within the respiratory bronchioles and the surrounding airspaces, variably, peribronchial fibrotic alveolar septal thickening, and minimal associated mural inflammation (see Wells et al. (2003) *Sem Respir. Crit. Care Med.* vol. 24).

DIP is a rare interstitial lung disease characterized by the accumulation of macrophages in large numbers in the alveolar spaces associated with interstitial inflammation and/or fibrosis. The macrophages frequently contain light brown pigment. Lymphoid nodules are common, as is a sparse but distinct eosinophil infiltrate. DIP is most common in smokers (see Tazelaar et at (Sep. 21, 2010) *Histopathology*).

NSIP is characterized pathologically by uniform interstitial inflammation and fibrosis appearing over a short period of time. NSIP differs from other interstitial lung diseases in that it has a generally good prognosis. In addition, the temporal uniformity of the parenchymal changes seen in NSIP contrasts greatly with the temporal heterogeneity of usual interstitial pneumonia (see Coche et al. (2001) *Brit J Radiol* 74:189).

BOOP, unlike NSIP, can be fatal within days of first acute symptoms. It is characterized by rapid onset of acute respiratory distress syndrome; therefore, clinically, rapidly progressive BOOP can be indistinguishable from acute interstitial pneumonia. Histological features include clusters of mononuclear inflammatory cells that form granulation tissue and plug the distal airways and alveolar spaces. These plugs of granulation tissue may form polyps that migrate within the alveolar ducts or may be focally attached to the wall. (see White & Ruth-Saad (2007) *Crit. Care Nurse* 27:53).

Further details about the characteristics and therapies available for these diseases can be found, e.g., on the website of the American Lung Association at lungusa.org/lung-disease/pulmonary-fibrosis.

Diagnostic indicators of pulmonary disorders include biopsy (e.g., VATS or surgical lung biopsy), high resolution computed tomography (HRTC) or breathing metrics, such as forced expiratory volume (FEV1), vital capacity (VC), forced vital capacity (FVC), and FEV1/FVC.

II. Methods

Provided herein, inter alia, are biomarkers (e.g. protein biomarkers) for diagnosing fibrotic pulmonary diseases as well as evaluation of progression, activity and treatment of fibrotic pulmonary diseases. Further provided herein are therapeutic targets for ameliorating fibrotic pulmonary diseases.

In one aspect, a method of determining an expression level of a fibrotic pulmonary disease marker protein set forth in Table 1A or Table 1B in a subject that has or is at risk for developing a fibrotic pulmonary disease is provided. The method includes (i) obtaining a biological sample from the subject and (ii) determining an expression level of a fibrotic pulmonary disease marker protein set forth in Table 1A or Table 1B in the biological sample. In some embodiments, the method includes selecting a subject that has or is at risk for developing a fibrotic pulmonary disease. The selected subject may be treated for fibrotic pulmonary disease.

In some embodiments, the subject is not treated for fibrotic pulmonary disease. The subject may be part of a plurality of subjects participating in a clinical trial. Wherein the subject is part of a clinical trial, the selecting is at least part based on the determining of an expression level as provided herein.

A fibrotic pulmonary disease marker protein is a biomarker protein useful to identify, predict, or monitor a fibrotic pulmonary disease or lack thereof or a therapy for fibrotic pulmonary disease in a subject or sample. A person of ordinary skill in the art will immediately recognize that determining an expression level of a fibrotic pulmonary disease marker protein described herein includes determining the level of one or more fibrotic pulmonary disease marker proteins in a sample (e.g. patient biological sample such as a blood-derived biological sample). Thus is some embodiments, the expression level of a plurality of fibrotic pulmonary disease marker proteins is determined. Wherein the expression level of a plurality of fibrotic pulmonary disease marker proteins is determined, the level of at least two (e.g. 3, 4, 5, 6, 7, 8, 9, 10 etc.) fibrotic pulmonary disease marker proteins is determined and the at least two fibrotic pulmonary disease marker proteins are independently different.

In some embodiments, the fibrotic pulmonary disease is idiopathic pulmonary fibrosis or familial interstitial pneumonia. In embodiments, the fibrotic pulmonary disease is a progressive form of idiopathic pulmonary fibrosis. In other embodiments, the fibrotic pulmonary disease marker protein is a progressive fibrotic pulmonary disease marker protein. A progressive fibrotic pulmonary disease maker protein is a biomarker protein indicative of a fibrotic pulmonary disease patient having or being at risk of developing progressive fibrotic pulmonary disease (e.g., a progressive form of a fibrotic pulmonary disease). Thus, in some embodiments, the subject has or is at risk for developing a progressive fibrotic pulmonary disease. In other embodiments, the progressive fibrotic pulmonary disease is idiopathic pulmonary fibrosis. A progressive fibrotic pulmonary disease is a disease wherein certain clinical or physiological parameters decline over the course of the disease. Commonly used parameters to determine fibrotic pulmonary disease progression include for example, breathing metrics, such as forced expiratory volume (FEV1), vital capacity (VC), forced vital capacity (FVC), FEV1/FVC and diffusing capacity of carbon monoxide ($DL_{CO}$). For example, a fibrotic pulmonary disease patient showing a 5% decline in FVC as compared to a control level may be considered a progressive fibrotic pulmonary disease patient. A control level may be the FVC of the same patient measured at an earlier stage of the fibrotic pulmonary disease or the FVC calculated from a number of subjects lacking the fibrotic pulmonary disease. Thus, in some embodiments, the FVC of a progressive fibrotic pulmonary disease patient is at least 5% less than a control level.

In other embodiments, the FVC of a progressive fibrotic pulmonary disease patient is about 5% less than a control level. In some embodiments, the FVC of a progressive fibrotic pulmonary disease patient is at least 10% less than a control level. In other embodiments, the FVC of a progressive fibrotic pulmonary disease patient is about 10% less than a control level.

Another parameter of progressive fibrotic pulmonary disease is a decline in the 6-minute walk test distance (6MWD). For example, a fibrotic pulmonary disease patient showing a decline of more than 50 meters in the 6MWD compared to a control distance may be considered a progressive fibrotic pulmonary disease patient. A control distance refers to the 6MWD of the same patient measured at an earlier stage of the fibrotic pulmonary disease or the 6MWD calculated from a number of subjects lacking the fibrotic pulmonary disease. In some embodiments, the decline in the 6MWD is at least 30 meters. In other embodiments, the decline in the 6MWD is about 50 meters.

Yet, another parameter of progressive fibrotic pulmonary disease is a decline in diffusing capacity of carbon monoxide ($DL_{CO}$). For example, a fibrotic pulmonary disease patient showing a decline of more than 15% in $DL_{CO}$ compared to a control level may be considered a progressive fibrotic pulmonary disease patient. A control level refers to the $DL_{CO}$ of the same patient measured at an earlier stage of the fibrotic pulmonary disease or the $DL_{CO}$ calculated from a number of subjects lacking the fibrotic pulmonary disease. Thus, in some embodiments, the $DL_{CO}$ of a progressive fibrotic pulmonary disease patient is at least 10% less compared to a control level. In other embodiments, the $DL_{CO}$ of a progressive fibrotic pulmonary disease patient is about 15% less than a control level.

In other embodiments, the biological sample is a blood-derived biological sample of the subject. In some further embodiments, the blood-derived biological sample is whole blood, serum or plasma. In some embodiments, the biological sample is urine, saliva, a pulmonary tissue, bronchoalveolar lavage sample, or exhaled breath condensate.

The methods provided herein including embodiments thereof further include treating a subject for fibrotic pulmonary diseases. As described above the expression level of one or more fibrotic pulmonary disease marker proteins is determined. In some embodiments, an expression level of a fibrotic pulmonary disease marker protein set forth in Table 1A is determined. In other embodiments, an expression level of a fibrotic pulmonary disease marker protein set forth in Table 1B is determined. In some embodiments, an expression level of a fibrotic pulmonary disease marker protein set forth in Table 2A is determined. In other embodiments, an expression level of a fibrotic pulmonary disease marker protein set forth in Table 2B is determined. In some embodiments, an expression level of a fibrotic pulmonary disease marker protein set forth in Table 4A is determined. In other embodiments, an expression level of a fibrotic pulmonary disease marker protein set forth in Table 4B is determined.

The expression levels of the one or more fibrotic pulmonary disease marker proteins set forth in Table 1A or Table 1B may be increased or decreased in a fibrotic pulmonary disease patient. The expression levels of the one or more fibrotic pulmonary disease marker proteins set forth in Table 2A or Table 2B may be increased or decreased in a fibrotic pulmonary disease patient. The expression levels of the one or more fibrotic pulmonary disease marker proteins set forth in Table 4A or Table 4B may be increased or decreased in a fibrotic pulmonary disease patient.

In some embodiments, the one or more fibrotic pulmonary disease marker proteins set forth in Table 1A, 2A or 4A is increased. In other embodiments, the one or more fibrotic pulmonary disease marker proteins set forth in Table 1A, 2A or 4A is decreased. In some embodiments, the one or more fibrotic pulmonary disease marker proteins set forth in Table 1B, 2B or 4B is increased. In other embodiments, the one or more fibrotic pulmonary disease marker proteins set forth in Table 1B, 2B or 4B is decreased.

In some embodiments, the expression level of the fibrotic pulmonary disease marker protein set forth in Table 1A is elevated relative to a standard control. In other embodiments, the expression level of the fibrotic pulmonary disease marker protein set forth in Table 1B is decreased relative to a standard control. In some embodiments, the expression level of the fibrotic pulmonary disease marker protein set forth in Table 2A is elevated relative to a standard control. In other embodiments, the expression level of the fibrotic pulmonary disease marker protein set forth in Table 2B is decreased relative to a standard control. In some embodiments, the expression level of the fibrotic pulmonary disease marker protein set forth in Table 4A is elevated relative to a standard control. In other embodiments, the expression level of the fibrotic pulmonary disease marker protein set forth in Table 4B is decreased relative to a standard control.

A treatment regimen for a fibrotic pulmonary disease patient with modulated expression levels of one or more fibrotic pulmonary disease marker proteins as disclosed herein (e.g. in Table 1A, 1B, 2A, 2B, 4A or 4B) may be administering to the patient an effective amount of a modulator affecting the one or more increased or decreased biomarker protein expression levels. Therefore, in some embodiments, the method includes administering to the subject an effective amount of a modulator of the fibrotic pulmonary disease marker protein set forth in Table 1A or 1B. In some embodiments, the method includes administering to the subject an effective amount of a modulator of the fibrotic pulmonary disease marker protein set forth in Table 2A or 2B. In some embodiments, the method includes administering to the subject an effective amount of a modulator of the fibrotic pulmonary disease marker protein set forth in Table 4A or 4B.

In some embodiments, the method includes administering to the subject an effective amount of a modulator of the fibrotic pulmonary disease marker protein set forth in Table 1A. In some embodiments, the method includes administering to the subject an effective amount of a modulator of the fibrotic pulmonary disease marker protein set forth in Table 2A. In some embodiments, the method includes administering to the subject an effective amount of a modulator of the fibrotic pulmonary disease marker protein set forth in Table 4A. In some embodiments, the method includes administering to the subject an effective amount of a modulator of the fibrotic pulmonary disease marker protein set forth in Table 1B. In some embodiments, the method includes administering to the subject an effective amount of a modulator of the fibrotic pulmonary disease marker protein set forth in Table 2B. In some embodiments, the method includes administering to the subject an effective amount of a modulator of the fibrotic pulmonary disease marker protein set forth in Table 4B. In some embodiments, the modulator is an antagonist. In other embodiments, the antagonist is a peptide, small molecule, nucleic acid, antibody or aptamer. In other embodiments, the modulator is an agonist. In other embodiments, the agonist is a peptide, small molecule, nucleic acid, antibody or aptamer. In embodiments, the agonist is a fibrotic pulmonary disease marker protein set forth in Table 1A or 1B. In embodiments, the agonist is a fibrotic pulmonary disease marker protein set forth in Table 2A or 2B. In embodiments, the agonist is a fibrotic pulmonary disease marker protein set forth in Table 4A or 4B.

The methods provided herein may include combinatorial treatment of a fibrotic pulmonary disease patient with a modulator of one or more fibrotic pulmonary disease marker proteins and a fibrotic pulmonary disease treatment. Thus, the method includes administering to the subject an effective amount of a further therapeutic agent. Exemplary therapeutic agents include, but are not limited to, the agents selected from the group consisting of steroids (including but not limited to prednisolone), cytotoxic agents (including but not limited to azathioprine and cyclophosphamide), bardoxolone, LPA agonists (including but not limited to AM152); Torisel (temsirolimus); PI3K inhibitors; pentraxin or serum amyloid P (including but not limited to Pentraxin-2 (PTX-2 or PRM-151)); MEK inhibitors (including but not limited to ARRY-162 and ARRY-300); p38 inhibitors; PAI-1 inhibitors (including but not limited to Tiplaxtinin); agents that reduce the activity of transforming growth factor-beta (TGF-β) (including but not limited to GC-1008 (Genzyme/MedImmune); lerdelimumab (CAT-152; Trabio, Cambridge Antibody); metelimumab (CAT-192, Cambridge Antibody,); LY-2157299 (Eli Lilly); ACU-HTR-028 (Opko Health)) including antibodies that target one or more TGF-β isoforms, inhibitors of TGF-β receptor kinases TGFBR1 (ALKS) and TGFBR2, and modulators of post-receptor signaling pathways; chemokine receptor signaling; endothelin receptor antagonists including inhibitors that target both endothelin receptor A and B and those that selectively target endothelin receptor A (including but not limited to ambrisentan; avosentan; bosentan; clazosentan, darusentan; BQ-153, FR-139317, L-744453; macitentan; PD-145065, PD-156252, PD163610; PS-433540, S-0139; sitaxentan sodium; TBC-3711; zibotentan); agents that reduce the activity of connective tissue growth factor (CTGF) (including but not limited to FG-3019, FibroGen), and including other CTGF-neutralizing antibodies; matrix metalloproteinase (MMP) inhibitors (including but not limited to MMPI-12, PUP-1 and tigapotide triflutate); agents that reduce the activity of epidermal growth factor receptor (EGFR) including but not limed to erlotinib, gefitinib, BMS-690514, cetuximab, antibodies targeting EGF receptor, inhibitors of EGF receptor kinase, and modulators of post-receptor signaling pathways; agents that reduce the activity of platelet derived growth factor (PDGF) (including but not limited to Imatinib mesylate (Novartis)) and also including PDGF neutralizing antibodies, antibodies targeting PDGF receptor (PDGFR), inhibitors of PDGFR kinase activity, and post-receptor signaling pathways; agents that reduce the activity of vascular endothelial growth factor (VEGF) (including but not limited to axitinib, bevacizumab, BIBF-1120, CDP-791, CT-322, IMC-18F1, PTC-299, and ramucirumab) and also including VEGF-neutralizing antibodies, antibodies targeting the VEGF receptor 1 (VEGFR1, Flt-1) and VEGF receptor 2 (VEGFR2, KDR), the soluble form of VEGFR1 (sFlt) and derivatives thereof which neutralize VEGF, and inhibitors of VEGF receptor kinase activity; inhibitors of multiple receptor kinases such as &BF-1120 which inhibits receptor kinases for vascular endothelial growth factor, fibroblast growth factor, and platelet derived growth factor; agents that interfere with integrin function (including but not limited to STX-100 and IMGN-388) and also including integrin targeted antibodies; agents that interfere with the pro-fibrotic activities of IL-4 (including but not limited to AER-001, AMG-317, APG-201, and sIL-4Ra) and IL-13 (including but not limited to AER-001, AMG-317, anrukinzumab, CAT-354, cintredekin besudotox, MK-6105, QAX-576, SB-313, SL-102, and TNX-650) and also including neutralizing anti-bodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly *pseudomonas* endotoxin, signaling though the JAK-STAT kinase pathway; agents that interfere with epithelial mesenchymal transition including inhibitors of mTor (including but not limited to AP-23573 or rapamycin); agents that reduce levels of copper such as tetrathiomolybdate; agents that reduce oxidative stress including N-acetyl cysteine and tetrathiomolybdate; and interferon gamma, inhibitors of phosphodiesterase 4 (PDE4) (including but not limited to Roflumilast); inhibitors of phosphodiesterase 5 (PDE5) (including but not limited to mirodenafil, PF-4480682, sildenafil citrate, SLx-2101, tadalafil, udenafil, UK-369003, vardenafil, and zaprinast); or modifiers of the arachidonic acid pathway including cyclooxygenase and 5-lipoxegenase inhibitors (including but not limited to Zileuton), compounds that reduce tissue remodeling or fibrosis including prolyl hydrolase inhibitors (including but not limited to 1016548, CG-0089, FG-2216, FG-4497, FG-5615, FG-6513, fibrostatin A (Takeda), lufironil, P-1894B, and safironil) and peroxisome proliferator-activated receptor (PPAR)-gamma agonists (including but not limited to pioglitazone and rosiglitazone), and combinations thereof. In some embodiments, the therapeutic agent is an anti-fibrotic drug. In some embodiments, the therapeutic agent is an idiopathic pulmonary fibrosis drug. In other embodiment, the idiopathic pulmonary fibrosis drug is a mucolytic drug.

In another aspect, a method of determining whether a subject has or is at risk of developing a fibrotic pulmonary disease is provided. The method includes (i) detecting an expression level of one or more fibrotic pulmonary disease marker proteins set forth in Table 1A or Table 1B in a subject; (ii) determining whether the expression level is increased or decreased relative to a standard control, wherein an elevated expression level of a fibrotic pulmonary disease marker protein in Table 1A or a decreased expression level of a fibrotic pulmonary disease marker protein in Table 1B relative to the standard control indicates that the subject has or is at risk of developing a fibrotic pulmonary disease; and (iii) based at least in part on the expression level in step (ii), determining whether the subject has or is at risk for developing a fibrotic pulmonary disease.

In some embodiments, the method includes selecting a subject that has or is at risk for developing a fibrotic pulmonary disease. In other embodiments, the fibrotic pulmonary disease is idiopathic pulmonary fibrosis or familial interstitial pneumonia. In some embodiments, the one or more fibrotic pulmonary disease marker proteins is a progressive fibrotic pulmonary disease marker protein. In other embodiments, the subject has or is at risk for developing a progressive fibrotic pulmonary disease. In some embodiments, the progressive fibrotic pulmonary disease is idiopathic pulmonary fibrosis.

The expression level of one or more fibrotic pulmonary disease marker proteins set forth in Table 1A or Table 1B is detected from a biological sample of the subject. In some embodiments, the biological sample is a blood-derived biological sample of the subject. In other embodiments, the blood-derived biological sample is whole blood, serum or plasma. In some embodiments, the biological sample is urine, saliva, a pulmonary tissue, bronchoalveolar lavage sample, or exhaled breath condensate.

As described above the methods provided herein include treating for fibrotic pulmonary disease. Thus, in some embodiments, the method includes administering to the subject an effective amount of a modulator of the fibrotic pulmonary disease marker protein set forth in Table 1A or 1B. In some embodiments, the method includes administering to the subject an effective amount of a modulator of the fibrotic pulmonary disease marker protein set forth in Table 1A. In some embodiments, the method includes administering to the subject an effective amount of a modulator of the fibrotic pulmonary disease marker protein set forth in Table 1B. In some embodiments, the method includes administering to the subject an effective amount of a modulator of the fibrotic pulmonary disease marker protein set forth in Table 2A. In some embodiments, the method includes administering to the subject an effective amount of a modulator of the fibrotic pulmonary disease marker protein set forth in Table 2B. In some embodiments, the method includes administering to the subject an effective amount of a modulator of the fibrotic pulmonary disease marker protein set forth in Table 4A. In some embodiments, the method includes administering to the subject an effective amount of a modulator of the fibrotic pulmonary disease marker protein set forth in Table 4B. In some embodiments, the modulator is an antagonist. In other embodiments, the antagonist is a peptide, small molecule, nucleic acid, antibody or aptamer. In one embodiment, the modulator is an agonist. In one embodiment, the agonist is a peptide, small molecule, nucleic acid, antibody or aptamer.

As described above the methods provided herein may further include administering to the subject an effective amount of a further therapeutic agent (e.g., as described above). In some further embodiments, the therapeutic agent is an idiopathic pulmonary fibrosis drug. In some other further embodiments, the idiopathic pulmonary fibrosis drug is a mucolytic drug.

In another aspect, a method of determining whether a fibrotic pulmonary disease patient is at risk for progression of the fibrotic pulmonary disease is provided. The method includes (i) detecting an expression level of one or more fibrotic pulmonary disease marker protein set forth in Table 1A or Table 1B in a fibrotic pulmonary disease patient (ii) determining whether the expression level is modulated relative to a standard control, wherein a modulated expression level of a fibrotic pulmonary disease marker protein in Table 1A or Table 1B relative to the standard control indicates that the fibrotic pulmonary disease patient is at risk for progression of the fibrotic pulmonary disease, and (iii) based at least in part on the expression level in step (ii), determining whether the fibrotic pulmonary disease patient is at risk for progression of the fibrotic pulmonary disease. In some embodiments, the determining whether the expression level is modulated relative to a standard control comprises determining whether the expression level is elevated or suppressed relative to other fibrotic pulmonary disease patients. In embodiments, the determining whether the expression level is modulated relative to a standard control includes determining whether the expression level is elevated or suppressed relative to an expression level of the same fibrotic pulmonary disease marker protein in other fibrotic pulmonary disease patients. In embodiments, the determining whether the expression level is modulated relative to a standard control includes determining whether the expression level is elevated or suppressed relative to an expression level of a different fibrotic pulmonary disease marker protein in the patient. In some embodiments, the fibrotic pulmonary disease is idiopathic pulmonary fibrosis or familial interstitial pneumonia. In other embodiments, the fibrotic pulmonary disease marker protein is a progressive fibrotic pulmonary disease marker protein.

In embodiments, an increased expression level of a fibrotic pulmonary disease marker protein in Table 1A relative to a standard control indicates an increased risk for progression of the fibrotic pulmonary disease. In embodiments, a decreased expression level of a fibrotic pulmonary disease marker protein in Table 1A relative to a standard control indicates an decreased risk for progression of the fibrotic pulmonary disease. In embodiments, an increased expression level of a fibrotic pulmonary disease marker protein in Table 1B relative to a standard control indicates an increased risk for progression of the fibrotic pulmonary disease. In embodiments, a decreased expression level of a fibrotic pulmonary disease marker protein in Table 1B relative to a standard control indicates an decreased risk for progression of the fibrotic pulmonary disease.

In some embodiments, the subject has or is at risk for developing a progressive fibrotic pulmonary disease. In other embodiments, the progressive fibrotic pulmonary disease is idiopathic pulmonary fibrosis. In other embodiments, the biological sample is a blood-derived biological sample of the subject. In some further embodiments, the blood-derived biological sample is whole blood, serum or plasma. In some embodiments, the biological sample is urine, saliva, a pulmonary tissue, bronchoalveolar lavage sample, or exhaled breath condensate.

In another aspect, a method of determining whether a fibrotic pulmonary disease patient is at risk for progression of the fibrotic pulmonary disease is provided. The method includes (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, wherein when the second expression level of a protein set forth in Table 1A is greater than the first level of a protein set forth in Table 1A; or wherein when the second expression level of a protein set forth in Table 1B is smaller than the first level of a protein set forth in Table 1B, the patient is at risk for progression of the fibrotic pulmonary disease. The patient at risk for progression of the fibrotic pulmonary disease may have received treatment for the fibrotic pulmonary disease prior to the determining in step (i). Where the patient at risk for progression of the fibrotic pulmonary disease has received treatment for the fibrotic pulmonary disease prior to the determining in step (i) the treatment may be altered after the determining in step (i) and before the determining in step (ii). Alternatively, the patient at risk for progression of the fibrotic pulmonary disease may not have received treatment for the fibrotic pulmonary disease prior to the determining in step (i). Where the patient at risk for progression of the fibrotic pulmonary disease has not received treatment for the fibrotic pulmonary disease prior to the determining in step (i) the patient may receive treatment after the determining in step (i). Thus, in some embodiments, the method includes administering a fibrotic pulmonary disease treatment after the determining in step (i). In some embodiments, the method further includes determining a rate of progression of the fibrotic pulmonary disease in the patient based on the comparing. In some embodiments, the method further includes predicting a rate of progression of the fibrotic pulmonary disease in the patient based on the comparing.

In other embodiments, the determining the first expression level of a protein set forth in Table 1A or Table 1B and the second expression level of a protein set forth in Table 1A or Table 1B includes normalizing the first expression level of a protein set forth in Table 1A or Table 1B and the second expression level of a protein set forth in Table 1A or Table 1B to a protein expressed from a standard gene in the patient. In some further embodiments, the standard gene is a so-called housekeeping gene, as is commonly known in the art, such as GAPDH or beta-actin. In embodiments, the standard gene is non-differentially expressed. Where the standard gene is non-differentially expressed, the expression level of the standard gene remains unchanged over the time course of the disease. In some embodiment, the first expression level is detected from a first biological sample of the subject and the second expression level is detected from a second biological sample of the subject. In some embodiment, the first biological sample is a first bodily fluid sample and the second biological sample is a second bodily fluid sample.

In another aspect, a method of determining a fibrotic pulmonary disease activity in a patient is provided. The method includes (i) detecting an expression level of one or more fibrotic pulmonary disease marker proteins set forth in Table 1A or Table 1B in a subject; (ii) determining whether the expression level is modulated relative to a standard control, thereby determining a fibrotic pulmonary disease activity in the patient; and (iii) based at least in part on the expression level in step (ii), determining the fibrotic pulmonary disease activity in the patient. In embodiments, the expression level of a fibrotic pulmonary disease marker protein in Table 1A is increased relative to the standard control. In embodiments, the expression level of a fibrotic pulmonary disease marker protein in Table 1B is decreased relative to the standard control.

In another aspect, a method of determining a fibrotic pulmonary disease activity in a patient is provided. The method includes (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, thereby determining the fibrotic pulmonary disease activity in the patient. In some embodiments, the method includes administering a fibrotic pulmonary disease treatment after the determining in step (i). In some embodiment, the method includes determining a change in a fibrotic pulmonary disease activity.

In another aspect, a method of treating a fibrotic pulmonary disease in a subject in need thereof is provided. The method includes administering to the subject an effective amount of an modulator of a fibrotic pulmonary disease marker protein set forth in Table 1A or Table 1B, thereby treating a fibrotic pulmonary disease in the subject. In some embodiments, the method includes administering to the subject an effective amount of a modulator of the fibrotic pulmonary disease marker protein set forth in Table 1A. In some embodiments, the method includes administering to the subject an effective amount of a modulator of the fibrotic pulmonary disease marker protein set forth in Table 2A. In some embodiments, the method includes administering to the subject an effective amount of a modulator of the fibrotic pulmonary disease marker protein set forth in Table 4A. In some embodiments, the method includes administering to the subject an effective amount of a modulator of the fibrotic pulmonary disease marker protein set forth in Table 1B. In some embodiments, the method includes administering to the subject an effective amount of a modulator of the fibrotic pulmonary disease marker protein set forth in Table 2B. In some embodiments, the method includes administering to the subject an effective amount of a modulator of the fibrotic pulmonary disease marker protein set forth in Table 4B. In other embodiments, the modulator is an antagonist. In some further embodiments, the antagonist is a peptide, small molecule, nucleic acid, antibody or aptamer. In some embodiments, the modulator is an agonist. In some other further embodiment, the agonist is a peptide, small molecule, nucleic acid, antibody or aptamer.

In one aspect, a method of treating a fibrotic pulmonary disease in a subject in need thereof is provided. The method includes (i) determining whether a subject expresses an elevated level of a fibrotic pulmonary disease marker protein as set forth in Table 1A or a decreased level of a fibrotic pulmonary disease marker protein as set forth in Table 1B relative to a standard control; and (ii) when an elevated expression level of the fibrotic pulmonary disease marker protein of Table 1A or a decreased expression level of the fibrotic pulmonary disease marker protein of Table 1B is found relative to the standard control, administering to the subject a fibrotic pulmonary disease treatment, an antagonist of a fibrotic pulmonary disease marker protein set forth in Table 1A or an agonist of a fibrotic pulmonary disease marker protein set forth in Table 1B, thereby treating the subject. In some embodiment, the fibrotic pulmonary disease treatment is a mucolytic drug.

The aspects provided herein including embodiments refer to one or more fibrotic pulmonary disease marker protein set forth in the tables provided herein. In some aspects, one or more fibrotic pulmonary disease marker proteins are set forth in Table 1A or Table 1B. In embodiments, the one or more fibrotic pulmonary disease marker protein set forth in Table 1A or Table 1B is a protein set forth in Table 2A or Table 2B. In embodiments, the one or more fibrotic pulmonary disease marker protein set forth in Table 1A or Table 1B is a protein set forth in Table 4A or Table 4B. In some embodiments, the one or more fibrotic pulmonary disease marker protein is set forth in Table 2A. In some embodiments, the one or more fibrotic pulmonary disease marker protein is set forth in Table 2B. In some embodiments, the one or more fibrotic pulmonary disease marker protein is set forth in Table 4A. In some embodiments, the one or more fibrotic pulmonary disease marker protein is set forth in Table 4B.

In some embodiments, the subject has or is at risk for developing a progressive fibrotic pulmonary disease. In other embodiments, the progressive fibrotic pulmonary disease is idiopathic pulmonary fibrosis. In embodiments, the progressive fibrotic pulmonary disease is a progressive form of idiopathic pulmonary fibrosis. In other embodiments, the biological sample is a blood-derived biological sample of the subject. In some further embodiments, the blood-derived biological sample is whole blood, serum or plasma. In some embodiments, the biological sample is urine, saliva, a pulmonary tissue, bronchoalveolar lavage sample, or exhaled breath condensate.

In some embodiments, an expression level of a fibrotic pulmonary disease marker protein set forth in Table 3A is determined. In other embodiments, an expression level of a fibrotic pulmonary disease marker protein set forth in Table 3B is determined. In embodiments, the risk for developing a progressive fibrotic pulmonary disease is increased relative to a standard control. In embodiments, the risk for developing a progressive fibrotic pulmonary disease is decreased relative to a standard control.

The expression levels of the one or more fibrotic pulmonary disease marker proteins set forth in Table 3A or Table 3B may be increased or decreased in a fibrotic pulmonary disease patient. In some embodiments, the expression level of the fibrotic pulmonary disease marker protein set forth in Table 3A is elevated relative to a standard control. In other embodiments, the expression level of the fibrotic pulmonary disease marker protein set forth in Table 3B is decreased relative to a standard control.

In some embodiments, the method includes administering to the subject an effective amount of a modulator of the fibrotic pulmonary disease marker protein set forth in Table 3A or 3B. In some embodiments, the method includes administering to the subject an effective amount of a modulator of the fibrotic pulmonary disease marker protein set forth in Table 3A. In some embodiments, the method includes administering to the subject an effective amount of a modulator of the fibrotic pulmonary disease marker protein set forth in Table 3B. Thus, the method includes administering to the subject an effective amount of a further therapeutic agent. In some embodiments, the therapeutic agent is an idiopathic pulmonary fibrosis drug. In other embodiment, the idiopathic pulmonary fibrosis drug is a mucolytic drug.

In another aspect, a method of determining an expression level of a fibrotic pulmonary disease marker protein set forth in Table 3A or Table 3B in a subject that has or is at risk for developing a fibrotic pulmonary disease is provided. The method includes (i) obtaining a biological sample from the subject, and (ii) determining an expression level of a fibrotic pulmonary disease marker protein set forth in Table 3A or Table 3B in the biological sample.

In some embodiments, the method includes selecting a subject that has or is at risk for developing a fibrotic pulmonary disease. In other embodiments, the fibrotic pulmonary disease is idiopathic pulmonary fibrosis or familial interstitial pneumonia. In some embodiments, the one or more fibrotic pulmonary disease marker proteins is a progressive fibrotic pulmonary disease marker protein. In other embodiments, the subject has or is at risk for developing a progressive fibrotic pulmonary disease. In some embodiments, the progressive fibrotic pulmonary disease is idiopathic pulmonary fibrosis. In embodiments, the progressive fibrotic pulmonary disease is a progressive form of idiopathic pulmonary fibrosis.

The expression level of one or more fibrotic pulmonary disease marker proteins set forth in Table 3A or Table 3B is detected from a biological sample of the subject. In some embodiments, the biological sample is a blood-derived biological sample of the subject. In other embodiments, the blood-derived biological sample is whole blood, serum or plasma. In some embodiments, the biological sample is urine, saliva, a pulmonary tissue, bronchoalveolar lavage sample, or exhaled breath condensate.

As described above the methods provided herein include treating for fibrotic pulmonary disease. Thus, in some embodiments, the method includes administering to the subject an effective amount of a modulator of the fibrotic pulmonary disease marker protein set forth in Table 3A or 3B. In some embodiments, the method includes administering to the subject an effective amount of a modulator of the fibrotic pulmonary disease marker protein set forth in Table 3A. In some embodiments, the method includes administering to the subject an effective amount of a modulator of the fibrotic pulmonary disease marker protein set forth in Table 3B.

As described above the methods provided herein may further include administering to the subject an effective amount of a further therapeutic agent. In some further embodiments, the therapeutic agent is an idiopathic pulmonary fibrosis drug. In some other further embodiments, the idiopathic pulmonary fibrosis drug is a mucolytic drug.

In another aspect, a method of determining whether a subject has or is at risk of developing a fibrotic pulmonary disease is provided. The method includes (i) detecting an expression level of one or more fibrotic pulmonary disease marker proteins set forth in Table 3A or Table 3B in a subject, (ii) determining whether said expression level is increased or decreased relative to a standard control, wherein an elevated expression level of a fibrotic pulmonary disease marker protein in Table 3A or a decreased expression level of a fibrotic pulmonary disease marker protein in Table 3B relative to the standard control indicates that the subject has or is at risk of developing a fibrotic pulmonary disease, and (iii) based at least in part on the expression level in step (ii), determining whether the subject has or is at risk for developing a fibrotic pulmonary disease.

In other embodiments, the determining the first expression level of a protein set forth in Table 3A or Table 3B and the second expression level of a protein set forth in Table 3A or Table 3B includes normalizing the first expression level of a protein set forth in Table 3A or Table 3B and the second expression level of a protein set forth in Table 3A or Table 3B to a protein expressed from a standard gene in the patient. In some further embodiments, the standard gene is a so-called housekeeping gene, as is commonly known in the art, such as GAPDH or beta-actin. In embodiments, the standard gene is non-differentially expressed. Where the standard gene is non-differentially expressed, the expression level of the standard gene remains unchanged over the time course of the disease. In some embodiment, the first expression level is detected from a first biological sample of the subject and the second expression level is detected from a second biological sample of the subject. In some embodiment, the first biological sample is a first bodily fluid sample and the second biological sample is a second bodily fluid sample.

In another aspect, a method of determining whether a fibrotic pulmonary disease patient is at risk for progression of the fibrotic pulmonary disease is provided. The method includes (i) detecting an expression level of one or more fibrotic pulmonary disease marker protein set forth in Table 3A or 3B in a fibrotic pulmonary disease patient, (ii) determining whether the expression level is modulated relative to a standard control, wherein a modulated expression level of a fibrotic pulmonary disease marker protein in Table 3A or 3B relative to the standard control indicates that the fibrotic pulmonary disease patient is at risk for progression of the fibrotic pulmonary disease, and (iii) based at least in part on the expression level in step (ii), determining whether the fibrotic pulmonary disease patient is at risk for progression of the fibrotic pulmonary disease. In some embodiments, the determining whether the expression level is modulated relative to a standard control comprises determining whether the expression level is elevated or suppressed relative to other fibrotic pulmonary disease patients. In embodiments, the determining whether the expression level is modulated relative to a standard control includes determining whether the expression level is elevated or suppressed relative to an expression level of the same fibrotic pulmonary disease marker protein in other fibrotic pulmonary disease patients. In embodiments, the determining whether the expression level is modulated relative to a standard control includes determining whether the expression level is elevated or suppressed relative to an expression level of a different fibrotic pulmonary disease marker protein in the patient. In some embodiments, the fibrotic pulmonary disease is idiopathic pulmonary fibrosis or familial interstitial pneumonia. In other embodiments, the fibrotic pulmonary disease marker protein is a progressive fibrotic pulmonary disease marker protein.

In embodiments, an increased expression level of a fibrotic pulmonary disease marker protein in Table 3A relative to a standard control indicates an increased risk for progression of the fibrotic pulmonary disease. In embodiments, a decreased expression level of a fibrotic pulmonary disease marker protein in Table 3A relative to a standard control indicates an decreased risk for progression of the fibrotic pulmonary disease. In embodiments, an increased expression level of a fibrotic pulmonary disease marker protein in Table 3B relative to a standard control indicates an increased risk for progression of the fibrotic pulmonary disease. In embodiments, a decreased expression level of a fibrotic pulmonary disease marker protein in Table 3B relative to a standard control indicates an decreased risk for progression of the fibrotic pulmonary disease.

In some embodiments, the subject has or is at risk for developing a progressive fibrotic pulmonary disease. In other embodiments, the progressive fibrotic pulmonary disease is idiopathic pulmonary fibrosis. In embodiments, the progressive fibrotic pulmonary disease is a progressive form of idiopathic pulmonary fibrosis. In other embodiments, the biological sample is a blood-derived biological sample of the subject. In some further embodiments, the blood-derived biological sample is whole blood, serum or plasma. In some embodiments, the biological sample is urine, saliva, a pulmonary tissue, bronchoalveolar lavage sample, or exhaled breath condensate.

In one aspect, a method of determining whether a fibrotic pulmonary disease patient is at risk for progression of the fibrotic pulmonary disease is provided. The method includes (i) determining a first expression level of a protein set forth in Table 3A or Table 3B in the patient at a first time point, (ii) determining a second expression level of a protein set forth in Table 3A or Table 3B in the patient at a second time point, (iii) comparing the second expression level of a protein set forth in Table 3A or Table 3B to the first expression level of a protein set forth in Table 3A or Table 3B, wherein when the second expression level of a protein set forth in Table 3A is greater than the first level of a protein set forth in Table 3A, or wherein when the second expression level of a protein set forth in Table 3B is smaller than the first level of a protein set forth in Table 3B, the patient is at risk for progression of the fibrotic pulmonary disease. The patient at risk for progression of the fibrotic pulmonary disease may have received treatment for the fibrotic pulmonary disease prior to the determining in step (i). Where the patient at risk for progression of the fibrotic pulmonary disease has received treatment for the fibrotic pulmonary disease prior to the determining in step (i) the treatment may be altered after the determining in step (i) and before the determining in step (ii). Alternatively, the patient at risk for progression of the fibrotic pulmonary disease may not have received treatment for the fibrotic pulmonary disease prior to the determining in step (i). Where the patient at risk for progression of the fibrotic pulmonary disease has not received treatment for the fibrotic pulmonary disease prior to the determining in step (i) the patient may receive treatment after the determining in step (i). Thus, in some embodiments, the method includes administering a fibrotic pulmonary disease treatment after the determining in step (i). In some embodiments, the method further includes determining a rate of progression of the fibrotic pulmonary disease in the patient based on the comparing.

In other embodiments, the determining the first expression level of a protein set forth in Table 3A or Table 3B and the second expression level of a protein set forth in Table 3A or Table 3B includes normalizing the first expression level of a protein set forth in Table 3A or Table 3B and the second expression level of a protein set forth in Table 3A or Table 3B to a protein expressed from a standard gene in the patient. In some further embodiments, the standard gene is a so-called housekeeping gene, as is commonly known in the art, such as GAPDH or beta-actin. In embodiments, the standard gene is non-differentially expressed. Where the standard gene is non-differentially expressed, the expression level of the standard gene remains unchanged over the time course of the disease. In some embodiment, the first expression level is detected from a first biological sample of the subject and the second expression level is detected from a second biological sample of the subject. In some embodiment, the first biological sample is a first bodily fluid sample and the second biological sample is a second bodily fluid sample.

In another aspect, a method of determining a fibrotic pulmonary disease activity in a patient is provided. The method includes (i) detecting an expression level of one or more fibrotic pulmonary disease marker proteins set forth in Table 3A or Table 3B in a subject; (ii) determining whether the expression level is modulated relative to a standard control, thereby determining a fibrotic pulmonary disease activity in the patient; and (iii) based at least in part on the expression level in step (ii), determining the fibrotic pulmonary disease activity in the patient. In embodiments, the expression level of a fibrotic pulmonary disease marker protein in Table 3A is increased relative to the standard control. In embodiments, the expression level of a fibrotic pulmonary disease marker protein in Table 3B is decreased relative to the standard control.

In another aspect, a method of determining a fibrotic pulmonary disease activity in a patient is provided. The method includes (i) determining a first expression level of a protein set forth in Table 3A or Table 3B in the patient at a first time point, (ii) determining a second expression level of a protein set forth in Table 3A or Table 3B in the patient at a second time point, (iii) comparing the second expression level of a protein set forth in Table 3A or Table 3B to the first expression level of a protein set forth in Table 3A or Table 3B, thereby determining the fibrotic pulmonary disease activity in the patient. In embodiments, the method includes determining a change in a fibrotic pulmonary disease activity.

In another aspect, a method of treating a fibrotic pulmonary disease in a subject in need thereof is provided. The method includes administering to the subject an effective amount of an modulator of a fibrotic pulmonary disease marker protein set forth in Table 3A or Table 3B, thereby treating a fibrotic pulmonary disease in the subject.

In another aspect, a method of treating a fibrotic pulmonary disease in a subject in need thereof is provided. The method includes (i) determining whether a subject expresses an elevated level of a fibrotic pulmonary disease marker protein as set forth in Table 3A or a decreased level of a fibrotic pulmonary disease marker protein as set forth in Table 3B relative to a standard control, and (ii) when an elevated expression level of the fibrotic pulmonary disease marker protein of Table 3A or a decreased expression level of the fibrotic pulmonary disease marker protein of Table 3B is found relative to the standard control, administering to the subject a fibrotic pulmonary disease treatment, an antagonist of a fibrotic pulmonary disease marker protein set forth in Table 3A or an agonist of a fibrotic pulmonary disease marker protein set forth in Table 3B, thereby treating the subject. In some embodiments, the determining whether the expression level is modulated relative to a standard control includes determining whether the expression level is elevated or suppressed relative to other fibrotic pulmonary disease patients. Therefore a standard control as referred to herein may include or may be an average value gathered from a population of pulmonary disease patients. In other embodiments, a standard control is an average value gathered from a population of normal patients.

III. Kits and Compositions

The invention provides kits for detection of fibrotic pulmonary disease marker proteins or fragments thereof in a subject. The kit can be for personal use or provided to medical professionals. The kit can be a kit for diagnosing or prognosing a fibrotic pulmonary disease, or for monitoring the progression of disease or the efficacy of treatment.

In one aspect a kit is provided. The kit includes a marker protein binding agent (e.g., an aptamer, optionally labeled) capable of binding to a substance within a biological sample (e.g., whole blood, serum or plasma) from a human subject having or at risk of developing a fibrotic pulmonary disease, wherein the substance is a fibrotic pulmonary disease marker protein or fragment thereof set forth in the tables provided herein (e.g., Table 1A, 1B, 2A, 2B, 3A, 3B, 4A, or 4B); and a detecting reagent or a detecting apparatus capable of indicating binding of the marker protein binding agent to the substance. The kit can further include assay containers (tubes), buffers, or enzymes necessary for carrying out the detection assay. In embodiments, the kit further includes a sample collection device for collecting a sample from a subject. In embodiments, the human subject has a fibrotic pulmonary disease.

In another aspect, a kit is provided. The kit includes a marker protein binding agent capable of binding to a substance within a biological sample from a human subject having a fibrotic pulmonary disease, wherein the substance is a fibrotic pulmonary disease marker protein or fragment thereof set forth in the tables provided herein (e.g., Table 1A, 1B, 2A, 2B, 3A, 3B, 4A, or 4B); and a detecting reagent or a detecting apparatus capable of indicating binding of the marker protein binding agent to the substance.

In some embodiments, the kit includes components to examine more than one fibrotic pulmonary disease marker protein or fragment thereof. For example, the kit can include more than one marker protein binding agent capable of binding to one or more fibrotic pulmonary disease marker proteins or fragments thereof set forth in Table 1A, 1B, 2A, 2B, 3A, 3B, 4A, or 4B. In embodiments, the kit includes a plurality of marker protein binding agents. Where the kit includes a plurality of marker protein binding agents a plurality of fibrotic pulmonary disease marker proteins or fragments thereof (e.g., as set forth in Table 1A, 1B, 2A, 2B, 3A, 3B, 4A, or 4B) are detected.

The kit will generally include at least one vial, test tube, flask, bottle, syringe or other container means, into which the testing agent, can be suitably reacted or aliquoted. Kits can also include components for comparing results such as a suitable control sample, for example a positive and/or negative control. The kit can also include a collection device for collecting and/or holding the sample from the subject. The collection device can include a sterile swab or needle (for collecting blood), and/or a sterile tube (e.g., for holding the swab or a bodily fluid sample).

In another aspect, a complex in vitro is provided. The complex includes a marker protein binding agent bound to a fibrotic pulmonary disease marker protein or fragment thereof set forth in the tables provided herein (e.g., Table 1A, 1B, 2A, 2B, 3A, 3B, 4A, or 4B), wherein the fibrotic pulmonary disease marker protein is extracted from a human subject having or at risk of developing a fibrotic pulmonary disease. In embodiments, the subject has a fibrotic pulmonary disease.

In another aspect, a complex in vitro is provided. The complex includes a marker protein binding agent bound to a fibrotic pulmonary disease marker protein or fragment thereof set forth in the tables provided herein (e.g., Table 1A, 1B, 2A, 2B, 3A, 3B, 4A, or 4B), wherein the fibrotic pulmonary disease marker protein is extracted from a human subject having a fibrotic pulmonary disease.

IV. Methods of Detection

The methods provided herein include the step of determining (detecting) an expression level of a fibrotic pulmonary disease marker protein or fragment thereof. Methods for detecting and identifying proteins and their interactions with other proteins or nucleic acid molecules involve conventional molecular biology, microbiology, and recombinant DNA techniques within the skill of the art. Such techniques are explained fully in the literature (see, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

"Determining an expression level of a protein" or "determining a level of expression of a protein" as provided herein includes methods and technologies well known in the art. For example, capture arrays for expression profiling may be used to determine an expression level of a protein. Capture arrays employ high affinity capture reagents, such as conventional antibodies, single domains, engineered scaffolds, peptides or nucleic acid aptamers, to bind and detect specific target ligands in high throughput manner. Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) are optionally useful in arrays.

The term scaffold refers to ligand-binding domains of proteins, which are engineered into multiple variants capable of binding diverse target molecules with antibody-like properties of specificity and affinity. The variants are produced in a genetic library format and selected against individual targets by phage, bacterial or ribosome display. Such ligand-binding scaffolds or frameworks include Affibodies based on *S. aureus* protein A (Affibody, Bromma, Sweden), Trinectins based on fibronectins (Phylos, Lexington, Mass.) and Anticalins based on the lipocalin structure (Pieris Proteolab, Freising-Weihenstephan, Germany). These are used on capture arrays in a similar fashion to antibodies and have advantages of robustness and ease of production.

Nonprotein capture molecules, notably the nucleic acid aptamers which bind protein ligands with high specificity and affinity, are also used in arrays (SomaLogic, Boulder, Colo.). Aptamers are selected from libraries of oligonucleotides by the Selex™ procedure (SomaLogic, Boulder, Colo.) and their interaction with protein is enhanced by covalent attachment, through incorporation of brominated deoxyuridine and UV-activated crosslinking (photoaptamers). Photocrosslinking to ligand reduces the cross reactivity of aptamers due to the specific steric requirements. Aptamers have the advantages of ease of production by automated oligonucleotide synthesis and the stability and robustness of DNA; on photoaptamer arrays, universal fluorescent protein stains are used to detect binding.

Protein analytes binding to antibody arrays are detected directly or indirectly, for example, via a secondary antibody. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately. Serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through molecular imprinting technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which is useful diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and are used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g., via a His tag and immobilized. Cell free protein transcription/translation is a viable alternative for synthesis of proteins which do not express well in bacterial or other in vivo systems.

In embodiments, determining (detecting) an expression level of a fibrotic pulmonary disease marker protein or fragment thereof as provided herein includes contacting a fibrotic pulmonary disease marker protein with a marker protein binding agent. A "marker protein binding agent" as provided herein refers to a substance capable of binding a fibrotic pulmonary disease marker protein. The marker protein binding agent may be a nucleic acid or a protein. In embodiments, the marker protein binding agent is an aptamer. In embodiments, the marker protein binding agent is peptide. In embodiments, the marker protein binding agent is a small molecule. In embodiments, the marker protein binding agent is an antibody. In embodiments, the fibrotic pulmonary disease marker protein or fragment thereof is contacted with a marker protein binding agent in a biological sample (e.g., whole blood, serum or plasma). In embodiments, the marker protein binding agent includes a detectable moiety. In embodiments, the detectable moiety is a fluorescent moiety. In embodiments, the marker protein binding agent includes a capturing moiety. A "capturing moiety" refers to a protein or nucleic acid, which is covalently, through a linker or a chemical bond, or noncovalently attached to the marker protein binding agent and is capable of interacting with a capturing agent. An example of a capturing moiety useful for the methods provided herein is biotin. In embodiments, the capturing moiety is biotin. In embodiments, the capturing moiety is a cleavable capturing moiety. In embodiments, the capturing moiety is photocleavable biotin.

A "capturing agent" as provided herein refers to an agent capable of binding a capturing moiety. The interaction between the capturing moiety and the capturing agent may be a high affinity interaction, wherein the capturing moiety and the capturing agent bind to each other (e.g., biotin, streptavidin). An example of a capturing agent useful for the methods provided herein are streptavidin coated beads. In embodiments, the capturing agent is a streptavidin coated bead. Without limitation any suitable affinity binding pairs known in the art may be used as capturing moiety and capturing agent in the methods provided herein. For example, the capturing moiety may be an antibody and the capturing agent may be an antigen-coated bead. In embodiments, the capturing moiety is biotin and the capturing agent is a streptavidin coated bead.

The marker protein binding agent may bind non-covalently to the fibrotic pulmonary disease marker protein through ionic, van der Waals, electrostatic or hydrogen bonds. Upon binding of the marker protein binding agent to the fibrotic pulmonary disease marker protein a disease marker-protein binding agent complex is formed. The methods provided herein including embodiments thereof include detecting the disease marker-protein binding agent complex, thereby determining the expression level of a fibrotic pulmonary disease marker protein or fragment thereof in a biological sample. Thus, in embodiments, the determining includes (a) contacting a fibrotic pulmonary disease marker protein with a marker protein binding agent in the biological sample, thereby forming a disease marker protein-binding agent complex; and (b) detecting the disease marker protein-binding agent complex. The disease marker protein-binding agent complex may be separated from the sample and unbound components contained therein by contacting the disease marker protein-binding agent complex with a capturing agent as described above (e.g., streptavidin-coated beads). Thus, in embodiments, the detecting includes contacting the disease marker protein-binding agent complex with a capturing agent, thereby forming a captured disease marker protein-binding agent complex. The captured disease marker protein-binding agent complex may be washed to remove any unbound components.

For the methods provided herein, the fibrotic pulmonary disease marker protein or fragment thereof may be contacted with a tagging moiety. A "tagging moiety" as provided herein is a composition capable of non-covalently binding to the fibrotic pulmonary disease marker protein or fragment thereof. In embodiments, the tagging moiety is biotin. Upon binding to the fibrotic pulmonary disease marker protein or fragment thereof, the tagging moiety may bind through high affinity interaction with a tagging agent (e.g., streptavidin). In embodiments, the fibrotic pulmonary disease marker protein or fragment thereof is contacted with a tagging moiety after the formation of a captured disease marker protein-binding agent complex. In embodiments, the fibrotic pulmonary disease marker protein or fragment thereof is contacted with a tagging moiety before the formation of a captured disease marker protein-binding agent complex. In embodiments, the fibrotic pulmonary disease marker protein or fragment thereof is contacted with a tagging moiety at the same time as the formation of a captured disease marker protein-binding agent complex. In embodiments, the detecting further includes (1) contacting the captured disease marker protein-binding agent complex with a tagging moiety; thereby forming a tagged disease marker protein-binding agent complex; and (2) separating the tagged disease marker protein-binding agent complex from the biological sample.

Once the tagged disease marker protein-binding agent complex is separated from the biological sample, the interaction between capturing moiety (e.g., photocleavable biotin) and capturing agent (e.g., streptavidin-coated beads) is reversed (e.g. through cleavage of the photocleavable biotin) and a cleaved disease marker protein-binding agent complex is formed. The cleaved disease marker protein-binding agent complex includes a fibrotic pulmonary disease marker protein or fragment thereof bound to a marker protein binding agent and a tagging moiety. Thus, in embodiments, the detecting further includes after the separating of step (2) separating the capturing binding agent from the tagged disease marker protein-binding agent complex, thereby forming a cleaved disease marker protein-binding agent complex.

The cleaved disease marker protein-binding agent complex may be contacted with a tagging agent (e.g., streptavidin-coated beads) and the tagging moiety (e.g., biotin) bound to the fibrotic pulmonary disease marker protein or fragment thereof may form a high affinity interaction with the tagging agent. The cleaved disease marker protein-binding agent complex may be captured by a tagging agent (e.g., streptavidin-coated beads) and the marker protein binding agent may be subsequently separated, (e.g., eluted by affinity chromatography) from the cleaved disease marker protein-binding agent complex. Once the marker protein binding agent (e.g., aptamer) is released (separated) from the cleaved disease marker protein-binding agent complex it may be quantified using standard techniques know in the art to quantify labeled nucleic acids molecules (e.g., hybridization to a custom DNA microarray). Thus, in embodiments, the detecting further includes (3) separating the marker protein binding agent from the cleaved disease marker protein-binding agent complex; thereby forming a released marker protein binding agent; and (4) determining an amount of released marker protein binding agent.

V. Marker Proteins

The fibrotic pulmonary disease marker proteins as provided herein (e.g., set forth in Table 1A, 1B, 2A, 2B, 3A, 3B, 4A, or 4B) are applicable to all methods, kits and compositions described herein. For the methods, kits and compositions described herein the expression level of one or more fibrotic pulmonary disease marker proteins may be determined (detected). In embodiments, the expression level of at least one fibrotic pulmonary disease marker protein is determined (detected). In embodiments, the expression level of a plurality (e.g., 2, 3, 4, 5, 6, 7, 8, 9, 10, 11, 12, 13, 14, 15, 16, 17, 18, 19, or 20) of fibrotic pulmonary disease marker proteins is determined (detected). Where the expression level of a plurality of fibrotic pulmonary disease marker proteins is determined (detected), the expression level of a combination of any one of the fibrotic pulmonary disease marker proteins provided herein is determined (detected).

For example, the expression level of a combination of fibrotic pulmonary disease marker proteins set forth in Table 4A and/or Table 4B may be determined (detected) in the methods, kits or compositions provided herein. In embodiments, the fibrotic pulmonary disease marker protein is a2-Macroglobulin, PUR8, iC3b, C4b, CAPG, PARC, Cathepsin H, Discoidin domain receptor 2, sICAM-5, LKHA4, MMP-7, MMP-9, NXPH1, OLR1, PTK6, or calgranulin B. In embodiments, the fibrotic pulmonary disease marker protein is a2-Macroglobulin, PUR8, iC3b, C4b, CAPG, PARC, Cathepsin H, Discoidin domain receptor 2, sICAM-5, LKHA4, MMP-7, MMP-9, NXPH1, OLR1, PTK6, and calgranulin B. In embodiments, the fibrotic pulmonary disease marker protein is a2-Macroglobulin. In embodiments, the fibrotic pulmonary disease marker protein is PUR8. In embodiments, the fibrotic pulmonary disease marker protein is iC3b. In embodiments, the fibrotic pulmonary disease marker protein is C4b. In embodiments, the fibrotic pulmonary disease marker protein is CAPG. In embodiments, the fibrotic pulmonary disease marker protein is PARC. In embodiments, the fibrotic pulmonary disease marker protein is Cathepsin H. In embodiments, the fibrotic pulmonary disease marker protein is Discoidin domain receptor 2. In embodiments, the fibrotic pulmonary disease marker protein is sICAM-5. In embodiments, the fibrotic pulmonary disease marker protein is LKHA4. In embodiments, the fibrotic pulmonary disease marker protein is MMP-7. In embodiments, the fibrotic pulmonary disease marker protein is MMP-9. In embodiments, the fibrotic pulmonary disease marker protein is NXPH1. In embodiments, the fibrotic pulmonary disease marker protein is OLR1. In embodiments, the fibrotic pulmonary disease marker protein is PTK6. In embodiments, the fibrotic pulmonary disease marker protein is calgranulin B. In embodiments, the expression level of a2-Macroglobulin, PUR8, iC3b, C4b, CAPG, PARC, Cathepsin H, Discoidin domain receptor 2, sICAM-5, LKHA4, MMP-7, MMP-9, NXPH1, OLR1, PTK6, or calgranulin B is determined. In embodiments, the expression level of a2-Macroglobulin, PUR8, iC3b, C4b, CAPG, PARC, Cathepsin H, Discoidin domain receptor 2, sICAM-5, LKHA4, MMP-7, MMP-9, NXPH1, OLR1, PTK6, and calgranulin B is determined.

In embodiments, the expression level of a2-Macroglobulin and one or more fibrotic pulmonary disease marker proteins as provided herein (e.g., set forth in Table 4A or 4B) is determined (detected). In embodiments, the expression level of PUR8 and one or more fibrotic pulmonary disease marker proteins as provided herein (e.g., set forth in Table 4A or 4B) is determined (detected). In embodiments, the expression level of iC3b and one or more fibrotic pulmonary disease marker proteins as provided herein (e.g., set forth in Table 4A or 4B) is determined (detected). In embodiments, the expression level of C4b and one or more fibrotic pulmonary disease marker proteins as provided herein (e.g., set forth in Table 4A or 4B) is determined (detected). In embodiments, the expression level of CAPG and one or more fibrotic pulmonary disease marker proteins as provided herein (e.g., set forth in Table 4A or 4B) is determined (detected). In embodiments, the expression level of PARC and one or more fibrotic pulmonary disease marker proteins as provided herein (e.g., set forth in Table 4A or 4B) is determined (detected). In embodiments, the expression level of Cathepsin H and one or more fibrotic pulmonary disease marker proteins as provided herein (e.g., set forth in Table 4A or 4B) is determined (detected). In embodiments, the expression level of Discoidin domain receptor 2 and one or more fibrotic pulmonary disease marker proteins as provided herein (e.g., set forth in Table 4A or 4B) is determined (detected). In embodiments, the expression level of sICAM-5 and one or more fibrotic pulmonary disease marker proteins as provided herein (e.g., set forth in Table 4A or 4B) is determined (detected). In embodiments, the expression level of LKHA4 and one or more fibrotic pulmonary disease marker proteins as provided herein (e.g., set forth in Table 4A or 4B) is determined (detected). In embodiments, the expression level of MMP-7 and one or more fibrotic pulmonary disease marker proteins as provided herein (e.g., set forth in Table 4A or 4B) is determined (detected). In embodiments, the expression level of MMP-9 and one or more fibrotic pulmonary disease marker proteins as provided herein (e.g., set forth in Table 4A or 4B) is determined (detected). In embodiments, the expression level of NXPH1 and one or more fibrotic pulmonary disease marker proteins as provided herein (e.g., set forth in Table 4A or 4B) is determined (detected). In embodiments, the expression level of OLR1 and one or more fibrotic pulmonary disease marker proteins as provided herein (e.g., set forth in Table 4A or 4B) is determined (detected). In embodiments, the expression level of PTK6 and one or more fibrotic pulmonary disease marker proteins as provided herein (e.g., set forth in Table 4A or 4B) is determined (detected). In embodiments, the expression level of calgranulin B and one or more fibrotic pulmonary disease marker proteins as provided herein (e.g., set forth in Table 4A or 4B) is determined (detected).

In embodiments, the fibrotic pulmonary disease marker protein is AMPK a2b2g1, CAMK2A, CAMK2B, CAMK2D, COMMD7, FER, FYN, Integrin a1b1, LYNB, METAP1, MMP-3, PDPK1, phosphoglycerate kinase 1, SHC1, or SRCN1. In embodiments, the fibrotic pulmonary disease marker protein is AMPK a2b2g1, CAMK2A, CAMK2B, CAMK2D, COMMD7, FER, FYN, Integrin a1b1, LYNB, METAP1, MMP-3, PDPK1, phosphoglycerate kinase 1, SHC1, and SRCN1. In embodiments, the fibrotic pulmonary disease marker protein is AMPK a2b2g1. In embodiments, the fibrotic pulmonary disease marker protein is CAMK2A. In embodiments, the fibrotic pulmonary disease marker protein is CAMK2B. In embodiments, the fibrotic pulmonary disease marker protein is CAMK2D. In embodiments, the fibrotic pulmonary disease marker protein is COMMD7. In embodiments, the fibrotic pulmonary disease marker protein is FER. In embodiments, the fibrotic pulmonary disease marker protein is FYN. In embodiments, the fibrotic pulmonary disease marker protein is Integrin a1b1. In embodiments, the fibrotic pulmonary disease marker protein is LYNB. In embodiments, the fibrotic pulmonary disease marker protein is METAP1. In embodiments, the fibrotic pulmonary disease marker protein is MMP-3. In embodiments, the fibrotic pulmonary disease marker protein is PDPK1. In embodiments, the fibrotic pulmonary disease marker protein is phosphoglycerate kinase 1. In embodiments, the fibrotic pulmonary disease marker protein is SHC1. In embodiments, the fibrotic pulmonary disease marker protein is SRCN1. In embodiments, the expression level of AMPK a2b2g1, CAMK2A, CAMK2B, CAMK2D, COMMD7, FER, FYN, Integrin a1b1, LYNB, METAP1, MMP-3, PDPK1, phosphoglycerate kinase 1, SHC1, or SRCN1 is determined. In embodiments, the expression level of AMPK a2b2g1, CAMK2A, CAMK2B, CAMK2D, COMMD7, FER, FYN, Integrin a1b1, LYNB, METAP1, MMP-3, PDPK1, phosphoglycerate kinase 1, SHC1, and SRCN1 is determined.

In embodiments, the expression level of AMPK a2b2g1 and one or more fibrotic pulmonary disease marker proteins as provided herein (e.g., set forth in Table 4A or 4B) is determined (detected). In embodiments, the expression level of CAMK2A and one or more fibrotic pulmonary disease marker proteins as provided herein (e.g., set forth in Table 4A or 4B) is determined (detected). In embodiments, the expression level of CAMK2B and one or more fibrotic pulmonary disease marker proteins as provided herein (e.g., set forth in Table 4A or 4B) is determined (detected). In embodiments, the expression level of CAMK2D and one or more fibrotic pulmonary disease marker proteins as provided herein (e.g., set forth in Table 4A or 4B) is determined (detected). In embodiments, the expression level of COMMD7 and one or more fibrotic pulmonary disease marker proteins as provided herein (e.g., set forth in Table 4A or 4B) is determined (detected). In embodiments, the expression level of FER and one or more fibrotic pulmonary disease marker proteins as provided herein (e.g., set forth in Table 4A or 4B) is determined (detected). In embodiments, the expression level of FYN and one or more fibrotic pulmonary disease marker proteins as provided herein (e.g., set forth in Table 4A or 4B) is determined (detected). In embodiments, the expression level of Integrin a1b1 and one or more fibrotic pulmonary disease marker proteins as provided herein (e.g., set forth in Table 4A or 4B) is determined (detected). In embodiments, the expression level of LYNB and one or more fibrotic pulmonary disease marker proteins as provided herein (e.g., set forth in Table 4A or 4B) is determined (detected). In embodiments, the expression level of METAP1 and one or more fibrotic pulmonary disease marker proteins as provided herein (e.g., set forth in Table 4A or 4B) is determined (detected). In embodiments, the expression level of MMP-3 and one or more fibrotic pulmonary disease marker proteins as provided herein (e.g., set forth in Table 4A or 4B) is determined (detected). In embodiments, the expression level of PDPK1 and one or more fibrotic pulmonary disease marker proteins as provided herein (e.g., set forth in Table 4A or 4B) is determined (detected). In embodiments, the expression level of phosphoglycerate kinase 1 and one or more fibrotic pulmonary disease marker proteins as provided herein (e.g., set forth in Table 4A or 4B) is determined (detected). In embodiments, the expression level of SHC1 and one or more fibrotic pulmonary disease marker proteins as provided herein (e.g., set forth in Table 4A or 4B) is determined (detected). In embodiments, the expression level of SRCN1 and one or more fibrotic pulmonary disease marker proteins as provided herein (e.g., set forth in Table 4A or 4B) is determined (detected).

As provided herein the methods, kits and compositions may include determining (detecting) the expression level of a fibrotic pulmonary disease marker protein set forth in Table 3A or Table 3B. Thus, in embodiments, the fibrotic pulmonary disease marker protein is TIMP-1, MMP-7, PTN, Activin A, HGF, Midkine, VEGF121, PDE3A, SBDS, Dkk-4, sICAM-5, SREC-I, ERK-1, DKK1, a2-Macroglobulin, NAGK, UFC1, or SGTA. In embodiments, the fibrotic pulmonary disease marker protein is TIMP-1, MMP-7, PTN, Activin A, HGF, Midkine, VEGF121, PDE3A, SBDS, Dkk-4, sICAM-5, SREC-I, ERK-1, DKK1, a2-Macroglobulin, NAGK, UFC1, and SGTA. In embodiments, the fibrotic pulmonary disease marker protein is TIMP-1. In embodiments, the fibrotic pulmonary disease marker protein is MMP-7. In embodiments, the fibrotic pulmonary disease marker protein is PTN. In embodiments, the fibrotic pulmonary disease marker protein is Activin A. In embodiments, the fibrotic pulmonary disease marker protein is HGF. In embodiments, the fibrotic pulmonary disease marker protein is Midkine. In embodiments, the fibrotic pulmonary disease marker protein is VEGF121. In embodiments, the fibrotic pulmonary disease marker protein is PDE3A. In embodiments, the fibrotic pulmonary disease marker protein is SBDS. In embodiments, the fibrotic pulmonary disease marker protein is Dkk-4. In embodiments, the fibrotic pulmonary disease marker protein is sICAM-5. In embodiments, the fibrotic pulmonary disease marker protein is SREC-I. In embodiments, the fibrotic pulmonary disease marker protein is ERK-1. In embodiments, the fibrotic pulmonary disease marker protein is DKK1. In embodiments, the fibrotic pulmonary disease marker protein is a2-Macroglobulin. In embodiments, the fibrotic pulmonary disease marker protein is NAGK. In embodiments, the fibrotic pulmonary disease marker protein is UFC1. In embodiments, the fibrotic pulmonary disease marker protein is SGTA. In embodiments, the expression level of TIMP-1, MMP-7, PTN, Activin A, HGF, Midkine, VEGF121, PDE3A, SBDS, Dkk-4, sICAM-5, SREC-I, ERK-1, DKK1, a2-Macroglobulin, NAGK, UFC1, or SGTA is determined. In embodiments, the expression level of TIMP-1, MMP-7, PTN, Activin A, HGF, Midkine, VEGF121, PDE3A, SBDS, Dkk-4, sICAM-5, SREC-I, ERK-1, DKK1, a2-Macroglobulin, NAGK, UFC1, and SGTA is determined.

In embodiments, the expression level of CCL18 and one or more fibrotic pulmonary disease marker proteins as provided herein (e.g., set forth in Table 3A or 3B) is determined (detected). In embodiments, the expression level of YKL40 and one or more fibrotic pulmonary disease marker proteins as provided herein (e.g., set forth in Table 3A or 3B) is determined (detected). In embodiments, the expression level of TIMP-1 and one or more fibrotic pulmonary disease marker proteins as provided herein (e.g., set forth in Table 3A or 3B) is determined (detected). In embodiments, the expression level of MMP-7 and one or more fibrotic pulmonary disease marker proteins as provided herein (e.g., set forth in Table 3A or 3B) is determined (detected). In embodiments, the expression level of PTN and one or more fibrotic pulmonary disease marker proteins as provided herein (e.g., set forth in Table 3A or 3B) is determined (detected). In embodiments, the expression level of Activin A and one or more fibrotic pulmonary disease marker proteins as provided herein (e.g., set forth in Table 3A or 3B) is determined (detected). In embodiments, the expression level of HGF and one or more fibrotic pulmonary disease marker proteins as provided herein (e.g., set forth in Table 3A or 3B) is determined (detected). In embodiments, the expression level of Midkine and one or more fibrotic pulmonary disease marker proteins as provided herein (e.g., set forth in Table 3A or 3B) is determined (detected). In embodiments, the expression level of VEGF121 and one or more fibrotic pulmonary disease marker proteins as provided herein (e.g., set forth in Table 3A or 3B) is determined (detected). In embodiments, the expression level of PDE3A and one or more fibrotic pulmonary disease marker proteins as provided herein (e.g., set forth in Table 3A or 3B) is determined (detected). In embodiments, the expression level of SBDS and one or more fibrotic pulmonary disease marker proteins as provided herein (e.g., set forth in Table 3A or 3B) is determined (detected). In embodiments, the expression level of Dkk-4 and one or more fibrotic pulmonary disease marker proteins as provided herein (e.g., set forth in Table 3A or 3B) is determined (detected). In embodiments, the expression level of sICAM-5 and one or more fibrotic pulmonary disease marker proteins as provided herein (e.g., set forth in Table 3A or 3B) is determined (detected). In embodiments, the expression level of SREC-I and one or more fibrotic pulmonary disease marker proteins as provided herein (e.g., set forth in Table 3A or 3B) is determined (detected). In embodiments, the expression level of ERK-1 and one or more fibrotic pulmonary disease marker proteins as provided herein (e.g., set forth in Table 3A or 3B) is determined (detected). In embodiments, the expression level of DKK1 and one or more fibrotic pulmonary disease marker proteins as provided herein (e.g., set forth in Table 3A or 3B) is determined (detected). In embodiments, the expression level of a2-Macroglobulin and one or more fibrotic pulmonary disease marker proteins as provided herein (e.g., set forth in Table 3A or 3B) is determined (detected). In embodiments, the expression level of NAGK and one or more fibrotic pulmonary disease marker proteins as provided herein (e.g., set forth in Table 3A or 3B) is determined (detected). In embodiments, the expression level of UFC1 and one or more fibrotic pulmonary disease marker proteins as provided herein (e.g., set forth in Table 3A or 3B) is determined (detected). In embodiments, the expression level of SGTA and one or more fibrotic pulmonary disease marker proteins as provided herein (e.g., set forth in Table 3A or 3B) is determined (detected).

In embodiments, the fibrotic pulmonary disease marker protein is PGRP-S, sFRP-3, P-Cadherin, SSRP1, a2-HS-Glycoprotein, Persephin, ABL2, SCF sR, EMR2, MSP, Marapsin, NXPH1, ZAP70, CHL1, Rb, CAD15, CK-MB, IL-1 sR9, Lymphotoxin a2/b1, PH, Survivin, IL-6 sRa, CLC7A, 17-beta-HSD 1, or NCAM-120. In embodiments, the fibrotic pulmonary disease marker protein is PGRP-S, sFRP-3, P-Cadherin, SSRP1, a2-HS-Glycoprotein, Persephin, ABL2, SCF sR, EMR2, MSP, Marapsin, NXPH1, ZAP70, CHL1, Rb, CAD15, CK-MB, IL-1 sR9, Lymphotoxin a2/b1, PH, Survivin, IL-6 sRa, CLC7A, 17-beta-HSD 1, and NCAM-120. In embodiments, the fibrotic pulmonary disease marker protein is PGRP-S. In embodiments, the fibrotic pulmonary disease marker protein is sFRP-3. In embodiments, the fibrotic pulmonary disease marker protein is P-Cadherin. In embodiments, the fibrotic pulmonary disease marker protein is SSRP1. In embodiments, the fibrotic pulmonary disease marker protein is a2-HS-Glycoprotein. In embodiments, the fibrotic pulmonary disease marker protein is Persephin. In embodiments, the fibrotic pulmonary disease marker protein is ABL2. In embodiments, the fibrotic pulmonary disease marker protein is SCF sR. In embodiments, the fibrotic pulmonary disease marker protein is EMR2. In embodiments, the fibrotic pulmonary disease marker protein is MSP. In embodiments, the fibrotic pulmonary disease marker protein is Marapsin. In embodiments, the fibrotic pulmonary disease marker protein is NXPH. In embodiments, the fibrotic pulmonary disease marker protein is ZAP70. In embodiments, the fibrotic pulmonary disease marker protein is CHL1. In embodiments, the fibrotic pulmonary disease marker protein is Rb. In embodiments, the fibrotic pulmonary disease marker protein is CAD15. In embodiments, the fibrotic pulmonary disease marker protein is CK-MB. In embodiments, the fibrotic pulmonary disease marker protein is IL-1 sR9. In embodiments, the fibrotic pulmonary disease marker protein is Lymphotoxin a2/b1. In embodiments, the fibrotic pulmonary disease marker protein is PH. In embodiments, the fibrotic pulmonary disease marker protein is Survivin. In embodiments, the fibrotic pulmonary disease marker protein is IL-6 sRa. In embodiments, the fibrotic pulmonary disease marker protein is CLC7A. In embodiments, the fibrotic pulmonary disease marker protein is 17-beta-HSD 1. In embodiments, the fibrotic pulmonary disease marker protein is NCAM-120. In embodiments, the expression level of PGRP-S, sFRP-3, P-Cadherin, SSRP1, a2-HS-Glycoprotein, Persephin, ABL2, SCF sR, EMR2, MSP, Marapsin, NXPH1, ZAP70, CHL1, Rb, CAD15, CK-MB, IL-1 sR9, Lymphotoxin a2/b1, PH, Survivin, IL-6 sRa, CLC7A, 17-beta-HSD 1, or NCAM-120 is determined. In embodiments, the expression level of PGRP-S, sFRP-3, P-Cadherin, SSRP1, a2-HS-Glycoprotein, Persephin, ABL2, SCF sR, EMR2, MSP, Marapsin, NXPH1, ZAP70, CHL1, Rb, CAD15, CK-MB, IL-1 sR9, Lymphotoxin a2/b1, PH, Survivin, sRa, CLC7A, 17-beta-HSD 1, and NCAM-120 is determined.

In embodiments, the expression level of PGRP-S and one or more fibrotic pulmonary disease marker proteins as provided herein (e.g., set forth in Table 3A or 3B) is determined (detected) (detected). In embodiments, the expression level of sFRP-3 and one or more fibrotic pulmonary disease marker proteins as provided herein (e.g., set forth in Table 3A or 3B) is determined (detected). In embodiments, the expression level of P-Cadherin and one or more fibrotic pulmonary disease marker proteins as provided herein (e.g., set forth in Table 3A or 3B) is determined (detected). In embodiments, the expression level of SSRP1 and one or more fibrotic pulmonary disease marker proteins as provided herein (e.g., set forth in Table 3A or 3B) is determined (detected). In embodiments, the expression level of a2-HS-Glycoprotein and one or more fibrotic pulmonary disease marker proteins as provided herein (e.g., set forth in Table 3A or 3B) is determined (detected). In embodiments, the expression level of Persephin and one or more fibrotic pulmonary disease marker proteins as provided herein (e.g., set forth in Table 3A or 3B) is determined (detected). In embodiments, the expression level of ABL2 and one or more fibrotic pulmonary disease marker proteins as provided herein (e.g., set forth in Table 3A or 3B) is determined (detected). In embodiments, the expression level of SCF sR and one or more fibrotic pulmonary disease marker proteins as provided herein (e.g., set forth in Table 3A or 3B) is determined (detected). In embodiments, the expression level of EMR2 and one or more fibrotic pulmonary disease marker proteins as provided herein (e.g., set forth in Table 3A or 3B) is determined (detected). In embodiments, the expression level of MSP and one or more fibrotic pulmonary disease marker proteins as provided herein (e.g., set forth in Table 3A or 3B) is determined (detected). In embodiments, the expression level of Marapsin and one or more fibrotic pulmonary disease marker proteins as provided herein (e.g., set forth in Table 3A or 3B) is determined (detected). In embodiments, the expression level of NXPH1 and one or more fibrotic pulmonary disease marker proteins as provided herein (e.g., set forth in Table 3A or 3B) is determined (detected). In embodiments, the expression level of ZAP70 and one or more fibrotic pulmonary disease marker proteins as provided herein (e.g., set forth in Table 3A or 3B) is determined (detected). In embodiments, the expression level of CHL1 and one or more fibrotic pulmonary disease marker proteins as provided herein (e.g., set forth in Table 3A or 3B) is determined (detected). In embodiments, the expression level of Rb and one or more fibrotic pulmonary disease marker proteins as provided herein (e.g., set forth in Table 3A or 3B) is determined (detected). In embodiments, the expression level of CAD15 and one or more fibrotic pulmonary disease marker proteins as provided herein (e.g., set forth in Table 3A or 3B) is determined (detected). In embodiments, the expression level of CK-MB and one or more fibrotic pulmonary disease marker proteins as provided herein (e.g., set forth in Table 3A or 3B) is determined (detected). In embodiments, the expression level of IL-1 sR9 and one or more fibrotic pulmonary disease marker proteins as provided herein (e.g., set forth in Table 3A or 3B) is determined (detected). In embodiments, the expression level of Lymphotoxin a2/b1 and one or more fibrotic pulmonary disease marker proteins as provided herein (e.g., set forth in Table 3A or 3B) is determined (detected). In embodiments, the expression level of PH and one or more fibrotic pulmonary disease marker proteins as provided herein (e.g., set forth in Table 3A or 3B) is determined (detected). In embodiments, the expression level of Survivin and one or more fibrotic pulmonary disease marker proteins as provided herein (e.g., set forth in Table 3A or 3B) is determined (detected). In embodiments, the expression level of IL-6 sRa and one or more fibrotic pulmonary disease marker proteins as provided herein (e.g., set forth in Table 3A or 3B) is determined (detected). In embodiments, the expression level of CLC7A and one or more fibrotic pulmonary disease marker proteins as provided herein (e.g., set forth in Table 3A or 3B) is determined (detected). In embodiments, the expression level of 17-beta-HSD 1 and one or more fibrotic pulmonary disease marker proteins as provided herein (e.g., set forth in Table 3A or 3B) is determined (detected). In embodiments, the expression level of NCAM-120 and one or more fibrotic pulmonary disease marker proteins as provided herein (e.g., set forth in Table 3A or 3B) is determined (detected).

For the methods, kits or compositions provided herein the expression level of one or more fibrotic pulmonary disease marker proteins set forth in Table 1A, 1B, 2A, 2B, 3A, 3B, 4A and/or Table 4B may be determined (detected) in combination with the expression level of known markers associated with fibrotic pulmonary diseases. In embodiments, the expression level of one or more fibrotic pulmonary disease marker proteins set forth in Table 1A, 1B, 2A, 2B, 3A, 3B, 4A or Table 4B is determined in combination with the expression level of MMP7, PARC/CCL18, YKL-40(Chitinase-Like-3), MMP3, SP-D, KL-6/Muc1, or Osteopontin (OPN). In embodiments, the expression level of one or more fibrotic pulmonary disease marker proteins set forth in Table 1A, 1B, 2A, 2B, 3A, 3B, 4A or Table 4B is determined in combination with the expression level of MMP7, PARC/CCL18, YKL-40(Chitinase-Like-3), MMP3, SP-D, KL-6/Muc1, and Osteopontin (OPN). In embodiments, the expression level of one or more fibrotic pulmonary disease marker proteins set forth in Table 1A, 1B, 2A, 2B, 3A, 3B, 4A or Table 4B is determined in combination with the expression level of MMP1, SP-A, S100a12 (enrage), Periostin, ICAM1, VCAM, IL8, VEGF, CD28, Hsp47, IL6, LDH, PAI-1, Protein C, Thrombomodulin, vonWillebrand Factor (vWF), MMP8, IL2Ralpha, IL2Rgamma, TGFB1, TGFb2, TGFb3, or TNFalpha. In embodiments, the expression level of one or more fibrotic pulmonary disease marker proteins set forth in Table 1A, 1B, 2A, 2B, 3A, 3B, 4A or Table 4B is determined in combination with the expression level of MMP1, SP-A, S100a12 (enrage), Periostin, ICAM1, VCAM, IL8, VEGF, CD28, Hsp47, IL6, LDH, PAI-1, Protein C, Thrombomodulin, vonWillebrand Factor (vWF), MMP8, IL2Ralpha, IL2Rgamma, TGFB1, TGFb2, TGFb3, and TNFalpha. In embodiments, the expression level of one or more fibrotic pulmonary disease marker proteins set forth in Table 1A, 1B, 2A, 2B, 3A, 3B, 4A or Table 4B is determined in combination with the expression level of BNP, albumin, COMP, CCL11, CCL13, CCL17, Serum amyloid A, or CXCL13. In embodiments, the expression level of one or more fibrotic pulmonary disease marker proteins set forth in Table 1A, 1B, 2A, 2B, 3A, 3B, 4A or Table 4B is determined in combination with the expression level of BNP, albumin, COMP, CCL11, CCL13, CCL17, Serum amyloid A, and CXCL13.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, UniProt numbers, and websites cited herein are hereby incorporated by reference in their entireties for all purposes.

VI. Specific Embodiments

Samples and Sample Selection

Plasma samples were obtained from IPF patients. Plasma samples for demographically matched healthy control subjects with a summary of health conditions and information regarding medication use were obtained from a separate collection protocol. All samples were obtained under appropriate written Informed Consent. Histories were reviewed to provide the best possible match of IPF and control groups. This excluded significant pulmonary disease from the healthy control group and recent use of prednisolone or other drugs (other than proton pump inhibitors) used off label in the treatment of IPF from the IPF cohort.

IPF patient samples were selected to include all patients that died. In addition, IPF patient samples were selected to include patients that experienced a broad range of subsequent FVC change. The ratio of male and female IPF patients (2.5:1) is similar to that in the IPF population. Control samples were selected for a balanced design across groups. Normal Healthy control subjects were selected to be demographically consistent with the IPF patient samples for consistency with the clinical trial population (age/gender). Normal Healthy control samples were collected into comparable collection vials (i.e. with matched preservatives). Both IPF and control samples were collected at multiple sites.

TABLE I

Summary demographics for IPF patients and healthy controls are shown below.

| | All | | Male | | Female | |
|---|---|---|---|---|---|---|
| | IPF | Controls | IPF | Controls | IPF | Controls |
| Patients (n) | 140 | 70 | 100 | 50 | 40 | 20 |
| Gender | | | | | | |
| Male | 100 (71.4%) | 50 (71.4%) | 100% | 100% | | |
| Female | 40 (28.6%) | 20 (28.6%) | | | 100% | 100% |
| Ethnic origin | | | | | | |
| White | 100% | 100% | 100% | 100% | 100% | 100% |

TABLE I-continued

Summary demographics for IPF patients and healthy controls are shown below.

|  | All | | Male | | Female | |
| --- | --- | --- | --- | --- | --- | --- |
|  | IPF | Controls | IPF | Controls | IPF | Controls |
| Smoking status | | | | | | |
| Never | 45 (32.1%) | 22 (31.4) | 31 (31%) | 16 (32%) | 14 (35%) | 6 (30%) |
| Previous | 92 (65.7%) | 46 (65.7) | 67 (67%) | 33 (66%) | 25 (62.5%) | 13 (65%) |
| Current | 3 (2.1%) | 2 (2.9%) | 2 (2%) | 1 (2%) | 1 (2.5%) | 1 (5%) |
| Region | | | | | | |
| United States | 98 (70.0%) | 100% | | | | |
| Canada | 10 (7.1%) | | | | | |
| Europe | 32 (22.9%) | | | | | |
| Age (year) | 66.9 (7.2) | 66.9 (7.3) | 66.9 (7.2) | 66.9 (7.7) | 67.6 (7.3) | 57.0 (6.5) |
| Weight (kg) | 87.4 (18.2) | 84.8 (17.1) | 91.1 (17.7) | 88.0 (15.7) | 78.4 (16.4) | 77.0 (18.2) |
| BMI | 30.1 (5.2) | | 30.1 (5.0) | | 30.1 (5.8) | |
| Baseline | | | | | | |
| FVC (% predicted) | 72.4 (13.2) | | 72.4 (12.5) | | 72.3 (14.9) | |
| Dlco (% predicted Hgb-corrected) | 45.9 (8.5) | | 45.4 (8.3) | | 46.8 (9.1) | |
| 6MWT (m) | 395.2 (95.1) | | 408.7 (90.4) | | 362.4 (99.3) | |
| Outcome | | | | | | |
| Death All patients that died were selected | 25 (17.9%) | | 16 (16%) | | 9 (22.5%) | |
| ΔFVC 24 weeks (% predicted) | −6.9 | | −6.7 | | −7.2 | |
| ΔFVC 48 weeks (% predicted) | −13.7 | | −12.7 | | −16.0 | |

From plasma of IPF patients and healthy controls, 1129 proteins were profiled using a broad aptamer-based proteomic platform (SomaLogic, Colorado, US). Briefly, the technology uses DNA aptamers containing chemically modified nucleotides as highly specific protein binding reagents in a multiplexed assay that transforms the quantity of each targeted protein into a corresponding quantify of the aptamer (FIG. 1). Protein quantities are then detected on a microarray platform and recorded as Relative Fluorescence Units (RFU). Data meeting quality control standards were obtained for 130/140 IPF patients and 69/70 controls.

From plasma of IPF patients and controls, proteins were profiled in commercially available sandwich immunoassays (ELISAs) from various companies (R&D Systems Inc., Minneapolis, Minn.; Abcam Inc., Cambridge, UK). In brief, the assay involves binding of the protein of interest to a capture matrix on a specific antibody and detection using a second enzymatically conjugated antibody, usually horse radish peroxidase. The HRP reacts with a chromogenic substrate to create a colorimetric reading which is read by a microplate reader and expressed as an OD. A standard curve is used to convert this to a defined concentration of protein. Data meeting quality control standards ranged from 191 to 213 in patient cohort #1 to 466 to 613 patients patient cohort #2. Survival and Progression Free Survival (PFS) Kaplan Meier Plots were generated using median and Rpart analysis.

Statistical analysis: Relative protein concentrations (measured in relative fluorescence units; RFU) were normalized against hybridization controls and median normalized (calibrated) across all groups. Normalized protein concentrations were log transformed for better fidelity with the Gaussian assumptions in the statistical models. Differential protein regulation was evaluated based on univariate tests (per protein). Differentially expressed proteins were identified by ANOVA with corrections for multiple comparisons (FDR<0.01 and fold change ≥1.2×). This resulted in the identification of 262 differentially expressed proteins of which 174 are up-regulated in IPF (Table 1A) relative to healthy controls and 88 are down-regulated (Table 1B). This analysis confirmed several previously known proteins that are differentially expressed in IPF including matrix metalloproteinase 7 (MMP7), chemokine (C—C motif) ligand (CCL18), and surfactant protein D (SFTPD).

Figure 2:
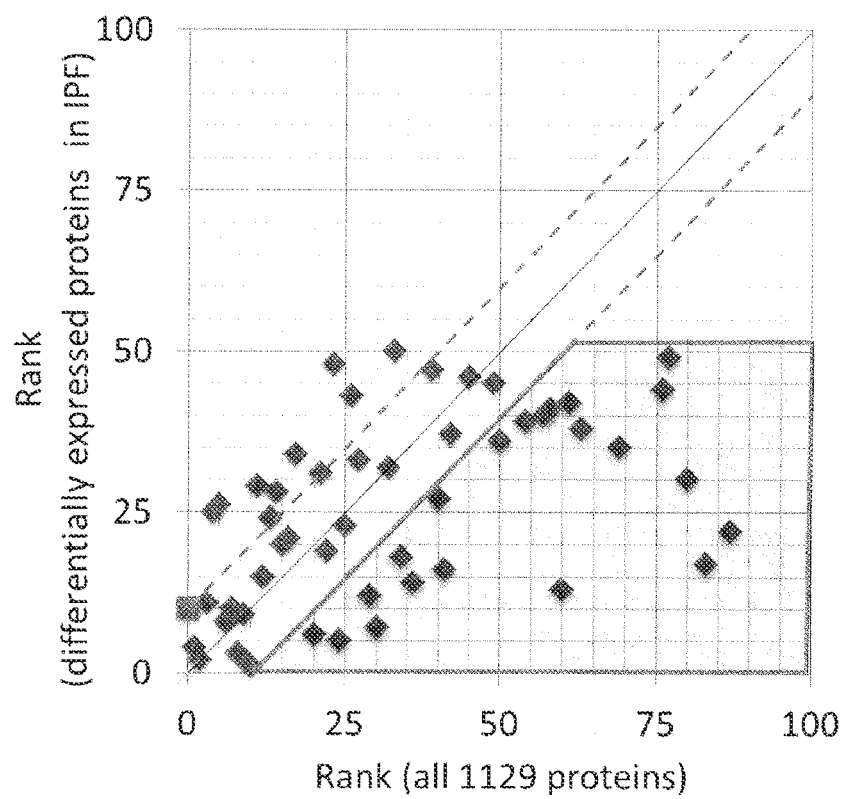
FIG. 2: Comparison of relative rank of pathways defined by differentially expressed proteins to those defined by the proteins on the panel as a whole.

In order to identify biological processes that are enriched in IPF, the pathways associated with differentially expressed proteins in IPF were compared to those associated with those on proteins on the 1129 protein panel as a whole. In each case, relevant processes were identified using MetaCore (Thomson Reuters, New York, N.Y.). To identify processes that are overrepresented by the differentially expressed proteins in IPF relative to the protein panel, the rank order of processes associated with each case were compared. FIG. 2 shows a plot of the highest ranked processes associated with differentially expressed proteins in IPF (Y axis) compared to the processes associated with the proteins on the panel as a whole (X axis). The processes highlighted in the red box (lower right section) are enriched in IPF. Table II lists the associated processes that show a shift of at least 10 positions between IPF and the panel as a whole (with processes associated with the greatest change in rank at the top). Among these processes are those involved in TGF-B signaling, cell adhesion, and epithelial mesenchymal transition (EMT). These processes are known to be associated with IPF and fibrotic conditions and suggest that the plasma proteomic signature obtained is consistent with disease state.

TABLE II

The IPF plasma protein profile shows activation of pathways involved in TGF-β signaling, cell adhesion, and EMT.

| Rank Increase (X-Y) | Rank in IPF (Y-axis) | Process Networks |
|---|---|---|
| 66 | 17 | Cardiac development BMP TGF beta signaling |
| 65 | 22 | Cell adhesion Synaptic contact |
| 50 | 30 | Cytoskeleton Maropinocytosis and its regulation |
| 47 | 13 | Apoptosis Anti-Apoptosis mediated by external signals by Estrogen |
| 34 | 35 | Reproduction Spermatogenesis, motility and copulation |
| 32 | 44 | Reproduction GnRH signaling pathway |
| 28 | 49 | Reproduction Gonadotropin regulation |
| 25 | 16 | Reproduction Male sex differentiation |
| 25 | 38 | Signal Transduction TGF-beta, GDF and Activin signaling |
| 23 | 7 | Cell cycle G1-S Growth factor regulation |
| 22 | 14 | Development Neurogenesis Axonal guidance |
| 19 | 5 | Development EMT Regulation of epithelial-to-mesenchymal transition |
| 19 | 42 | Inflammation MIF signaling |
| 17 | 12 | Cell adhesion Attractive and repulsive receptors |
| 17 | 40 | Development Synaptogenesis |
| 17 | 41 | Cell adhesion Cadherins |
| 16 | 18 | Inflammation Amphoterin signaling |
| 15 | 39 | Immune response Phagosome in antigen presentation |
| 14 | 6 | Apoptosis Anti-Apoptosis mediated by external signals via MAPK and JAK/STAT |
| 14 | 36 | Cell adhesion Cell-matrix interactions |
| 13 | 27 | Signal transduction WNT signaling |

Identification of proteins that predict disease progression: Protein concentrations and patient outcomes (particularly time to death or disease progression) were analyzed using R. For this analysis, disease progression was defined as death or a ≥10% absolute decrease in percent predicted FVC or a ≥15% absolute decrease in percent predicted DLCO (corrected for Hb) at any time compared to baseline, documented by at 2 consecutive assessments performed at least 6 weeks apart. Patients were followed from Baseline to last known survival date or completion of study, whichever is shortest. Patients undergoing lung transplant were censored at the time of transplant.

For each of 1129 proteins, an initial analysis using a method tree-based model (CART, R package), partitioned patients into a high and low risk range of protein concentration that would maximize the difference in Hazard Ratios (HR) for mortality or progression free survival. The output from this analysis was a protein concentration threshold (in RFU) for further evaluation. In a further analysis, the HR and p value associated with this threshold were determined and reported using a Cox proportional hazard (PH) model (survival package of R). An additional analysis stratified the patients by protein expression (in quartiles) and reported associated differences in either survival or PFS compared to the patients in the lowest quartile. The resultant Kaplan-Meier curves were manually evaluated resulting in the identification of 43 proteins that predict mortality, progression free survival, or both (Table 3; FIG. 5-FIG. 47). This list includes MMP-7, a previously reported marker of disease progression in IPF.

Figure 3:
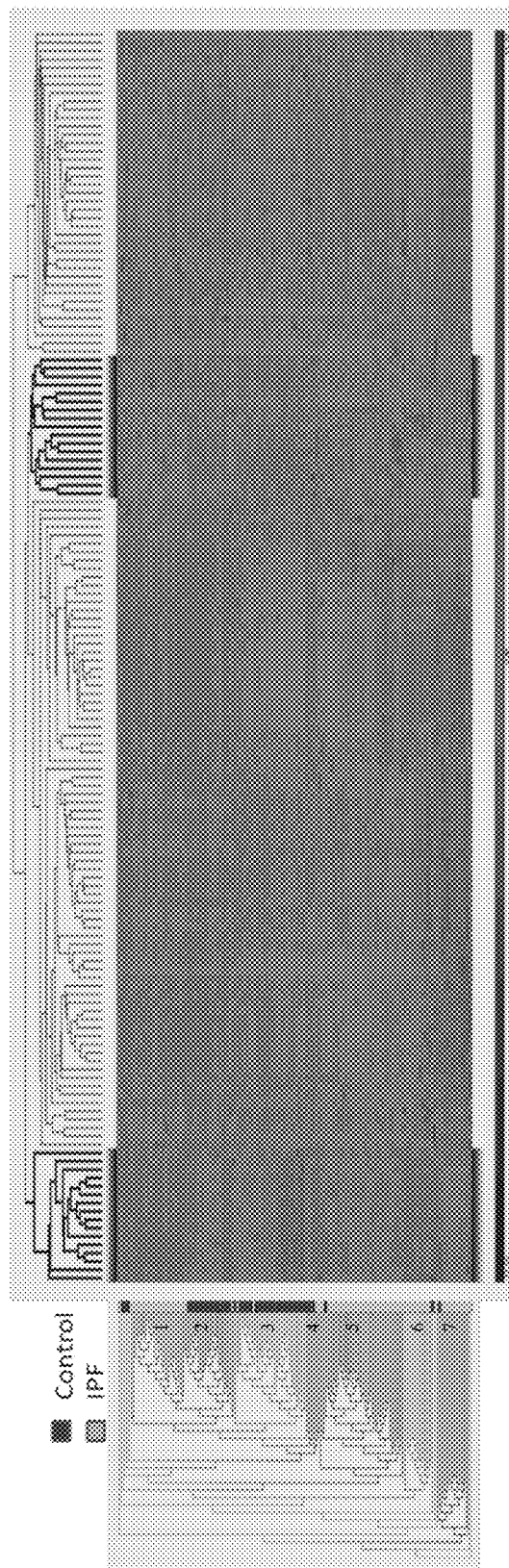
FIG. 3: Hierarchical Clustering of IPF patients.
Figure 4:
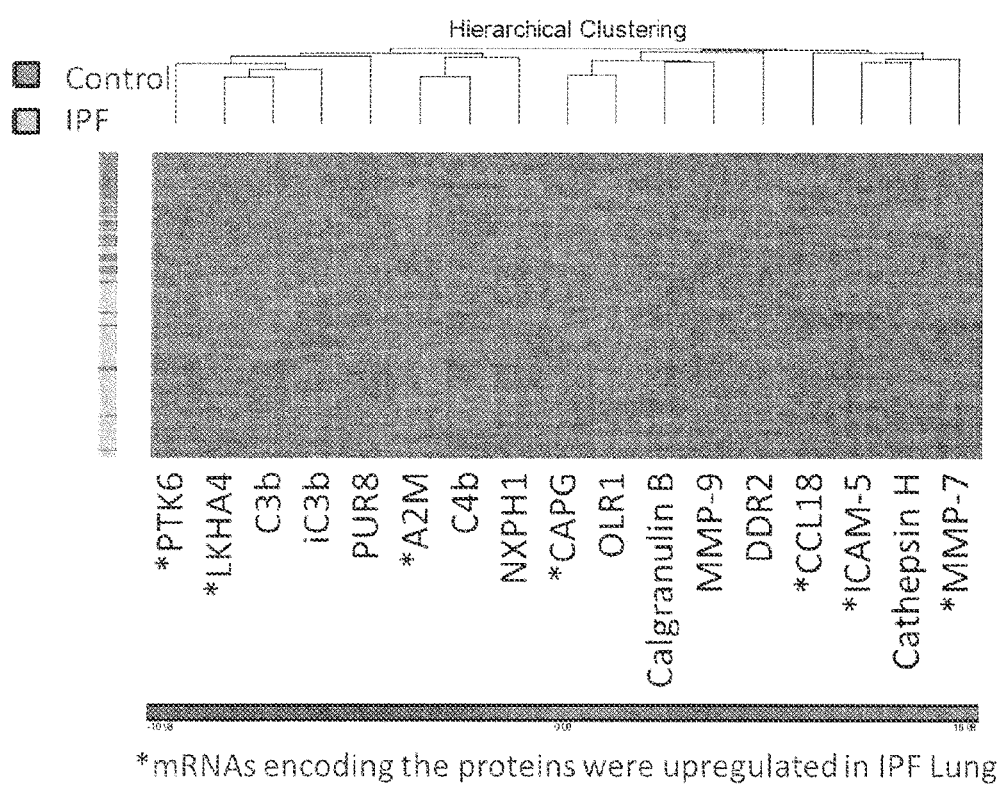
FIG. 4: Hierarchical Clustering of IPF patients.
Figure 5:
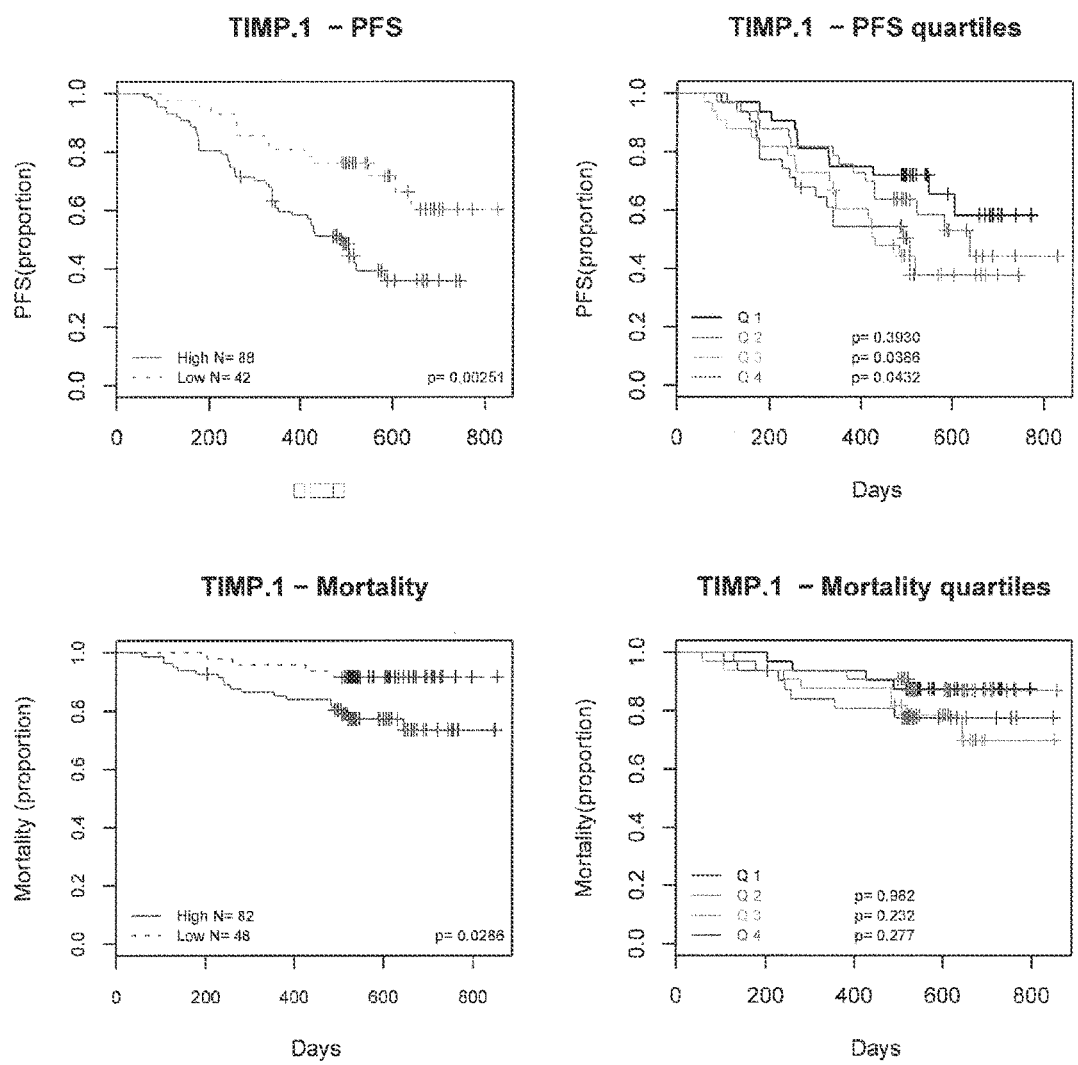
FIG. 5-FIG. 47: Fibrotic pulmonary disease biomarker proteins that predict disease progression in patient cohort #1 using aptamer based proteomic platform for determination of protein levels. The following description applies to the histograms shown in FIG. 5-FIG. 47.
Figure 6:
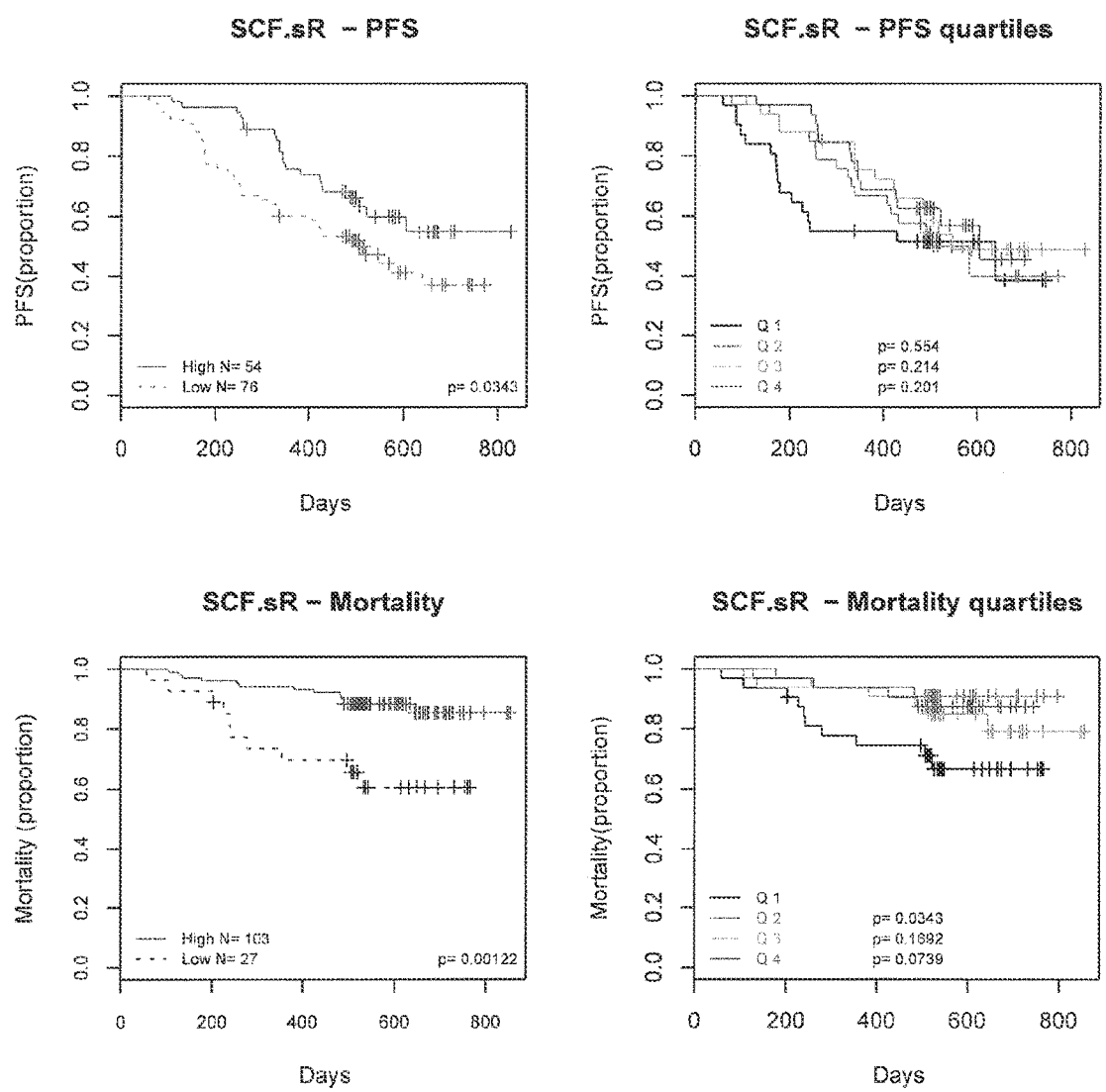
Figure 7:
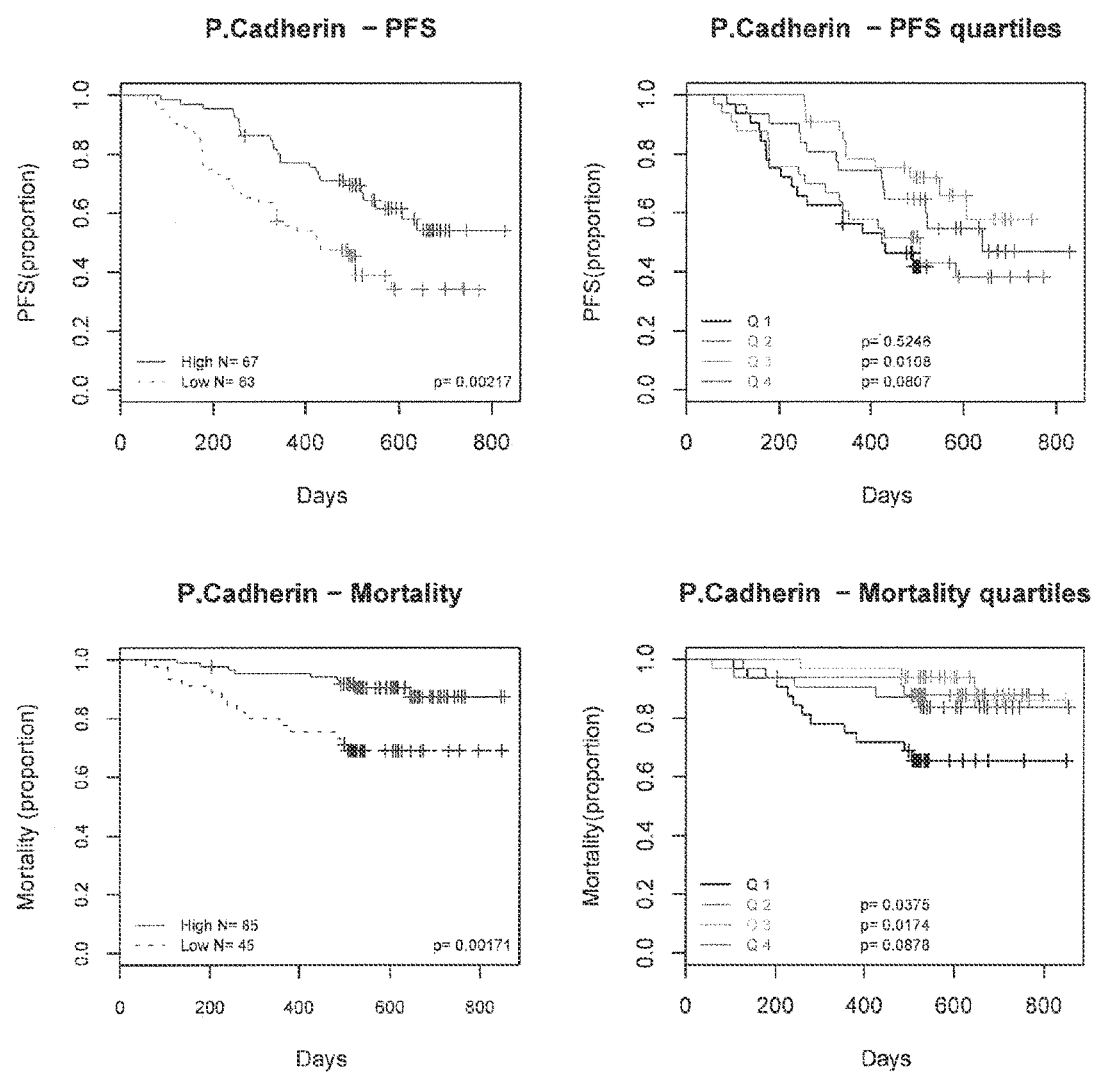
Figure 8:
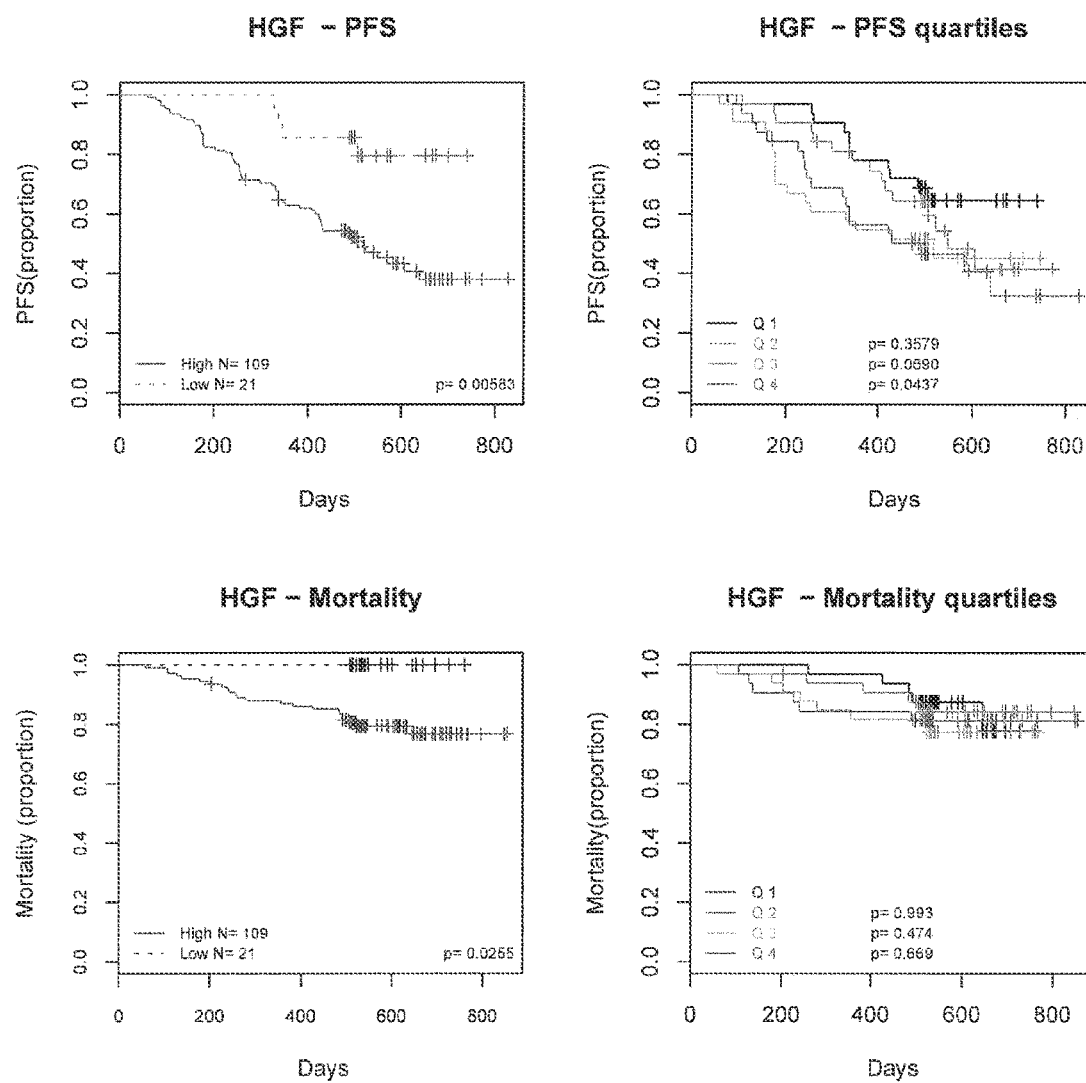
Figure 9:
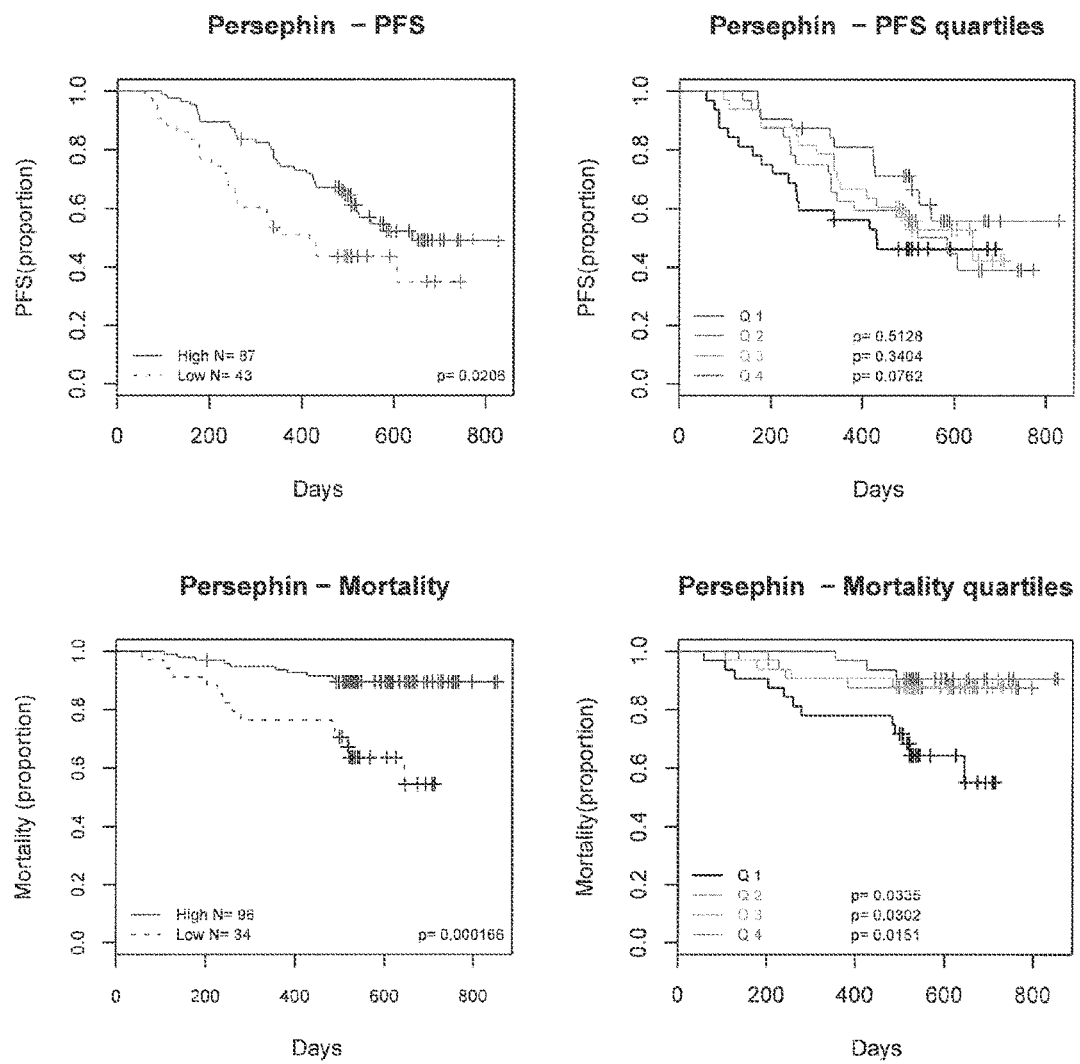
Figure 10:
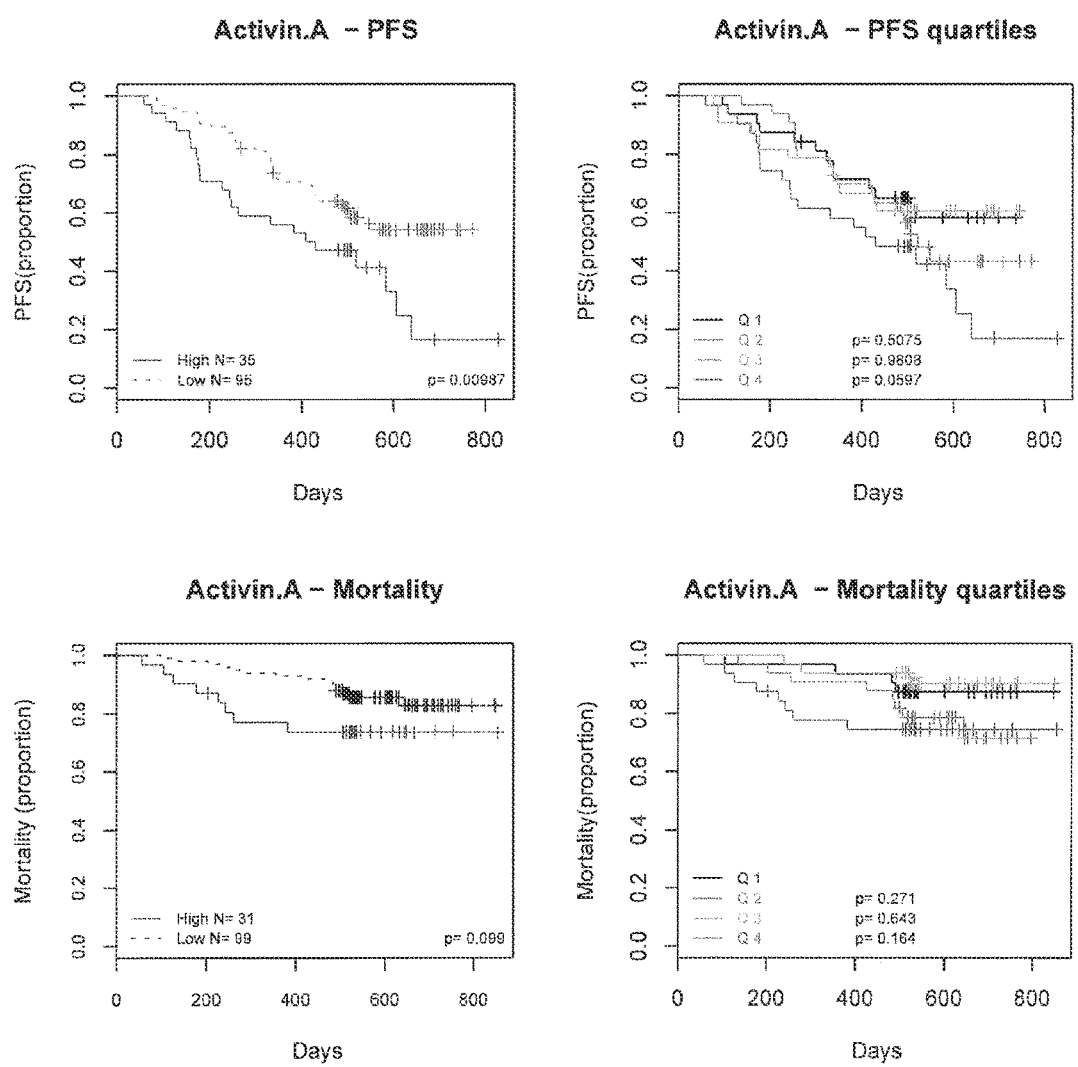
Figure 11:
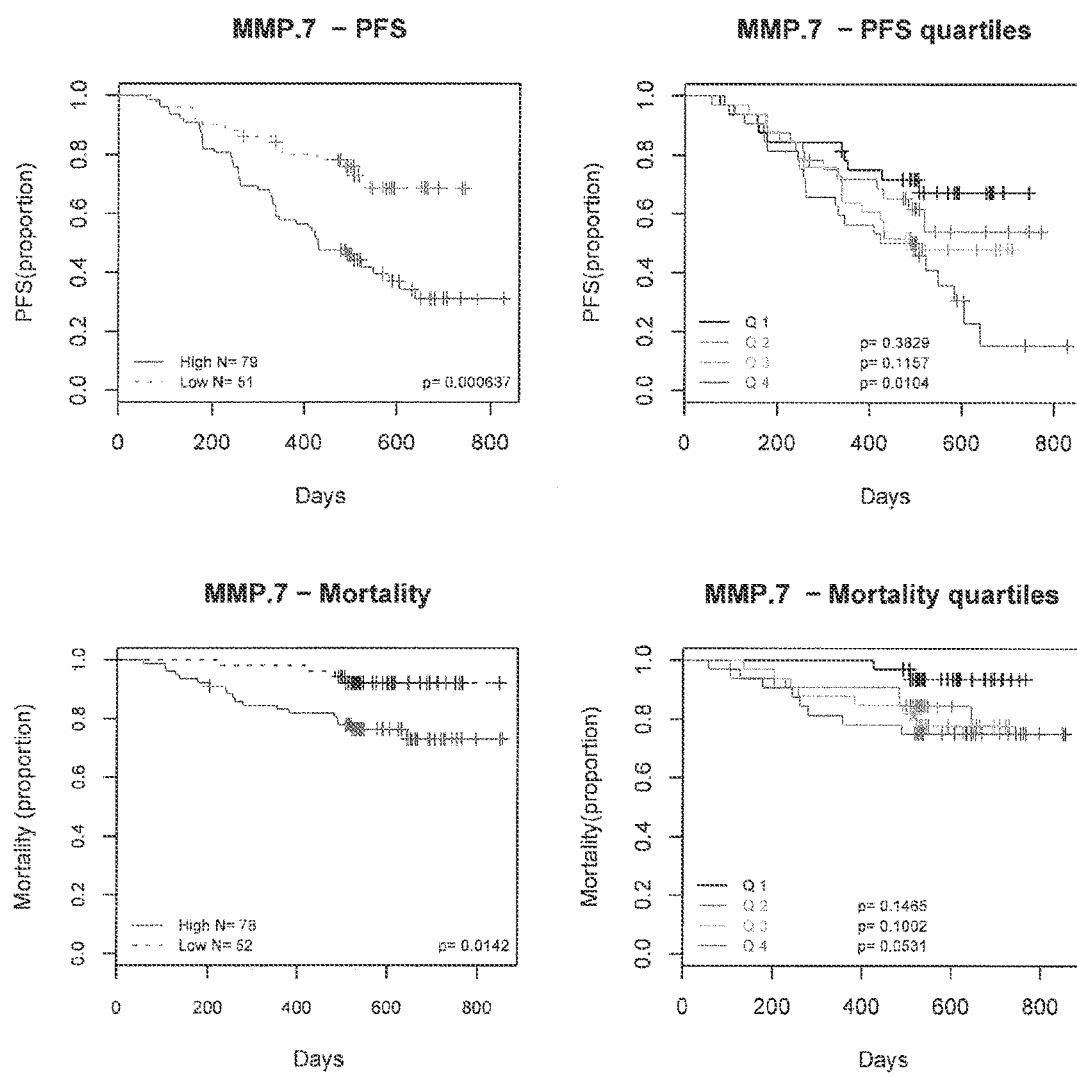
Figure 12:
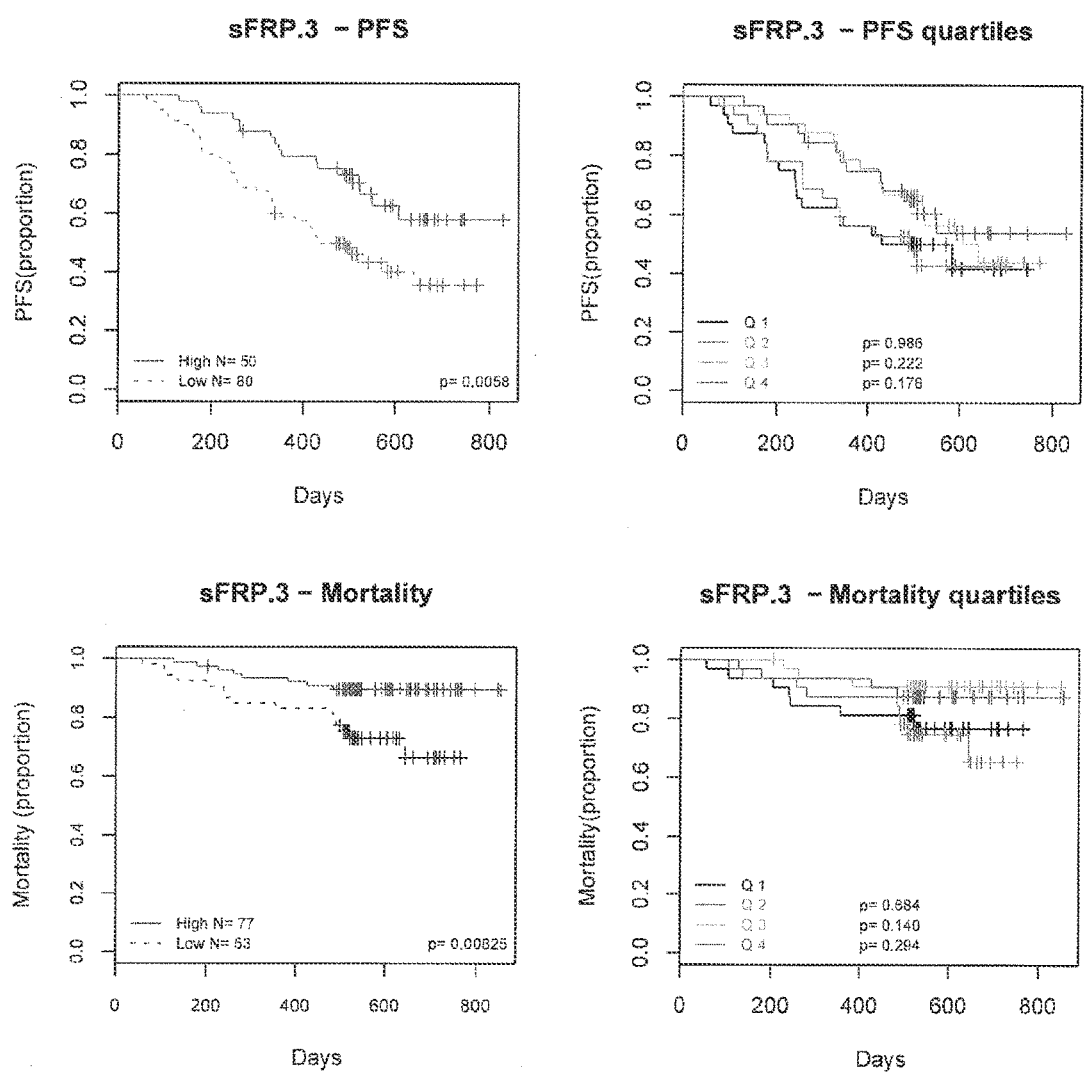
Figure 13:
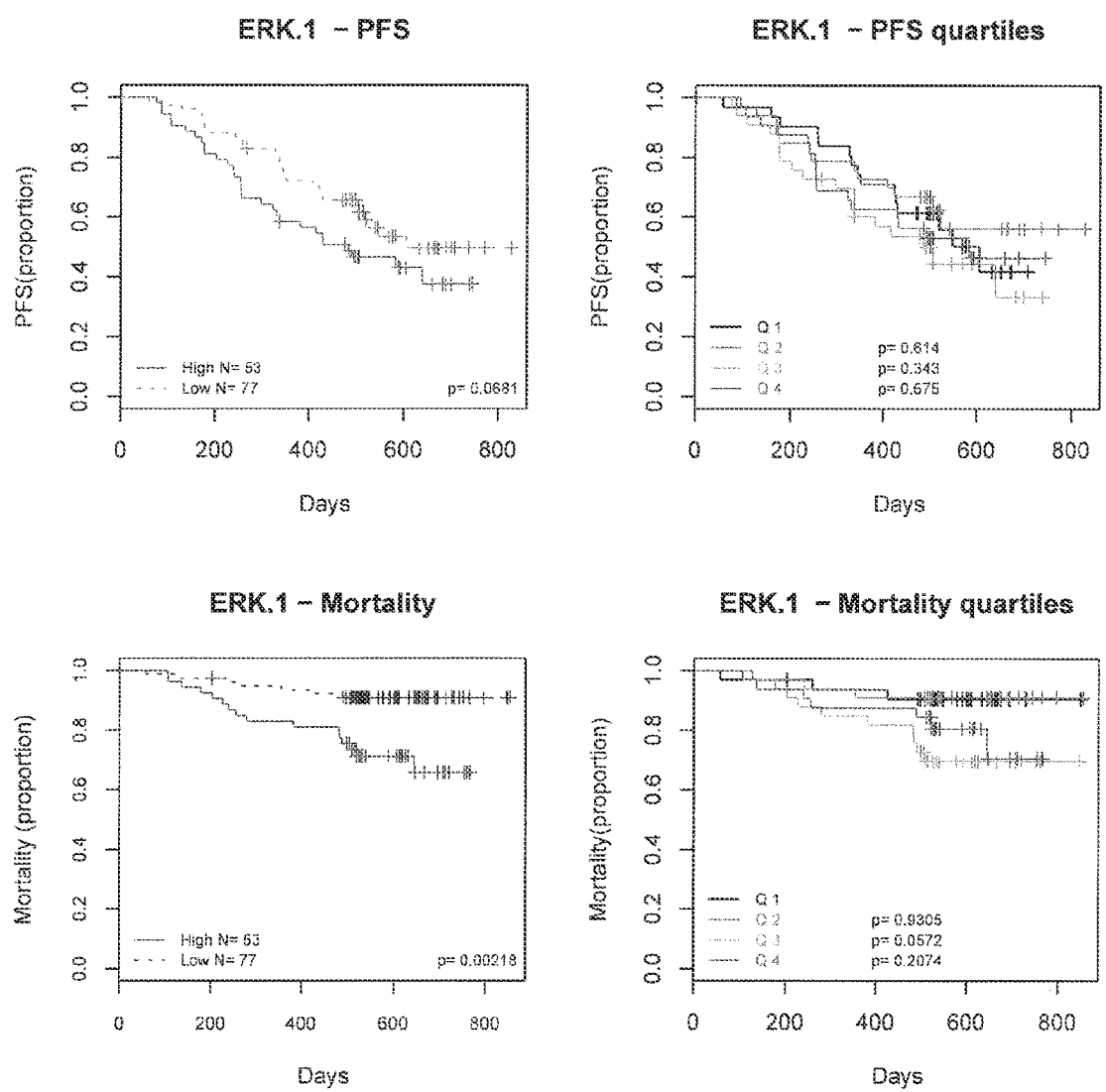
Figure 14:
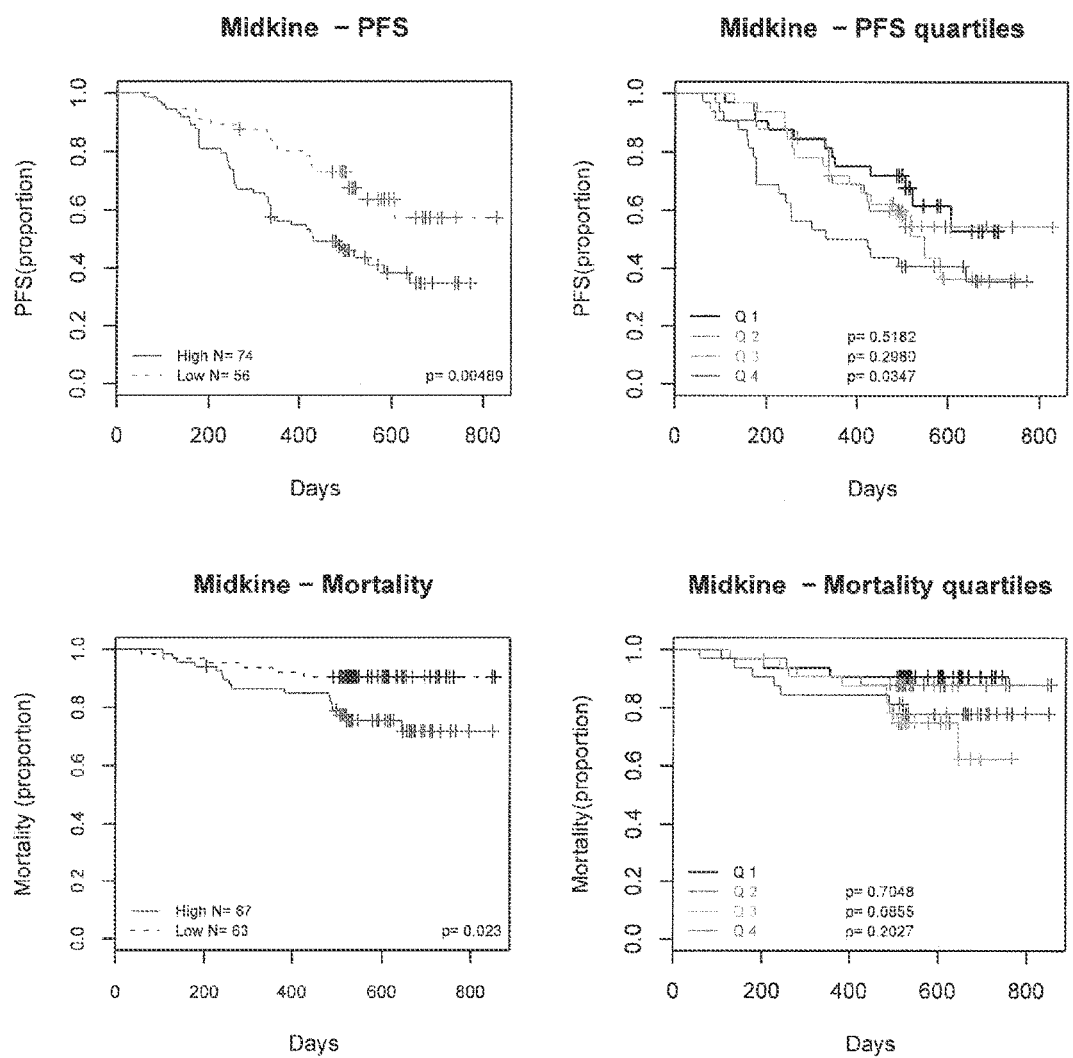
Figure 15:
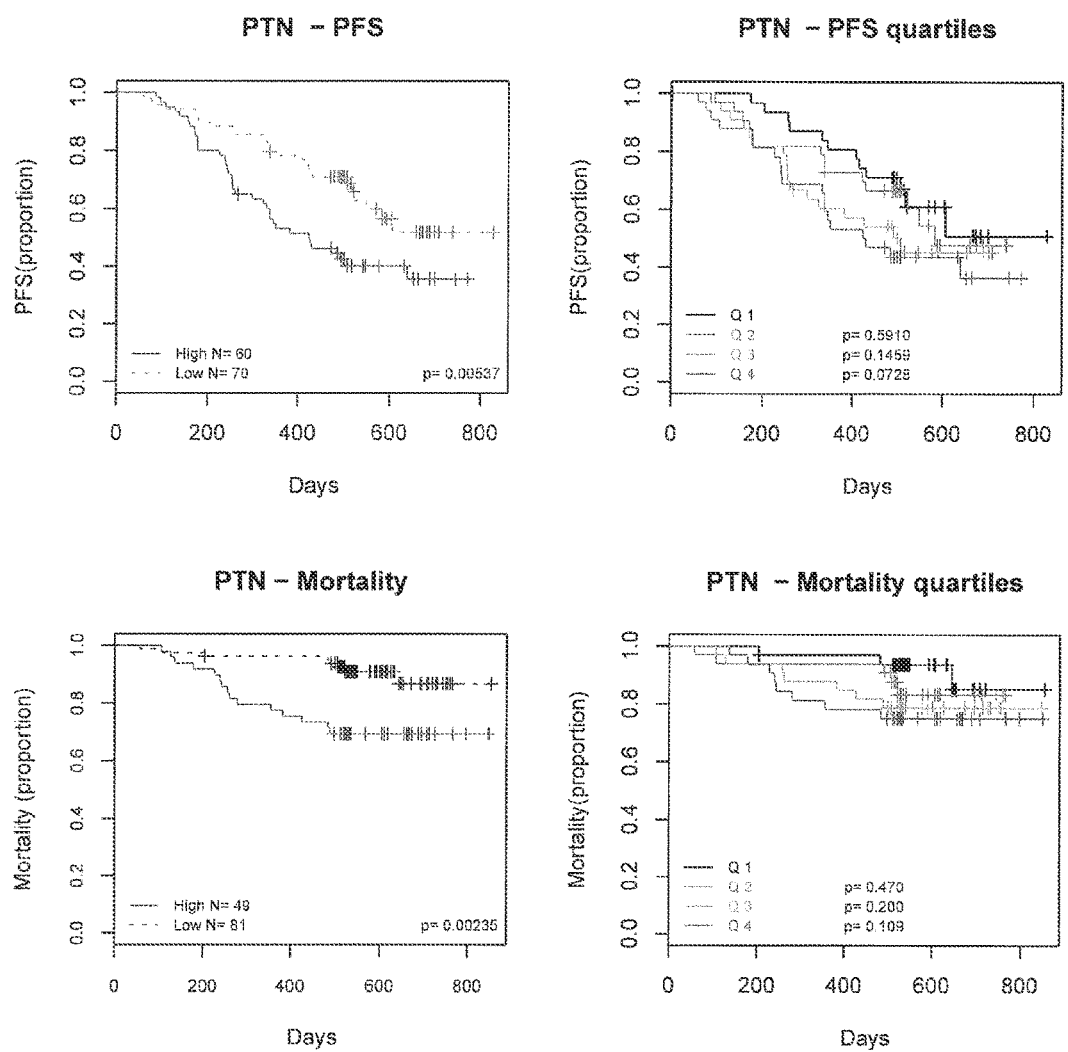
Figure 16:
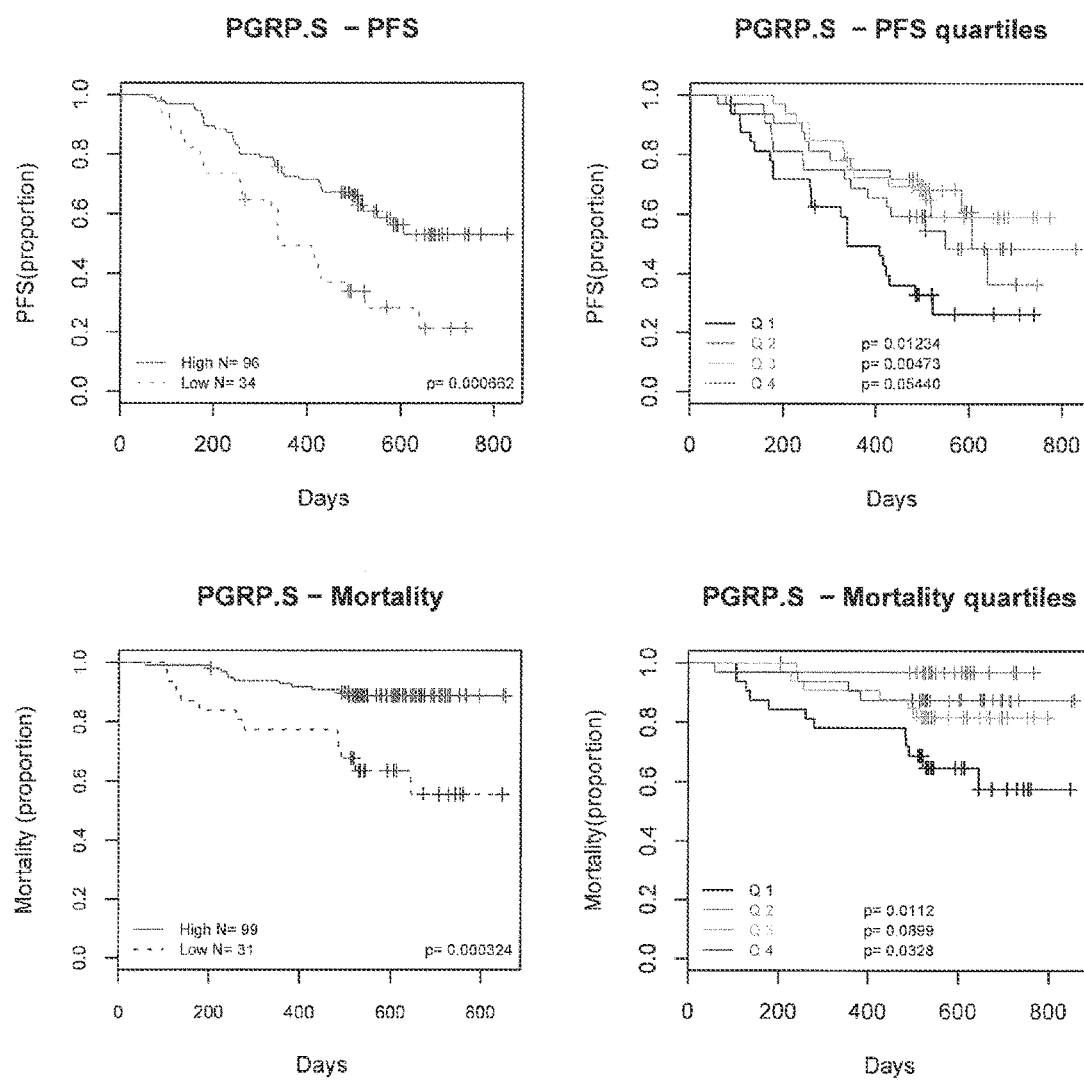
Figure 17:
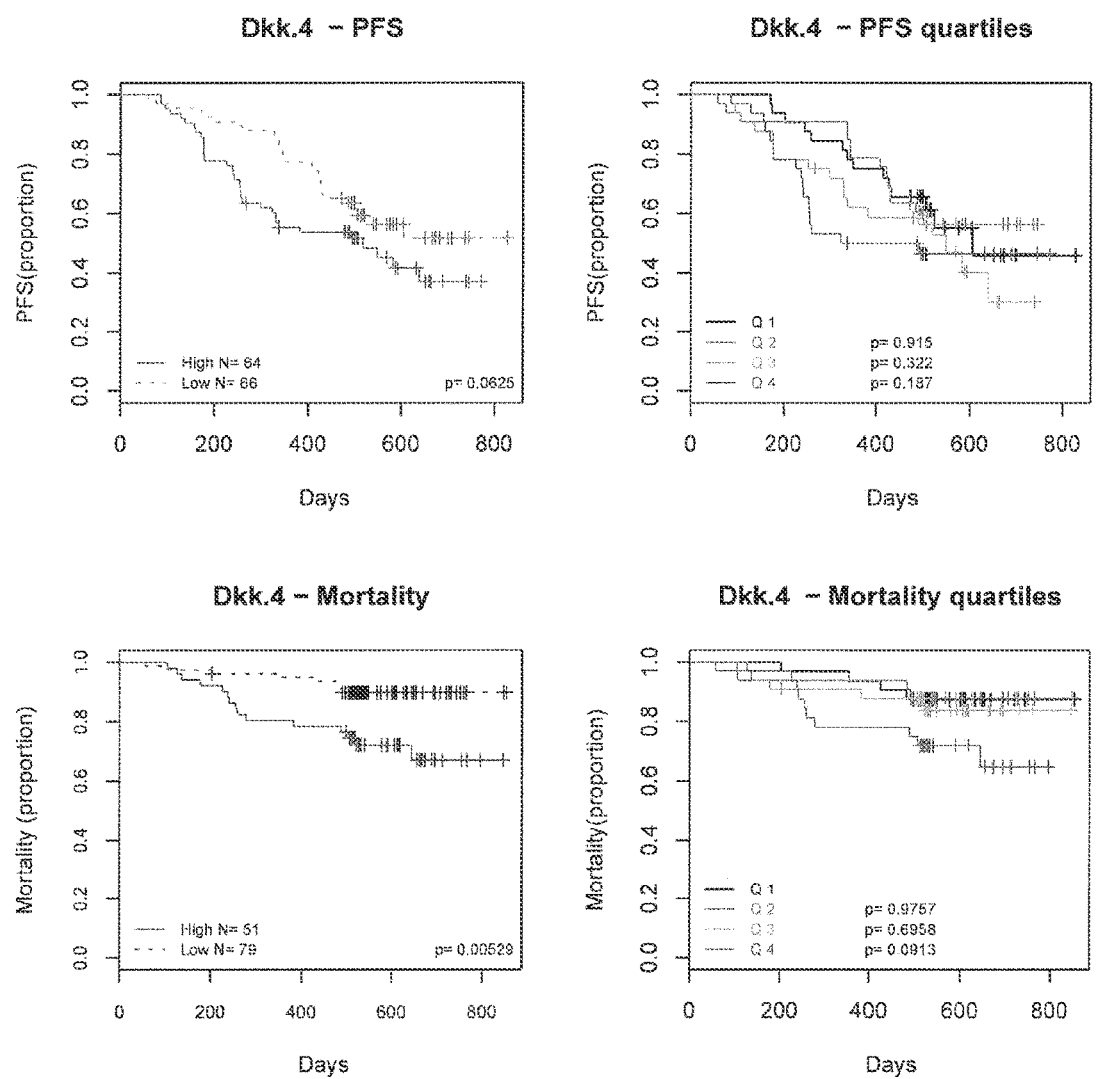
Figure 18:
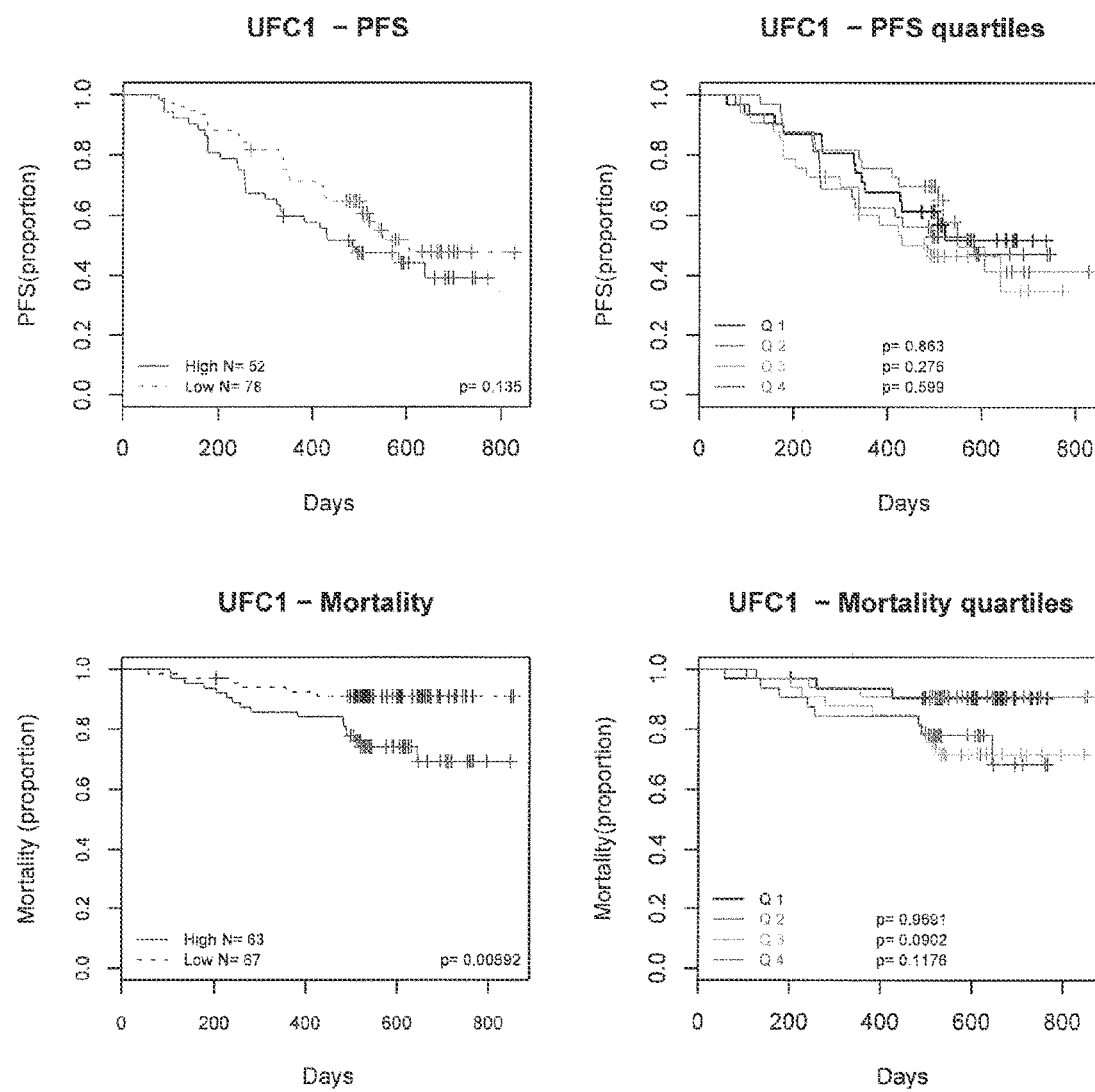
Figure 19:
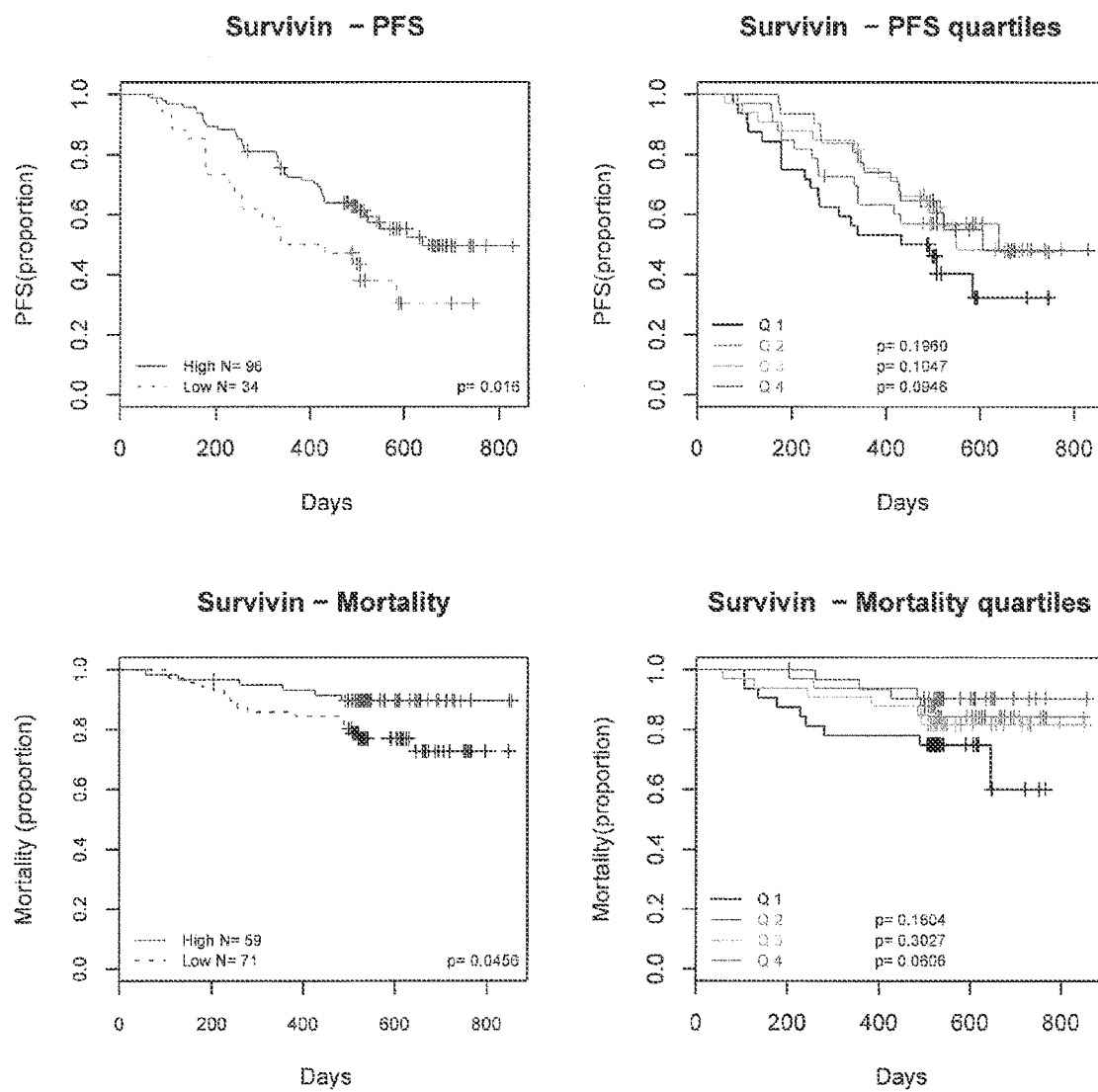
Figure 20:
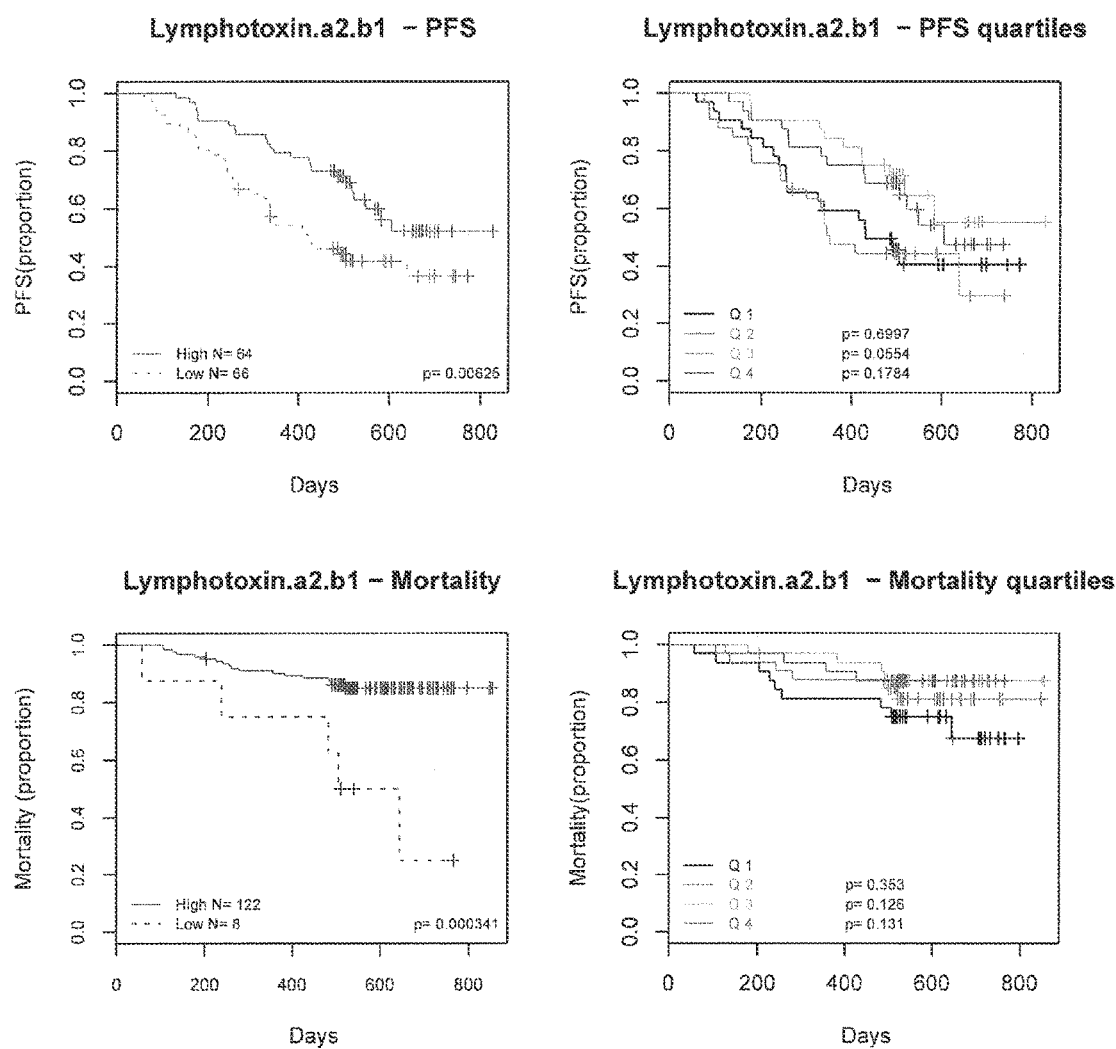
Figure 21:
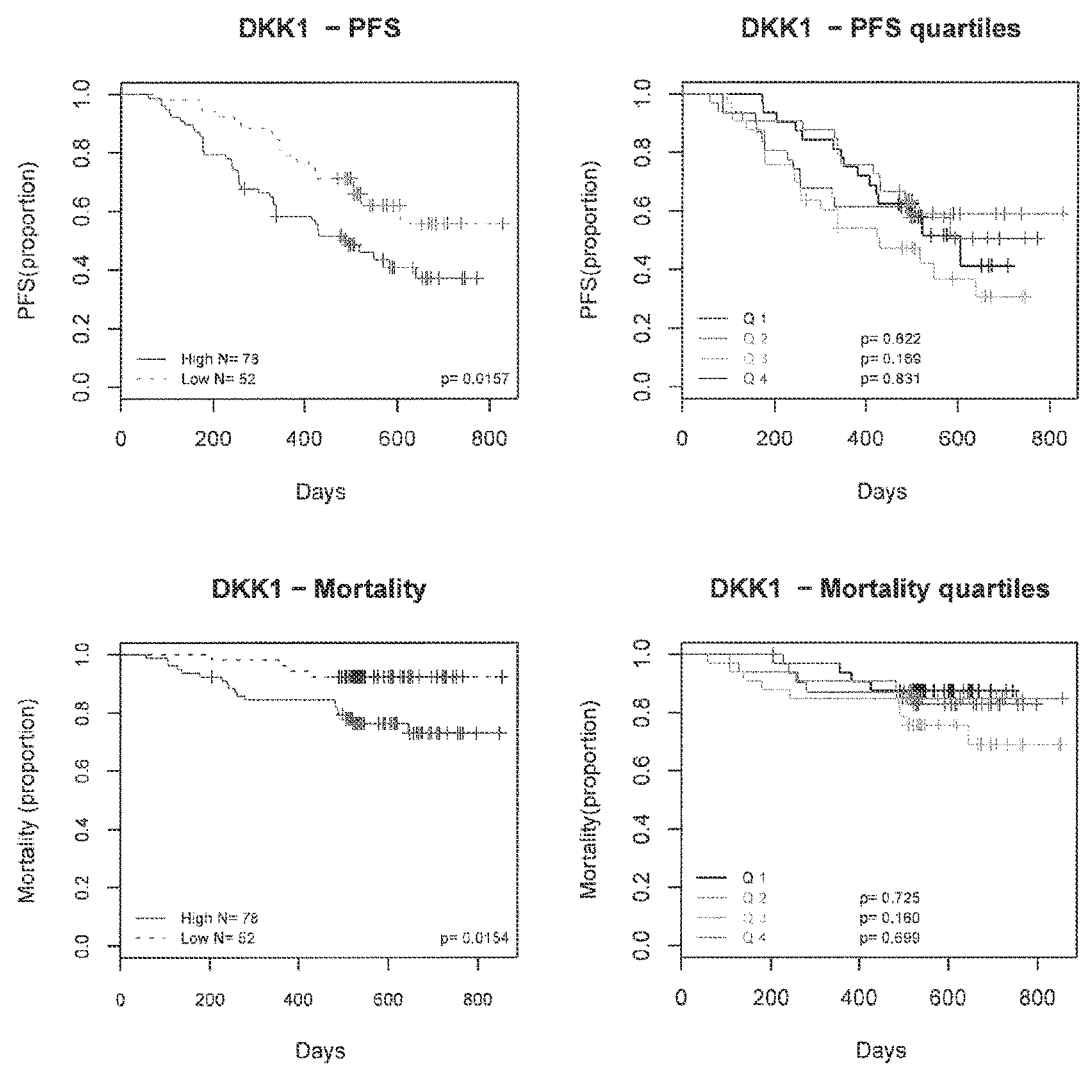
Figure 22:
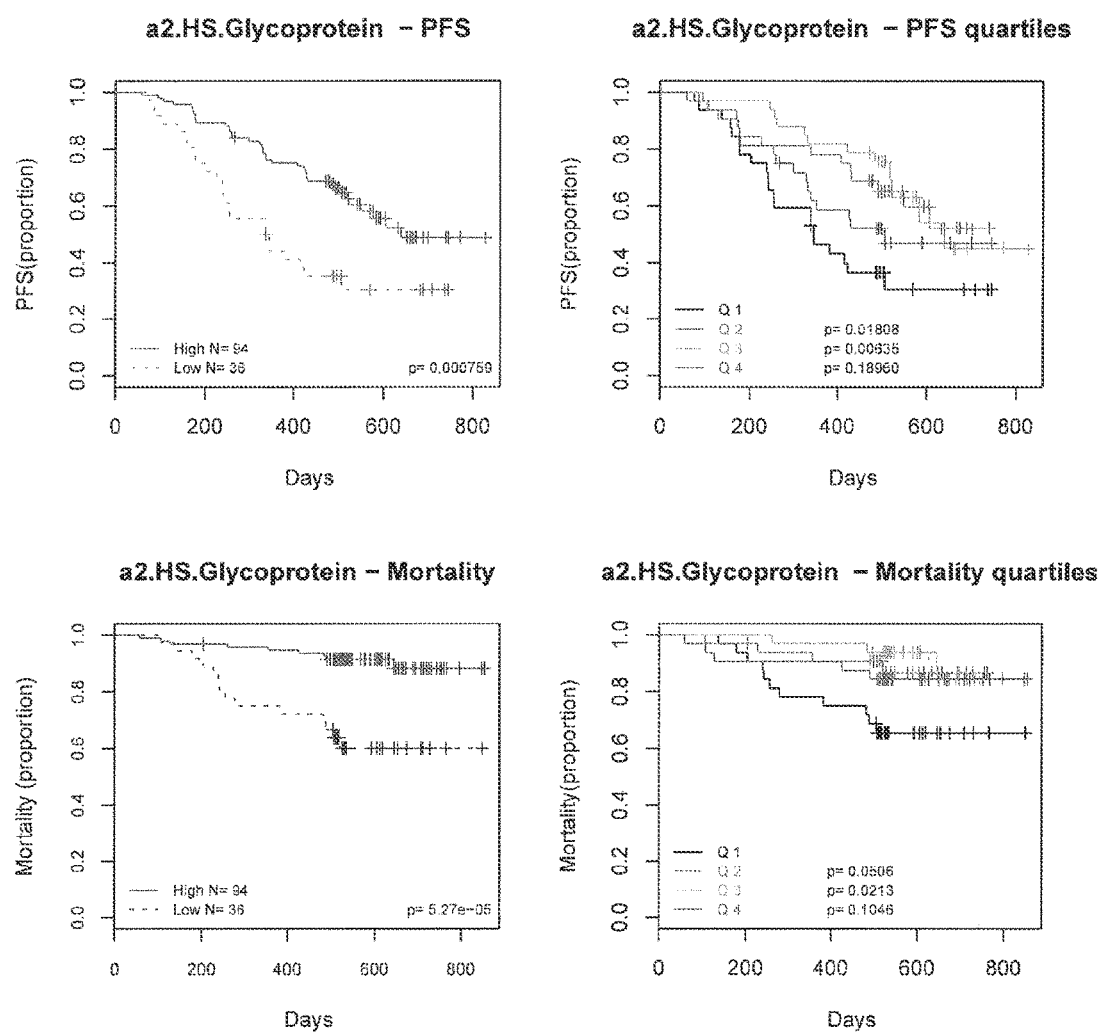
Figure 23:
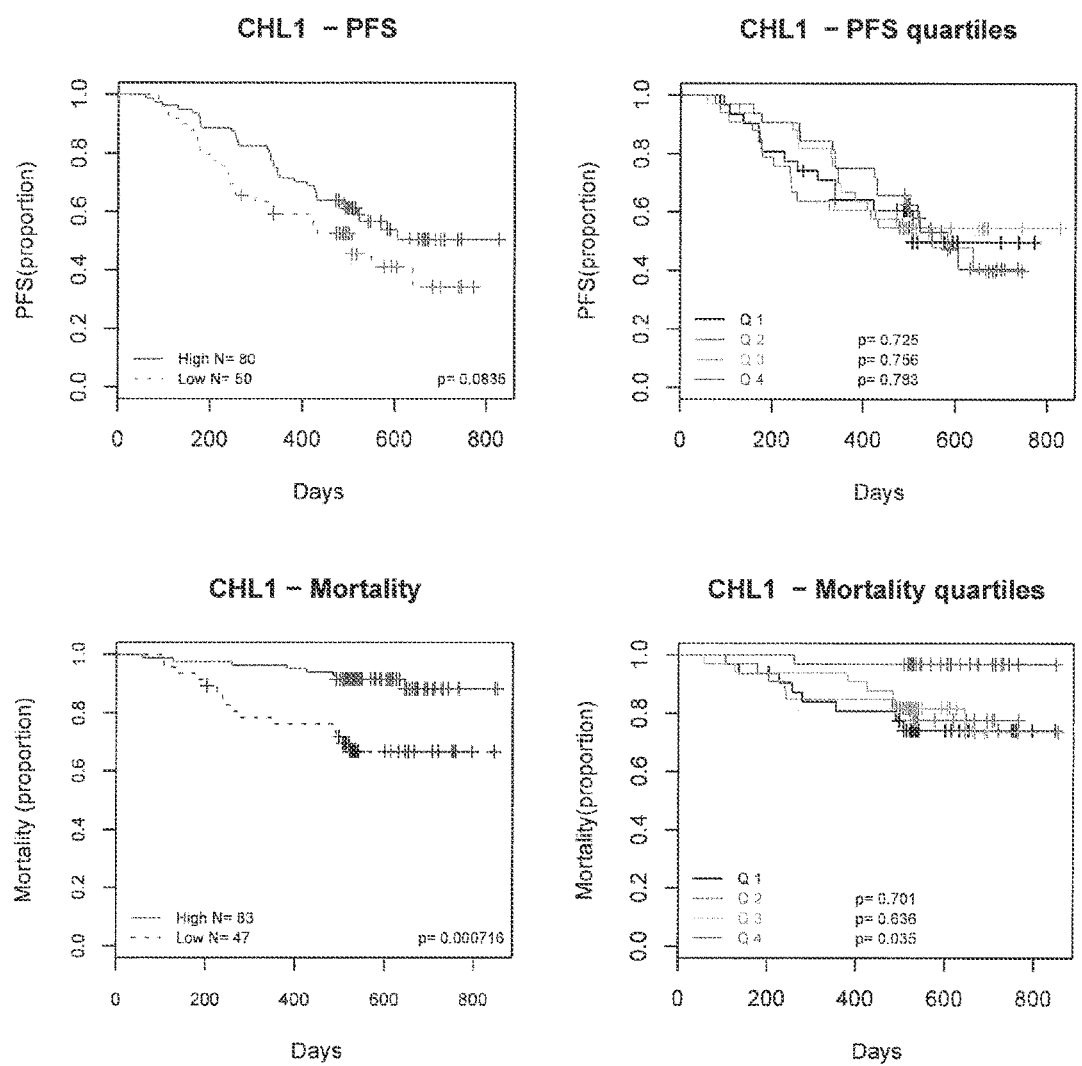
Figure 24:
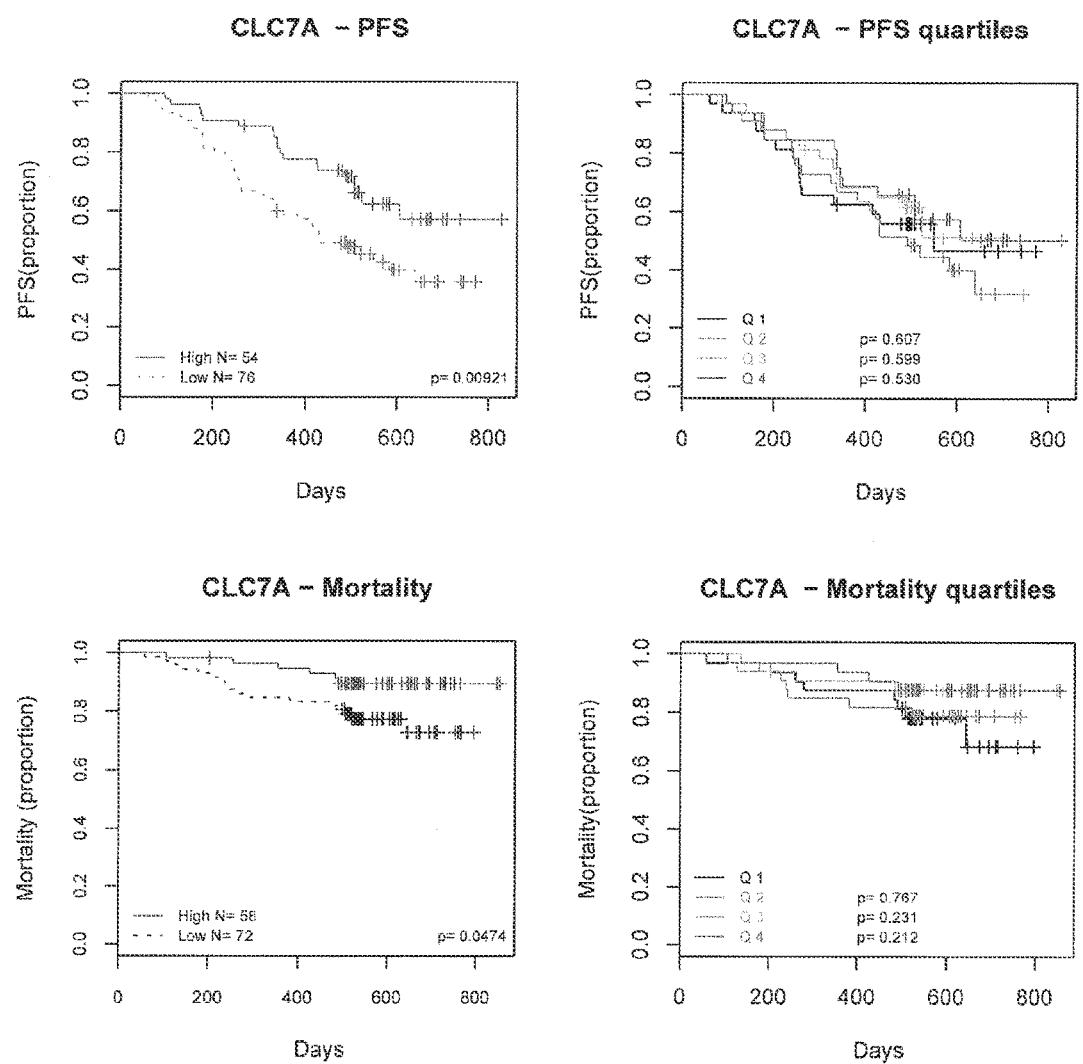
Figure 25:
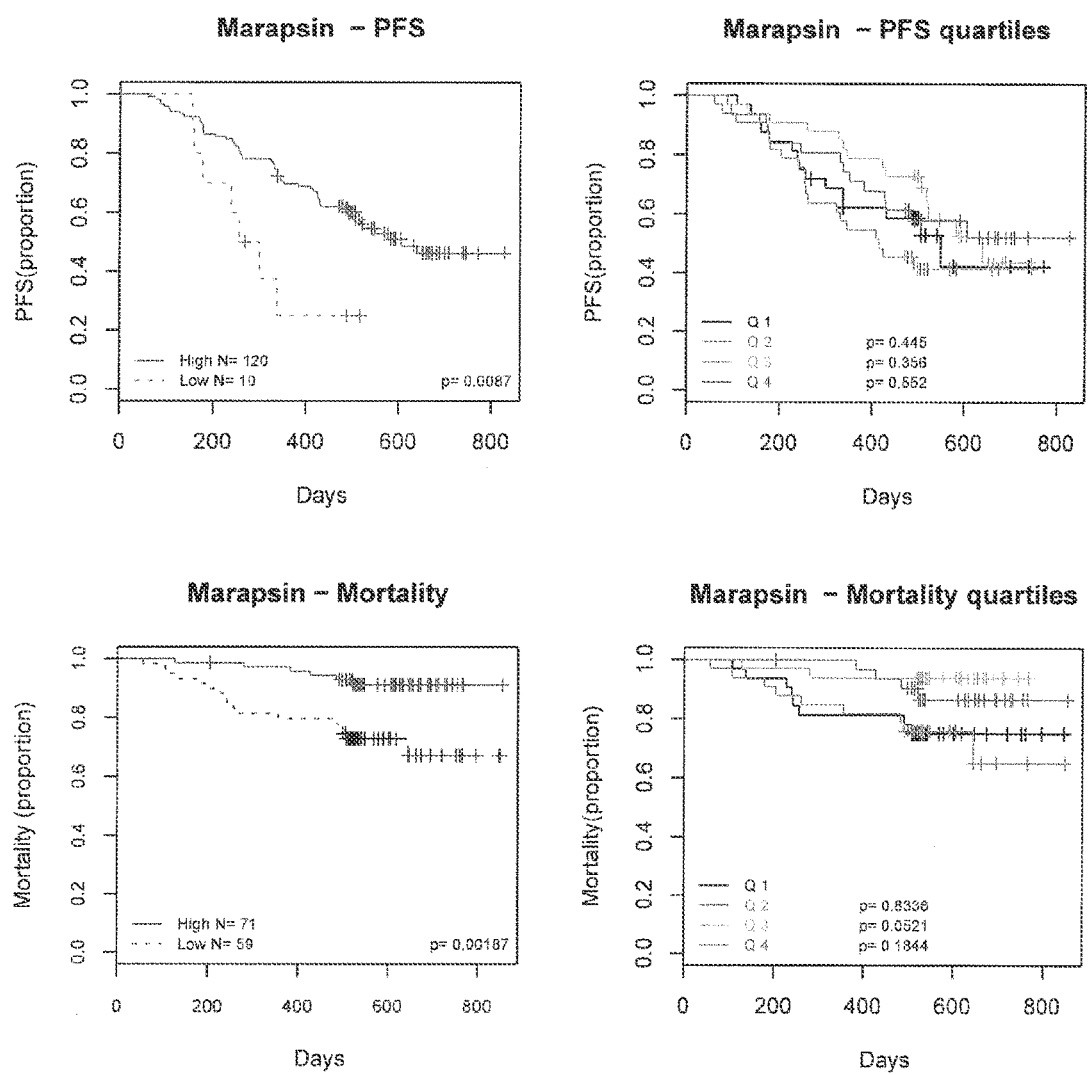
Figure 26:
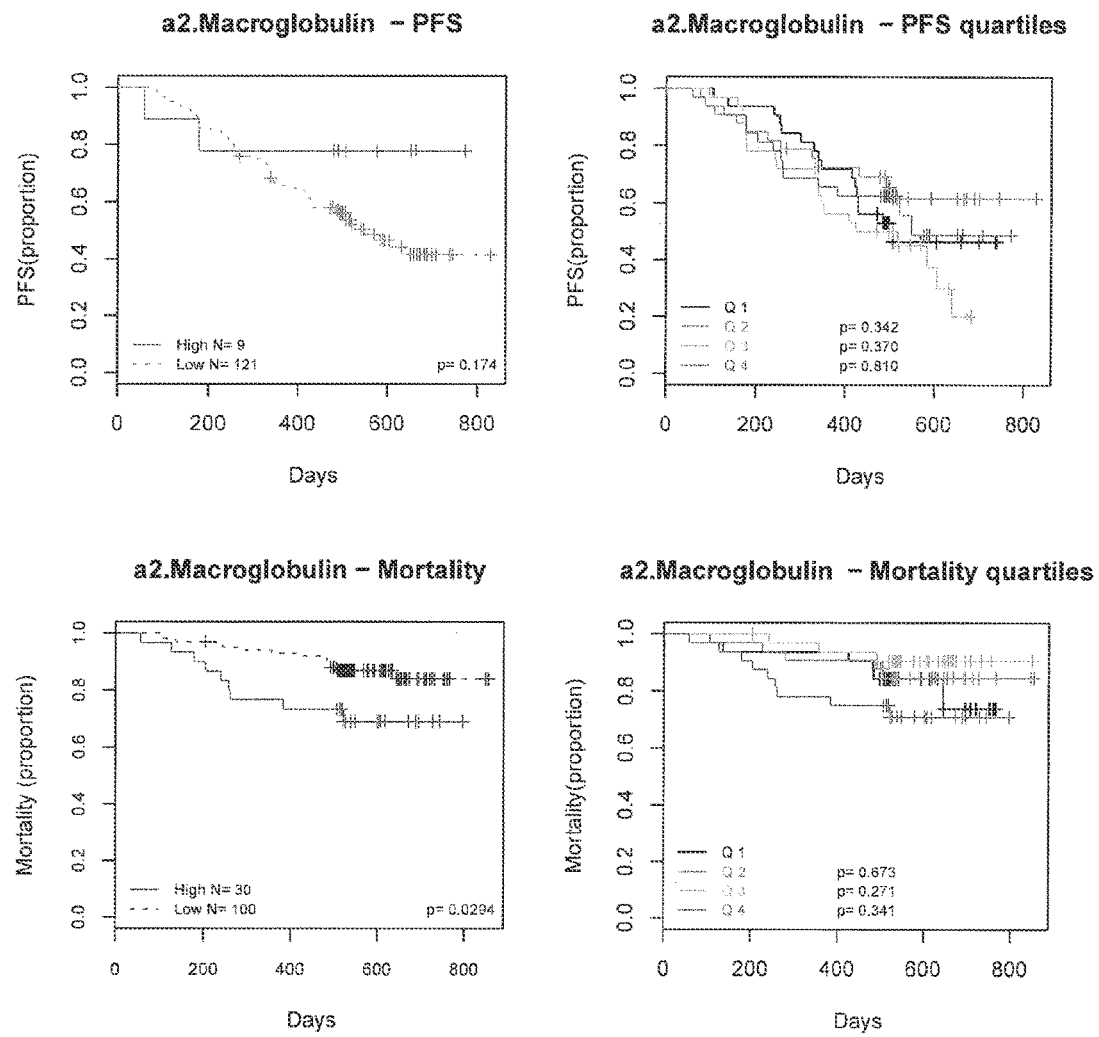
Figure 27:
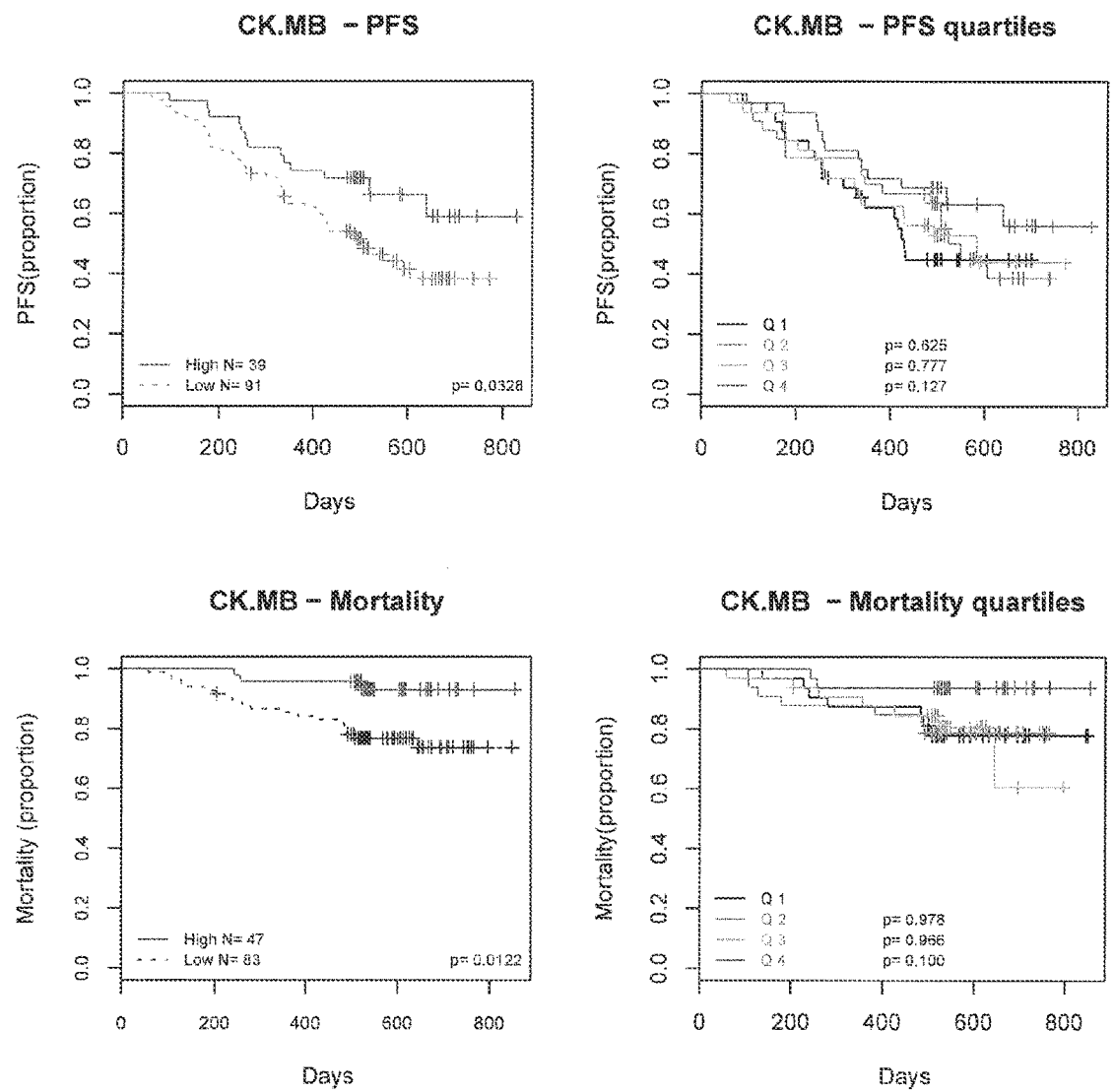
Figure 28:
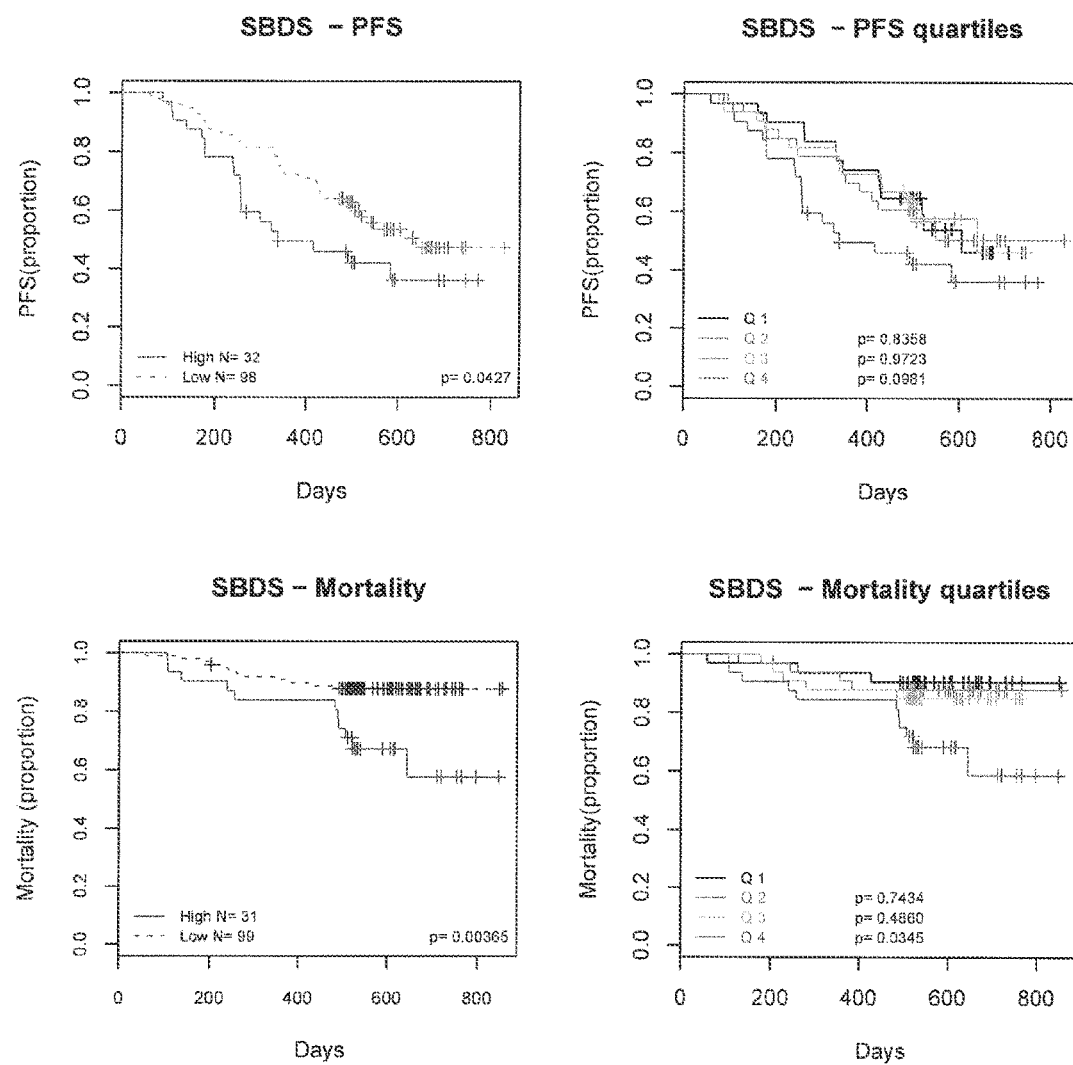
Figure 29:
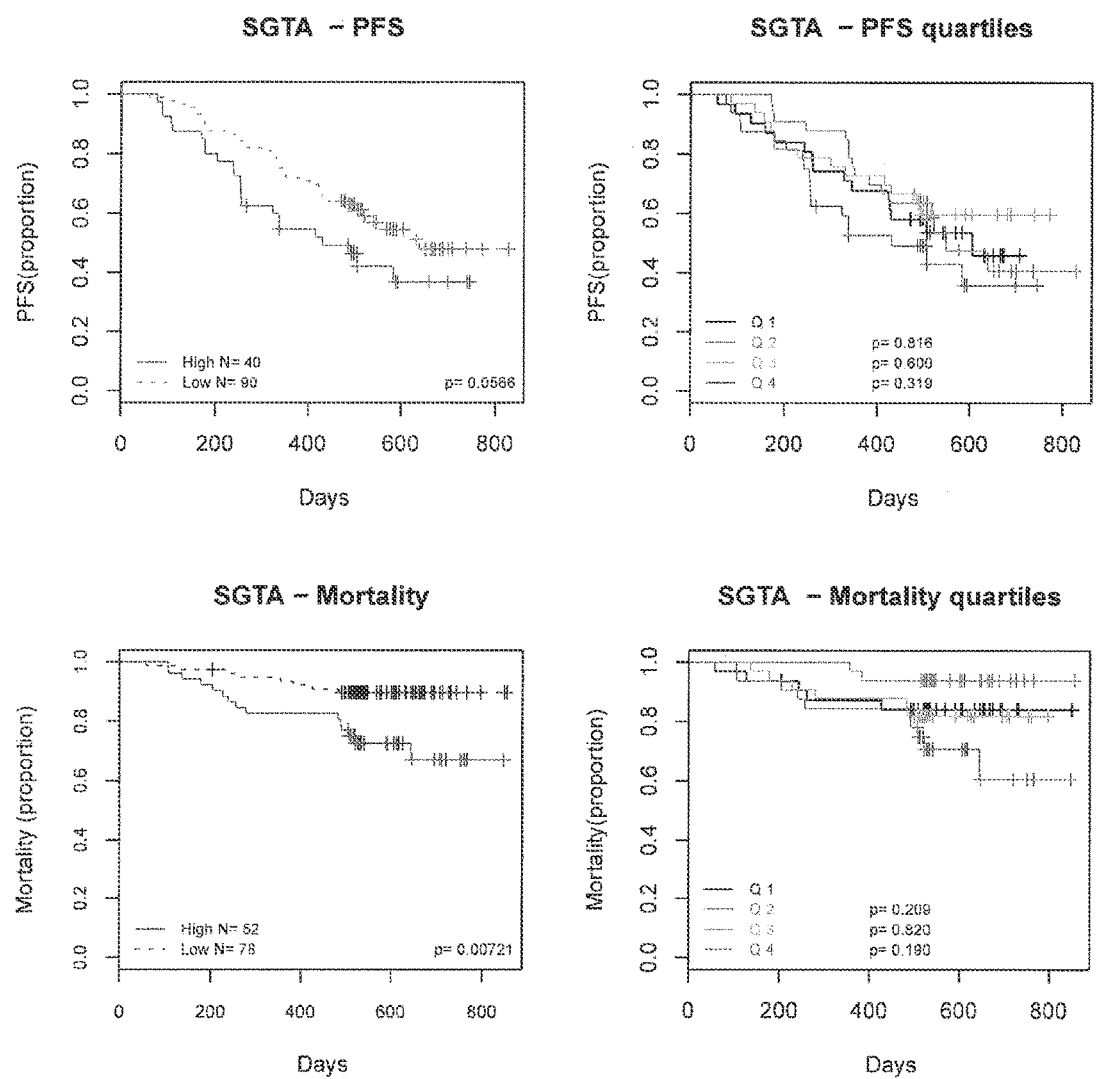
Figure 30:
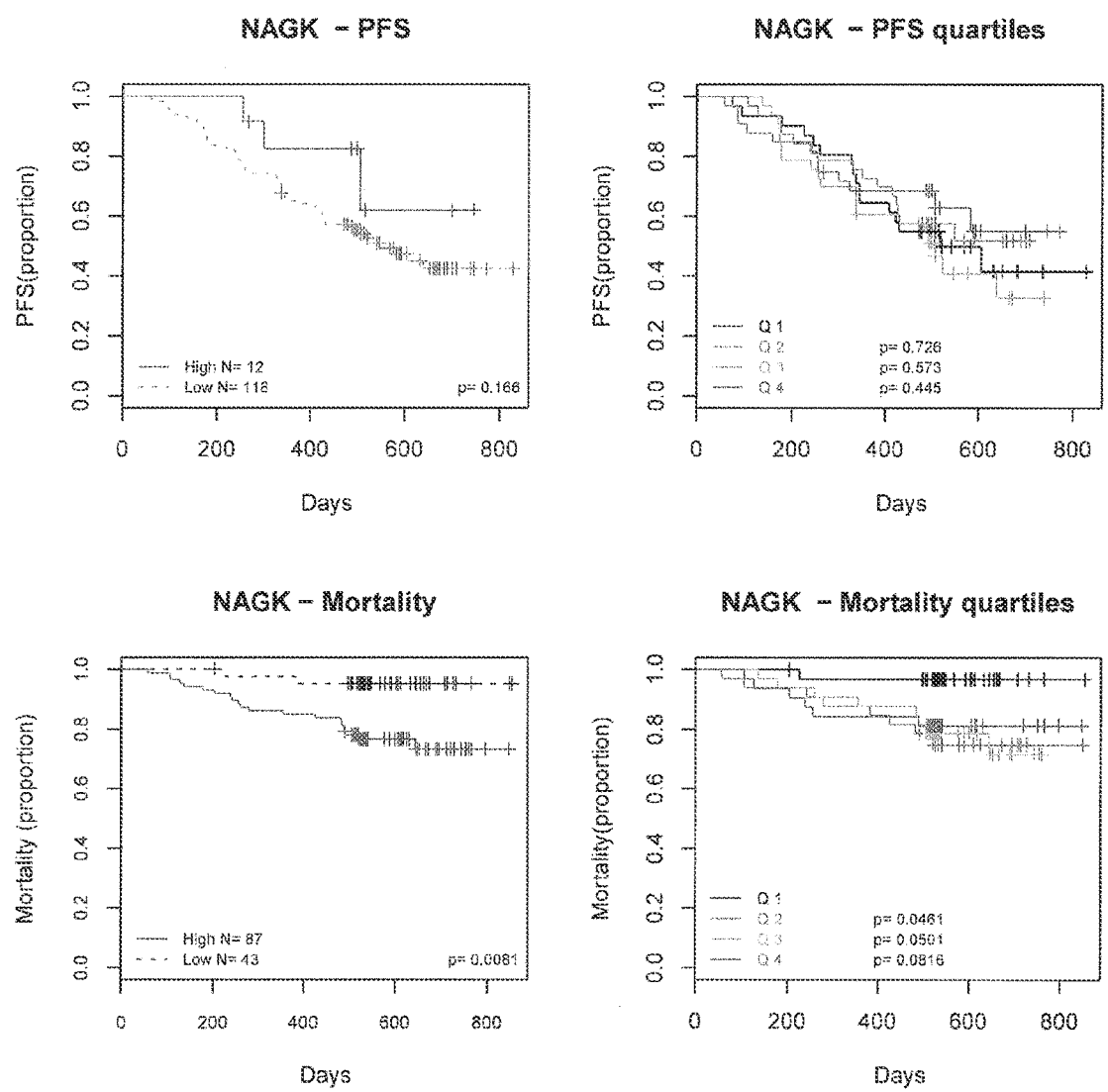
Figure 31:
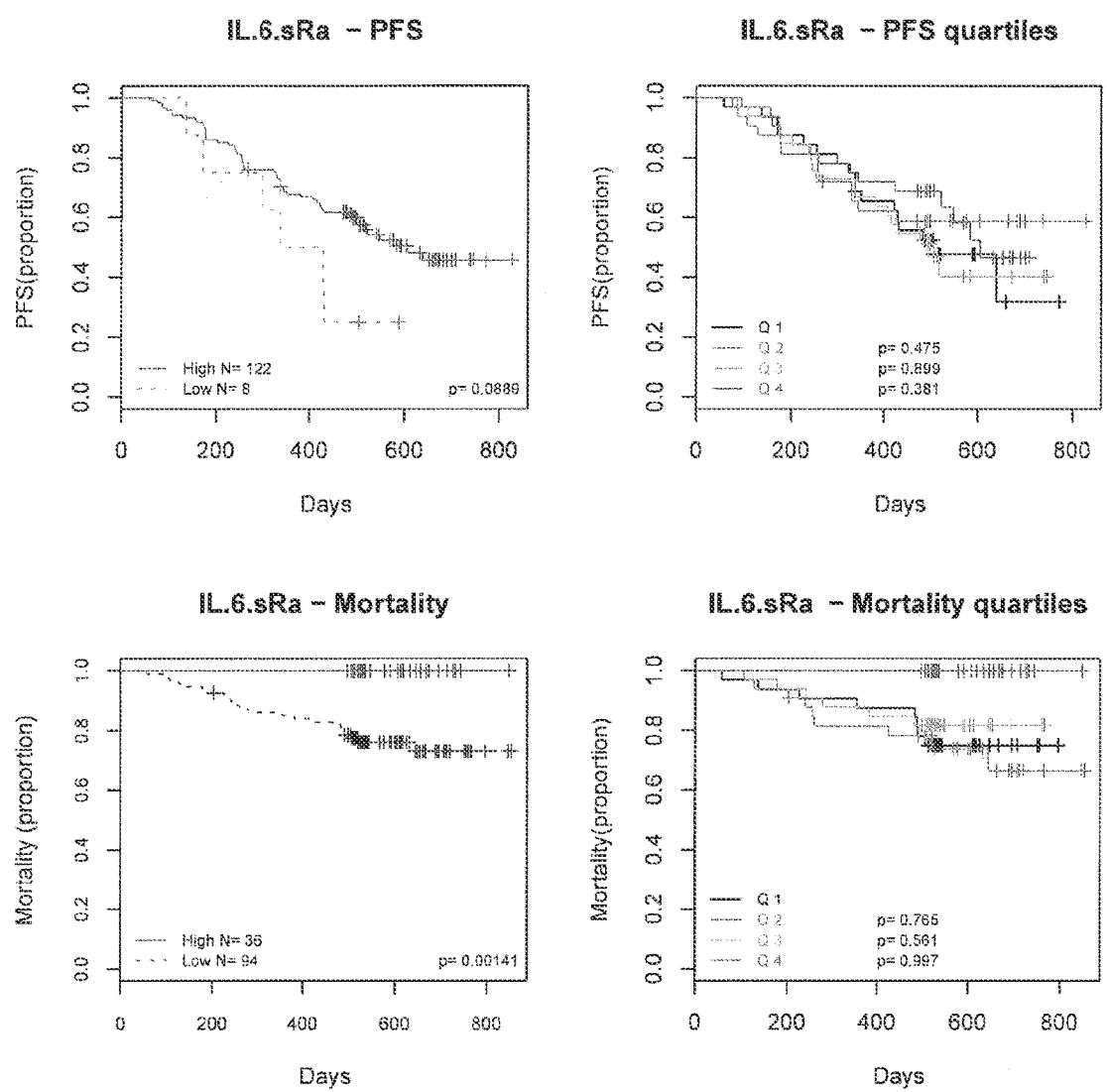
Figure 32:
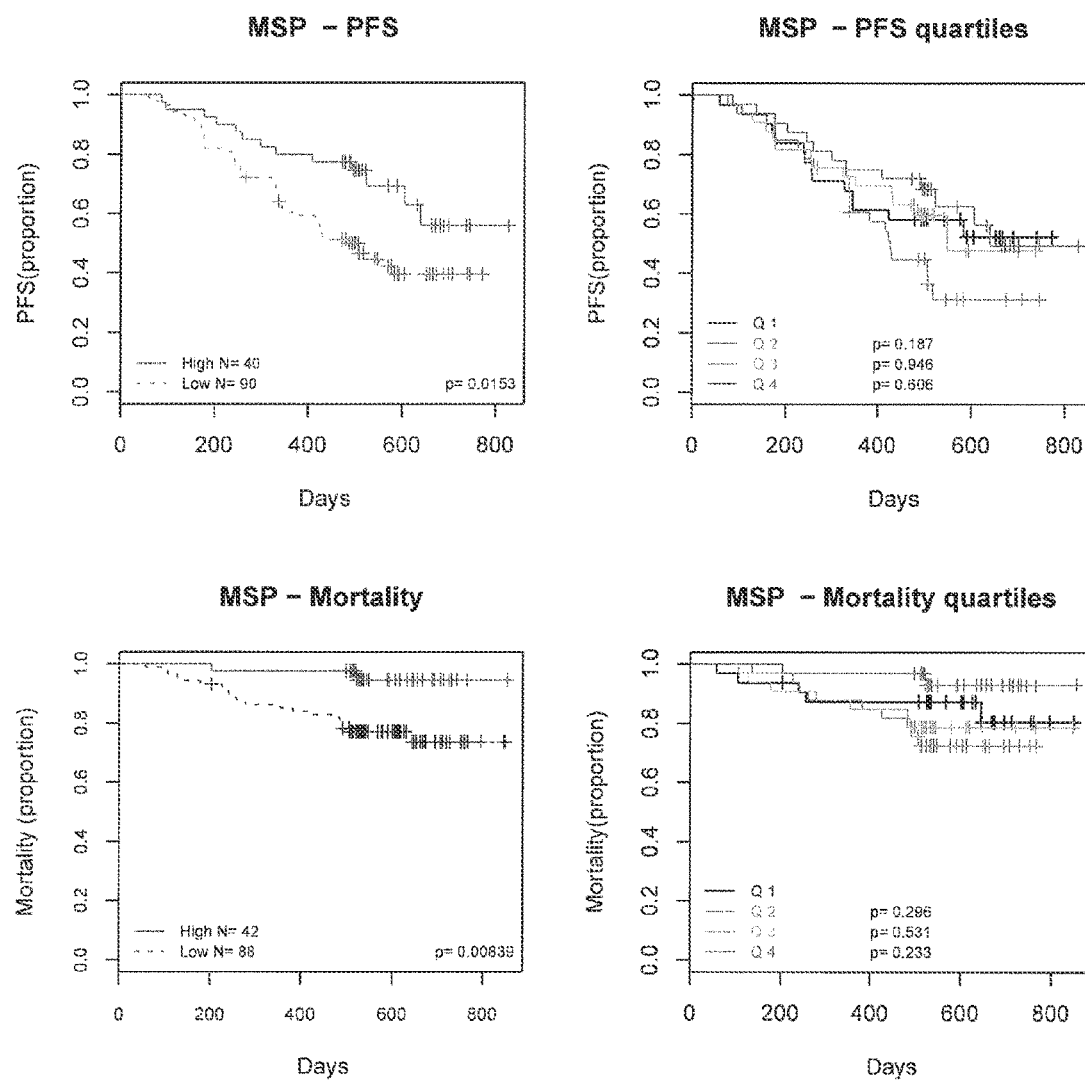
Figure 33:
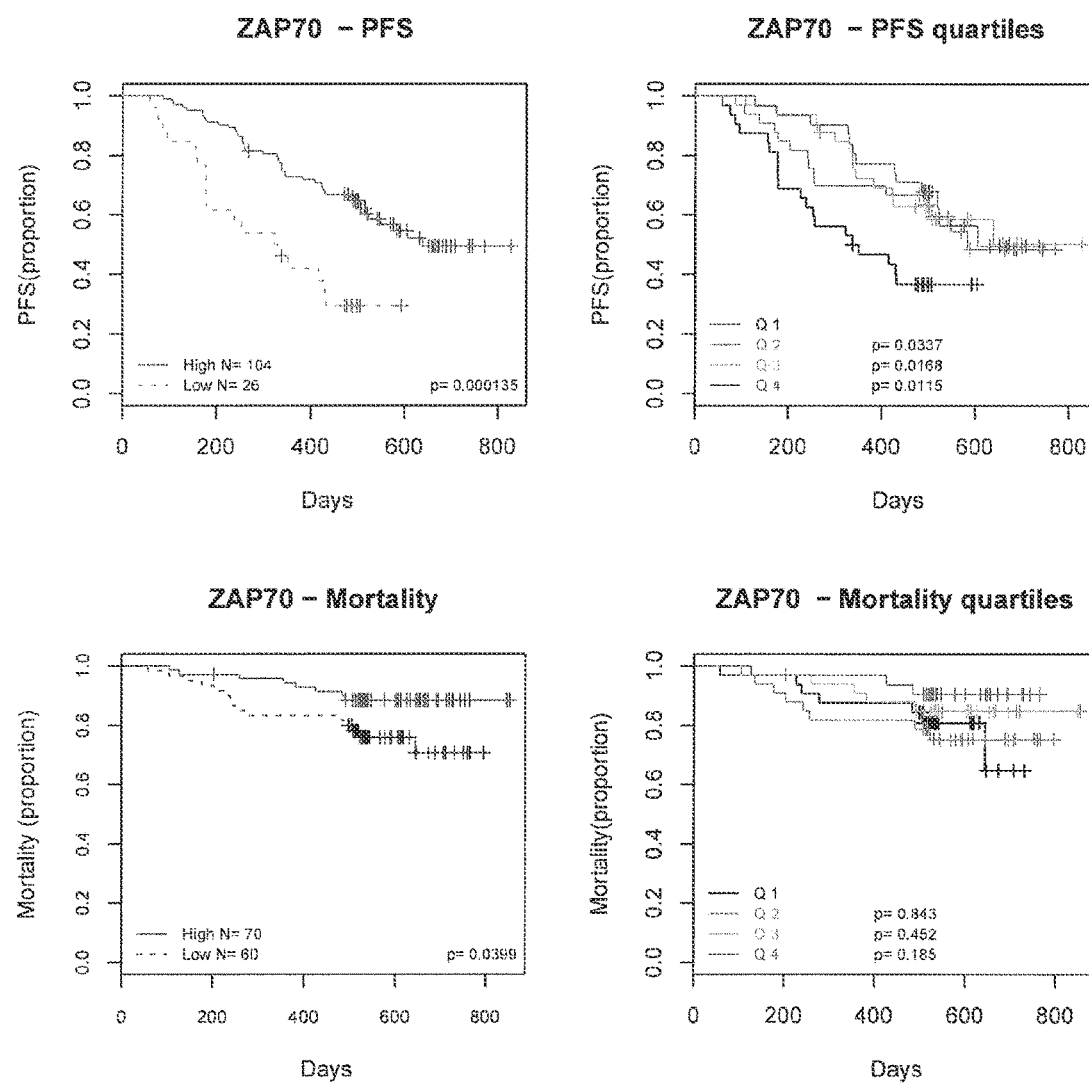
Figure 34:
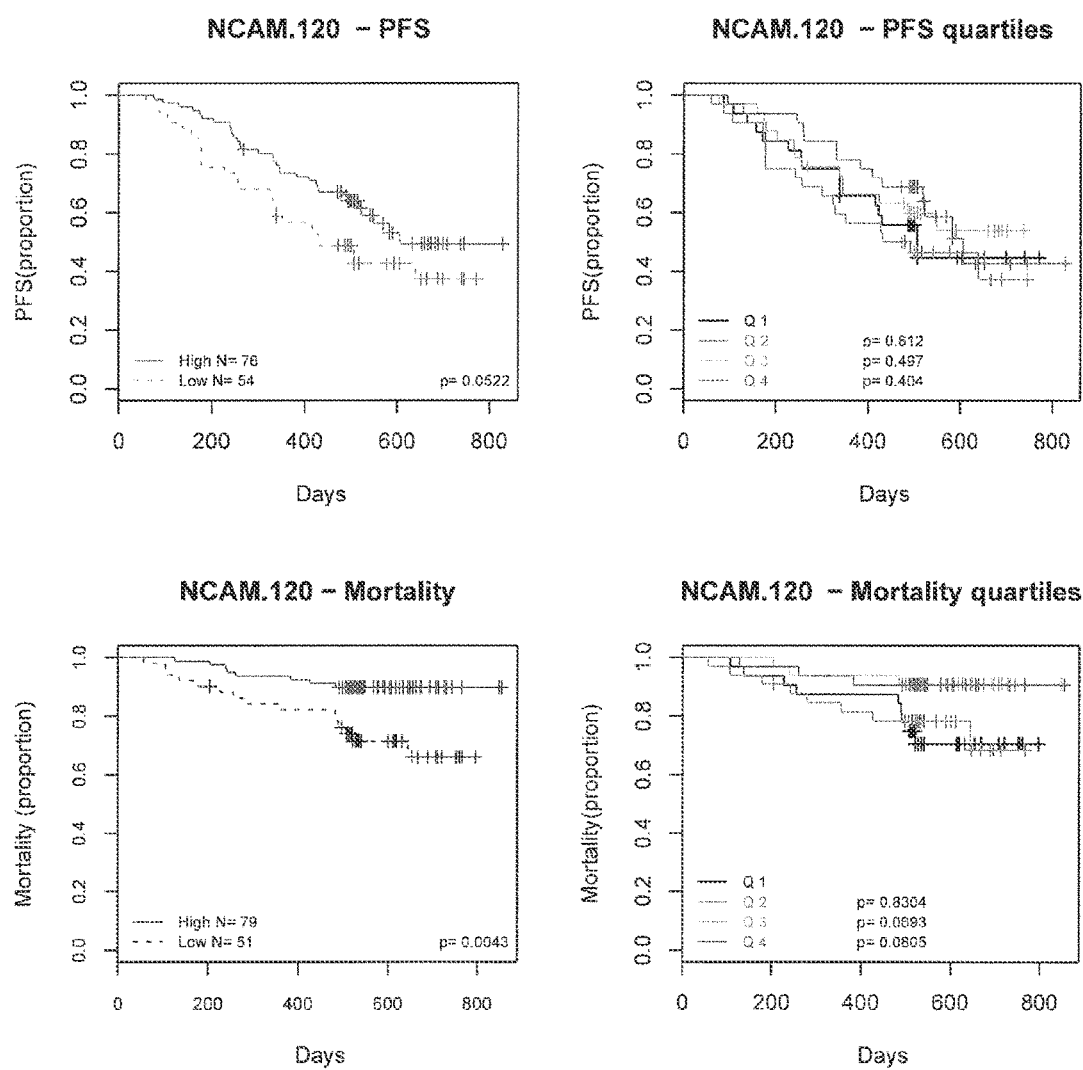
Figure 35:
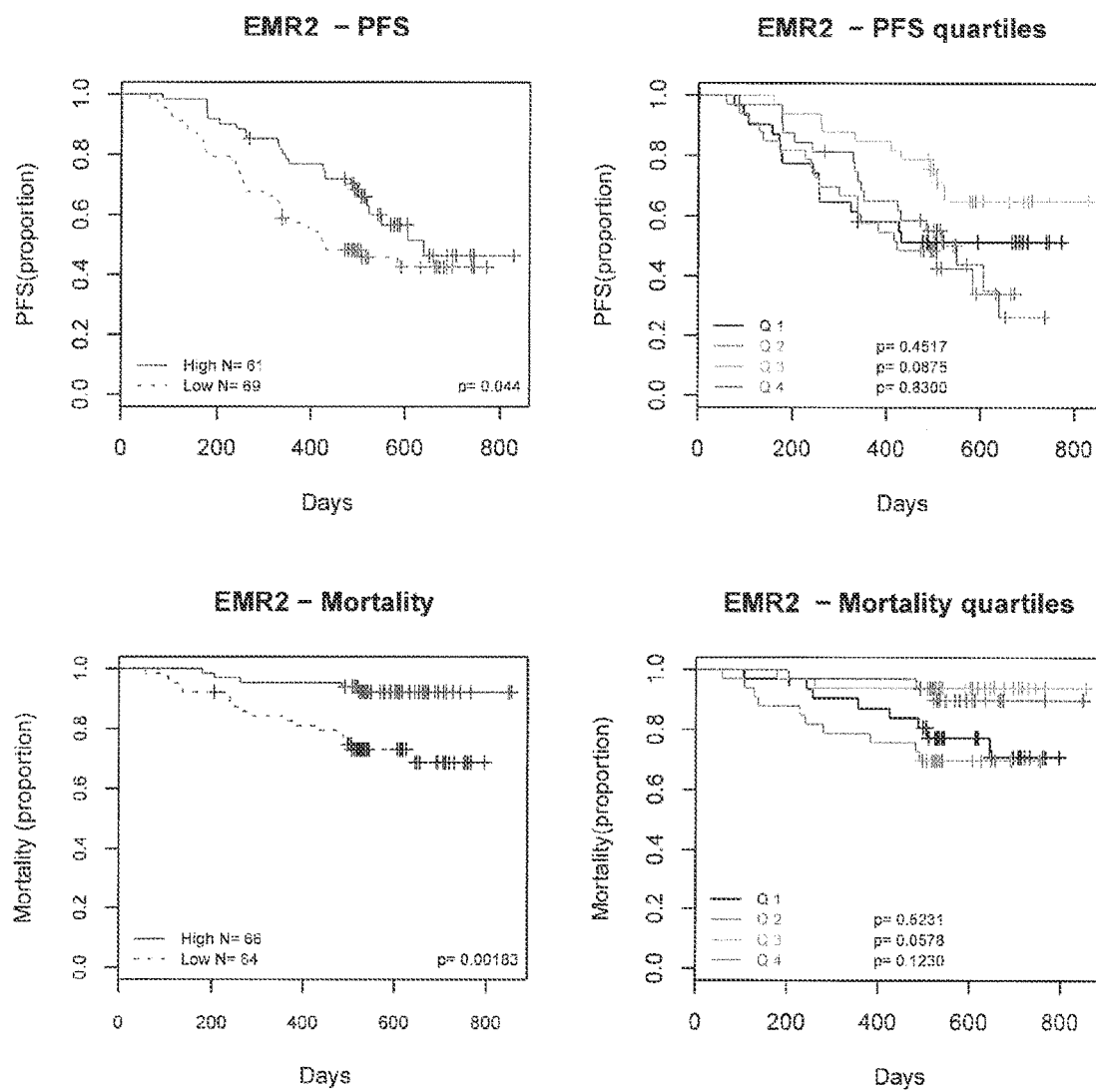
Figure 36:
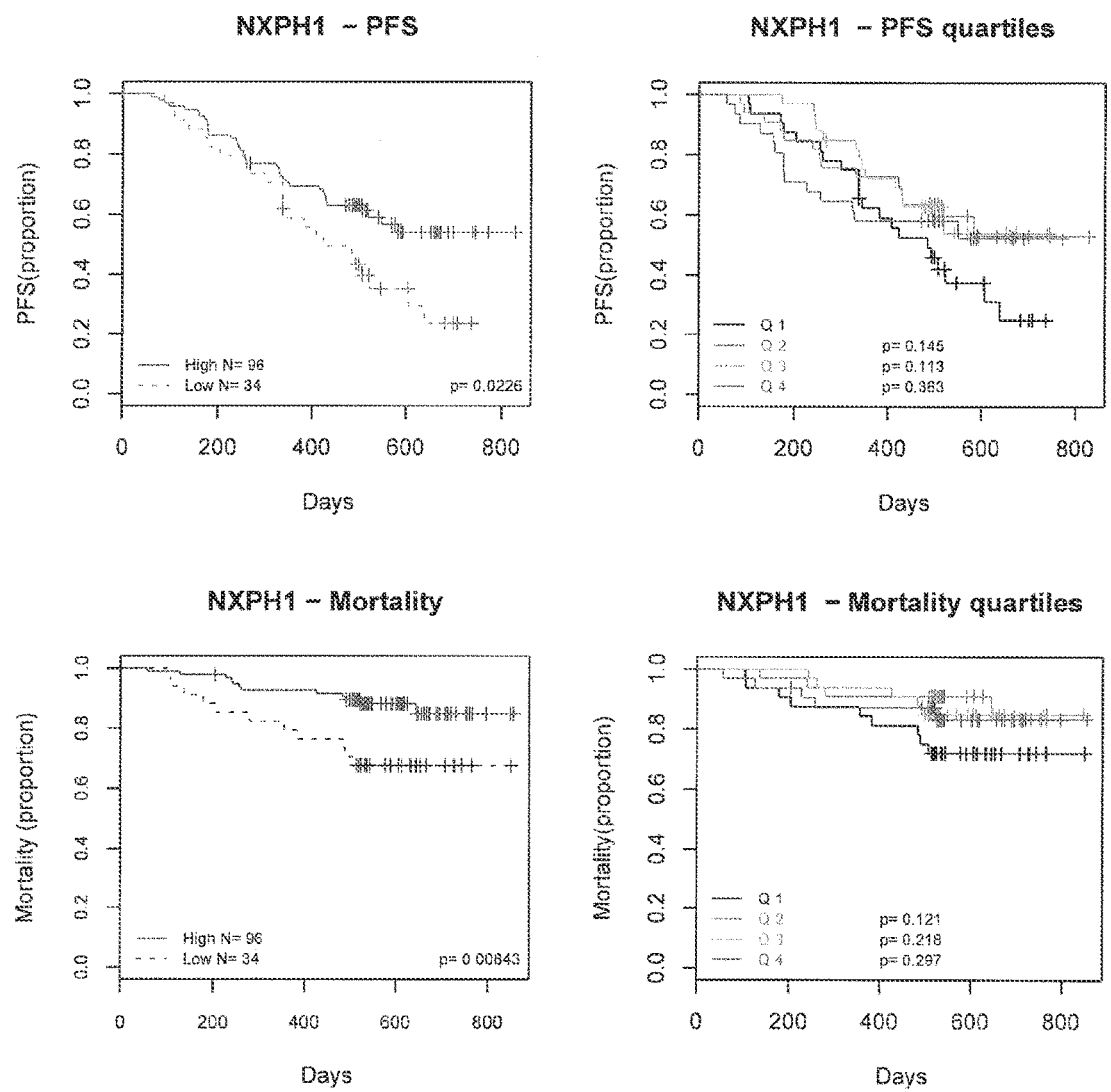
Figure 37:
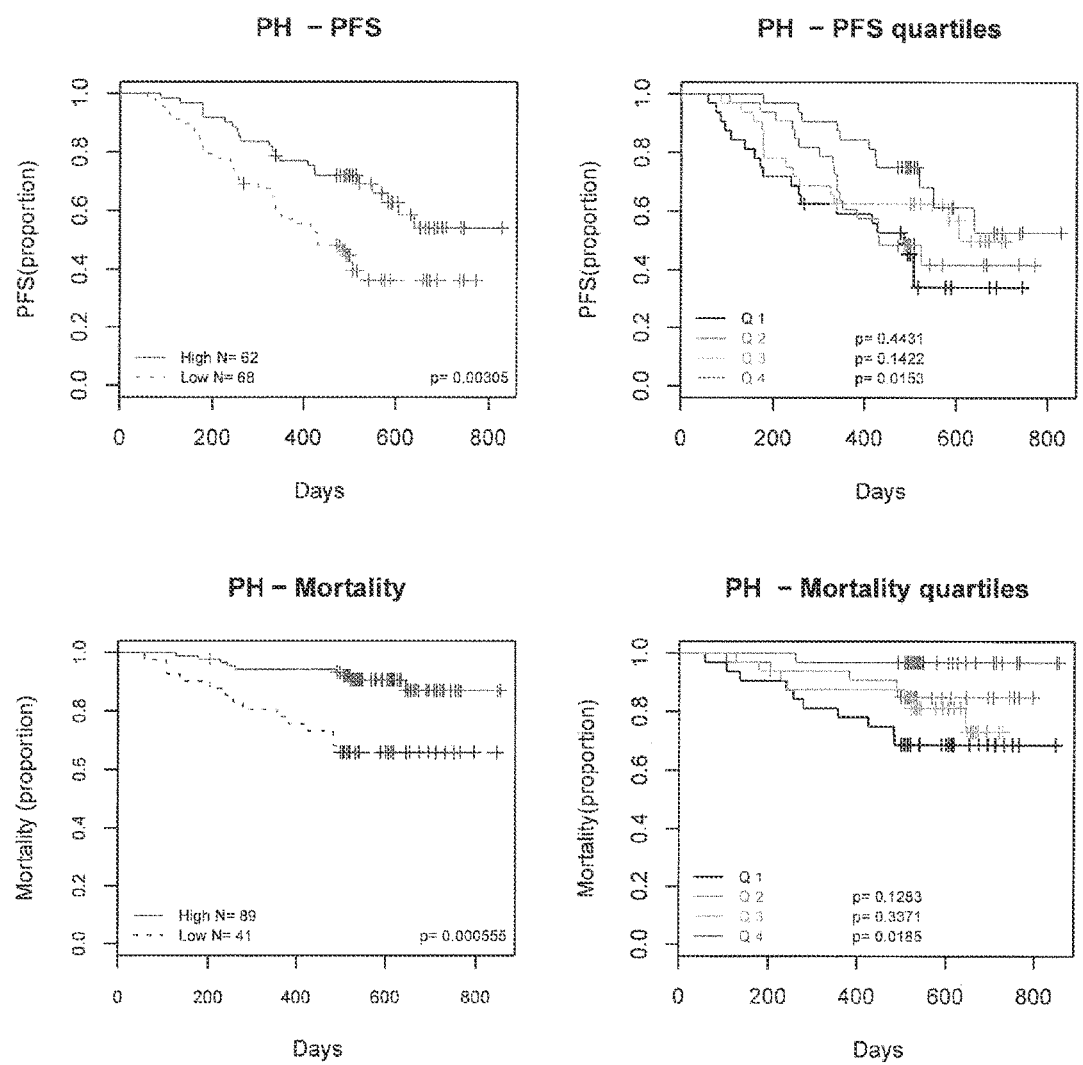
Figure 38:
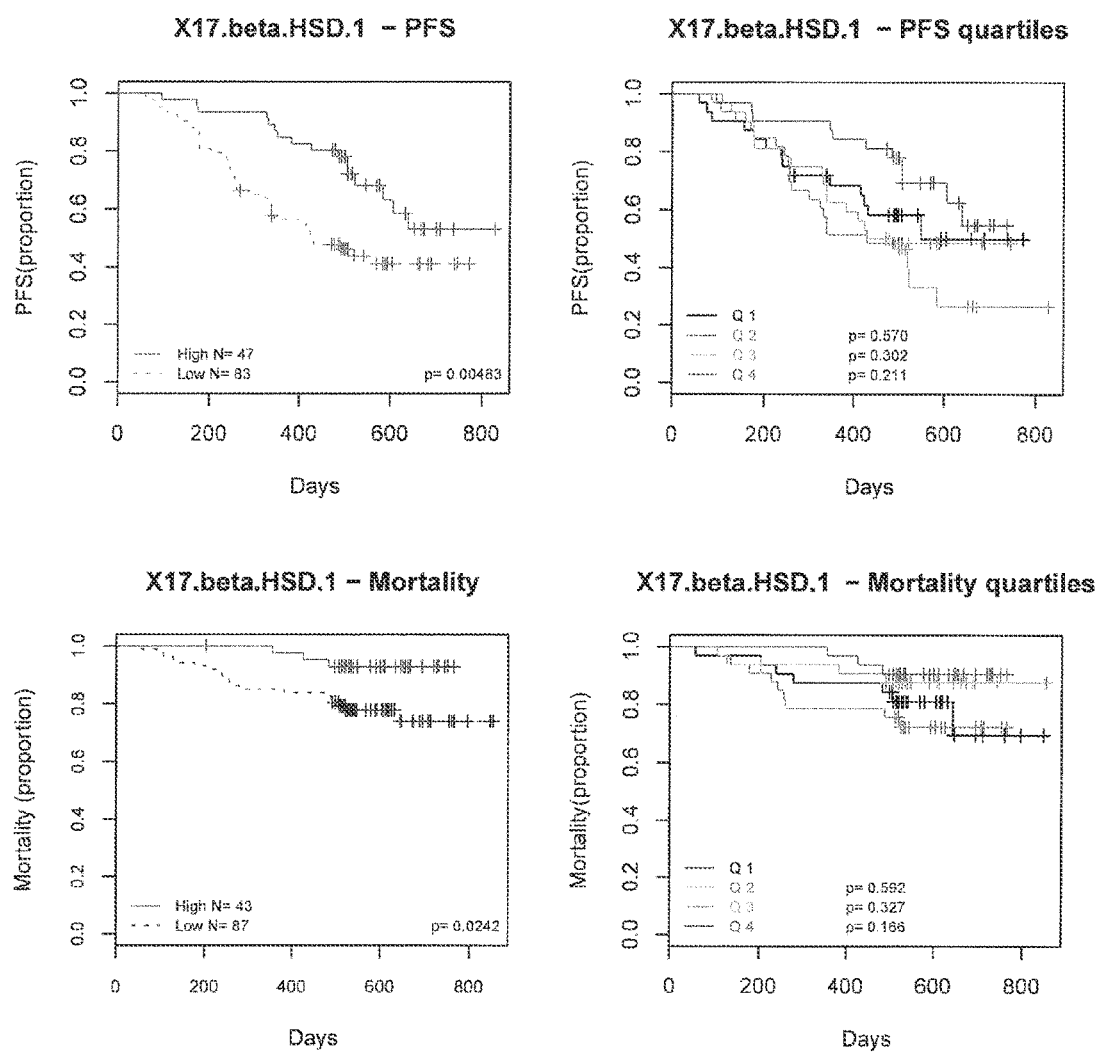
Figure 39:
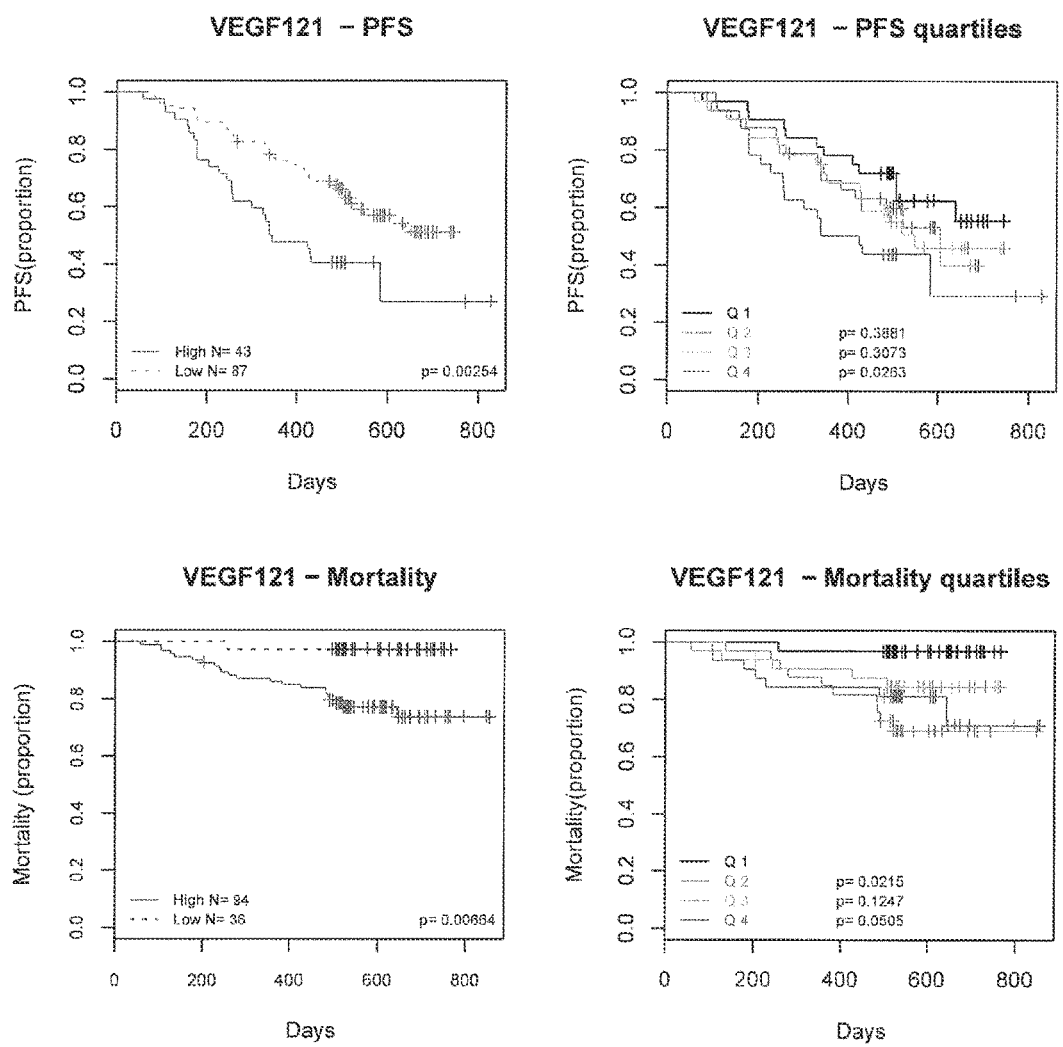
Figure 40:
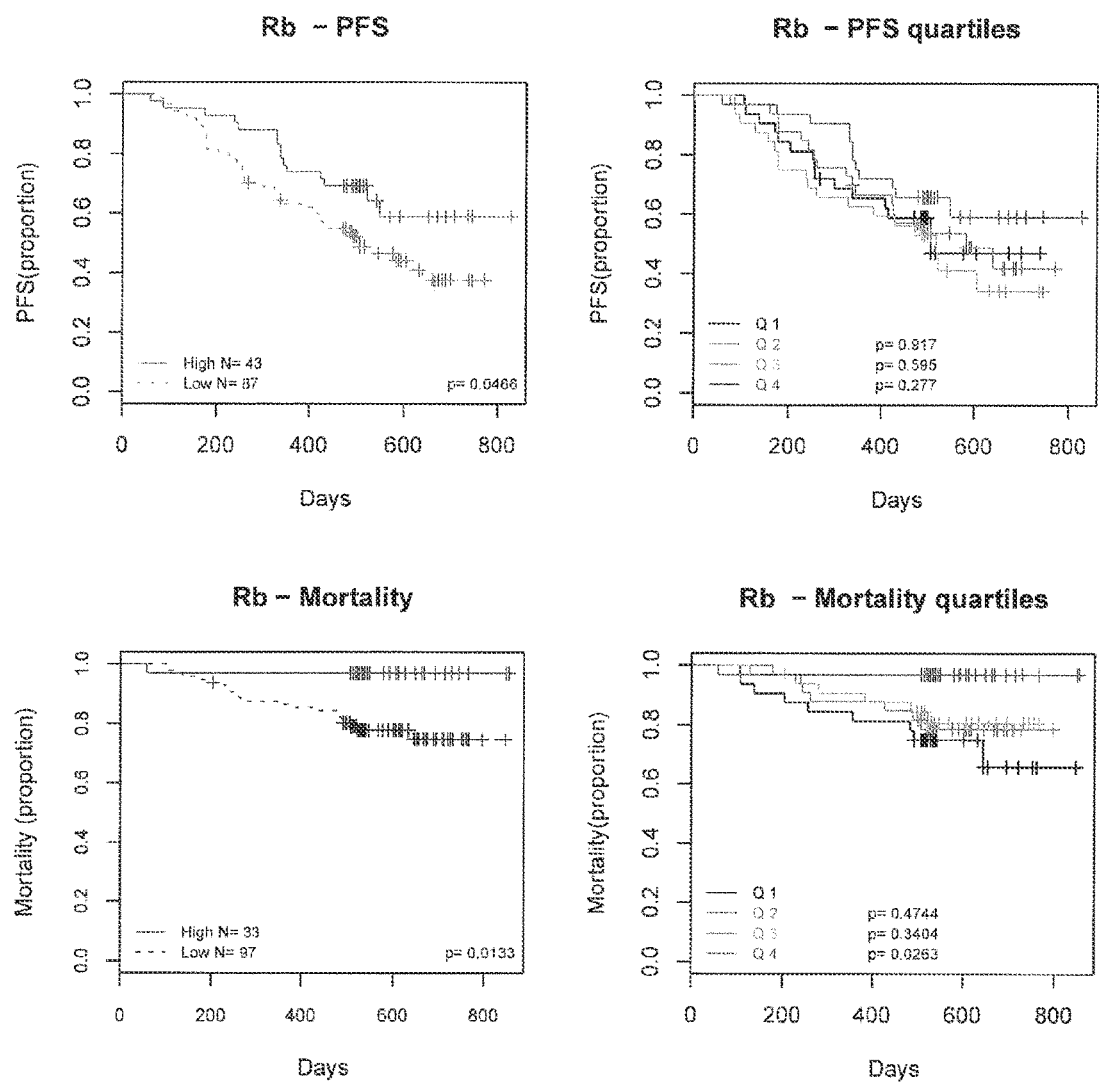
Figure 41:
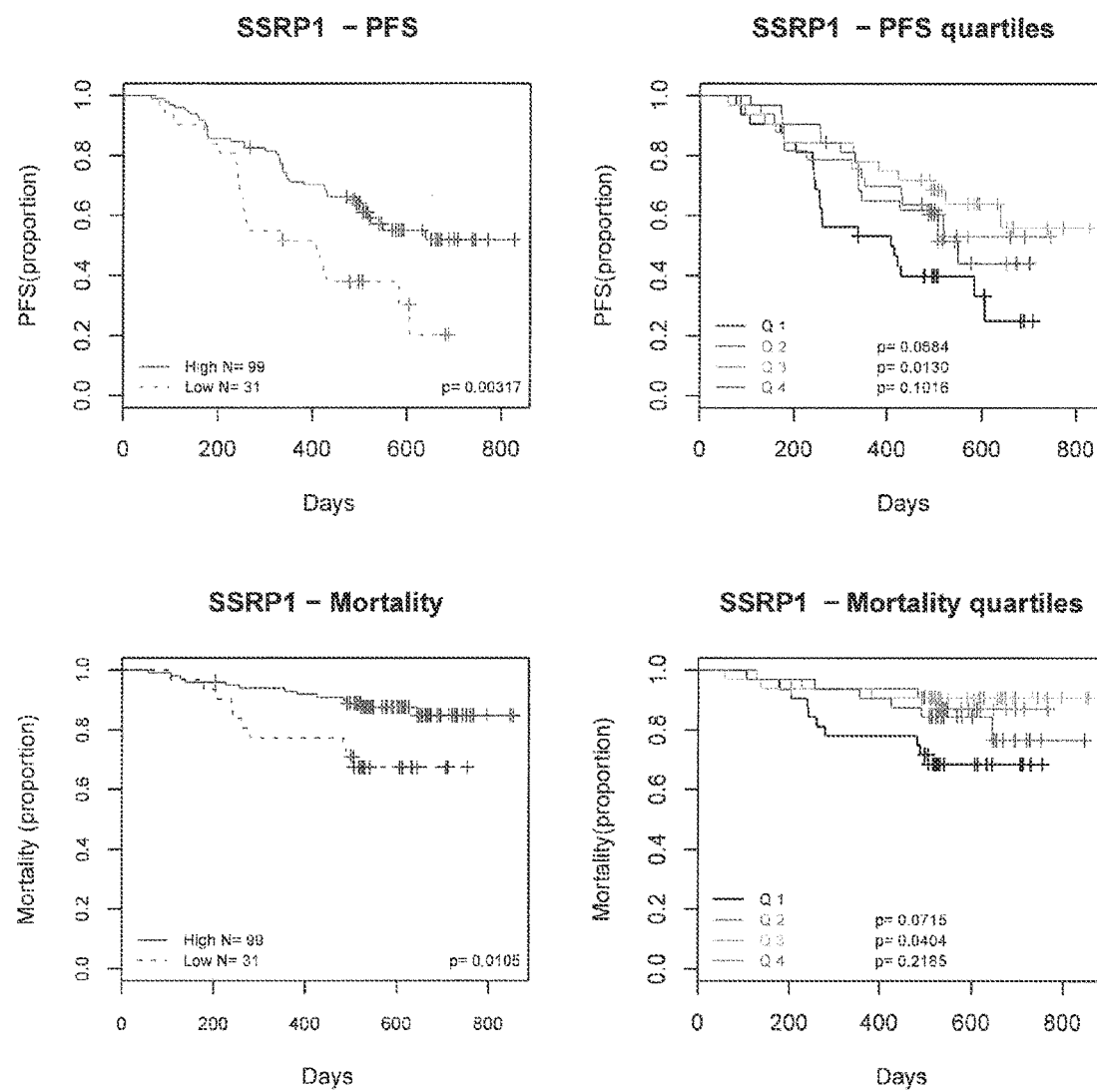
Figure 42:
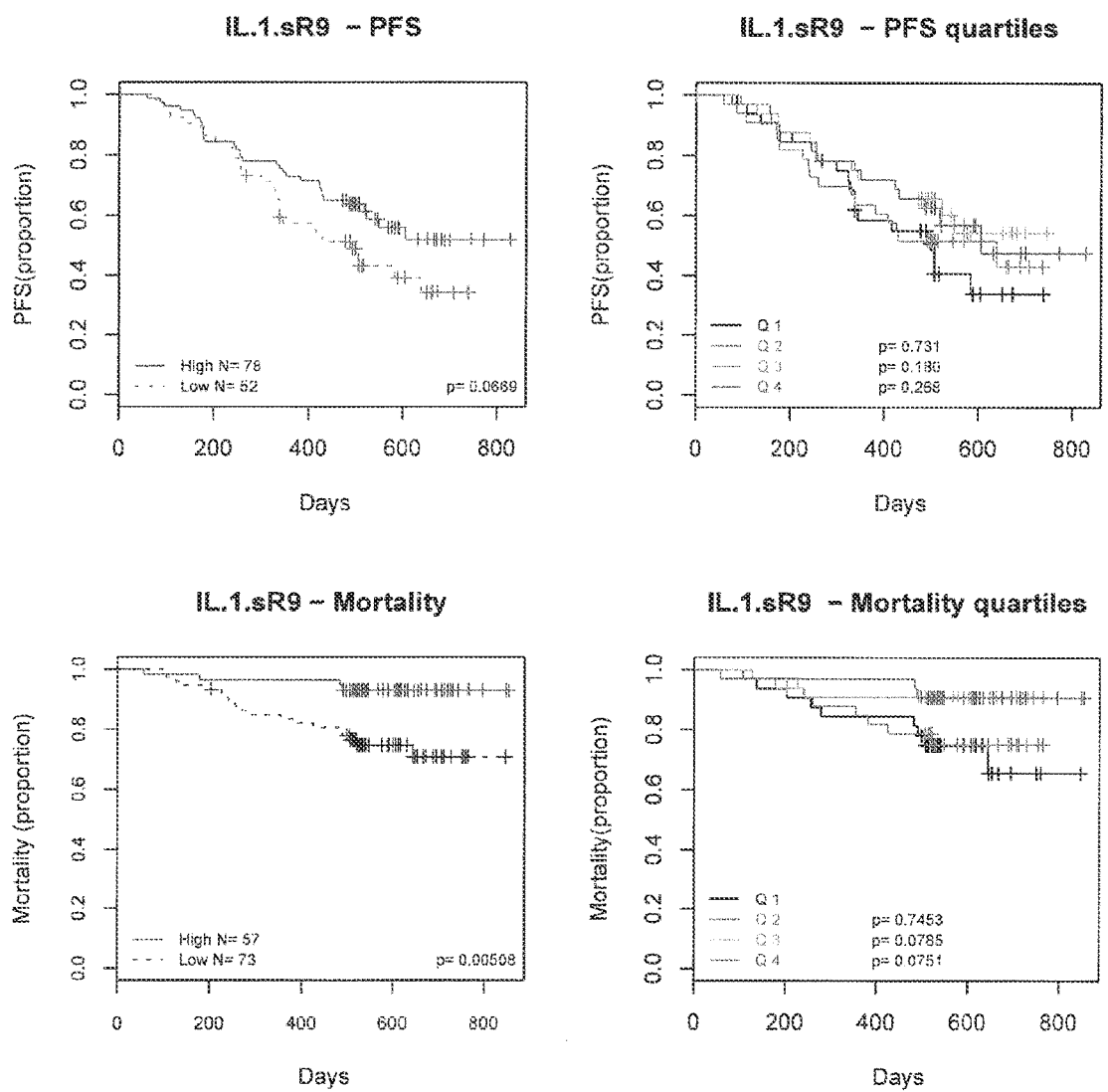
Figure 43:
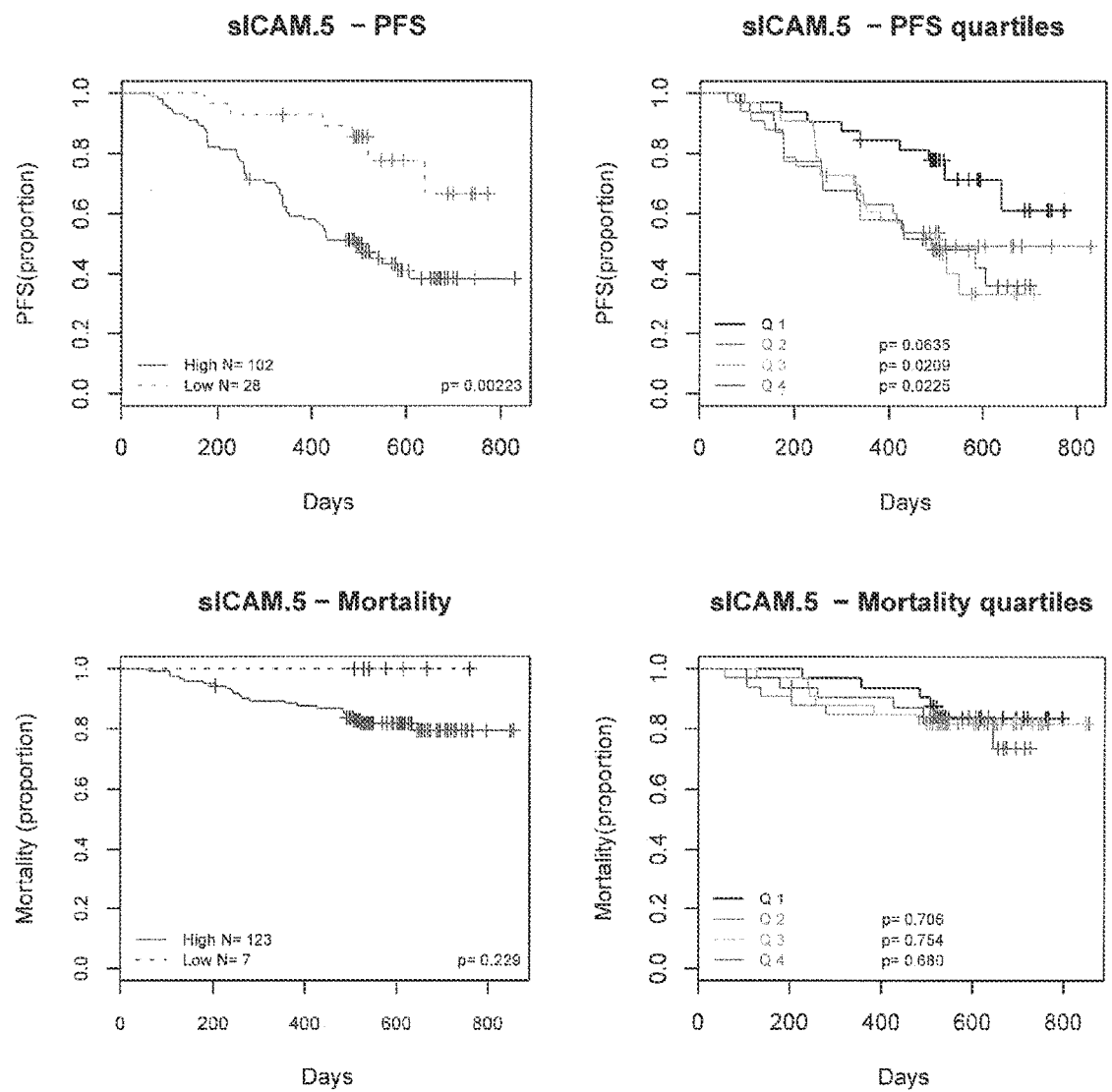
Figure 44:
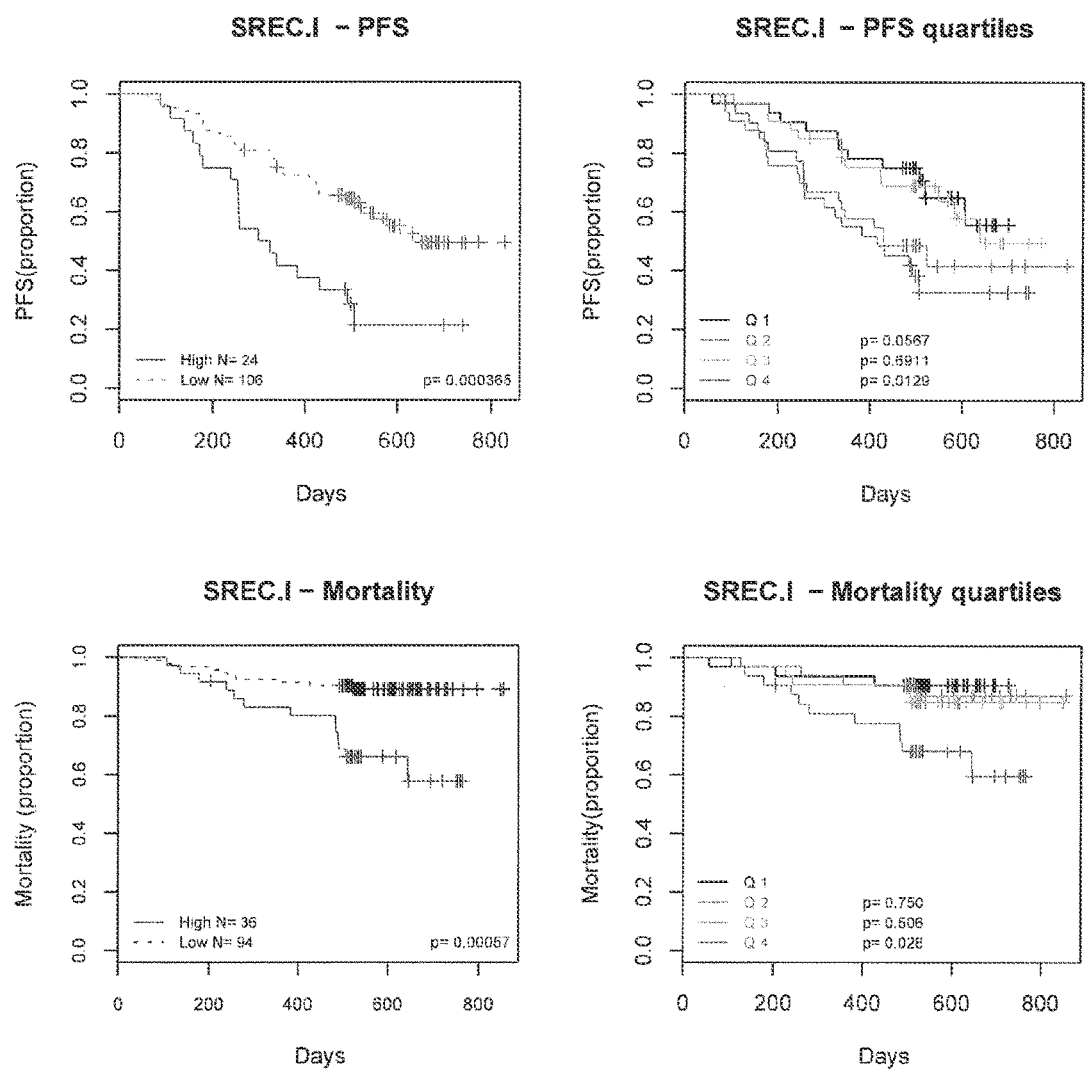
Figure 45:
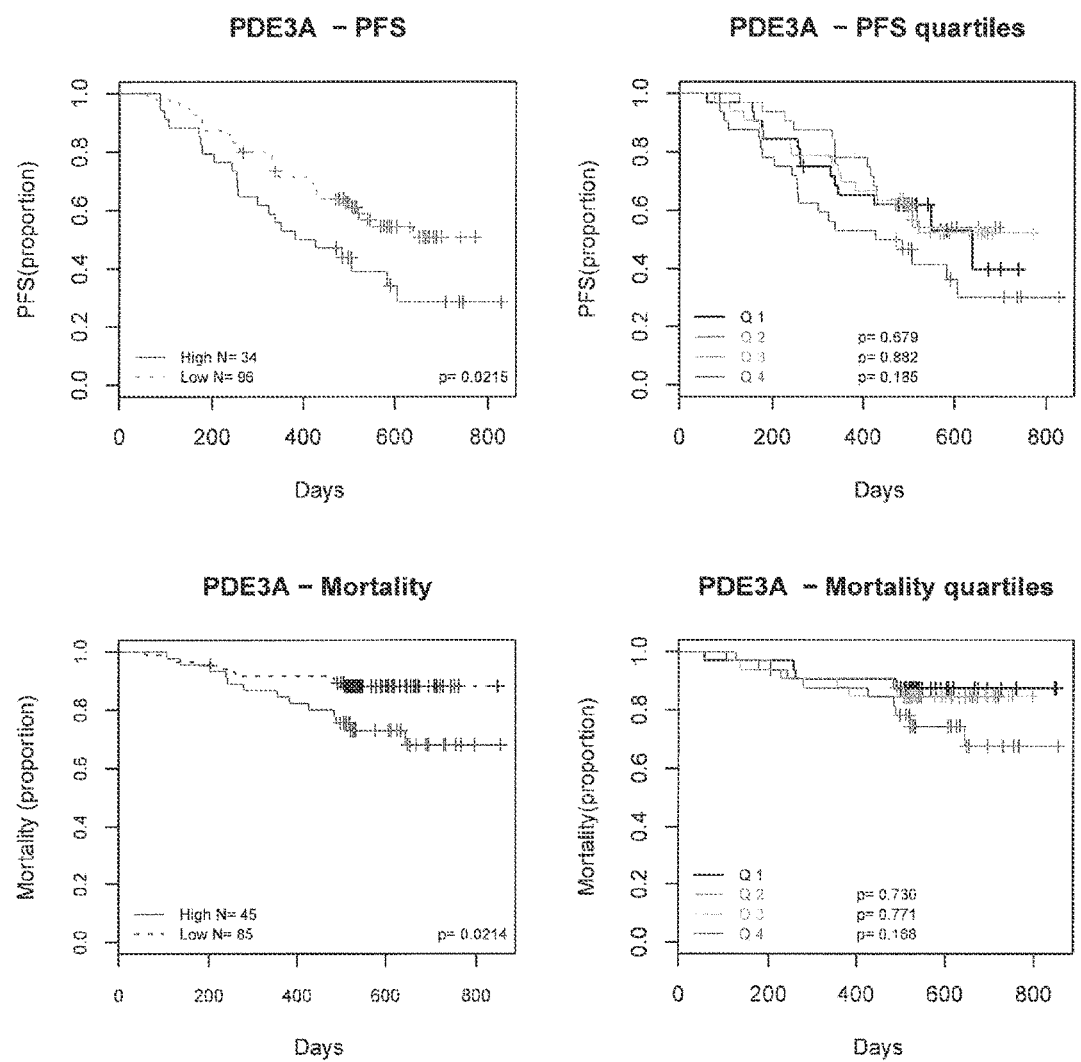
Figure 46:
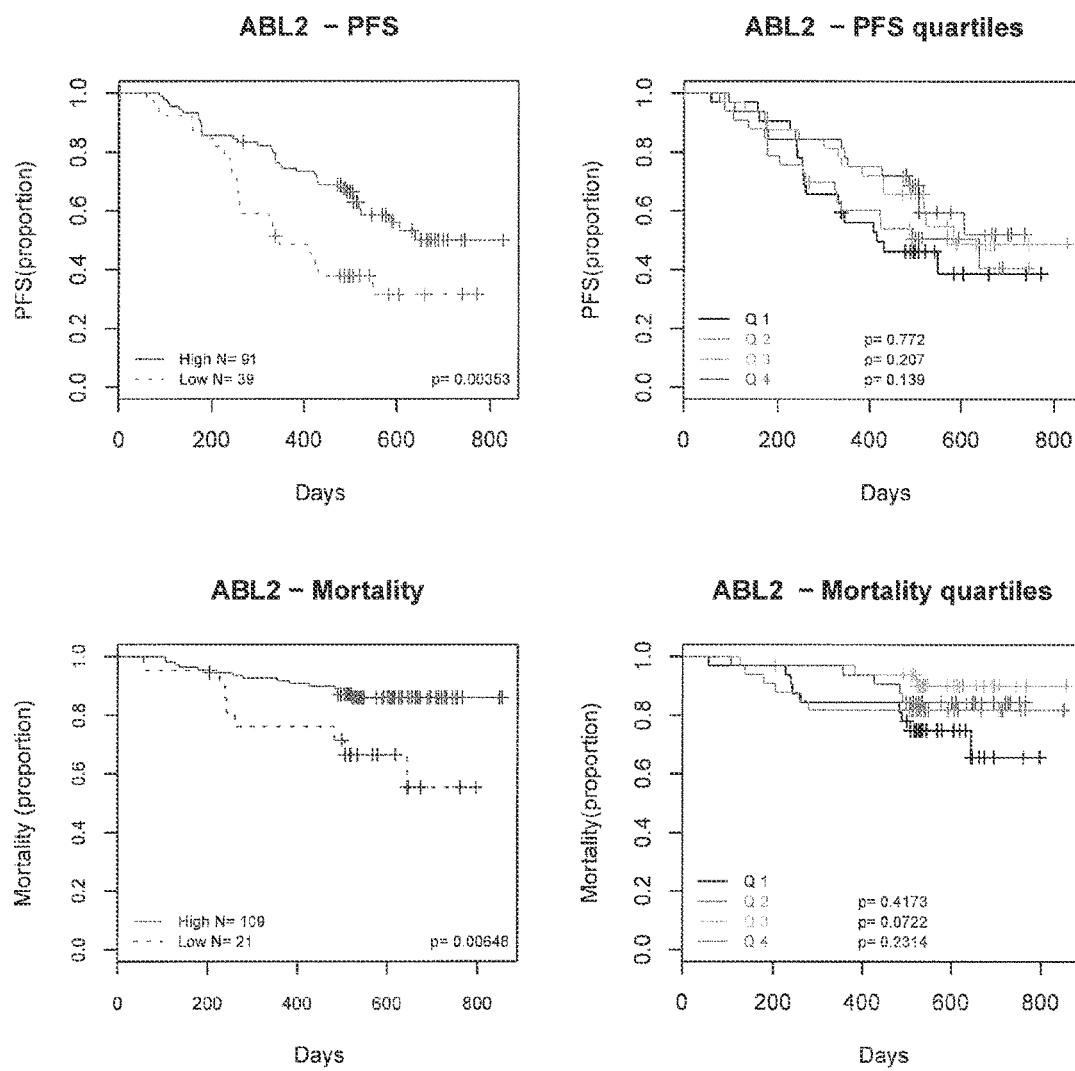
Figure 47:
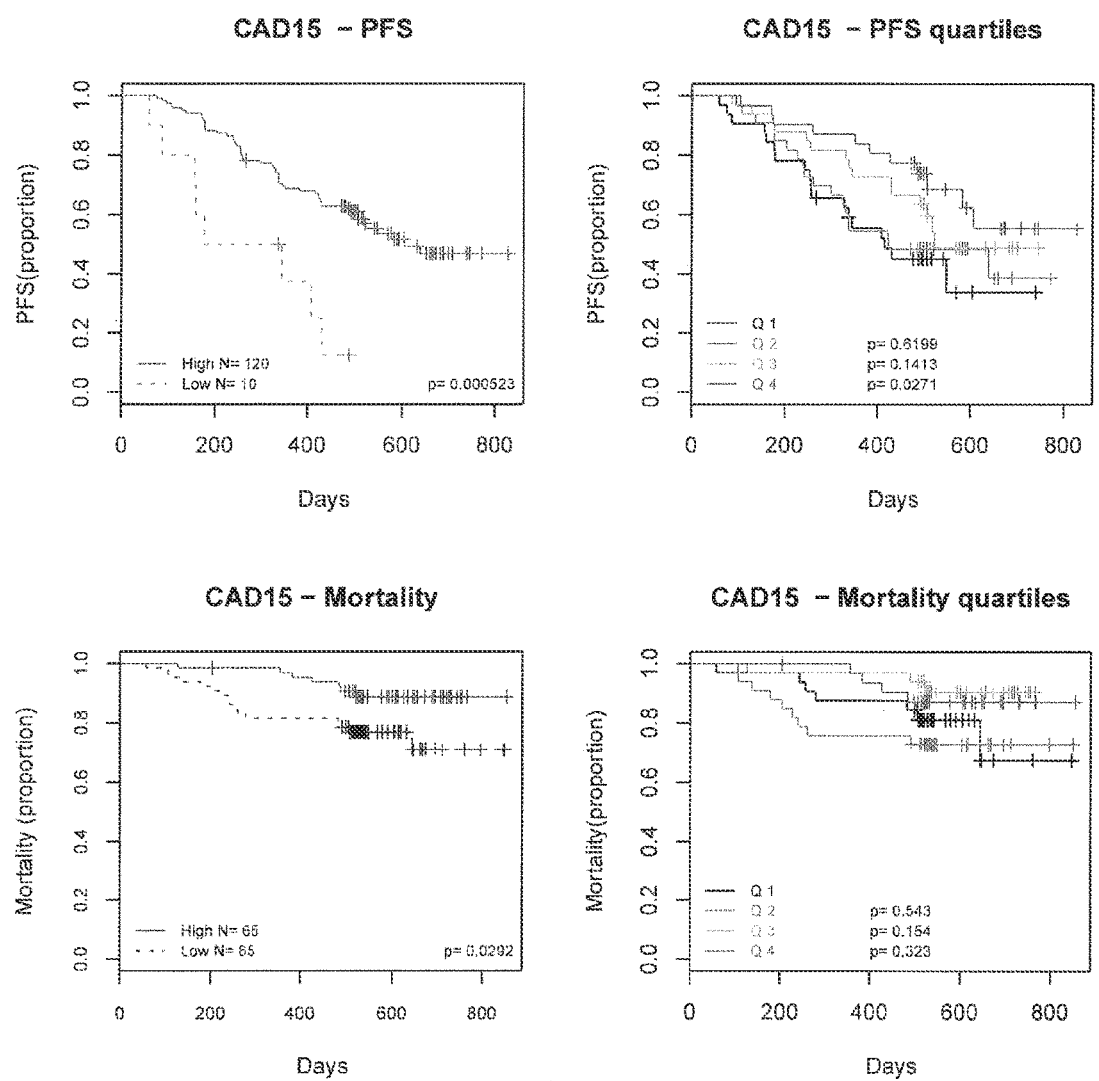
Figure 48:
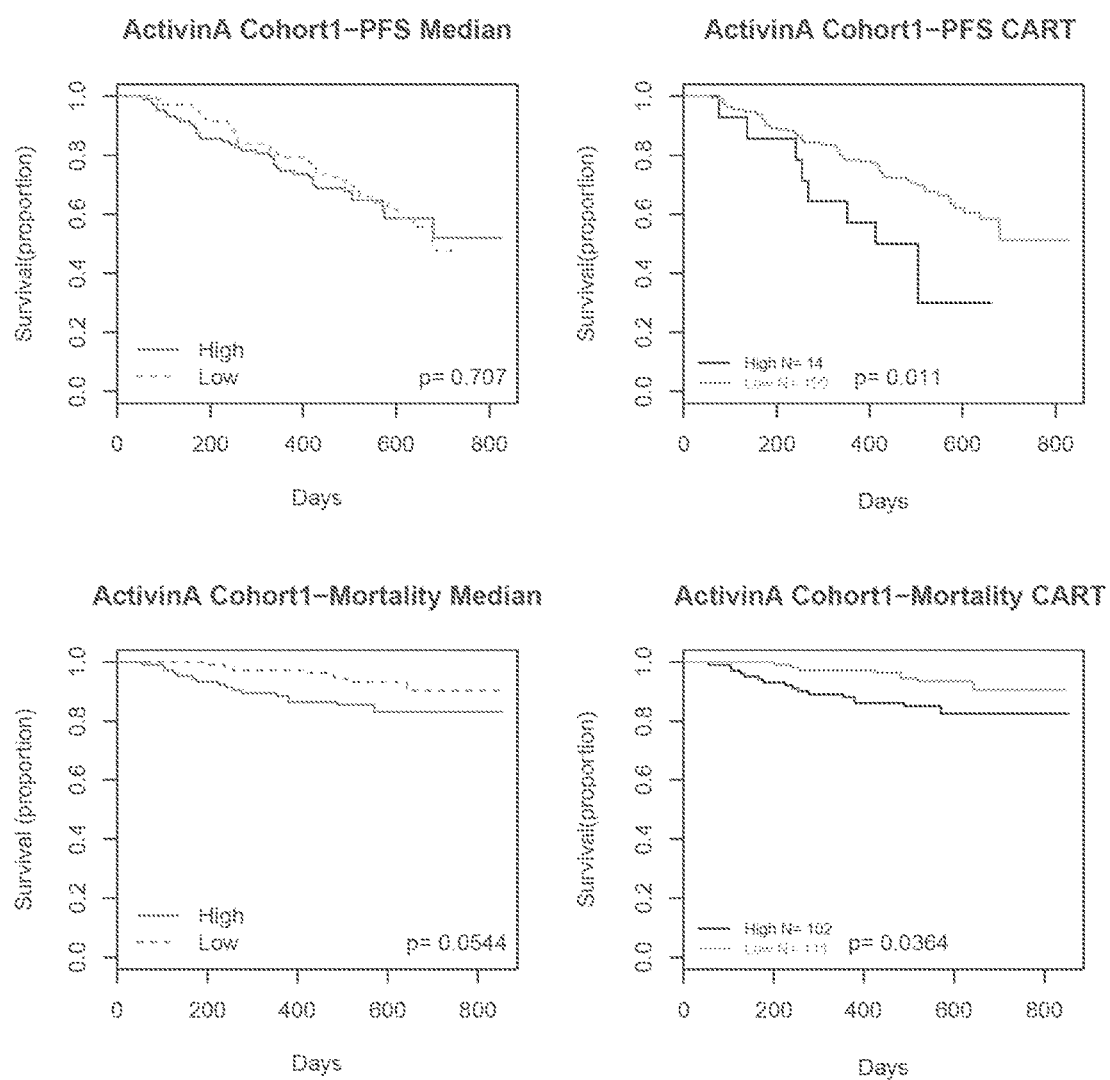
Figure 49:
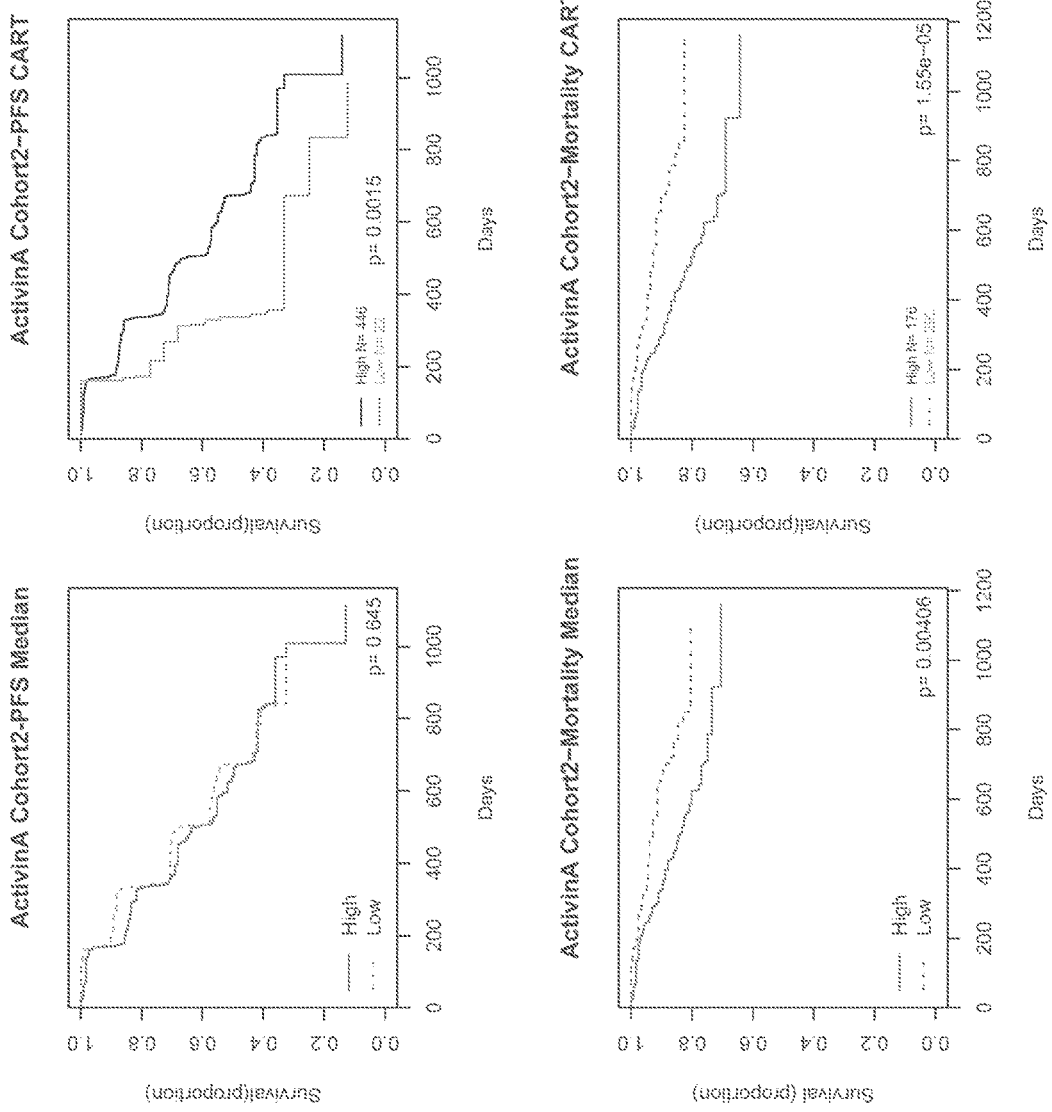
Figure 50:
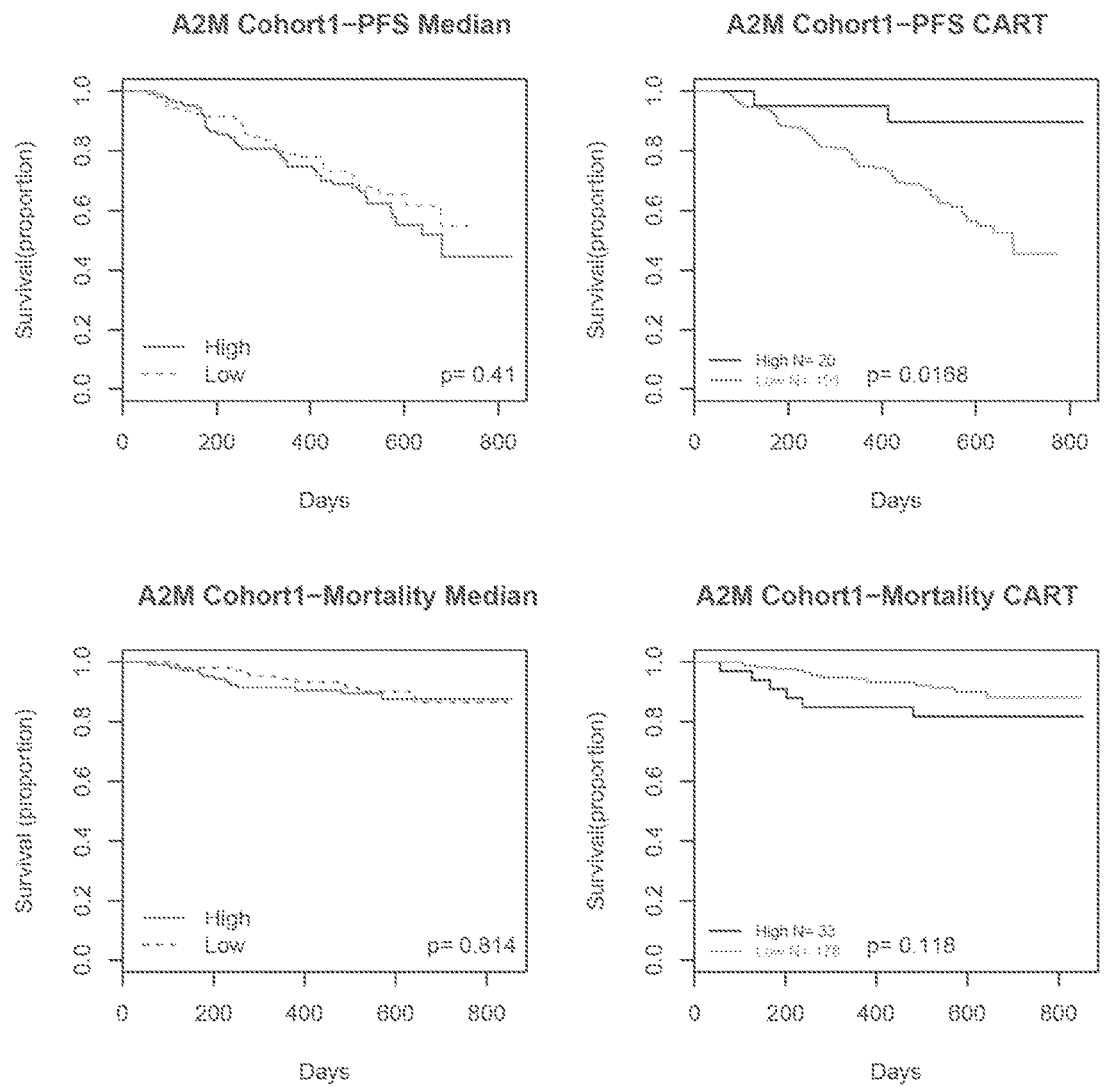
Figure 51:
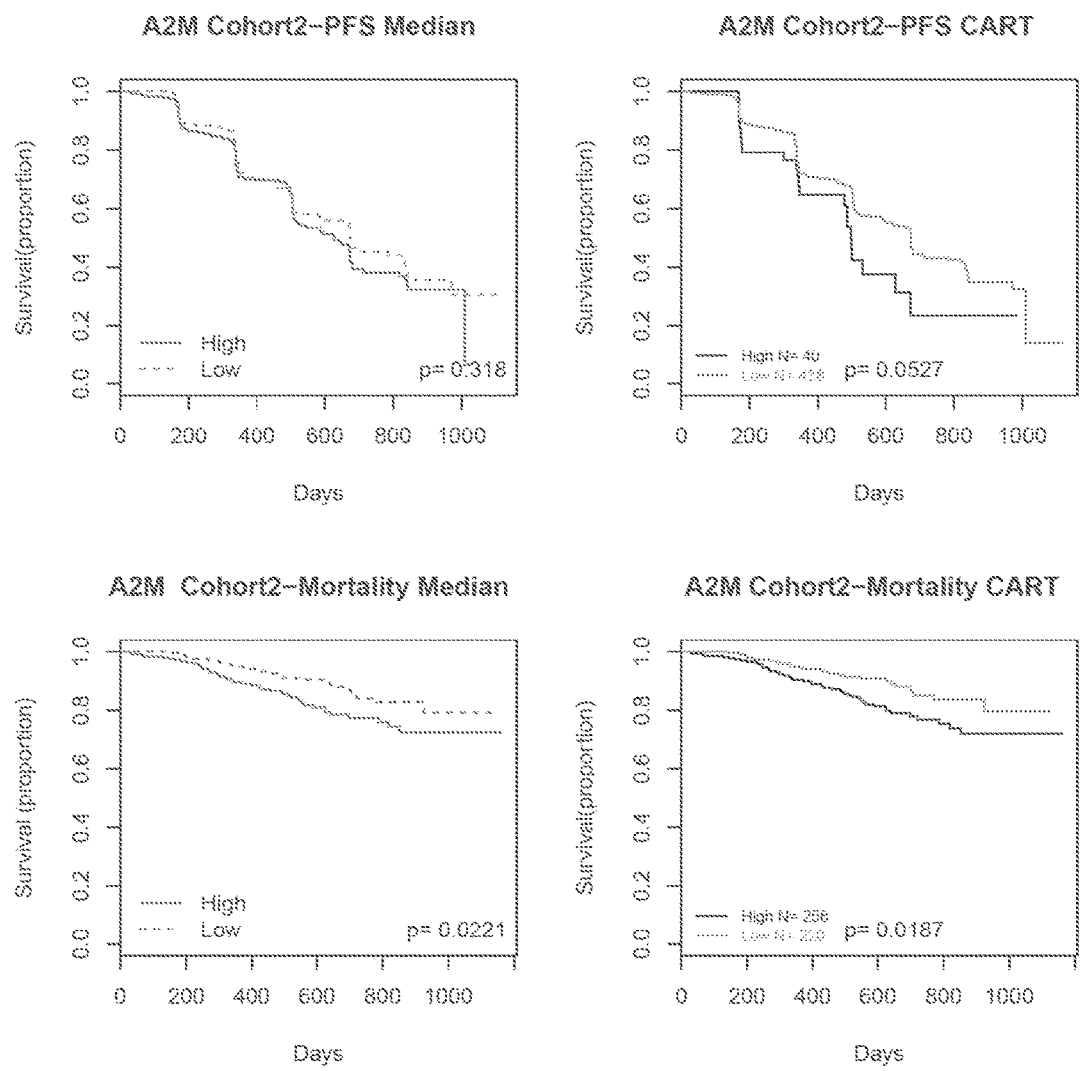
Figure 52:
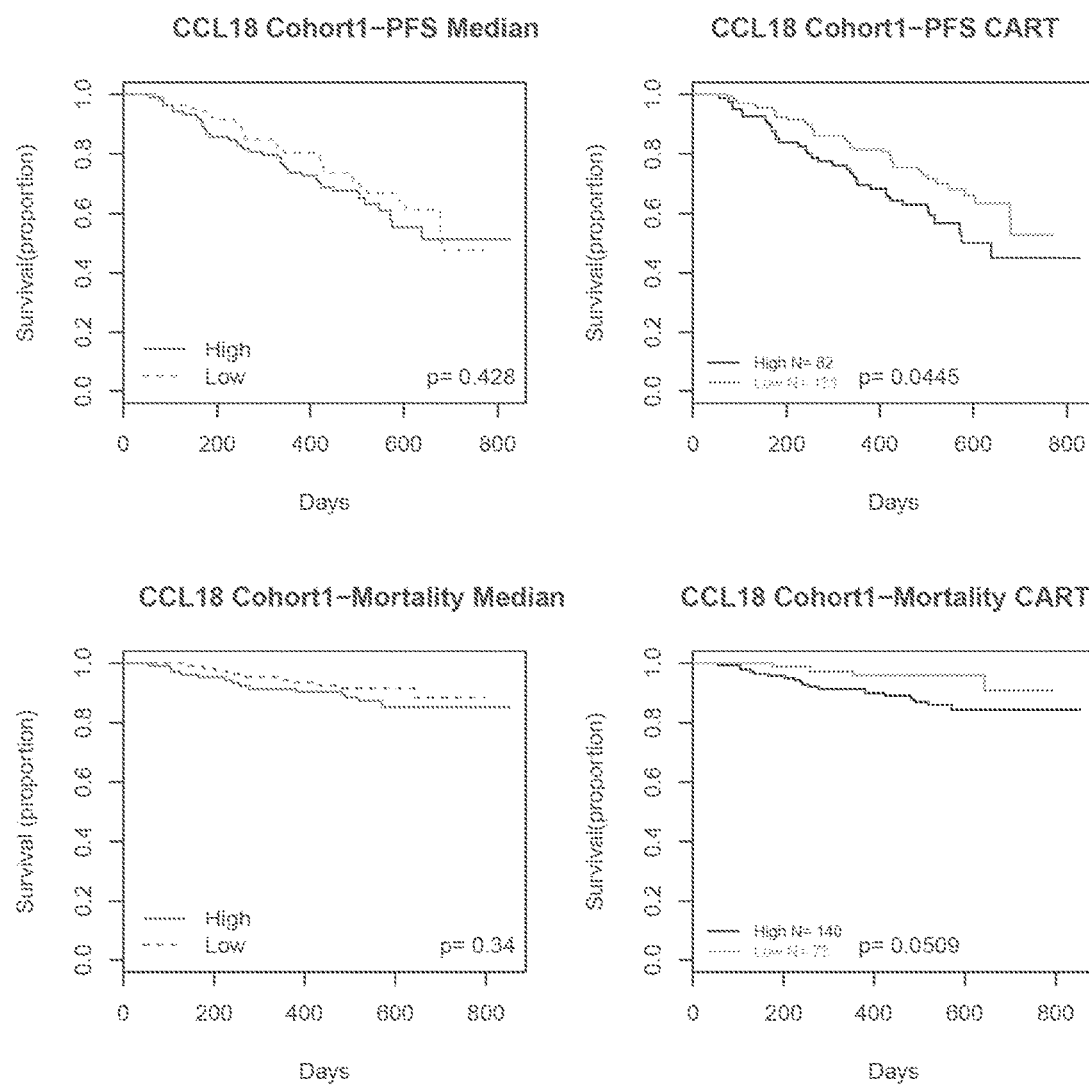
Figure 53:
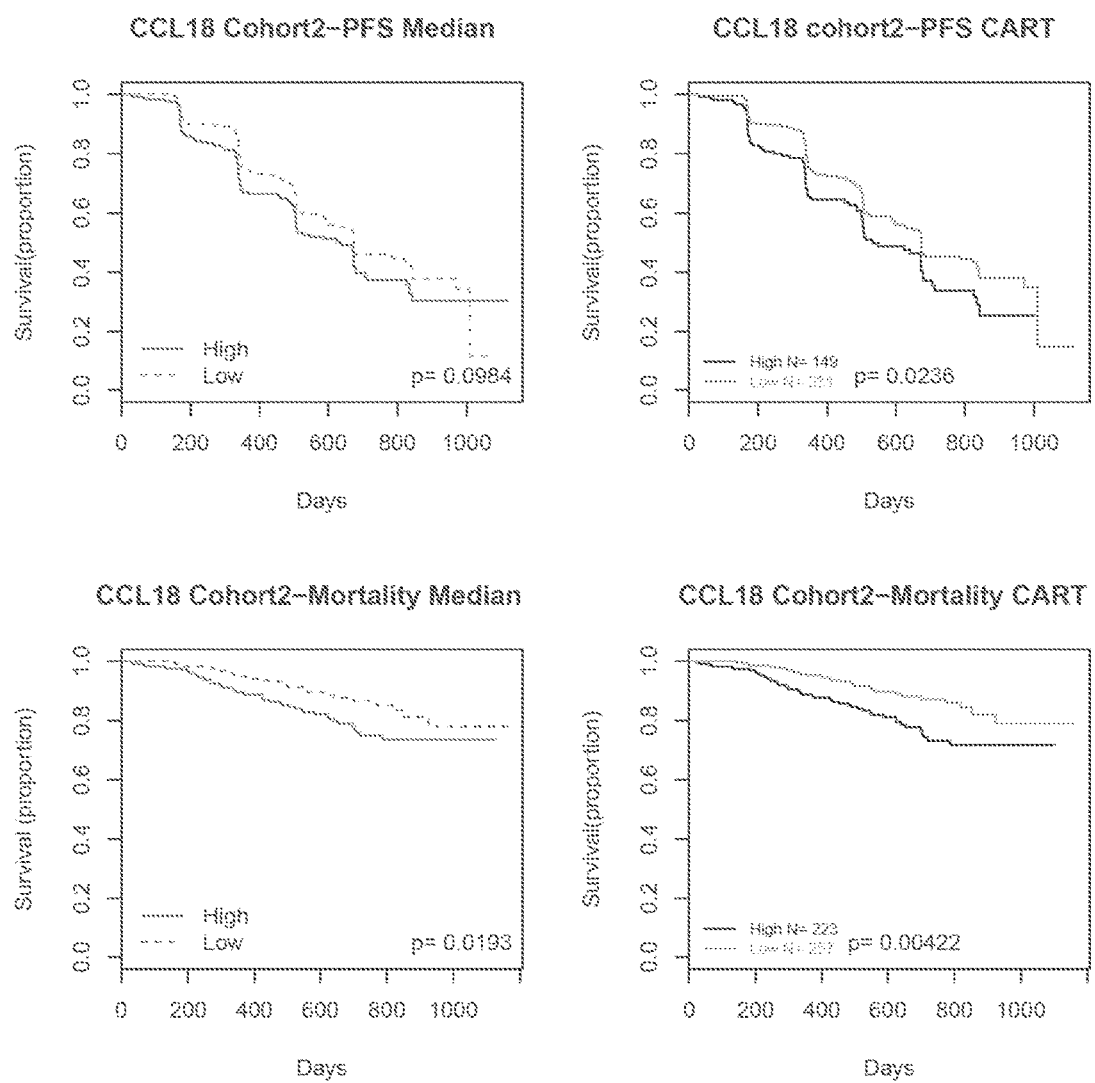
Figure 54:
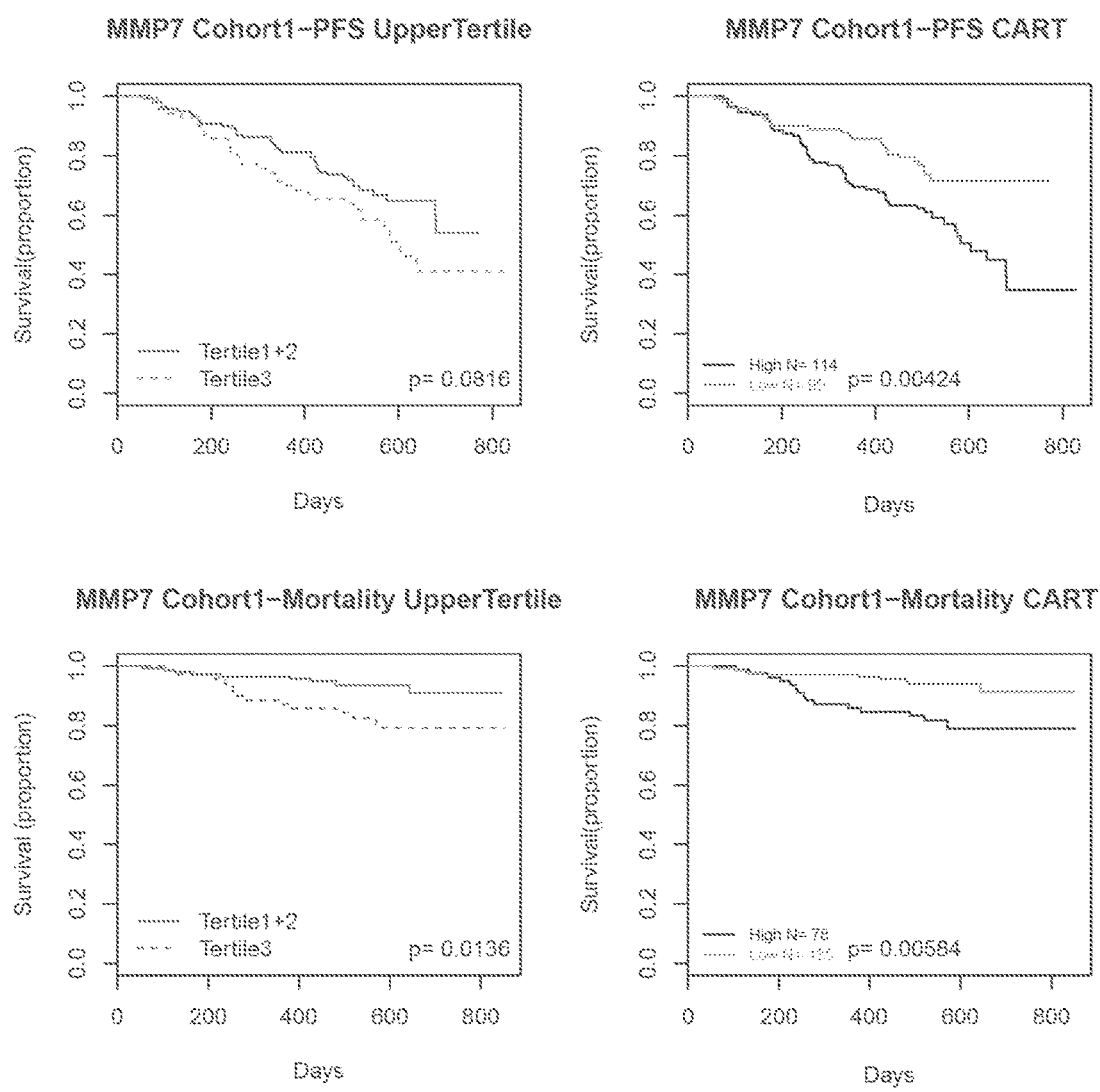
Figure 55:
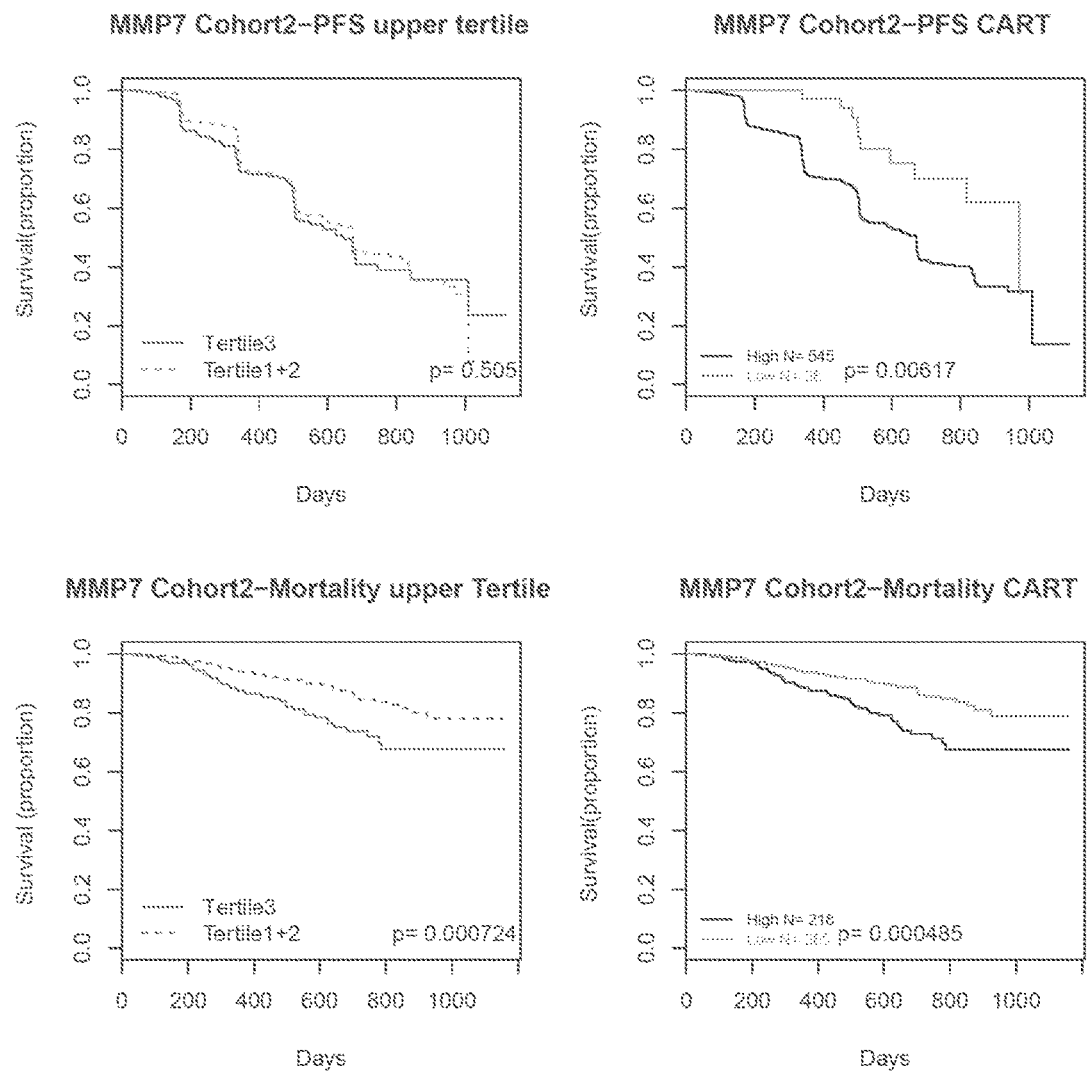
Figure 56:
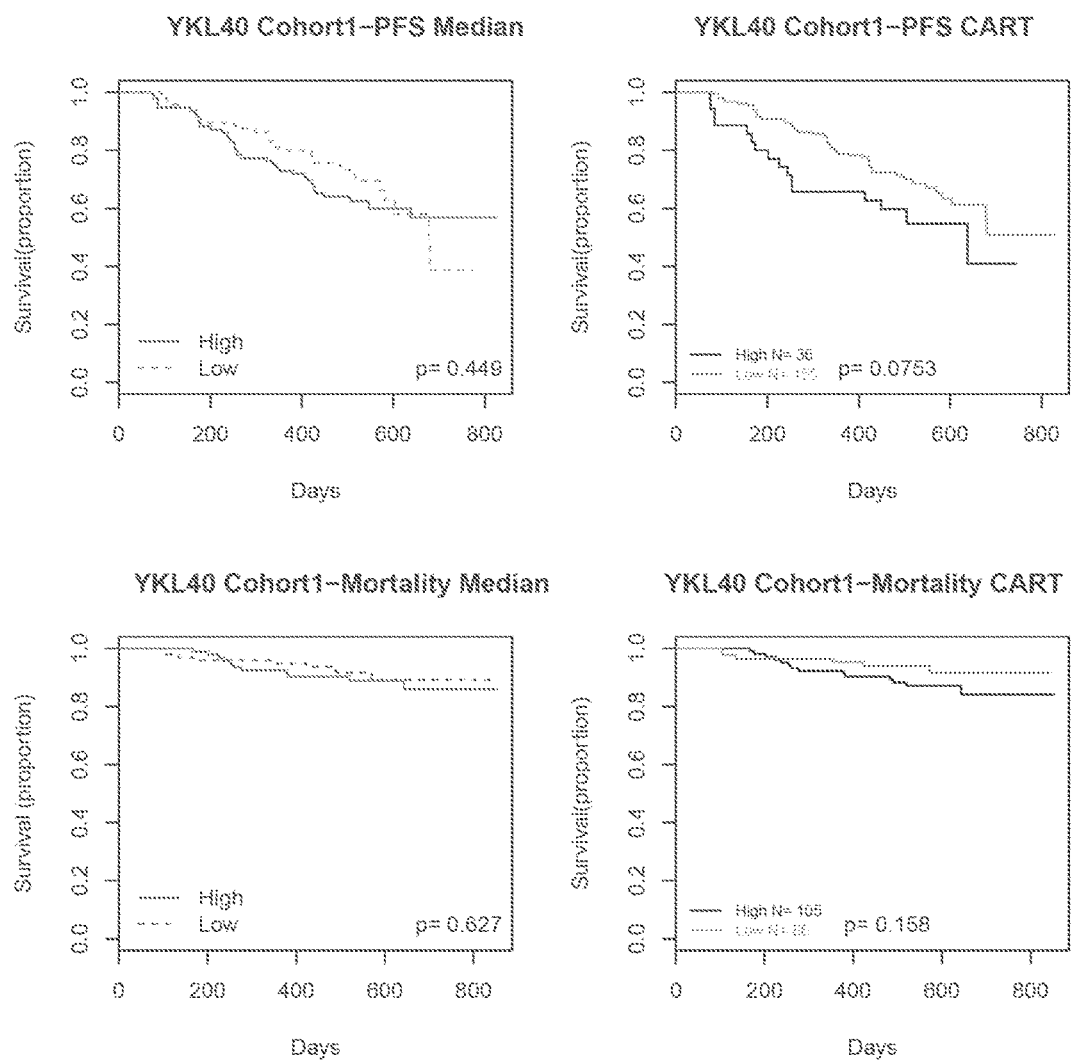
Figure 57:
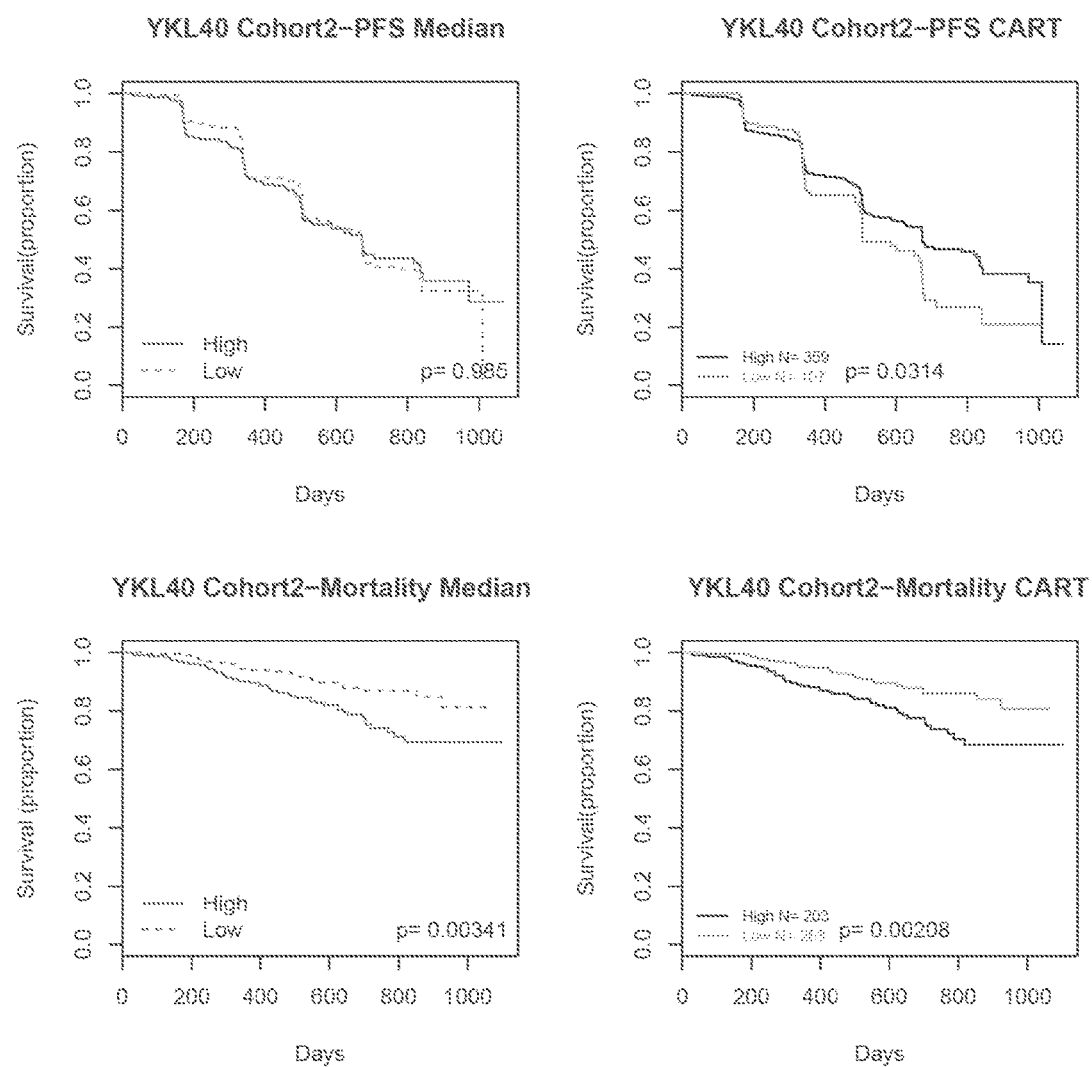

Unsupervised Hierarchical Clustering: Unsupervised hierarchical clustering was performed based on a subset of 150 differentially expressed proteins that met more stringent inclusion criteria (FDR<0.001 and FC>1.25). The Partek Genomics Suite was used for this analysis (Partek, St. Louis, Mo.). In this analysis, the majority IPF patients cluster together (FIG. 3 branches 5-7). Most of the remaining patients form a secondary cluster has increased similarity to healthy controls (FIG. 3; branch 1). One cluster of upregulated proteins and one cluster of downregulated proteins are consistent across the majority of IPF patients. The consistently upregulated proteins (FIG. 4) includes the previously reported IPF plasma protein markers MMP-7 and CCL-18. Seven of the 17 protein in this cluster are differentially upregulated at the mRNA level in IPF lung tissue (InterMune analysis of data in the GEO database).

In addition, several differentially expressed proteins correspond to mRNAs previously shown to be differentially expressed in IPF lung tissue

| p-value (FDR) threshold | 0.01 | 0.01 | 0.01 | 0.01 | 0.01 |
|---|---|---|---|---|---|
| Fold Change threshold | none | 1.15 | 1.2 | 1.5 | 2 |
| number of proteins above the threshold | 351 | 311 | 262 | 94 | 20 |

Table IIIA and IIIB. Bivariate analysis of the association between mortality and plasma protein levels (i.e. MMP-7, CCL-18, YKL-40, Activin A and A2M) by Cox proportional hazards regression model. Protein levels were quantitated by ELISA in two independent patient cohorts (i.e. Cohort 1 in Table IIIA and Cohort 2 in Table IIIB).

TABLE IIIA

| | Cohort 1 | | | | | |
|---|---|---|---|---|---|---|
| | N | Death | N High Conc. | HR | 95% CI | p-value |
| MMP-7 | 221 | 25 | 74 | 2.3 | 1.0-5.0 | 0.041 |
| CCL-18 | 213 | 24 | 140 | 2.8 | 1.0-8.1 | 0.062 |
| YKL-40 | 191 | 20 | 105 | 2.0 | 0.8-5.1 | 0.165 |
| Activin A | 213 | 24 | 102 | 2.4 | 1.0-5.6 | 0.043 |
| A2-macroglobulin | 211 | 23 | 33 | 2.1 | 0.8-5.2 | 0.126 |

TABLE IIIB

| | Cohort 2 | | | | | |
|---|---|---|---|---|---|---|
| | N | Death | N High Conc. | HR | 95% CI | p-value |
| MMP-7 | 613 | 97 | 205 | 1.8 | 1.2-2.6 | 0.006 |
| CCL-18 | 480 | 77 | 223 | 1.9 | 1.2-3.0 | 0.005 |
| YKL-40 | 466 | 75 | 203 | 2.0 | 1.3-3.2 | 0.003 |
| Activin A | 468 | 76 | 176 | 2.6 | 1.7-4.2 | 3.23e−05 |
| A2-macroglobulin | 478 | 77 | 258 | 1.7 | 1.1-2.8 | 0.02 |

TABLE IV

Mortality risk of CCL18 and YKL40 determined by ELISA with 2 separate patient cohorts.

| EntrezGeneID | EntrezGeneSymbol | UniProt | Target | Correlation with risk |
|---|---|---|---|---|
| 6362 | CCL18 | P55774 | PARC | positive |
| 1116 | CHI3L1 | P36222 | YKL40 | positive |

TABLE 1A

Fibrotic pulmonary disease biomarker proteins (upregulated). Marker proteins have been identified with p(FDR) < 0.01, FC > 1.2x, n = 262; 174 proteins upregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| sICAM-5 | 7087 | ICAM5 | Q9UMF0 | 5.36E−16 | 1.6161 | IPF-Baseline up vs Control |
| PUR8 | 158 | ADSL | P30566 | 3.05E−14 | 2.87734 | IPF-Baseline up vs Control |
| Cathepsin H | 1512 | CTSH | P09668 | 5.68E−13 | 1.30088 | IPF-Baseline up vs Control |
| STRATIFIN | 2810 | SFN | P31947 | 1.15E−12 | 1.62451 | IPF-Baseline up vs Control |
| iC3b | 718 | C3 | P01024 | 6.55E−10 | 1.73599 | IPF-Baseline up vs Control |
| MMP-7 | 4316 | MMP7 | P09237 | 2.06E−09 | 1.5265 | IPF-Baseline up vs Control |
| LKHA4 | 4048 | LTA4H | P09960 | 3.44E−09 | 8.53381 | IPF-Baseline up vs Control |
| Soggy-1 | 27120 | DKKL1 | Q9UK85 | 9.10E−09 | 1.50067 | IPF-Baseline up vs Control |
| C3b | 718 | C3 | P01024 | 2.16E−08 | 2.31267 | IPF-Baseline up vs Control |
| CLC7A | 64581 | CLEC7A | Q9BXN2 | 3.87E−08 | 1.48678 | IPF-Baseline up vs Control |
| BASI | 682 | BSG | P35613 | 4.77E−08 | 1.76885 | IPF-Baseline up vs Control |
| ER | 2099 | ESR1 | P03372 | 4.82E−08 | 1.48871 | IPF-Baseline up vs Control |
| calgranulin B | 6280 | S100A9 | P06702 | 6.55E−08 | 1.83576 | IPF-Baseline up vs Control |
| SOD | 6647 | SOD1 | P00441 | 7.89E−08 | 1.45524 | IPF-Baseline up vs Control |
| Cathepsin A | 5476 | CTSA | P10619 | 1.34E−07 | 1.3084 | IPF-Baseline up vs Control |
| cGMP-stimulated PDE | 5138 | PDE2A | O00408 | 1.54E−07 | 1.42056 | IPF-Baseline up vs Control |
| PARC | 6362 | CCL18 | P55774 | 1.84E−07 | 1.40298 | IPF-Baseline up vs Control |
| NID2 | 22795 | NID2 | Q14112 | 2.97E−07 | 1.44597 | IPF-Baseline up vs Control |
| Cadherin-6 | 1004 | CDH6 | P55285 | 3.74E−07 | 1.6071 | IPF-Baseline up vs Control |
| LGMN | 5641 | LGMN | Q99538 | 4.82E−07 | 1.28215 | IPF-Baseline up vs Control |
| WISP-1 | 8840 | WISP1 | O95388 | 5.92E−07 | 1.39604 | IPF-Baseline up vs Control |
| tau | 4137 | MAPT | P10636 | 6.96E−07 | 1.83756 | IPF-Baseline up vs Control |
| 41 | 2035 | EPB41 | P11171 | 8.08E−07 | 1.53461 | IPF-Baseline up vs Control |
| RANTES | 6352 | CCL5 | P13501 | 9.62E−07 | 1.55401 | IPF-Baseline up vs Control |
| Histone H1.2 | 3006 | HIST1H1C | P16403 | 9.96E−07 | 3.83001 | IPF-Baseline up vs Control |
| Bcl-2 | 596 | BCL2 | P10415 | 1.08E−06 | 1.60709 | IPF-Baseline up vs Control |
| PRL | 5617 | PRL | P01236 | 1.25E−06 | 1.42039 | IPF-Baseline up vs Control |
| Cadherin-12 | 1010 | CDH12 | P55289 | 1.29E−06 | 1.88342 | IPF-Baseline up vs Control |
| PKC-Z | 5590 | PRKCZ | Q05513 | 1.45E−06 | 1.90214 | IPF-Baseline up vs Control |
| PSA1 | 5682 | PSMA1 | P25786 | 1.47E−06 | 1.22511 | IPF-Baseline up vs Control |
| BMP10 | 27302 | BMP10 | O95393 | 1.56E−06 | 1.52213 | IPF-Baseline up vs Control |
| Ephrin-B3 | 1949 | EFNB3 | Q15768 | 1.64E−06 | 1.58277 | IPF-Baseline up vs Control |
| EphB4 | 2050 | EPHB4 | P54760 | 1.73E−06 | 1.47915 | IPF-Baseline up vs Control |
| TGF-b3 | 7043 | TGFB3 | P10600 | 2.09E−06 | 1.40029 | IPF-Baseline up vs Control |
| GFRa-3 | 2676 | GFRA3 | O60609 | 2.25E−06 | 1.29682 | IPF-Baseline up vs Control |
| MMP-9 | 4318 | MMP9 | P14780 | 2.58E−06 | 1.48952 | IPF-Baseline up vs Control |

TABLE 1A-continued

Fibrotic pulmonary disease biomarker proteins (upregulated). Marker proteins have been identified with p(FDR) < 0.01, FC > 1.2x, n = 262; 174 proteins upregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| Protease nexin I | 5270 | SERPINE2 | P07093 | 3.09E−06 | 1.98673 | IPF-Baseline up vs Control |
| Calcineurin B a | 5534 | PPP3R1 | P63098 | 3.23E−06 | 1.39475 | IPF-Baseline up vs Control |
| PTP-1C | 5777 | PTPN6 | P29350 | 3.91E−06 | 1.90799 | IPF-Baseline up vs Control |
| MMP-17 | 4326 | MMP17 | Q9ULZ9 | 4.58E−06 | 1.92995 | IPF-Baseline up vs Control |
| HMG-1 | 3146 | HMGB1 | P09429 | 5.23E−06 | 1.97342 | IPF-Baseline up vs Control |
| NCC27 | 1192 | CLIC1 | O00299 | 5.67E−06 | 2.043 | IPF-Baseline up vs Control |
| TYK2 | 7297 | TYK2 | P29597 | 6.51E−06 | 1.51262 | IPF-Baseline up vs Control |
| IL22RA1 | 58985 | IL22RA1 | Q8N6P7 | 7.73E−06 | 1.70245 | IPF-Baseline up vs Control |
| RBM39 | 9584 | RBM39 | Q14498 | 7.90E−06 | 1.95172 | IPF-Baseline up vs Control |
| Peroxiredoxin-6 | 9588 | PRDX6 | P30041 | 8.15E−06 | 1.74142 | IPF-Baseline up vs Control |
| FCGR1 | 2209 | FCGR1A | P12314 | 8.71E−06 | 1.59004 | IPF-Baseline up vs Control |
| MOZ | 7994 | KAT6A | Q92794 | 8.86E−06 | 1.28366 | IPF-Baseline up vs Control |
| SP-D | 6441 | SFTPD | P35247 | 9.08E−06 | 4.00143 | IPF-Baseline up vs Control |
| Ubiquitin+1 | 6233 | RPS27A | P62979 | 9.17E−06 | 1.32953 | IPF-Baseline up vs Control |
| Histone H2A.z | 3015 | H2AFZ | P0C0S5 | 1.04E−05 | 2.20185 | IPF-Baseline up vs Control |
| a2-Macroglobulin | 2 | A2M | P01023 | 1.19E−05 | 1.60132 | IPF-Baseline up vs Control |
| PECAM-1 | 5175 | PECAM1 | P16284 | 1.21E−05 | 1.23637 | IPF-Baseline up vs Control |
| ON | 6678 | SPARC | P09486 | 1.25E−05 | 1.38543 | IPF-Baseline up vs Control |
| MIF | 4282 | MIF | P14174 | 1.37E−05 | 1.62735 | IPF-Baseline up vs Control |
| CaMKK alpha | 84254 | CAMKK1 | Q8N5S9 | 1.69E−05 | 1.684 | IPF-Baseline up vs Control |
| PSME1 | 5720 | PSME1 | Q06323 | 1.75E−05 | 1.7017 | IPF-Baseline up vs Control |
| LY86 | 9450 | LY86 | O95711 | 2.03E−05 | 1.25277 | IPF-Baseline up vs Control |
| HPG- | 3248 | HPGD | P15428 | 2.61E−05 | 1.36537 | IPF-Baseline up vs Control |
| TrkA | 4914 | NTRK1 | P04629 | 2.64E−05 | 1.20709 | IPF-Baseline up vs Control |
| Rab GDP dissociation inhibitor beta | 2665 | GDI2 | P50395 | 3.61E−05 | 1.36366 | IPF-Baseline up vs Control |
| PBEF | 10135 | NAMPT | P43490 | 3.63E−05 | 2.23087 | IPF-Baseline up vs Control |
| CAPG | 822 | CAPG | P40121 | 3.69E−05 | 1.90263 | IPF-Baseline up vs Control |
| PAI-1 | 5054 | SERPINE1 | P05121 | 3.80E−05 | 1.52823 | IPF-Baseline up vs Control |
| BDNF | 627 | BDNF | P23560 | 3.90E−05 | 1.6203 | IPF-Baseline up vs Control |
| ANGL3 | 27329 | ANGPTL3 | Q9Y5C1 | 4.07E−05 | 1.30295 | IPF-Baseline up vs Control |
| CD30 | 943 | TNFRSF8 | P28908 | 4.28E−05 | 1.25432 | IPF-Baseline up vs Control |
| Flt-3 | 2322 | FLT3 | P36888 | 4.47E−05 | 1.45412 | IPF-Baseline up vs Control |
| G-CSF-R | 1441 | CSF3R | Q99062 | 4.55E−05 | 1.25163 | IPF-Baseline up vs Control |
| tPA | 5327 | PLAT | P00750 | 4.88E−05 | 1.2056 | IPF-Baseline up vs Control |
| IL-12 | 3592 3593 | IL12A IL12B | P29459 P29460 | 5.19E−05 | 1.24153 | IPF-Baseline up vs Control |
| XPNPEP1 | 7511 | XPNPEP1 | Q9NQW7 | 6.32E−05 | 1.57494 | IPF-Baseline up vs Control |

TABLE 1A-continued

Fibrotic pulmonary disease biomarker proteins (upregulated). Marker proteins have been identified with p(FDR) < 0.01, FC > 1.2x, n = 262; 174 proteins upregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| PAK6 | 56924 | PAK6 | Q9NQU5 | 6.40E−05 | 1.7035 | IPF-Baseline up vs Control |
| Gro-b/g | None | CXCL3 CXCL2 | P19876 P19875 | 6.56E−05 | 1.61602 | IPF-Baseline up vs Control |
| HDGR2 | 84717 | HDGFRP2 | Q7Z4V5 | 6.57E−05 | 1.34838 | IPF-Baseline up vs Control |
| PTK6 | 5753 | PTK6 | Q13882 | 6.80E−05 | 1.54905 | IPF-Baseline up vs Control |
| NET4 | 59277 | NTN4 | Q9HB63 | 7.40E−05 | 1.27615 | IPF-Baseline up vs Control |
| C4b | 720 721 | C4A C4B | P0C0L4 P0C0L5 | 8.41E−05 | 2.21215 | IPF-Baseline up vs Control |
| a1-Antitrypsin | 5265 | SERPINA1 | P01009 | 8.42E−05 | 1.21183 | IPF-Baseline up vs Control |
| prostatic binding protein | 5037 | PEBP1 | P30086 | 8.56E−05 | 1.4349 | IPF-Baseline up vs Control |
| OLR1 | 4973 | OLR1 | P78380 | 9.39E−05 | 1.77154 | IPF-Baseline up vs Control |
| GHC2 | 83733 | SLC25A18 | Q9H1K4 | 9.52E−05 | 1.28086 | IPF-Baseline up vs Control |
| GAS1 | 2619 | GAS1 | P54826 | 9.60E−05 | 1.58615 | IPF-Baseline up vs Control |
| Nucleoside diphosphate kinase A | 4830 | NME1 | P15531 | 9.93E−05 | 1.31321 | IPF-Baseline up vs Control |
| IMDH2 | 3615 | IMPDH2 | P12268 | 9.96E−05 | 1.37417 | IPF-Baseline up vs Control |
| PGP9.5 | 7345 | UCHL1 | P09936 | 0.000102138 | 1.44393 | IPF-Baseline up vs Control |
| 4EBP2 | 1979 | EIF4EBP2 | Q13542 | 0.000102548 | 1.27799 | IPF-Baseline up vs Control |
| Discoidin domain receptor 2 | 4921 | DDR2 | Q16832 | 0.000105013 | 1.25463 | IPF-Baseline up vs Control |
| hnRNP A2/B1 | 3181 | HNRNPA2B1 | P22626 | 0.000105496 | 3.10531 | IPF-Baseline up vs Control |
| TARC | 6361 | CCL17 | Q92583 | 0.000111088 | 1.62767 | IPF-Baseline up vs Control |
| Peroxiredoxin-1 | 5052 | PRDX1 | Q06830 | 0.000111533 | 1.4596 | IPF-Baseline up vs Control |
| IL-12 Rb1 | 3594 | IL12RB1 | P42701 | 0.00011327 | 1.23088 | IPF-Baseline up vs Control |
| MDHC | 4190 | MDH1 | P40925 | 0.000115994 | 1.32468 | IPF-Baseline up vs Control |
| HO-2 | 3163 | HMOX2 | P30519 | 0.000124116 | 1.51311 | IPF-Baseline up vs Control |
| IFN-lambda 2 | 282616 | IL28A | Q8IZJ0 | 0.000126914 | 1.36754 | IPF-Baseline up vs Control |
| RAP | 4043 | LRPAP1 | P30533 | 0.000127158 | 1.4188 | IPF-Baseline up vs Control |
| LDH-H 1 | 3945 | LDHB | P07195 | 0.000133641 | 1.42348 | IPF-Baseline up vs Control |
| MFRP | 83552 | MFRP | Q9BY79 | 0.000139768 | 2.08405 | IPF-Baseline up vs Control |
| Epo | 2056 | EPO | P01588 | 0.00014028 | 1.65765 | IPF-Baseline up vs Control |
| Myokinase human | 203 | AK1 | P00568 | 0.000141109 | 1.31277 | IPF-Baseline up vs Control |
| AK1A1 | 10327 | AKR1A1 | P14550 | 0.000147383 | 1.43383 | IPF-Baseline up vs Control |
| GREM1 | 26585 | GREM1 | O60565 | 0.00015057 | 1.57243 | IPF-Baseline up vs Control |
| NXPH1 | 30010 | NXPH1 | P58417 | 0.000152003 | 1.40755 | IPF-Baseline up vs Control |
| CAMK1 | 8536 | CAMK1 | Q14012 | 0.000155007 | 1.23113 | IPF-Baseline up vs Control |
| C3 | 718 | C3 | P01024 | 0.000157238 | 1.23997 | IPF-Baseline up vs Control |
| PSA6 | 5687 | PSMA6 | P60900 | 0.000194759 | 1.44708 | IPF-Baseline up vs Control |
| 17-beta-HSD 1 | 3292 | HSD17B1 | P14061 | 0.000214675 | 1.27653 | IPF-Baseline up vs Control |
| STX1a | 6804 | STX1A | Q16623 | 0.000239348 | 1.31737 | IPF-Baseline up vs Control |

TABLE 1A-continued

Fibrotic pulmonary disease biomarker proteins (upregulated). Marker proteins have been identified with p(FDR) < 0.01, FC > 1.2x, n = 262; 174 proteins upregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| DnaJ homolog | 131118 | DNAJC19 | Q96DA6 | 0.000247922 | 1.21217 | IPF-Baseline up vs Control |
| UBE2N | 7334 | UBE2N | P61088 | 0.00028064 | 1.51364 | IPF-Baseline up vs Control |
| P-Selectin | 6403 | SELP | P16109 | 0.00028186 | 1.25965 | IPF-Baseline up vs Control |
| RS7 | 6201 | RPS7 | P62081 | 0.000283023 | 2.12908 | IPF-Baseline up vs Control |
| IDUA | 3425 | IDUA | P35475 | 0.000297778 | 1.20044 | IPF-Baseline up vs Control |
| Triosephosphate isomerase | 7167 | TPI1 | P60174 | 0.000298866 | 1.48785 | IPF-Baseline up vs Control |
| AIF1 | 199 | AIF1 | P55008 | 0.000300015 | 1.39219 | IPF-Baseline up vs Control |
| Topoisomerase I | 7150 | TOP1 | P11387 | 0.000302245 | 2.53892 | IPF-Baseline up vs Control |
| UBC9 | 7329 | UBE2I | P63279 | 0.000323054 | 1.61829 | IPF-Baseline up vs Control |
| TSLP R | 64109 | CRLF2 | Q9HC73 | 0.000341473 | 1.27071 | IPF-Baseline up vs Control |
| Cytochrome P450 3A4 | 1576 | CYP3A4 | P08684 | 0.000343888 | 1.38319 | IPF-Baseline up vs Control |
| eIF-5 | 1983 | EIF5 | P55010 | 0.000349155 | 1.36514 | IPF-Baseline up vs Control |
| PIGR | 5284 | PIGR | P01833 | 0.000373112 | 1.49802 | IPF-Baseline up vs Control |
| complement factor H-related 5 | 81494 | CFHR5 | Q9BXR6 | 0.000468351 | 1.45947 | IPF-Baseline up vs Control |
| Ubiquitin | 6233 | RPS27A | P62979 | 0.00049552 | 1.82873 | IPF-Baseline up vs Control |
| kallikrein 14 | 43847 | KLK14 | Q9P0G3 | 0.000500586 | 1.22009 | IPF-Baseline up vs Control |
| HPV E7 Type 16 | 1489079 | Human-virus | P03129 | 0.000510247 | 1.23204 | IPF-Baseline up vs Control |
| amyloid precursor protein | 351 | APP | P05067 | 0.000579533 | 1.33454 | IPF-Baseline up vs Control |
| TCTP | 7178 | TPT1 | P13693 | 0.000631081 | 1.51891 | IPF-Baseline up vs Control |
| IL-1b | 3553 | IL1B | P01584 | 0.000635989 | 1.33065 | IPF-Baseline up vs Control |
| PPIE | 10450 | PPIE | Q9UNP9 | 0.000647066 | 1.46298 | IPF-Baseline up vs Control |
| NAGK | 55577 | NAGK | Q9UJ70 | 0.000653108 | 1.28239 | IPF-Baseline up vs Control |
| RBP | 5950 | RBP4 | P02753 | 0.000660154 | 1.52463 | IPF-Baseline up vs Control |
| PA2G4 | 5036 | PA2G4 | Q9UQ80 | 0.000692109 | 1.50882 | IPF-Baseline up vs Control |
| NAP-2 | 5473 | PPBP | P02775 | 0.000711716 | 1.52551 | IPF-Baseline up vs Control |
| KREM2 | 79412 | KREMEN2 | Q8NCW0 | 0.000824472 | 1.54929 | IPF-Baseline up vs Control |
| TGF-b1 | 7040 | TGFB1 | P01137 | 0.00087606 | 1.2611 | IPF-Baseline up vs Control |
| Angiopoietin-1 | 284 | ANGPT1 | Q15389 | 0.000895193 | 1.35839 | IPF-Baseline up vs Control |
| PSA2 | 5683 | PSMA2 | P25787 | 0.000896019 | 1.30114 | IPF-Baseline up vs Control |
| PF-4 | 5196 | PF4 | P02776 | 0.000907416 | 1.52612 | IPF-Baseline up vs Control |
| YES | 7525 | YES1 | P07947 | 0.000923612 | 1.24438 | IPF-Baseline up vs Control |
| CTAP-III | 5473 | PPBP | P02775 | 0.000967891 | 1.42696 | IPF-Baseline up vs Control |
| TWEAK | 8742 | TNFSF12 | O43508 | 0.00098247 | 1.38582 | IPF-Baseline up vs Control |
| CSF-1 | 1435 | CSF1 | P09603 | 0.000999988 | 1.66978 | IPF-Baseline up vs Control |
| FLRT1 | 23769 | FLRT1 | Q9NZU1 | 0.00109578 | 1.28199 | IPF-Baseline up vs Control |
| EP15R | 58513 | EPS15L1 | Q9UBC2 | 0.00110187 | 1.27645 | IPF-Baseline up vs Control |

TABLE 1A-continued

Fibrotic pulmonary disease biomarker proteins (upregulated). Marker proteins have been identified with p(FDR) < 0.01, FC > 1.2x, n = 262; 174 proteins upregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| Azurocidin | 566 | AZU1 | P20160 | 0.0011022 | 1.33249 | IPF-Baseline up vs Control |
| COX-2 | 5743 | PTGS2 | P35354 | 0.00112433 | 1.51298 | IPF-Baseline up vs Control |
| ASM3A | 10924 | SMPDL3A | Q92484 | 0.00113407 | 1.45068 | IPF-Baseline up vs Control |
| MCP-4 | 6357 | CCL13 | O99616 | 0.00123469 | 1.53294 | IPF-Baseline up vs Control |
| Myeloperoxidase | 4353 | MPO | P05164 | 0.00127381 | 1.43084 | IPF-Baseline up vs Control |
| SKP1 | 6500 | SKP1 | P63208 | 0.00128357 | 1.29436 | IPF-Baseline up vs Control |
| MMP-1 | 4312 | MMP1 | P03956 | 0.00137452 | 1.50942 | IPF-Baseline up vs Control |
| RAN | 5901 | RAN | P62826 | 0.00138722 | 1.35935 | IPF-Baseline up vs Control |
| PACAP-27 | 116 | ADCYAP1 | P18509 | 0.00147735 | 1.26374 | IPF-Baseline up vs Control |
| NG36 | 10919 | EHMT2 | Q96KQ7 | 0.00155681 | 1.21559 | IPF-Baseline up vs Control |
| MBD4 | 8930 | MBD4 | O95243 | 0.00157949 | 1.46935 | IPF-Baseline up vs Control |
| PSA-ACT | 354 12 | KLK3 SERPINA3 | P07288 P01011 | 0.00175059 | 1.49302 | IPF-Baseline up vs Control |
| PAFAH beta subunit | 5049 | PAFAH1B2 | P68402 | 0.00176448 | 1.26625 | IPF-Baseline up vs Control |
| OBCAM | 4978 | OPCML | Q14982 | 0.00177672 | 1.23158 | IPF-Baseline up vs Control |
| BMPER | 168667 | BMPER | Q8N8U9 | 0.00180385 | 1.26938 | IPF-Baseline up vs Control |
| BPI | 671 | BPI | P17213 | 0.00183319 | 4.13979 | IPF-Baseline up vs Control |
| MATK | 4145 | MATK | P42679 | 0.00204296 | 1.57543 | IPF-Baseline up vs Control |
| CATE | 1510 | CTSE | P14091 | 0.00209243 | 1.55577 | IPF-Baseline up vs Control |
| Plasmin | 5340 | PLG | P00747 | 0.00216666 | 1.33246 | IPF-Baseline up vs Control |
| CPNE1 | 8904 | CPNE1 | Q99829 | 0.00217877 | 1.55166 | IPF-Baseline up vs Control |
| ULBP-3 | 79465 | ULBP3 | Q9BZM4 | 0.00223735 | 1.27446 | IPF-Baseline up vs Control |
| Cripto | 6997 | TDGF1 | P13385 | 0.00225129 | 1.30062 | IPF-Baseline up vs Control |
| Calpain I | 823 826 | CAPN1 CAPNS1 | P07384 P04632 | 0.00234514 | 1.27918 | IPF-Baseline up vs Control |
| Thrombospondin-1 | 7057 | THBS1 | P07996 | 0.00248811 | 1.46794 | IPF-Baseline up vs Control |
| CHST6 | 4166 | CHST6 | Q9GZX3 | 0.00249809 | 1.23918 | IPF-Baseline up vs Control |
| Testican-1 | 6695 | SPOCK1 | Q08629 | 0.00253377 | 1.26887 | IPF-Baseline up vs Control |
| TIMP-3 | 7078 | TIMP3 | P35625 | 0.00261046 | 1.42678 | IPF-Baseline up vs Control |
| GX | 8399 | PLA2G10 | O15496 | 0.00279047 | 1.23456 | IPF-Baseline up vs Control |
| PDE7A | 5150 | PDE7A | Q13946 | 0.00292702 | 1.23995 | IPF-Baseline up vs Control |
| SSRP1 | 6749 | SSRP1 | Q08945 | 0.00300883 | 2.08277 | IPF-Baseline up vs Control |

TABLE 1B

Fibrotic pulmonary disease biomarker proteins (downregulated). Marker
proteins have been identified with p(FDR) < 0.01, FC > 1.2x, n = 262;
88 proteins downregulated in IPF vs. control are shown.
Study 2 differentially expressed protein

| Target | Entrez GeneID | Entrez GeneSymbol | UniProt | p-value | FoldChange (IPF vs. Control) | FoldChange (Description) |
|---|---|---|---|---|---|---|
| METAP1 | 23173 | METAP1 | P53582 | 9.21E−22 | −3.52411 | IPF-Baseline down vs Control |
| SLIK5 | 26050 | SLITRK5 | O94991 | 1.26E−16 | −1.53867 | IPF-Baseline down vs Control |
| sRAGE | 177 | AGER | Q15109 | 1.96E−15 | −1.69619 | IPF-Baseline down vs Control |
| TGF-b R III | 7049 | TGFBR3 | Q03167 | 4.54E−14 | −1.30835 | IPF-Baseline down vs Control |
| RGM-C | 148738 | HFE2 | Q6ZVN8 | 5.48E−13 | −1.31264 | IPF-Baseline down vs Control |
| NCAM-120 | 4684 | NCAM1 | P13591 | 6.20E−13 | −1.30594 | IPF-Baseline down vs Control |
| NCAM-L1 | 3897 | L1CAM | P32004 | 1.37E−12 | −1.33744 | IPF-Baseline down vs Control |
| phosphoglycerate kinase 1 | 5230 | PGK1 | P00558 | 1.45E−12 | −1.85791 | IPF-Baseline down vs Control |
| CNTFR alpha | 1271 | CNTFR | P26992 | 2.18E−12 | −1.49834 | IPF-Baseline down vs Control |
| IL-1 sRI | 3554 | IL1R1 | P14778 | 3.36E−12 | −1.44229 | IPF-Baseline down vs Control |
| Lymphotoxin a1/b2 | 4049 4050 | LTA LTB | P01374 Q06643 | 4.79E−12 | −1.28121 | IPF-Baseline down vs Control |
| bFGF-R | 2260 | FGFR1 | P11362 | 4.84E−12 | −1.23515 | IPF-Baseline down vs Control |
| Endoglin | 2022 | ENG | P17813 | 3.75E−11 | −1.44841 | IPF-Baseline down vs Control |
| ATS13 | 11093 | ADAMTS13 | Q76LX8 | 3.76E−11 | −1.34398 | IPF-Baseline down vs Control |
| UNC5H4 | 137970 | UNC5D | Q6UXZ4 | 3.77E−11 | −1.50039 | IPF-Baseline down vs Control |
| MATN2 | 4147 | MATN2 | O00339 | 4.08E−11 | −1.2313 | IPF-Baseline down vs Control |
| LRIG3 | 121227 | LRIG3 | Q6UXM1 | 6.28E−11 | −1.38206 | IPF-Baseline down vs Control |
| DAF | 1604 | CD55 | P08174 | 1.59E−10 | −1.23646 | IPF-Baseline down vs Control |
| Sonic Hedgehog | 6469 | SHH | Q15465 | 2.58E−10 | −1.52834 | IPF-Baseline down vs Control |
| CAMK2D | 817 | CAMK2D | Q13557 | 3.80E−10 | −1.77385 | IPF-Baseline down vs Control |
| LYNB | 4067 | LYN | P07948 | 1.87E−09 | −1.70397 | IPF-Baseline down vs Control |
| Semaphorin-6A | 57556 | SEMA6A | Q9H2E6 | 2.14E−09 | −1.34688 | IPF-Baseline down vs Control |
| AMPK a2b2g1 | 5563 5565 5571 | PRKAA2 PRKAB2 PRKAG1 | P54646 O43741 P54619 | 2.59E−09 | −1.84555 | IPF-Baseline down vs Control |
| FER | 2241 | FER | P16591 | 2.94E−09 | −2.17179 | IPF-Baseline down vs Control |
| CAMK2B | 816 | CAMK2B | Q13554 | 4.33E−09 | −1.74339 | IPF-Baseline down vs Control |
| MMP-3 | 4314 | MMP3 | P08254 | 8.42E−09 | −2.73309 | IPF-Baseline down vs Control |
| Carbonic anhydrase 6 | 765 | CA6 | P23280 | 1.00E−08 | −1.6323 | IPF-Baseline down vs Control |
| EphB6 | 2051 | EPHB6 | O15197 | 1.10E−08 | −1.20157 | IPF-Baseline down vs Control |
| EphA1 | 2041 | EPHA1 | P21709 | 1.67E−08 | −1.37492 | IPF-Baseline down vs Control |
| ERBB1 | 1956 | EGFR | P00533 | 1.74E−08 | −1.21591 | IPF-Baseline down vs Control |
| Ephrin-A5 | 1946 | EFNA5 | P52803 | 2.03E−08 | −1.36768 | IPF-Baseline down vs Control |
| CAMK2A | 815 | CAMK2A | Q9UQM7 | 2.05E−08 | −1.66666 | IPF-Baseline down vs Control |
| TrkC | 4916 | NTRK3 | Q16288 | 2.39E−08 | −1.24118 | IPF-Baseline down vs Control |
| WFKN2 | 124857 | WFIKKN2 | Q8TEU8 | 3.40E−08 | −1.34719 | IPF-Baseline down vs Control |
| RGMA | 56963 | RGMA | Q96B86 | 4.41E−08 | −1.35993 | IPF-Baseline down vs Control |
| IDS | 3423 | IDS | P22304 | 5.26E−08 | −1.3268 | IPF-Baseline down vs Control |
| TrkB | 4915 | NTRK2 | Q16620 | 6.60E−08 | −1.2045 | IPF-Baseline down vs Control |
| Cathepsin V | 1515 | CTSL2 | O60911 | 8.41E−08 | −1.42082 | IPF-Baseline down vs Control |
| Mn SOD | 6648 | SOD2 | P04179 | 9.06E−08 | −1.22193 | IPF-Baseline down vs Control |
| MP2K4 | 6416 | MAP2K4 | P45985 | 9.30E−08 | −1.30101 | IPF-Baseline down vs Control |
| Cadherin-5 | 1003 | CDH5 | P33151 | 1.23E−07 | −1.24254 | IPF-Baseline down vs Control |
| PCSK7 | 9159 | PCSK7 | Q16549 | 3.02E−07 | −1.39555 | IPF-Baseline down vs Control |
| IL-1 R AcP | 3556 | IL1RAP | Q9NPH3 | 1.42E−06 | −1.28716 | IPF-Baseline down vs Control |
| EDA | 1896 | EDA | Q92838 | 1.45E−06 | −1.40884 | IPF-Baseline down vs Control |
| BOC | 91653 | BOC | Q9BWV1 | 1.78E−06 | −1.30703 | IPF-Baseline down vs Control |
| COMMD7 | 149951 | COMMD7 | Q86VX2 | 5.50E−06 | −1.3293 | IPF-Baseline down vs Control |
| FYN | 2534 | FYN | P06241 | 6.42E−06 | −2.37353 | IPF-Baseline down vs Control |
| SHC1 | 6464 | SHC1 | P29353 | 9.32E−06 | −1.41344 | IPF-Baseline down vs Control |
| PDGF Rb | 5159 | PDGFRB | P09619 | 1.47E−05 | −1.40369 | IPF-Baseline down vs Control |
| IGF-I sR | 3480 | IGF1R | P08069 | 1.63E−05 | −1.25281 | IPF-Baseline down vs Control |
| IGFBP-2 | 3485 | IGFBP2 | P18065 | 1.79E−05 | −1.27751 | IPF-Baseline down vs Control |
| sTie-2 | 7010 | TEK | Q02763 | 2.29E−05 | −1.2446 | IPF-Baseline down vs Control |
| LY9 | 4063 | LY9 | Q9HBG7 | 2.42E−05 | −1.30885 | IPF-Baseline down vs Control |
| CD109 | 135228 | CD109 | Q6YHK3 | 2.86E−05 | −1.42742 | IPF-Baseline down vs Control |
| CYTT | 1470 | CST2 | P09228 | 3.39E−05 | −1.36018 | IPF-Baseline down vs Control |
| LYN | 4067 | LYN | P07948 | 3.60E−05 | −1.51471 | IPF-Baseline down vs Control |
| XTP3A | 79077 | DCTPP1 | Q9H773 | 4.51E−05 | −1.23348 | IPF-Baseline down vs Control |
| BGN | 633 | BGN | P21810 | 4.93E−05 | −1.2413 | IPF-Baseline down vs Control |
| ART | 181 | AGRP | O00253 | 5.06E−05 | −1.31411 | IPF-Baseline down vs Control |
| Elafin | 5266 | PI3 | P19957 | 5.83E−05 | −1.40487 | IPF-Baseline down vs Control |
| ADAM 9 | 8754 | ADAM9 | Q13443 | 7.47E−05 | −1.65831 | IPF-Baseline down vs Control |
| PDPK1 | 5170 | PDPK1 | O15530 | 8.30E−05 | −1.81173 | IPF-Baseline down vs Control |
| sLeptin R | 3953 | LEPR | P48357 | 9.45E−05 | −1.27922 | IPF-Baseline down vs Control |
| BMP-7 | 655 | BMP7 | P18075 | 9.59E−05 | −1.2765 | IPF-Baseline down vs Control |
| Integrin a1b1 | 3672 3688 | ITGA1 ITGB1 | P56199 P05556 | 0.000113895 | −1.54663 | IPF-Baseline down vs Control |

TABLE 1B-continued

Fibrotic pulmonary disease biomarker proteins (downregulated). Marker proteins have been identified with p(FDR) < 0.01, FC > 1.2x, n = 262; 88 proteins downregulated in IPF vs. control are shown.
Study 2 differentially expressed protein

| Target | Entrez GeneID | Entrez GeneSymbol | UniProt | p-value | FoldChange (IPF vs. Control) | FoldChange (Description) |
|---|---|---|---|---|---|---|
| SRCN1 | 6714 | SRC | P12931 | 0.000147453 | −1.41024 | IPF-Baseline down vs Control |
| JNK2 | 5601 | MAPK9 | P45984 | 0.000168267 | −1.21905 | IPF-Baseline down vs Control |
| IR | 3643 | INSR | P06213 | 0.000171593 | −1.24842 | IPF-Baseline down vs Control |
| GASP-2 | 114928 | GPRASP2 | Q96D09 | 0.000215307 | −1.24857 | IPF-Baseline down vs Control |
| b-ECGF | 2246 | FGF1 | P05230 | 0.000217493 | −1.20768 | IPF-Baseline down vs Control |
| Siglec-3 | 945 | CD33 | P20138 | 0.000285117 | −1.33873 | IPF-Baseline down vs Control |
| CYTN | 1469 | CST1 | P01037 | 0.000526955 | −1.25847 | IPF-Baseline down vs Control |
| LAG-3 | 3902 | LAG3 | P18627 | 0.000543879 | −1.28161 | IPF-Baseline down vs Control |
| Cystatin M | 1474 | CST6 | Q15828 | 0.000602595 | −1.23413 | IPF-Baseline down vs Control |
| Adiponectin | 9370 | ADIPOQ | Q15848 | 0.000685824 | −1.24709 | IPF-Baseline down vs Control |
| DC-SIGN | 30835 | CD209 | Q9NNX6 | 0.000768396 | −1.20751 | IPF-Baseline down vs Control |
| PDK1 | 5163 | PDK1 | Q15118 | 0.00105885 | −2.05488 | IPF-Baseline down vs Control |
| PERL | 4025 | LPO | P22079 | 0.00108209 | −1.23178 | IPF-Baseline down vs Control |
| Nectin-like protein 2 | 23705 | CADM1 | Q9BY67 | 0.00130427 | −1.20929 | IPF-Baseline down vs Control |
| TEC | 7006 | TEC | P42680 | 0.00144851 | −1.30303 | IPF-Baseline down vs Control |
| Ck-b-8-1 | 6368 | CCL23 | P55773 | 0.00156062 | −1.20917 | IPF-Baseline down vs Control |
| Activin A | 3624 | INHBA | P08476 | 0.001905 | −1.20745 | IPF-Baseline down vs Control |
| Cofilin-1 | 1072 | CFL1 | P23528 | 0.00192739 | −1.22991 | IPF-Baseline down vs Control |
| PKC-A | 5578 | PRKCA | P17252 | 0.00215465 | −1.31513 | IPF-Baseline down vs Control |
| KPCT | 5588 | PRKCQ | Q04759 | 0.00227261 | −1.79846 | IPF-Baseline down vs Control |
| IL-5 Ra | 3568 | IL5RA | Q01344 | 0.00245521 | −1.27362 | IPF-Baseline down vs Control |
| BST1 | 683 | BST1 | Q10588 | 0.00295217 | −1.22839 | IPF-Baseline down vs Control |
| FGF-19 | 9965 | FGF19 | O95750 | 0.00303264 | −1.42081 | IPF-Baseline down vs Control |

TABLE 2A

Fibrotic pulmonary disease biomarker proteins overlapping between study 1 and study 2 (upregulated). Marker proteins (n = 8) that have been identified with p(FDR) < 0.01, FC > 1.2, up-regulated in study 2 (Table 1A, n = 174) and that have been identified with p(FDR) < 0.01, FC > 1.15, up-regulated in study 1 (n = 125); and are upregulated in IPF vs. control are shown.

| Consistent differentially expressed proteins in Study 1 and 2 | | | | | Study 2 data | | Study 1 data | |
|---|---|---|---|---|---|---|---|---|
| Entrez GeneID | Entrez GeneSymbol | UniProt | Target | Fold-Change | p-value | Fold Change | p-value | Fold Change |
| 7087 | ICAM5 | Q9UMF0 | sICAM-5 | IPF1 up vs control | 5.36E−16 | 1.6161 | 2.42E−08 | 2.07 |
| 1512 | CTSH | P09668 | Cathepsin H | IPF1 up vs control | 5.68E−13 | 1.30088 | 1.37E−06 | 1.45 |
| 718 | C3 | P01024 | iC3b | IPF1 up vs control | 6.55E−10 | 1.73599 | 3.15E−03 | 1.44 |
| 4316 | MMP7 | P09237 | MMP-7 | IPF1 up vs control | 2.06E−09 | 1.5265 | 2.38E−07 | 2.71 |
| 4048 | LTA4H | P09960 | LKHA4 | IPF1 up vs control | 3.44E−09 | 8.53381 | 4.48E−03 | 3.24 |
| 6362 | CCL18 | P55774 | PARC | IPF1 up vs control | 1.84E−07 | 1.40298 | 3.15E−03 | 1.5 |
| 2 | A2M | P01023 | a2-Macroglobulin | IPF1 up vs control | 1.19E−05 | 1.60132 | 1.76E−03 | 1.36 |
| 3425 | IDUA | P35475 | IDUA | IPF1 up vs control | 0.000297778 | 1.20044 | 7.00E−03 | 1.36 |

TABLE 2B

Fibrotic pulmonary disease biomarker proteins overlapping between study 1 and study 2 (downregulated). Marker proteins (n = 20) that have been identified with p(FDR) < 0.01, FC > 1.2, down-regulated in study 2 (Table 1A, n = 88) and that have been identified with p(FDR) < 0.01, FC > 1.15, down-regulated in study 1 (n = 175); and are downregulated in IPF vs. control are shown.

| Consistent differentially expressed proteins in Study 1 and 2 | | | | | Study 2 data | | Study 1 data | |
|---|---|---|---|---|---|---|---|---|
| Entrez GeneID | Entrez GeneSymbol | UniProt | Target | Fold-Change | p-value | Fold Change | p-value | Fold Change |
| 5230 | PGK1 | P00558 | phosphoglycerate kinase 1 | IPF1 down vs control | 1.45E−12 | −1.85791 | 9.50E−05 | −1.42 |
| 817 | CAMK2D | Q13557 | CAMK2D | IPF1 down vs control | 3.80E−10 | −1.77385 | 2.38E−07 | −3.21 |
| 4067 | LYN | P07948 | LYNB | IPF1 down vs control | 1.87E−09 | −1.70397 | 1.75E−04 | −2.08 |
| 5563 5565 5571 | PRKAA2 PRKAB2 PRKAG1 | P54646 O43741 P54619 | AMPK a2b2g1 | IPF1 down vs control | 2.59E−09 | −1.84555 | 4.56E−06 | −3.5 |
| 2241 | FER | P16591 | FER | IPF1 down vs control | 2.94E−09 | −2.17179 | 3.13E−05 | −2.8 |
| 816 | CAMK2B | Q13554 | CAMK2B | IPF1 down vs control | 4.33E−09 | −1.74339 | 2.38E−07 | −3.79 |
| 815 | CAMK2A | Q9UQM7 | CAMK2A | IPF1 down vs control | 2.05E−08 | −1.66666 | 1.38E−07 | −3.43 |

TABLE 2B-continued

Fibrotic pulmonary disease biomarker proteins overlapping between study 1 and study 2 (downregulated). Marker proteins (n = 20) that have been identified with p(FDR) < 0.01, FC > 1.2, down-regulated in study 2 (Table 1A, n = 88) and that have been identified with p(FDR) < 0.01, FC > 1.15, down-regulated in study 1 (n = 175); and are downregulated in IPF vs. control are shown.

| Entrez GeneID | Entrez GeneSymbol | UniProt | Target | Fold-Change | Study 2 data p-value | Study 2 data Fold Change | Study 1 data p-value | Study 1 data Fold Change |
|---|---|---|---|---|---|---|---|---|
| 4916 | NTRK3 | Q16288 | TrkC | IPF1 down vs control | 2.39E-08 | -1.24118 | 2.71E-02 | -1.24 |
| 3423 | IDS | P22304 | IDS | IPF1 down vs control | 5.26E-08 | -1.3268 | 4.46E-02 | -1.5 |
| 149951 | COMMD7 | Q86VX2 | COMMD7 | IPF1 down vs control | 5.50E-06 | -1.3293 | 1.48E-08 | -2.09 |
| 2534 | FYN | P06241 | FYN | IPF1 down vs control | 6.42E-06 | -2.37353 | 5.08E-07 | -2.71 |
| 6464 | SHC1 | P29353 | SHC1 | IPF1 down vs control | 9.32E-06 | -1.41344 | 6.01E-08 | -2.11 |
| 4067 | LYN | P07948 | LYN | IPF1 down vs control | 3.60E-05 | -1.51471 | 3.21E-03 | -2.01 |
| 633 | BGN | P21810 | BGN | IPF1 down vs control | 4.93E-05 | -1.2413 | 3.71E-05 | -1.57 |
| 5170 | PDPK1 | O15530 | PDPK1 | IPF1 down vs control | 8.30E-05 | -1.81173 | 7.91E-05 | -3.74 |
| 3672 3688 | ITGA1 ITGB1 | P56199 P05556 | Integrin a1b1 | IPF1 down vs control | 0.000113895 | -1.54663 | 3.30E-04 | -1.95 |
| 7006 | TEC | P42680 | TEC | IPF1 down vs control | 0.00144851 | -1.30303 | 4.48E-03 | -1.25 |
| 1072 | CFL1 | P23528 | Cofilin-1 | IPF1 down vs control | 0.00192739 | -1.22991 | 2.42E-08 | -2.34 |
| 5578 | PRKCA | P17252 | PKC-A | IPF1 down vs control | 0.00215465 | -1.31513 | 7.99E-03 | -1.65 |
| 5588 | PRKCQ | Q04759 | KPCT | IPF1 down vs control | 0.00227261 | -1.79846 | 4.48E-03 | -1.53 |

TABLE 3A

Fibrotic pulmonary disease biomarker proteins that predict disease progression (positively correlated with risk).

| Entrez GeneID | Entrez GeneSymbol | UniProt | Target | Mortality high risk | PFS high risk | correlation with risk | Mortality p-value | PFS p-value |
|---|---|---|---|---|---|---|---|---|
| 7076 | TIMP1 | P01033 | TIMP-1 | High 82 | High 88 | positive | 0.0286 | 0.00251 |
| 4316 | MMP7 | P09237 | MMP-7 | High 78 | High 79 | positive | 0.0142 | 0.000637 |
| 5764 | PTN | P21246 | PTN | High 49 | High 60 | positive | 0.00235 | 0.00537 |
| 3624 | INHBA | P08476 | Activin A | High 31 | High 35 | positive | 0.099 | 0.00987 |
| 3082 | HGF | P14210 | HGF | High 109 | High 109 | positive | 0.0255 | 0.00583 |
| 4192 | MDK | P21741 | Midkine | High 67 | High 74 | positive | 0.023 | 0.00489 |
| 7422 | VEGFA | P15692 | VEGF121 | High 94 | High 43 | positive | 0.00664 | 0.00254 |
| 5139 | PDE3A | Q14432 | PDE3A | High 45 | High 34 | positive | 0.0214 | 0.0215 |
| 51119 | SBDS | Q9Y3A5 | SBDS | High 31 | High 32 | positive | 0.00365 | 0.0427 |
| 27121 | DKK4 | Q9UBT3 | Dkk-4 | High 51 | High 64 | positive | 0.00529 | 0.0625 |
| 7087 | ICAM5 | Q9UMF0 | sICAM-5 | High 123 | High 102 | positive | 0.229 | 0.00223 |
| 8578 | SCARF1 | Q14162 | SREC-I | High 36 | High 24 | positive | 0.00057 | 0.000365 |
| 5595 | MAPK3 | P27361 | ERK-1 | High 53 | High 53 | positive | 0.00218 | 0.0681 |
| 22943 | DKK1 | O94907 | DKK1 | High 78 | High 78 | positive | 0.0154 | 0.0157 |
| 2 | A2M | P01023 | a2-Macroglobulin | High 30 | Low 121 | positive | 0.0294 | 0.174 |
| 55577 | NAGK | Q9UJ70 | NAGK | High 87 | Low 118 | positive | 0.0081 | 0.166 |
| 51506 | UFC1 | O9Y3C8 | UFC1 | High 63 | High 52 | positive | 0.00892 | 0.135 |
| 6449 | SGTA | O43765 | SGTA | High 52 | High 40 | positive | 0.00721 | 0.0566 |

TABLE 3B

Fibrotic pulmonary disease biomarker proteins that predict disease progression (negatively correlated with risk).

| Entrez GeneID | Entrez GeneSymbol | UniProt | Target | Mortality high risk | PFS high risk | correlation with risk | Mortality p-value | PFS p-value | Rank |
|---|---|---|---|---|---|---|---|---|---|
| 8993 | PGLYRP1 | O75594 | PGRP-S | Low 31 | Low 34 | negative | 0.000324 | 0.000662 | 3 |
| 2487 | FRZB | Q92765 | sFRP-3 | Low 53 | Low 80 | negative | 0.00825 | 0.0058 | 3 |
| 1001 | CDH3 | P22223 | P-Cadherin | Low 45 | Low 63 | negative | 0.00171 | 0.00217 | 4 |
| 6749 | SSRP1 | Q08945 | SSRP1 | Low 31 | Low 31 | negative | 0.0105 | 0.00317 | 5 |
| 197 | AHSG | P02765 | a2-HS-Glycoprotein | Low 36 | Low 36 | negative | 5.27e-05 | 0.000759 | 6 |
| 5623 | PSPN | O60542 | Persephin | Low 34 | Low 43 | negative | 0.000166 | 0.0206 | 6 |
| 27 | ABL2 | P42684 | ABL2 | Low 21 | Low 39 | negative | 0.00648 | 0.00353 | 7 |
| 3815 | KIT | P10721 | SCF sR | Low 27 | Low 76 | negative | 0.00122 | 0.0343 | 7 |
| 30817 | EMR2 | Q9UHX3 | EMR2 | Low 64 | Low 69 | negative | 0.00183 | 0.044 | 9 |
| 4485 | MST1 | P26927 | MSP | Low 88 | Low 90 | negative | 0.00839 | 0.0153 | 9 |
| 83886 | PRSS27 | Q9BQR3 | Marapsin | Low 59 | Low 10 | negative | 0.00187 | 0.0087 | 10 |
| 30010 | NXPH1 | P58417 | NXPH1 | Low 34 | Low 34 | negative | 0.00843 | 0.0226 | 10 |
| 7535 | ZAP70 | P43403 | ZAP70 | Low 60 | Low 26 | negative | 0.0399 | 0.000135 | 10 |
| 10752 | CHL1 | O00533 | CHL1 | Low 47 | Low 50 | negative | 0.000716 | 0.0835 | 11 |
| 5925 | RB1 | P06400 | Rb | Low 97 | Low 87 | negative | 0.0133 | 0.0466 | 11 |
| 1013 | CDH15 | P55291 | CAD15 | Low 65 | Low 10 | negative | 0.0292 | 0.000523 | 12 |

TABLE 3B-continued

Fibrotic pulmonary disease biomarker proteins that predict disease progression (negatively correlated with risk).

| Entrez GeneID | Entrez GeneSymbol | UniProt | Target | Mortality high risk | PFS high risk | correlation with risk | Mortality p-value | PFS p-value | Rank |
|---|---|---|---|---|---|---|---|---|---|
| 1152 1158 | CKB CKM | P12277 P06732 | CK-MB | Low 83 | Low 91 | negative | 0.0122 | 0.0328 | 12 |
| 26280 | IL1RAPL2 | Q9NP60 | IL-1 sR9 | Low 73 | Low 52 | negative | 0.00508 | 0.0669 | 12 |
| 4049 4050 | LTA LTB | P01374 Q06643 | Lymphotoxin a2/b1 | Low 8 | Low 66 | negative | 0.000341 | 0.00625 | 12 |
| 5539 | PPY | P01298 | PH | Low 41 | Low 68 | negative | 0.000555 | 0.00305 | 12 |
| 332 | BIRC5 | O15392 | Survivin | Low 71 | Low 34 | negative | 0.0456 | 0.016 | 12 |
| 3570 | IL6R | P08887 | IL-6 sRa | Low 94 | Low 8 | negative | 0.00141 | 0.0889 | 13 |
| 64581 | CLEC7A | Q9BXN2 | CLC7A | Low 72 | Low 76 | negative | 0.0474 | 0.00921 | 13 |
| 3292 | HSD17B1 | P14061 | 17-beta-HSD 1 | Low 87 | Low 83 | negative | 0.0242 | 0.00483 | 14 |
| 4684 | NCAM1 | P13591 | NCAM-120 | Low 51 | Low 54 | negative | 0.0043 | 0.0522 | 14 |

TABLE 4A

Fibrotic pulmonary disease biomarker proteins (upregulated). Marker proteins have been identified with p(FDR) < 0.01, FC > 1.2x, n = 262; 16 proteins upregulated in IPF vs. control are shown.

| Target | Entrez GeneID | Entrez GeneSymbol | UniProt | p-value | FoldChange (IPF vs. Control) | Foldchange (Description) |
|---|---|---|---|---|---|---|
| a2-Macroglobulin | 2 | A2M | P01023 | 1.19E−05 | 1.60132 | IPF-Baseline up vs Control |
| PUR8 | 158 | ADSL | P30566 | 3.05E−14 | 2.87734 | IPF-Baseline up vs Control |
| iC3b | 718 | C3 | P01024 | 6.55E−10 | 1.73599 | IPF-Baseline up vs Control |
| C4b | 720 721 | C4A C4B | P0C0L4 P0C0L5 | 8.41E−05 | 2.21215 | IPF-Baseline up vs Control |
| CAPG | 822 | CAPG | P40121 | 3.69E−05 | 1.90263 | IPF-Baseline up vs Control |
| PARC | 6362 | CCL18 | P55774 | 1.84E−07 | 1.40298 | IPF-Baseline up vs Control |
| Cathepsin H | 1512 | CTSH | P09668 | 5.68E−13 | 1.30088 | IPF-Baseline up vs Control |
| Discoidin domain receptor 2 | 4921 | DDR2 | Q16832 | 0.000105 | 1.25463 | IPF-Baseline up vs Control |
| sICAM-5 | 7087 | ICAM5 | Q9UMF0 | 5.36E−16 | 1.6161 | IPF-Baseline up vs Control |
| LKHA4 | 4048 | LTA4H | P09960 | 3.44E−09 | 8.53381 | IPF-Baseline up vs Control |
| MMP-7 | 4316 | MMP7 | P09237 | 2.06E−09 | 1.5265 | IPF-Baseline up vs Control |
| MMP-9 | 4318 | MMP9 | P14780 | 2.58E−06 | 1.48952 | IPF-Baseline up vs Control |
| NXPH1 | 30010 | NXPH1 | P58417 | 0.000152 | 1.40755 | IPF-Baseline up vs Control |
| OLR1 | 4973 | OLR1 | P78380 | 9.39E−05 | 1.77154 | IPF-Baseline up vs Control |
| PTK6 | 5753 | PTK6 | Q13882 | 6.80E−05 | 1.54905 | IPF-Baseline up vs Control |
| calgranulin B | 6280 | S100A9 | P06702 | 6.55E−08 | 1.83576 | IPF-Baseline up vs Control |

TABLE 4B

Fibrotic pulmonary disease biomarker proteins (downregulated). Marker proteins have been identified with p(FDR) < 0.01, FC > 1.2x, n = 262; 15 proteins downregulated in IPF vs. control are shown.

| Target | Entrez GeneID | Entrez GeneSymbol | UniProt | p-value | FoldChange (IPF vs. Control) | FoldChange (Description) |
|---|---|---|---|---|---|---|
| AMPK a2b2g1 | 5563 5565 5571 | PRKAA2 PRKAB2 PRKAG1 | P54646 O43741 P54619 | 2.59E−09 | −1.84555 | IPF-Baseline down vs Control |
| CAMK2A | 815 | CAMK2A | Q9UQM7 | 2.05E−08 | −1.66666 | IPF-Baseline down vs Control |
| CAMK2B | 816 | CAMK2B | Q13554 | 4.33E−09 | −1.74339 | IPF-Baseline down vs Control |
| CAMK2D | 817 | CAMK2D | Q13557 | 3.80E−10 | −1.77385 | IPF-Baseline down vs Control |
| COMMD7 | 149951 | COMMD7 | O86VX2 | 5.50E−06 | −1.3293 | IPF-Baseline down vs Control |
| FER | 2241 | FER | P16591 | 2.94E−09 | −2.17179 | IPF-Baseline down vs Control |
| FYN | 2534 | FYN | P06241 | 6.42E−06 | −2.37353 | IPF-Baseline down vs Control |
| Integrin a1b1 | 3672 3688 | ITGA1 ITGB1 | P56199 P05556 | 0.000114 | −1.54663 | IPF-Baseline down vs Control |
| LYNB | 4067 | LYN | P07948 | 1.87E−09 | −1.70397 | IPF-Baseline down vs Control |
| METAP1 | 23173 | METAP1 | P53582 | 9.21E−22 | −3.52411 | IPF-Baseline down vs Control |
| MMP-3 | 4314 | MMP3 | P08254 | 8.42E−09 | −2.73309 | IPF-Baseline down vs Control |
| PDPK1 | 5170 | PDPK1 | O15530 | 8.30E−05 | −1.81173 | IPF-Baseline down vs Control |
| phosphoglycerate kinase 1 | 5230 | PGK1 | P00558 | 1.45E−12 | −1.85791 | IPF-Baseline down vs Control |
| SHC1 | 6464 | SHC1 | P29353 | 9.32E−06 | −1.41344 | IPF-Baseline down vs Control |
| SRCN1 | 6714 | SRC | P12931 | 0.000147 | −1.41024 | IPF-Baseline down vs Control |

VIII. Embodiments

Embodiment 1

A method of determining an expression level of a fibrotic pulmonary disease marker protein set forth in Table 1A or Table 1B in a subject that has or is at risk for developing a fibrotic pulmonary disease, said method comprising: (i) obtaining a biological sample from said subject; (ii) determining an expression level of a fibrotic pulmonary disease marker protein or fragment thereof set forth in Table 1A or Table 1B in said biological sample.

Embodiment 2

The method of embodiment 1, wherein said determining comprises: (a) contacting a fibrotic pulmonary disease marker protein with a marker protein binding agent in said biological sample, thereby forming a disease marker protein-binding agent complex; and (b) detecting said disease marker protein-binding agent complex.

Embodiment 3

The method of embodiment 2, wherein said marker protein binding agent comprises a detectable moiety.

Embodiment 4

The method of embodiment 3, wherein said marker protein binding agent comprises a capturing moiety.

Embodiment 5

The method of embodiment 4, wherein said capturing moiety is a cleavable capturing moiety.

Embodiment 6

The method of any one of embodiments 2-5, wherein said detecting comprises contacting said disease marker protein-binding agent complex with a capturing agent, thereby forming a captured disease marker protein-binding agent complex.

Embodiment 7

The method of embodiment 6, wherein said detecting further comprises: (1) contacting said captured disease marker protein-binding agent complex with a tagging moiety; thereby forming a tagged disease marker protein-binding agent complex; and (2) separating said tagged disease marker protein-binding agent complex from said biological sample.

Embodiment 8

The method of embodiment 7, wherein said detecting further comprises after said separating of step (2) separating said capturing binding agent from said tagged disease marker protein-binding agent complex, thereby forming a cleaved disease marker protein-binding agent complex.

Embodiment 9

The method of embodiment 8, wherein said detecting further comprises: (3) separating said marker protein binding agent from said cleaved disease marker protein-binding agent complex; thereby forming a released marker protein binding agent; and (4) determining an amount of released marker protein binding agent.

Embodiment 10

The method of any one of embodiments 1-9, further comprising selecting a subject that has or is at risk for developing a fibrotic pulmonary disease.

Embodiment 11

The method of any one of embodiments 1-9, wherein said fibrotic pulmonary disease is idiopathic pulmonary fibrosis or familial interstitial pneumonia.

Embodiment 12

The method of any one of embodiments 1-9, wherein said fibrotic pulmonary disease marker protein is a progressive fibrotic pulmonary disease marker protein.

Embodiment 13

The method of embodiment 12, wherein said subject has or is at risk for developing a progressive fibrotic pulmonary disease.

Embodiment 14

The method of embodiment 13, wherein said progressive fibrotic pulmonary disease is idiopathic pulmonary fibrosis.

Embodiment 15

The method of embodiment 1, wherein said biological sample is a blood-derived biological sample of said subject.

Embodiment 16

The method of embodiment 15, wherein said blood-derived biological sample is whole blood, serum or plasma.

Embodiment 17

The method of embodiment 1, wherein said biological sample is urine, saliva, a pulmonary tissue, bronchoalveolar lavage sample, or exhaled breath condensate.

Embodiment 18

The method of embodiment 1, wherein an expression level of a fibrotic pulmonary disease marker protein set forth in Table 1A is determined.

Embodiment 19

The method of embodiment 18, further comprising administering to said subject an effective amount of a modulator of said fibrotic pulmonary disease marker protein set forth in Table 1A.

Embodiment 20

The method of embodiment 19, wherein said modulator is an antagonist.

Embodiment 21

The method of embodiment 20, wherein said antagonist is a peptide, small molecule, nucleic acid, antibody or aptamer.

Embodiment 22

The method of embodiment 20, wherein said expression level of said fibrotic pulmonary disease marker protein set forth in Table 1A is elevated relative to a standard control.

Embodiment 23

The method of embodiment 1, wherein an expression level of a fibrotic pulmonary disease marker protein set forth in Table 1B is determined.

Embodiment 24

The method of embodiment 23, further comprising administering to said subject an effective amount of a modulator of said fibrotic pulmonary disease marker protein set forth in Table 1B.

Embodiment 25

The method of embodiment 24, wherein said modulator is an agonist.

Embodiment 26

The method of embodiment 24, wherein said agonist is a peptide, small molecule, nucleic acid, antibody or aptamer.

Embodiment 27

The method of embodiment 25, wherein said expression level of said fibrotic pulmonary disease marker protein set forth in Table 1B is decreased relative to a standard control.

Embodiment 28

The method of embodiment 19 or 24, further comprising administering to said subject an effective amount of a further therapeutic agent.

Embodiment 29

The method of embodiment 28, wherein said therapeutic agent is an idiopathic pulmonary fibrosis drug or an anti-fibrotic drug.

Embodiment 30

The method of embodiment 28, wherein said idiopathic pulmonary fibrosis drug is a mucolytic drug.

Embodiment 31

A method of determining whether a subject has or is at risk of developing a fibrotic pulmonary disease, said method comprising: (i) detecting an expression level of one or more fibrotic pulmonary disease marker proteins set forth in Table 1A or Table 1B in a subject; (ii) determining whether said expression level is increased or decreased relative to a standard control, wherein an elevated expression level of a fibrotic pulmonary disease marker protein in Table 1A or a decreased expression level of a fibrotic pulmonary disease marker protein in Table 1B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 32

The method of embodiment 31, further comprising selecting a subject that has or is at risk for developing a fibrotic pulmonary disease.

Embodiment 33

The method of embodiment 31, wherein said fibrotic pulmonary disease is idiopathic pulmonary fibrosis or familial interstitial pneumonia.

Embodiment 34

The method of embodiment 31, wherein said one or more fibrotic pulmonary disease marker proteins is a progressive fibrotic pulmonary disease marker protein.

Embodiment 35

The method of embodiment 34, wherein said subject has or is at risk for developing a progressive fibrotic pulmonary disease.

Embodiment 36

The method of embodiment 35, wherein said progressive fibrotic pulmonary disease is idiopathic pulmonary fibrosis.

Embodiment 37

The method of embodiment 31, wherein said expression level of one or more fibrotic pulmonary disease marker proteins set forth in Table 1A or Table 1B is detected from a biological sample of said subject.

Embodiment 38

The method of embodiment 37, wherein said biological sample is a blood-derived biological sample of said subject.

Embodiment 39

The method of embodiment 38, wherein said blood-derived biological sample is whole blood, serum or plasma.

Embodiment 40

The method embodiment 37, wherein said biological sample is urine, saliva, a pulmonary tissue, bronchoalveolar lavage sample, or exhaled breath condensate.

Embodiment 41

The method of embodiment 31, further comprising administering to said subject an effective amount of a modulator of said fibrotic pulmonary disease marker protein set forth in Table 1A.

Embodiment 42

The method of embodiment 41, wherein said modulator is an antagonist.

Embodiment 43

The method of embodiment 42, wherein said antagonist is a peptide, small molecule, nucleic acid, antibody or aptamer.

Embodiment 44

The method of embodiment 31, further comprising administering to said subject an effective amount of a modulator of said fibrotic pulmonary disease marker protein set forth in Table 1B.

Embodiment 45

The method of embodiment 44, wherein said modulator is an agonist.

Embodiment 46

The method of embodiment 45, wherein said agonist is a peptide, small molecule, nucleic acid, antibody or aptamer.

Embodiment 47

The method of embodiments 41 or 44, further comprising administering to said subject an effective amount of a further therapeutic agent.

Embodiment 48

The method of embodiment 47, wherein said therapeutic agent is an idiopathic pulmonary fibrosis drug or an anti-fibrotic drug.

Embodiment 49

The method of embodiment 48, wherein said idiopathic pulmonary fibrosis drug is a mucolytic drug.

Embodiment 50

A method of determining whether a fibrotic pulmonary disease patient is at risk for progression of the fibrotic pulmonary disease, the method comprising: (i) detecting an expression level of one or more fibrotic pulmonary disease marker protein set forth in Table 1A or Table 1B in a fibrotic pulmonary disease patient; (ii) determining whether said expression level is modulated relative to a standard control, wherein a modulated expression level of a fibrotic pulmonary disease marker protein in Table 1A or Table 1B relative to said standard control indicates that said fibrotic pulmonary disease patient is at risk for progression of said fibrotic pulmonary disease; and (iii) based at least in part on said expression level in step (ii), determining whether said fibrotic pulmonary disease patient is at risk for progression of said fibrotic pulmonary disease.

Embodiment 51

The method of embodiment 50, wherein said determining whether the expression level is modulated relative to a standard control comprises determining whether the expression level is elevated or suppressed relative to other fibrotic pulmonary disease patients.

Embodiment 52

A method of determining whether a fibrotic pulmonary disease patient is at risk for progression of the fibrotic pulmonary disease, said method comprising: (i) determining a first expression level of a protein set forth in Table 1A or Table 1B in said patient at a first time point; (ii) determining a second expression level of a protein set forth in Table 1A or Table 1B in said patient at a second time point; (iii) comparing said second expression level of a protein set forth in Table 1A or Table 1B to said first expression level of a protein set forth in Table 1A or Table 1B, wherein when said second expression level of a protein set forth in Table 1A is greater than said first level of a protein set forth in Table 1A, or wherein when said second expression level of a protein set forth in Table 1B is smaller than said first level of a protein set forth in Table 1B, the patient is at risk for progression of the fibrotic pulmonary disease.

Embodiment 53

The method of embodiment 52 further comprising administering a fibrotic pulmonary disease treatment after said determining in step (i).

Embodiment 54

The method of embodiment 52, further comprising predicting a rate of progression of said fibrotic pulmonary disease in said patient based on said comparing.

Embodiment 55

The method of embodiment 52, wherein said determining said first expression level of a protein set forth in Table 1A or Table 1B and said second expression level of a protein set forth in Table 1A or Table 1B comprises normalizing said first expression level of a protein set forth in Table 1A or Table 1B and said second expression level of a protein set forth in Table 1A or Table 1B to a protein expressed from a standard gene in said patient.

Embodiment 56

The method of embodiment 55, wherein said first expression level is detected from a first biological sample of said subject and said second expression level is detected from a second biological sample of said subject.

Embodiment 57

The method of embodiment 56, wherein said first biological sample is a first bodily fluid sample and said second biological sample is a second bodily fluid sample.

Embodiment 58

A method of determining a fibrotic pulmonary disease activity in a patient, said method comprising: (i) detecting an expression level of one or more fibrotic pulmonary disease marker proteins set forth in Table 1A or Table 1B in a subject; (ii) determining whether said expression level is modulated relative to a standard control, thereby determining a fibrotic pulmonary disease activity in said patient; and (iii) based at least in part on said expression level in step (ii), determining said fibrotic pulmonary disease activity in said patient.

Embodiment 59

The method of embodiment 58, wherein said expression level of a fibrotic pulmonary disease marker protein in Table 1A is increased relative to said standard control.

Embodiment 60

The method of embodiment 58, wherein said expression level of a fibrotic pulmonary disease marker protein in Table 1B is decreased relative to said standard control.

Embodiment 61

A method of determining a fibrotic pulmonary disease activity in a patient, said method comprising: (i) determining a first expression level of a protein set forth in Table 1A or Table 1B in said patient at a first time point; (ii) determining a second expression level of a protein set forth in Table 1A or Table 1B in said patient at a second time point; (iii) comparing said second expression level of a protein set forth in Table 1A or Table 1B to said first expression level of a protein set forth in Table 1A or Table 1B, thereby determining said fibrotic pulmonary disease activity in said patient.

Embodiment 62

The method of embodiment 61, further comprising administering a fibrotic pulmonary disease treatment after said determining in step (i).

Embodiment 63

A method of determining a change in fibrotic pulmonary disease activity in a patient, said comprising: (i) determining a first expression level of a protein set forth in Table 1A or Table 1B in a patient at a first time point; (ii) determining a second expression level of a protein set forth in Table 1A or Table 1B in said patient at a second time point; and (iii) comparing said second expression level of a protein set forth in Table 1A or Table 1B to said first expression level of a protein set forth in Table 1A or Table 1B, thereby determining said change in fibrotic pulmonary disease activity in the patient.

Embodiment 64

A method of determining a change in fibrotic pulmonary disease activity in a patient, said method comprising: (i) detecting an expression level of one or more fibrotic pulmonary disease marker proteins set forth in Table 1A or Table 1B in a subject; (ii) determining whether said expression level is modulated relative to a standard control, thereby determining a change in fibrotic pulmonary disease activity in said patient; and (iii) based at least in part on said expression level in step (ii), determining said change in fibrotic pulmonary disease activity in said patient.

Embodiment 65

A method of monitoring the effect of treatment for a fibrotic pulmonary disease in a patient undergoing fibrotic pulmonary disease therapy or a patient that has received fibrotic pulmonary disease therapy comprising: (i) determining a first expression level of a protein set forth in Table 1A or Table 1B in the patient at a first time point; (ii) determining a second expression level of a protein set forth in Table 1A or Table 1B in the patient at a second time point; and (iii) comparing the second expression level of a protein set forth in Table 1A or Table 1B to the first expression level of a protein set forth in Table 1A or Table 1B, thereby determining the effect of treatment for a fibrotic pulmonary disease in the patient.

Embodiment 66

A method of monitoring the effect of treatment for a fibrotic pulmonary disease in a patient undergoing fibrotic pulmonary disease therapy or a patient that has received fibrotic pulmonary disease therapy comprising: (i) detecting an expression level of one or more fibrotic pulmonary disease marker proteins set forth in Table 1A or Table 1B in a subject; (ii) determining whether the expression level is modulated relative to a standard control, thereby monitoring the effect of treatment for a fibrotic pulmonary disease in the patient; and (iii) based at least in part on the expression level in step (ii), monitoring the effect of treatment for a fibrotic pulmonary disease in the patient.

Embodiment 67

A method of treating a fibrotic pulmonary disease in a subject in need thereof, said method comprising administering to said subject an effective amount of an modulator of a fibrotic pulmonary disease marker protein set forth in Table 1A or Table 1B, thereby treating a fibrotic pulmonary disease in said subject.

Embodiment 68

The method of embodiment 67, comprising administering to said subject an effective amount of a modulator of said fibrotic pulmonary disease marker protein set forth in Table 1A.

Embodiment 69

The method of embodiment 68, wherein said modulator is an antagonist.

Embodiment 70

The method of embodiment 69, wherein said antagonist is a peptide, small molecule, nucleic acid, antibody or aptamer.

Embodiment 71

The method of embodiment 67, comprising administering to said subject an effective amount of a modulator of said fibrotic pulmonary disease marker protein set forth in Table 1B.

Embodiment 72

The method of embodiment 71, wherein said modulator is an agonist.

Embodiment 73

The method of embodiment 72, wherein said agonist is a peptide, small molecule, nucleic acid, antibody or aptamer.

Embodiment 74

A method of treating a fibrotic pulmonary disease in a subject in need thereof, said method comprising: (i) determining whether a subject expresses an elevated level of a fibrotic pulmonary disease marker protein as set forth in Table 1A or a decreased level of a fibrotic pulmonary disease marker protein as set forth in Table 1B relative to a standard control; and (ii) when an elevated expression level of said fibrotic pulmonary disease marker protein of Table 1A or a decreased expression level of said fibrotic pulmonary disease marker protein of Table 1B is found relative to said standard control, administering to said subject a fibrotic pulmonary disease treatment, an antagonist of a fibrotic pulmonary disease marker protein set forth in Table 1A or an agonist of a fibrotic pulmonary disease marker protein set forth in Table 1B, thereby treating said subject.

Embodiment 75

The method of embodiment 74, wherein said fibrotic pulmonary disease treatment is a mucolytic drug.

Embodiment 76

A method of determining an expression level of a fibrotic pulmonary disease marker protein set forth in Table 3A or Table 3B in a subject that has or is at risk for developing a fibrotic pulmonary disease, said method comprising: (i) obtaining a biological sample from said subject; and (ii) determining an expression level of a fibrotic pulmonary disease marker protein set forth in Table 3A or Table 3B in said biological sample.

Embodiment 77

A method of determining whether a subject has or is at risk of developing a fibrotic pulmonary disease, said method comprising: (i) detecting an expression level of one or more fibrotic pulmonary disease marker proteins set forth in Table 3A or Table 3B in a subject; (ii) determining whether said expression level is increased or decreased relative to a standard control, wherein an elevated expression level of a fibrotic pulmonary disease marker protein in Table 3A or a decreased expression level of a fibrotic pulmonary disease marker protein in Table 3B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 78

A method of determining whether a fibrotic pulmonary disease patient is at risk for progression of the fibrotic pulmonary disease, the method comprising: (i) detecting an expression level of one or more fibrotic pulmonary disease marker protein set forth in Table 3A or 3B in a fibrotic pulmonary disease patient; (ii) determining whether said expression level is modulated relative to a standard control, wherein a modulated expression level of a fibrotic pulmonary disease marker protein in Table 3A or 3B relative to said standard control indicates that said fibrotic pulmonary disease patient is at risk for progression of said fibrotic pulmonary disease; and (iii) based at least in part on said expression level in step (ii), determining whether said fibrotic pulmonary disease patient is at risk for progression of said fibrotic pulmonary disease.

Embodiment 79

The method of embodiment 78, wherein said expression level of a fibrotic pulmonary disease marker protein in Table 3A is increased relative to said standard control.

Embodiment 80

The method of embodiment 78, wherein said expression level of a fibrotic pulmonary disease marker protein in Table 3B is decreased relative to said standard control.

Embodiment 81

The method of embodiment 78, wherein said determining whether the expression level is modulated relative to a standard control comprises determining whether the expression level is elevated or suppressed relative to other fibrotic pulmonary disease patients.

Embodiment 82

A method of determining whether a fibrotic pulmonary disease patient is at risk for progression of the fibrotic pulmonary disease, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, wherein when said second expression level of a protein set forth in Table 3A or Table 3B is greater than said first level of a protein set forth in Table 3A or Table 3B, or wherein when said second expression level of a protein set forth in Table 3A or Table 3B is smaller than said first level of a protein set forth in Table 3A or Table 3B, the patient is at risk for progression of the fibrotic pulmonary disease.

Embodiment 83

A method of determining a fibrotic pulmonary disease activity in a patient, said method comprising: (i) detecting an expression level of one or more fibrotic pulmonary disease marker proteins set forth in Table 3A or Table 3B in a subject; (ii) determining whether said expression level is modulated relative to a standard control, thereby determining a fibrotic pulmonary disease activity in said patient; and (iii) based at least in part on said expression level in step (ii), determining said fibrotic pulmonary disease activity in said patient.

Embodiment 84

The method of embodiment 83, wherein said expression level of a fibrotic pulmonary disease marker protein in Table 3A is increased relative to said standard control.

Embodiment 85

The method of embodiment 83, wherein said expression level of a fibrotic pulmonary disease marker protein in Table 3B is decreased relative to said standard control.

Embodiment 86

A method of determining a fibrotic pulmonary disease activity in a patient, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, thereby determining said fibrotic pulmonary disease activity in said patient.

Embodiment 87

A method of determining a change in fibrotic pulmonary disease activity in a patient, said comprising: (i) determining a first expression level of a protein set forth in Table 3A or Table 3B in a patient at a first time point; (ii) determining a second expression level of a protein set forth in Table 3A or Table 3B in said patient at a second time point; and (iii) comparing said second expression level of a protein set forth in Table 3A or Table 3B to said first expression level of a protein set forth in Table 3A or Table 3B, thereby determining said change in fibrotic pulmonary disease activity in the patient.

Embodiment 88

A method of determining a change in fibrotic pulmonary disease activity in a patient, said comprising: (i) detecting an expression level of one or more fibrotic pulmonary disease marker proteins set forth in Table 3A or Table 3B in a subject; (ii) determining whether said expression level is modulated relative to a standard control, thereby determining a change in fibrotic pulmonary disease activity in said patient; and (iii) based at least in part on said expression level in step (ii), determining said change in fibrotic pulmonary disease activity in said patient.

Embodiment 89

A method of monitoring the effect of treatment for a fibrotic pulmonary disease in a patient undergoing fibrotic pulmonary disease therapy or a patient that has received fibrotic pulmonary disease therapy comprising: (i) determining a first expression level of a protein set forth in Table 3A or Table 3B in the patient at a first time point; (ii) determining a second expression level of a protein set forth in Table 3A or Table 3B in the patient at a second time point; and (iii) comparing the second expression level of a protein set forth in Table 3A or Table 3B to the first expression level of a protein set forth in Table 3A or Table 3B, thereby determining the effect of treatment for a fibrotic pulmonary disease in the patient.

Embodiment 90

A method of monitoring the effect of treatment for a fibrotic pulmonary disease in a patient undergoing fibrotic pulmonary disease therapy or a patient that has received fibrotic pulmonary disease therapy comprising: (i) detecting an expression level of one or more fibrotic pulmonary disease marker proteins set forth in Table 3A or Table 3B in a subject; (ii) determining whether the expression level is modulated relative to a standard control, thereby monitoring the effect of treatment for a fibrotic pulmonary disease in the patient; and (iii) based at least in part on the expression level in step (ii), monitoring the effect of treatment for a fibrotic pulmonary disease in the patient.

Embodiment 91

A method of treating a fibrotic pulmonary disease in a subject in need thereof, said method comprising administering to said subject an effective amount of an modulator of a fibrotic pulmonary disease marker protein set forth in Table 3A or Table 3B, thereby treating a fibrotic pulmonary disease in said subject.

Embodiment 92

A method of treating a fibrotic pulmonary disease in a subject in need thereof, said method comprising: (i) determining whether a subject expresses an elevated level of a fibrotic pulmonary disease marker protein as set forth in Table 3A or a decreased level of a fibrotic pulmonary disease marker protein as set forth in Table 3B relative to a standard control; and (ii) when an elevated expression level of said fibrotic pulmonary disease marker protein of Table 3A or a decreased expression level of said fibrotic pulmonary disease marker protein of Table 3B is found relative to said standard control, administering to said subject a fibrotic pulmonary disease treatment, an antagonist of a fibrotic pulmonary disease marker protein set forth in Table 3A or an agonist of a fibrotic pulmonary disease marker protein set forth in Table 3B, thereby treating said subject.

Embodiment 93

The method of embodiment 92, wherein said determining whether the expression level is modulated relative to a standard control comprises determining whether the expression level is elevated or suppressed relative to other fibrotic pulmonary disease patients.

Embodiment 94

A kit comprising: (a) a marker protein binding agent capable of binding to a substance within a biological sample from a human subject having or at risk of developing a fibrotic pulmonary disease; wherein said substance is a fibrotic pulmonary disease marker protein or fragment thereof set forth in Table 1A, 1B, 2A, 2B, 3A, 3B, 4A, or 4B; (b) a detecting reagent or a detecting apparatus capable of indicating binding of said marker protein binding agent to said substance.

Embodiment 95

The kit of embodiment 94, further comprising: c) a sample collection device for collecting a sample from a subject.

Embodiment 96

The kit of embodiment 94 or 95, wherein said subject has a fibrotic pulmonary disease.

Embodiment 97

A complex in vitro comprising a marker protein binding agent bound to a fibrotic pulmonary disease marker protein or fragment thereof set forth in Table 1A, 1B, 2A, 2B, 3A, 3B, 4A, or 4B, wherein said fibrotic pulmonary disease marker protein is extracted from a human subject having or at risk of developing a fibrotic pulmonary disease.

Embodiment 98

The complex of embodiment 97, wherein said subject has a fibrotic pulmonary disease.

Embodiment 99

A method of determining an expression level of a fibrotic pulmonary disease marker protein set forth in Table 1A or Table 1B in a subject that has or is at risk for developing a fibrotic pulmonary disease, said method comprising: (i) obtaining a biological sample from said subject; and (ii) determining an expression level of a fibrotic pulmonary disease marker protein set forth in Table 1A or Table 1B in said biological sample.

Embodiment 100

The method of embodiment 99, further comprising selecting a subject that has or is at risk for developing a fibrotic pulmonary disease.

Embodiment 101

The method of embodiment 99, wherein said fibrotic pulmonary disease is idiopathic pulmonary fibrosis or familial interstitial pneumonia.

Embodiment 102

The method of embodiment 99, wherein said fibrotic pulmonary disease marker protein is a progressive fibrotic pulmonary disease marker protein.

Embodiment 103

The method of embodiment 102, wherein said subject has or is at risk for developing a progressive fibrotic pulmonary disease.

Embodiment 104

The method of embodiment 103, wherein said progressive fibrotic pulmonary disease is progressive idiopathic pulmonary fibrosis.

Embodiment 105

The method of embodiment 99, wherein said biological sample is a blood-derived biological sample of said subject.

Embodiment 106

The method of embodiment 105, wherein said blood-derived biological sample is whole blood, serum or plasma.

Embodiment 107

The method of embodiment 99, wherein said biological sample is urine, saliva, a pulmonary tissue, bronchoalveolar lavage sample, or exhaled breath condensate.

Embodiment 108

The method of embodiment 99, wherein an expression level of a fibrotic pulmonary disease marker protein set forth in Table 1A is determined.

Embodiment 109

The method of embodiment 108, further comprising administering to said subject an effective amount of a modulator of said fibrotic pulmonary disease marker protein set forth in Table 1A.

Embodiment 110

The method of embodiment 109, wherein said modulator is an antagonist.

Embodiment 111

The method of embodiment 110, wherein said antagonist is a peptide, small molecule, nucleic acid, antibody or aptamer.

Embodiment 112

The method of embodiment 110, wherein said expression level of said fibrotic pulmonary disease marker protein set forth in Table 1A is elevated relative to a standard control.

Embodiment 113

The method of embodiment 99, wherein an expression level of a fibrotic pulmonary disease marker protein set forth in Table 1B is determined.

Embodiment 114

The method of embodiment 113, further comprising administering to said subject an effective amount of a modulator of said fibrotic pulmonary disease marker protein set forth in Table 1B.

Embodiment 115

The method of embodiment 114, wherein said modulator is an agonist.

Embodiment 116

The method of embodiment 114, wherein said agonist is a peptide, small molecule, nucleic acid, antibody or aptamer.

Embodiment 117

The method of embodiment 115, wherein said expression level of said fibrotic pulmonary disease marker protein set forth in Table 1B is decreased relative to a standard control.

Embodiment 118

The method of embodiment 109 or 114, further comprising administering to said subject an effective amount of a further therapeutic agent.

Embodiment 119

The method of embodiment 118, wherein said therapeutic agent is an idiopathic pulmonary fibrosis drug.

Embodiment 120

The method of embodiment 118, wherein said idiopathic pulmonary fibrosis drug is a mucolytic drug.

Embodiment 121

A method of determining whether a subject has or is at risk of developing a fibrotic pulmonary disease, said method comprising: (i) detecting an expression level of one or more fibrotic pulmonary disease marker proteins set forth in Table 1A or Table 1B in a subject; (ii) determining whether said expression level is increased or decreased relative to a standard control, wherein an elevated expression level of a fibrotic pulmonary disease marker protein in Table 1A or a decreased expression level of a fibrotic pulmonary disease marker protein in Table 1B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 122

The method of embodiment 121, further comprising selecting a subject that has or is at risk for developing a fibrotic pulmonary disease.

Embodiment 123

The method of embodiment 121, wherein said fibrotic pulmonary disease is idiopathic pulmonary fibrosis or familial interstitial pneumonia.

Embodiment 124

The method of embodiment 121, wherein said one or more fibrotic pulmonary disease marker proteins is a progressive fibrotic pulmonary disease marker protein.

Embodiment 125

The method of embodiment 124, wherein said subject has or is at risk for developing a progressive fibrotic pulmonary disease.

Embodiment 126

The method of embodiment 125, wherein said progressive fibrotic pulmonary disease is progressive idiopathic pulmonary fibrosis.

Embodiment 127

The method of embodiment 121, wherein said expression level of one or more fibrotic pulmonary disease marker proteins set forth in Table 1A or Table 1B is detected from a biological sample of said subject.

Embodiment 128

The method of embodiment 127, wherein said biological sample is a blood-derived biological sample of said subject.

Embodiment 129

The method of embodiment 128, wherein said blood-derived biological sample is whole blood, serum or plasma.

Embodiment 130

The method embodiment 127, wherein said biological sample is urine, saliva, a pulmonary tissue, bronchoalveolar lavage sample, or exhaled breath condensate.

Embodiment 131

The method of embodiment 121, further comprising administering to said subject an effective amount of a modulator of said fibrotic pulmonary disease marker protein set forth in Table 1A.

Embodiment 132

The method of embodiment 131, wherein said modulator is an antagonist.

Embodiment 133

The method of embodiment 132, wherein said antagonist is a peptide, small molecule, nucleic acid, antibody or aptamer.

Embodiment 134

The method of embodiment 121, further comprising administering to said subject an effective amount of a modulator of said fibrotic pulmonary disease marker protein set forth in Table 1B.

Embodiment 135

The method of embodiment 134, wherein said modulator is an agonist.

Embodiment 136

The method of embodiment 135, wherein said agonist is a peptide, small molecule, nucleic acid, antibody or aptamer.

Embodiment 137

The method of embodiments 131 or 134, further comprising administering to said subject an effective amount of a further therapeutic agent.

Embodiment 138

The method of embodiment 137, wherein said therapeutic agent is an idiopathic pulmonary fibrosis drug.

Embodiment 139

The method of embodiment 138, wherein said idiopathic pulmonary fibrosis drug is a mucolytic drug.

Embodiment 140

A method of determining whether a fibrotic pulmonary disease patient is at risk for progression of the fibrotic pulmonary disease, said method comprising: (i) determining a first expression level of a protein set forth in Table 1A or Table 1B in said patient at a first time point; (ii) determining a second expression level of a protein set forth in Table 1A or Table 1B in said patient at a second time point; (iii) comparing said second expression level of a protein set forth in Table 1A or Table 1B to said first expression level of a protein set forth in Table 1A or Table 1B, wherein when said second expression level of a protein set forth in Table 1A is greater than said first level of a protein set forth in Table 1A, or wherein when said second expression level of a protein set forth in Table 1B is smaller than said first level of a protein set forth in Table 1B, the patient is at risk for progression of the fibrotic pulmonary disease.

Embodiment 141

The method of embodiment 140 further comprising administering a fibrotic pulmonary disease treatment after said determining in step (i).

Embodiment 142

The method of embodiment 140, further comprising determining a rate of progression of said fibrotic pulmonary disease in said patient based on said comparing.

Embodiment 143

The method of embodiment 140, wherein said determining said first expression level of a protein set forth in Table 1A or Table 1B and said second expression level of a protein set forth in Table 1A or Table 1B comprises normalizing said first expression level of a protein set forth in Table 1A or Table 1B and said second expression level of a protein set forth in Table 1A or Table 1B to a protein expressed from a standard gene in said patient.

Embodiment 144

The method of embodiment 143, wherein said standard gene is a GAPDH or beta-actin.

Embodiment 145

The method of embodiment 144, wherein said first expression level is detected from a first biological sample of said subject and said second expression level is detected from a second biological sample of said subject.

Embodiment 146

The method of embodiment 145, wherein said first biological sample is a first bodily fluid sample and said second biological sample is a second bodily fluid sample.

Embodiment 147

A method of determining a fibrotic pulmonary disease activity in a patient, said method comprising: (i) determining a first expression level of a protein set forth in Table 1A or Table 1B in said patient at a first time point; (ii) determining a second expression level of a protein set forth in Table 1A or Table 1B in said patient at a second time point; (iii) comparing said second expression level of a protein set forth in Table 1A or Table 1B to said first expression level of a protein set forth in Table 1A or Table 1B, thereby determining said fibrotic pulmonary disease activity in said patient.

Embodiment 148

The method of embodiment 147, further comprising administering a fibrotic pulmonary disease treatment after said determining in step (i).

Embodiment 149

A method of treating a fibrotic pulmonary disease in a subject in need thereof, said method comprising administering to said subject an effective amount of an modulator of a fibrotic pulmonary disease marker protein set forth in Table 1A or Table 1B, thereby treating a fibrotic pulmonary disease in said subject.

Embodiment 150

The method of embodiment 149, comprising administering to said subject an effective amount of a modulator of said fibrotic pulmonary disease marker protein set forth in Table 1A.

Embodiment 151

The method of embodiment 150, wherein said modulator is an antagonist.

Embodiment 152

The method of embodiment 151, wherein said antagonist is a peptide, small molecule, nucleic acid, antibody or aptamer.

Embodiment 153

The method of embodiment 149, comprising administering to said subject an effective amount of a modulator of said fibrotic pulmonary disease marker protein set forth in Table 1B.

Embodiment 154

The method of embodiment 153, wherein said modulator is an agonist.

Embodiment 155

The method of embodiment 154, wherein said agonist is a peptide, small molecule, nucleic acid, antibody or aptamer.

Embodiment 156

A method of treating a fibrotic pulmonary disease in a subject in need thereof, said method comprising: (i) determining whether a subject expresses an elevated level of a fibrotic pulmonary disease marker protein as set forth in Table 1A or a decreased level of a fibrotic pulmonary disease marker protein as set forth in Table 1B relative to a standard control; and (ii) when an elevated expression level of said fibrotic pulmonary disease marker protein of Table 1A or a decreased expression level of said fibrotic pulmonary disease marker protein of Table 1B is found relative to said standard control, administering to said subject a fibrotic pulmonary disease treatment, an antagonist of a fibrotic pulmonary disease marker protein set forth in Table 1A or an agonist of a fibrotic pulmonary disease marker protein set forth in Table 1B, thereby treating said subject.

Embodiment 157

The method of embodiment 156, wherein said fibrotic pulmonary disease treatment is a mucolytic drug.

Embodiment 158

A method of determining whether a fibrotic pulmonary disease patient is at risk for progression of the fibrotic pulmonary disease, the method comprising: (i) detecting an expression level of one or more fibrotic pulmonary disease marker protein set forth in Table 1A or 1B in a fibrotic pulmonary disease patient; (ii) determining whether said expression level is modulated relative to a standard control, wherein a modulated expression level of a fibrotic pulmonary disease marker protein in Table 1A or 1B relative to said standard control indicates that said fibrotic pulmonary disease patient is at risk for progression of said fibrotic pulmonary disease; and (iii) based at least in part on said expression level in step (ii), determining whether said fibrotic pulmonary disease patient is at risk for progression of said fibrotic pulmonary disease.

Embodiment 159

The method of embodiment 158, wherein said determining whether the expression level is modulated relative to a standard control comprises determining whether the expression level is elevated or suppressed relative to other fibrotic pulmonary disease patients.

Embodiment 160

A method of determining an expression level of a fibrotic pulmonary disease marker protein set forth in Table 3A or Table 3B in a subject that has or is at risk for developing a fibrotic pulmonary disease, said method comprising: (i) obtaining a biological sample from said subject; and (ii) determining an expression level of a fibrotic pulmonary disease marker protein set forth in Table 3A or Table 3B in said biological sample.

Embodiment 161

A method of determining whether a subject has or is at risk of developing a fibrotic pulmonary disease, said method comprising: (i) detecting an expression level of one or more fibrotic pulmonary disease marker proteins set forth in Table 3A or Table 3B in a subject; (ii) determining whether said expression level is increased or decreased relative to a standard control, wherein an elevated expression level of a fibrotic pulmonary disease marker protein in Table 3A or a decreased expression level of a fibrotic pulmonary disease marker protein in Table 3B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 162

A method of determining whether a fibrotic pulmonary disease patient is at risk for progression of the fibrotic pulmonary disease, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, wherein when said second expression level of a protein set forth in Table 3A is greater than said first level of a protein set forth in Table 3A, or wherein when said second expression level of a protein set forth in Table 1B is smaller than said first level of a protein set forth in Table 1B, the patient is at risk for progression of the fibrotic pulmonary disease.

Embodiment 163

A method of determining a fibrotic pulmonary disease activity in a patient, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, thereby determining said fibrotic pulmonary disease activity in said patient.

Embodiment 164

A method of treating a fibrotic pulmonary disease in a subject in need thereof, said method comprising administering to said subject an effective amount of an modulator of a fibrotic pulmonary disease marker protein set forth in Table 3A or Table 3B, thereby treating a fibrotic pulmonary disease in said subject.

Embodiment 165

A method of treating a fibrotic pulmonary disease in a subject in need thereof, said method comprising: (i) determining whether a subject expresses an elevated level of a fibrotic pulmonary disease marker protein as set forth in Table 3A or a decreased level of a fibrotic pulmonary disease marker protein as set forth in Table 3B relative to a standard control; and (ii) when an elevated expression level of said fibrotic pulmonary disease marker protein of Table 3A or a decreased expression level of said fibrotic pulmonary disease marker protein of Table 3B is found relative to said standard control, administering to said subject a fibrotic pulmonary disease treatment, an antagonist of a fibrotic pulmonary disease marker protein set forth in Table 3A or an agonist of a fibrotic pulmonary disease marker protein set forth in Table 3B, thereby treating said subject.

Embodiment 166

The method of embodiment 165, wherein said determining whether the expression level is modulated relative to a standard control comprises determining whether the expression level is elevated or suppressed relative to other fibrotic pulmonary disease patients.

Embodiment 167

A method of determining whether a fibrotic pulmonary disease patient is at risk for progression of the fibrotic pulmonary disease, the method comprising: (i) detecting an expression level of one or more fibrotic pulmonary disease marker protein set forth in Table 3A or 3B in a fibrotic pulmonary disease patient; (ii) determining whether the expression level is modulated relative to a standard control, wherein a modulated expression level of a fibrotic pulmonary disease marker protein in Table 3A or 3B relative to said standard control indicates that said fibrotic pulmonary disease patient is at risk for progression of the fibrotic pulmonary disease; and (iii) based at least in part on the expression level in step (ii), determining whether said fibrotic pulmonary disease patient is at risk for progression of the fibrotic pulmonary disease.

Embodiment 168

The method of embodiment 167, wherein said determining whether the expression level is modulated relative to a standard control comprises determining whether the expression level is elevated or suppressed relative to other fibrotic pulmonary disease patients.

Embodiment 169

A method of determining an expression level of a fibrotic pulmonary disease marker protein set forth in Table 2A or Table 2B in a subject that has or is at risk for developing a fibrotic pulmonary disease, said method comprising: (i) obtaining a biological sample from said subject; and (ii) determining an expression level of a fibrotic pulmonary disease marker protein set forth in Table 2A or Table 2B in said biological sample.

Embodiment 170

The method of embodiment 169, further comprising selecting a subject that has or is at risk for developing a fibrotic pulmonary disease.

Embodiment 171

The method of embodiment 169, wherein said fibrotic pulmonary disease is idiopathic pulmonary fibrosis or familial interstitial pneumonia.

Embodiment 172

The method of embodiment 169, wherein said fibrotic pulmonary disease marker protein is a progressive fibrotic pulmonary disease marker protein.

Embodiment 173

The method of embodiment 172, wherein said subject has or is at risk for developing a progressive fibrotic pulmonary disease.

Embodiment 174

The method of embodiment 173, wherein said progressive fibrotic pulmonary disease is progressive idiopathic pulmonary fibrosis.

Embodiment 175

The method of embodiment 169, wherein said biological sample is a blood-derived biological sample of said subject.

Embodiment 176

The method of embodiment 175, wherein said blood-derived biological sample is whole blood, serum or plasma.

Embodiment 177

The method of embodiment 169, wherein said biological sample is urine, saliva, a pulmonary tissue, bronchoalveolar lavage sample, or exhaled breath condensate.

Embodiment 178

The method of embodiment 169, wherein an expression level of a fibrotic pulmonary disease marker protein set forth in Table 2A is determined.

Embodiment 179

The method of embodiment 178, further comprising administering to said subject an effective amount of a modulator of said fibrotic pulmonary disease marker protein set forth in Table 2A.

Embodiment 180

The method of embodiment 179, wherein said modulator is an antagonist.

Embodiment 181

The method of embodiment 180, wherein said antagonist is a peptide, small molecule, nucleic acid, antibody or aptamer.

Embodiment 182

The method of embodiment 180, wherein said expression level of said fibrotic pulmonary disease marker protein set forth in Table 2A is elevated relative to a standard control.

Embodiment 183

The method of embodiment 169, wherein an expression level of a fibrotic pulmonary disease marker protein set forth in Table 2B is determined.

Embodiment 184

The method of embodiment 183, further comprising administering to said subject an effective amount of a modulator of said fibrotic pulmonary disease marker protein set forth in Table 2B.

Embodiment 185

The method of embodiment 184, wherein said modulator is an agonist.

Embodiment 186

The method of embodiment 184, wherein said agonist is a peptide, small molecule, nucleic acid, antibody or aptamer.

Embodiment 187

The method of embodiment 185, wherein said expression level of said fibrotic pulmonary disease marker protein set forth in Table 2B is decreased relative to a standard control.

Embodiment 188

The method of embodiment 179 or 184, further comprising administering to said subject an effective amount of a further therapeutic agent.

Embodiment 189

The method of embodiment 188, wherein said therapeutic agent is an idiopathic pulmonary fibrosis drug.

Embodiment 190

The method of embodiment 188, wherein said idiopathic pulmonary fibrosis drug is a mucolytic drug.

Embodiment 191

A method of determining whether a subject has or is at risk of developing a fibrotic pulmonary disease, said method comprising: (i) detecting an expression level of one or more fibrotic pulmonary disease marker proteins set forth in Table 2A or Table 2B in a subject; (ii) determining whether said expression level is increased or decreased relative to a standard control, wherein an elevated expression level of a fibrotic pulmonary disease marker protein in Table 2A or a decreased expression level of a fibrotic pulmonary disease marker protein in Table 2B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 192

The method of embodiment 191, further comprising selecting a subject that has or is at risk for developing a fibrotic pulmonary disease.

Embodiment 193

The method of embodiment 191, wherein said fibrotic pulmonary disease is idiopathic pulmonary fibrosis or familial interstitial pneumonia.

Embodiment 194

The method of embodiment 191, wherein said one or more fibrotic pulmonary disease marker proteins is a progressive fibrotic pulmonary disease marker protein.

Embodiment 195

The method of embodiment 194, wherein said subject has or is at risk for developing a progressive fibrotic pulmonary disease.

Embodiment 196

The method of embodiment 195, wherein said progressive fibrotic pulmonary disease is progressive idiopathic pulmonary fibrosis.

Embodiment 197

The method of embodiment 191, wherein said expression level of one or more fibrotic pulmonary disease marker proteins set forth in Table 2A or Table 2B is detected from a biological sample of said subject.

Embodiment 198

The method of embodiment 197, wherein said biological sample is a blood-derived biological sample of said subject.

Embodiment 199

The method of embodiment 198, wherein said blood-derived biological sample is whole blood, serum or plasma.

Embodiment 200

The method embodiment 197, wherein said biological sample is urine, saliva, a pulmonary tissue, bronchoalveolar lavage sample, or exhaled breath condensate.

Embodiment 201

The method of embodiment 191, further comprising administering to said subject an effective amount of a modulator of said fibrotic pulmonary disease marker protein set forth in Table 2A.

Embodiment 202

The method of embodiment 201, wherein said modulator is an antagonist.

Embodiment 203

The method of embodiment 202, wherein said antagonist is a peptide, small molecule, nucleic acid, antibody or aptamer.

Embodiment 204

The method of embodiment 191, further comprising administering to said subject an effective amount of a modulator of said fibrotic pulmonary disease marker protein set forth in Table 2B.

Embodiment 205

The method of embodiment 204, wherein said modulator is an agonist.

Embodiment 206

The method of embodiment 205, wherein said agonist is a peptide, small molecule, nucleic acid, antibody or aptamer.

Embodiment 207

The method of embodiments 201 or 204, further comprising administering to said subject an effective amount of a further therapeutic agent.

Embodiment 208

The method of embodiment 207, wherein said therapeutic agent is an idiopathic pulmonary fibrosis drug.

Embodiment 209

The method of embodiment 208, wherein said idiopathic pulmonary fibrosis drug is a mucolytic drug.

Embodiment 210

A method of determining whether a fibrotic pulmonary disease patient is at risk for progression of the fibrotic pulmonary disease, said method comprising: (i) determining a first expression level of a protein set forth in Table 2A or Table 2B in said patient at a first time point; (ii) determining a second expression level of a protein set forth in Table 2A or Table 2B in said patient at a second time point; (iii) comparing said second expression level of a protein set forth in Table 2A or Table 2B to said first expression level of a protein set forth in Table 2A or Table 2B, wherein when said second expression level of a protein set forth in Table 2A is greater than said first level of a protein set forth in Table 2A, or wherein when said second expression level of a protein set forth in Table 2B is smaller than said first level of a protein set forth in Table 2B, the patient is at risk for progression of the fibrotic pulmonary disease.

Embodiment 211

The method of embodiment 210 further comprising administering a fibrotic pulmonary disease treatment after said determining in step (i).

Embodiment 212

The method of embodiment 210, further comprising determining a rate of progression of said fibrotic pulmonary disease in said patient based on said comparing.

Embodiment 213

The method of embodiment 210, wherein said determining said first expression level of a protein set forth in Table 2A or Table 2B and said second expression level of a protein set forth in Table 2A or Table 2B comprises normalizing said first expression level of a protein set forth in Table 2A or Table 2B and said second expression level of a protein set forth in Table 2A or Table 2B to a protein expressed from a standard gene in said patient.

Embodiment 214

The method of embodiment 213, wherein said standard gene is a GAPDH or beta-actin.

Embodiment 215

The method of embodiment 214, wherein said first expression level is detected from a first biological sample of said subject and said second expression level is detected from a second biological sample of said subject.

Embodiment 216

The method of embodiment 215, wherein said first biological sample is a first bodily fluid sample and said second biological sample is a second bodily fluid sample.

Embodiment 217

A method of determining a fibrotic pulmonary disease activity in a patient, said method comprising: (i) determining a first expression level of a protein set forth in Table 2A or Table 2B in said patient at a first time point; (ii) determining a second expression level of a protein set forth in Table 2A or Table 2B in said patient at a second time point; (iii) comparing said second expression level of a protein set forth in Table 2A or Table 2B to said first expression level of a protein set forth in Table 2A or Table 2B, thereby determining said fibrotic pulmonary disease activity in said patient.

Embodiment 218

The method of embodiment 217, further comprising administering a fibrotic pulmonary disease treatment after said determining in step (i).

Embodiment 219

A method of treating a fibrotic pulmonary disease in a subject in need thereof, said method comprising administering to said subject an effective amount of an modulator of a fibrotic pulmonary disease marker protein set forth in Table 2A or Table 2B, thereby treating a fibrotic pulmonary disease in said subject.

Embodiment 220

The method of embodiment 219, comprising administering to said subject an effective amount of a modulator of said fibrotic pulmonary disease marker protein set forth in Table 2A.

Embodiment 221

The method of embodiment 220, wherein said modulator is an antagonist.

Embodiment 222

The method of embodiment 221, wherein said antagonist is a peptide, small molecule, nucleic acid, antibody or aptamer.

Embodiment 223

The method of embodiment 219, comprising administering to said subject an effective amount of a modulator of said fibrotic pulmonary disease marker protein set forth in Table 2B.

Embodiment 224

The method of embodiment 223, wherein said modulator is an agonist.

Embodiment 225

The method of embodiment 224, wherein said agonist is a peptide, small molecule, nucleic acid, antibody or aptamer.

Embodiment 226

A method of treating a fibrotic pulmonary disease in a subject in need thereof, said method comprising: (i) determining whether a subject expresses an elevated level of a fibrotic pulmonary disease marker protein as set forth in Table 2A or a decreased level of a fibrotic pulmonary disease marker protein as set forth in Table 2B relative to a standard control; and (ii) when an elevated expression level of said fibrotic pulmonary disease marker protein of Table 2A or a decreased expression level of said fibrotic pulmonary disease marker protein of Table 2B is found relative to said standard control, administering to said subject a fibrotic pulmonary disease treatment, an antagonist of a fibrotic pulmonary disease marker protein set forth in Table 2A or an agonist of a fibrotic pulmonary disease marker protein set forth in Table 2B, thereby treating said subject.

Embodiment 227

The method of embodiment 226, wherein said fibrotic pulmonary disease treatment is a mucolytic drug.

Embodiment 228

A method of determining whether a fibrotic pulmonary disease patient is at risk for progression of the fibrotic pulmonary disease, the method comprising: (i) detecting an expression level of one or more fibrotic pulmonary disease marker protein set forth in Table 2A or 2B in a fibrotic pulmonary disease patient; (ii) determining whether said expression level is modulated relative to a standard control, wherein a modulated expression level of a fibrotic pulmonary disease marker protein in Table 2A or 2B relative to said standard control indicates that said fibrotic pulmonary disease patient is at risk for progression of said fibrotic pulmonary disease; and (iii) based at least in part on said expression level in step (ii), determining whether said fibrotic pulmonary disease patient is at risk for progression of said fibrotic pulmonary disease.

Embodiment 229

The method of embodiment 228, wherein said determining whether the expression level is modulated relative to a standard control comprises determining whether the expression level is elevated or suppressed relative to other fibrotic pulmonary disease patients.

Embodiment 230

A method of determining an expression level of a fibrotic pulmonary disease marker protein set forth in Table 3A or Table 3B in a subject that has or is at risk for developing a fibrotic pulmonary disease, said method comprising: (i) obtaining a biological sample from said subject; and (ii) determining an expression level of a fibrotic pulmonary disease marker protein set forth in Table 3A or Table 3B in said biological sample.

Embodiment 231

A method of determining whether a subject has or is at risk of developing a fibrotic pulmonary disease, said method comprising: (i) detecting an expression level of one or more fibrotic pulmonary disease marker proteins set forth in Table 3A or Table 3B in a subject; (ii) determining whether said expression level is increased or decreased relative to a standard control, wherein an elevated expression level of a fibrotic pulmonary disease marker protein in Table 3A or a decreased expression level of a fibrotic pulmonary disease marker protein in Table 3B relative to said standard control indicates that said subject has or is at risk of developing a fibrotic pulmonary disease; and (iii) based at least in part on said expression level in step (ii), determining whether said subject has or is at risk for developing a fibrotic pulmonary disease.

Embodiment 232

A method of determining whether a fibrotic pulmonary disease patient is at risk for progression of the fibrotic pulmonary disease, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, wherein when said second expression level of a protein set forth in Table 3A is greater than said first level of a protein set forth in Table 3A, or wherein when said second expression level of a protein set forth in Table 3B is smaller than said first level of a protein set forth in Table 3B, the patient is at risk for progression of the fibrotic pulmonary disease.

Embodiment 233

A method of determining a fibrotic pulmonary disease activity in a patient, said method comprising: (i) determining a first expression level of a protein set forth in Table 3A or Table 3B in said patient at a first time point; (ii) determining a second expression level of a protein set forth in Table 3A or Table 3B in said patient at a second time point; (iii) comparing said second expression level of a protein set forth in Table 3A or Table 3B to said first expression level of a protein set forth in Table 3A or Table 3B, thereby determining said fibrotic pulmonary disease activity in said patient.

Embodiment 234

A method of treating a fibrotic pulmonary disease in a subject in need thereof, said method comprising administering to said subject an effective amount of an modulator of a fibrotic pulmonary disease marker protein set forth in Table 3A or Table 3B, thereby treating a fibrotic pulmonary disease in said subject.

Embodiment 235

A method of treating a fibrotic pulmonary disease in a subject in need thereof, said method comprising: (i) determining whether a subject expresses an elevated level of a fibrotic pulmonary disease marker protein as set forth in Table 3A or a decreased level of a fibrotic pulmonary disease marker protein as set forth in Table 3B relative to a standard control; and (ii) when an elevated expression level of said fibrotic pulmonary disease marker protein of Table 3A or a decreased expression level of said fibrotic pulmonary disease marker protein of Table 3B is found relative to said standard control, administering to said subject a fibrotic pulmonary disease treatment, an antagonist of a fibrotic pulmonary disease marker protein set forth in Table 3A or an agonist of a fibrotic pulmonary disease marker protein set forth in Table 3B, thereby treating said subject.

Embodiment 236

The method of embodiment 235, wherein said determining whether the expression level is modulated relative to a standard control comprises determining whether the expression level is elevated or suppressed relative to other fibrotic pulmonary disease patients.

Embodiment 237

A method of determining whether a fibrotic pulmonary disease patient is at risk for progression of the fibrotic pulmonary disease, the method comprising: (i) detecting an expression level of one or more fibrotic pulmonary disease marker protein set forth in Table 3A or 3B in a fibrotic pulmonary disease patient; (ii) determining whether the expression level is modulated relative to a standard control, wherein a modulated expression level of a fibrotic pulmonary disease marker protein in Table 3A or 3B relative to said standard control indicates that said fibrotic pulmonary disease patient is at risk for progression of the fibrotic pulmonary disease; and (iii) based at least in part on the expression level in step (ii), determining whether said fibrotic pulmonary disease patient is at risk for progression of the fibrotic pulmonary disease.

Embodiment 238

The method of embodiment 237, wherein said determining whether the expression level is modulated relative to a standard control comprises determining whether the expression level is elevated or suppressed relative to other fibrotic pulmonary disease patients.

What is claimed is:
1. A method of determining an expression level of each of a plurality of fibrotic pulmonary disease marker proteins in a subject that has or is at risk for developing a fibrotic pulmonary disease, said method comprising:
  (i) obtaining a biological sample from said subject;
  (ii) contacting each of said plurality of fibrotic pulmonary disease marker proteins with a marker protein binding agent for each of said plurality of fibrotic pulmonary disease marker proteins in said biological sample thereby forming disease marker protein-binding agent complexes; and
  (iii) detecting said disease marker protein-binding agent complexes thereby determining an expression level of each of said plurality of fibrotic pulmonary disease marker proteins in said biological sample,
wherein said plurality of fibrotic pulmonary disease marker proteins consists of TIMP-1, MMP-7, PTN, Activin A, HGF, Midkine, SIEGE-121, PDE3A, SBDS, DKK-4, SICAM-5, SREC-I, ERIK-1, DKK-1, α2-Macroglobulin, NAGK, UFC1 and SGTA.

2. The method of claim 1, further comprising selecting a subject that has or is at risk for developing a fibrotic pulmonary disease for treatment of said fibrotic pulmonary disease when said expression level of one or more of said plurality of pulmonary disease marker proteins as set forth in claim 1 is elevated relative to a standard control.

3. The method of claim 1, wherein said fibrotic pulmonary disease is idiopathic pulmonary fibrosis or familial interstitial pneumonia.

4. The method of claim 1, wherein said subject has or is at risk for developing a progressive fibrotic pulmonary disease.

5. The method of claim 4, wherein said progressive fibrotic pulmonary disease is progressive idiopathic pulmonary fibrosis.

6. The method of claim 1, wherein said biological sample is a blood-derived biological sample of said subject.

7. The method of claim 1, wherein said expression level of one or more of said plurality of fibrotic pulmonary disease marker proteins as set forth in claim 1 is elevated relative to a standard control.

8. The method of claim 1, wherein said expression level of one or more of said plurality of fibrotic pulmonary disease marker proteins as set forth in claim 1 is decreased relative to a standard control.

9. A method of treating a fibrotic pulmonary disease in a subject said method comprising:
  (i) obtaining a biological sample from said subject;
  (ii) contacting one or more fibrotic pulmonary disease marker proteins with a marker protein binding agent for each of said one or more of fibrotic pulmonary disease marker proteins in said biological sample thereby forming one or more disease marker protein-binding agent complexes;
  (iii) detecting said one or more disease marker protein-binding agent complexes thereby detecting an expression level of said one or more fibrotic pulmonary disease marker proteins in said subject;
  (iv) determining whether said expression level of said one or more fibrotic pulmonary marker proteins is increased or decreased relative to a standard control, wherein an elevated expression level of said one or more fibrotic pulmonary disease marker proteins or a decreased expression level of said one or more fibrotic pulmonary disease marker proteins relative to said standard control indicates that said subject has or is at risk of developing a fibrotic pulmonary disease; and
  (v) based at least in part on said expression level detected in step (iii) and the presence of one or more additional characteristics of fibrotic pulmonary disease in said subject determining said subject has or is at risk for developing a fibrotic pulmonary disease; and
  (vi) administering to said subject that has or is at risk for developing a fibrotic pulmonary disease an effective amount of a steroid or a TGF-β inhibitor;
  wherein said one or more fibrotic pulmonary disease marker proteins is selected from the group consisting of:
    (a) a plurality of fibrotic pulmonary disease marker proteins consisting of TIMP-1, MMP-7, PTN, Activin A, HGF, Midkine, VEGF-121, PDE3A, SBDS, DKK-4, SICAM-5, SREC-I, ERK-1, DKK-1, α2-Macroglobulin, NAGK, UFC1 and SGTA wherein the expression level of each of said plurality of fibrotic pulmonary disease marker proteins is determined;
    (b) SREC-I; and
    (c) PTN.

10. The method of claim 9, wherein said subject has or is at risk for developing a progressive fibrotic pulmonary disease.

11. The method of claim 10, wherein said progressive fibrotic pulmonary disease is progressive idiopathic pulmonary fibrosis.

12. A method of treating a fibrotic pulmonary disease in a subject in need thereof the method comprising:
- (i) obtaining a biological sample from said subject;
- (ii) contacting one or more fibrotic pulmonary disease marker proteins with a marker protein binding agent for each of said one or more of fibrotic pulmonary disease marker proteins in said biological sample forming thereby one or more disease marker protein-binding agent complexes;
- (iii) detecting said one or more disease marker protein-binding agent complexes thereby detecting an expression level of said one or more fibrotic pulmonary disease marker proteins in said fibrotic pulmonary disease patient;
- (iv) determining whether said expression level of said one or more fibrotic pulmonary marker proteins is modulated relative to a standard control, wherein a modulated expression level of said one or more fibrotic pulmonary disease marker protein relative to said standard control indicates that said fibrotic pulmonary disease patient is at risk for progression of said fibrotic pulmonary disease; and
- (v) based at least in part on said expression level in step (iv) and the presence of one or more additional characteristics of fibrotic pulmonary disease in said subject, determining said fibrotic pulmonary disease patient is at risk for progression of said fibrotic pulmonary disease; and
- (vi) administering to said subject that has or is at risk for developing a fibrotic pulmonary disease an effective amount of a steroid or a TGF-$\beta$ inhibitor, wherein said one or more fibrotic pulmonary disease marker proteins is selected from the group consisting of:
- (a) a plurality of fibrotic pulmonary disease marker proteins consisting of TIMP-1, MMP-7, PTN, Activin A, HGF, Midkine, VEGF-121, PDE3A, SBDS, DKK-4, SCAM-5, SREC-I, ERK-1, DKK-1, $\alpha$2-Macroglobulin, NAGK, UFC1 and SGTA wherein the expression level of each of said plurality of fibrotic pulmonary disease marker proteins is determined;
- (b) SREC-I; and
- (c) PTN.

* * * * *